United States Patent
Nyce et al.

(10) Patent No.: US 9,512,047 B2
(45) Date of Patent: *Dec. 6, 2016

(54) ETHYLENE-TO-LIQUIDS SYSTEMS AND METHODS

(71) Applicant: Siluria Technologies, Inc., San Francisco, CA (US)

(72) Inventors: Greg Nyce, Pleasanton, CA (US); Peter Czerpak, San Francisco, CA (US); Carlos Faz, Hayward, CA (US); Jarod McCormick, San Carlos, CA (US); William Michalak, Redwood City, CA (US); Bipinkumar Patel, Richmond, TX (US); Guido Radaelli, South San Francisco, CA (US); Tim A. Rappold, San Francisco, CA (US); Ron Runnebaum, Sacramento, CA (US); Erik C. Scher, San Francisco, CA (US); Aihua Zhang, Daly City, CA (US); Joel Cizeron, Redwood City, CA (US)

(73) Assignee: SILURIA TECHNOLOGIES, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/076,512

(22) Filed: Mar. 21, 2016

(65) Prior Publication Data
US 2016/0200643 A1 Jul. 14, 2016

Related U.S. Application Data

(63) Continuation of application No. 14/789,917, filed on Jul. 1, 2015, now Pat. No. 9,321,702, which is a continuation of application No. 14/591,850, filed on Jan. 7, 2015.

(Continued)

(51) Int. Cl.
*C07C 1/00* (2006.01)
*C07C 27/00* (2006.01)
(Continued)

(52) U.S. Cl.
CPC ............... *C07C 2/12* (2013.01); *B01J 19/24* (2013.01); *B01J 19/245* (2013.01); *C07C 1/0425* (2013.01);
(Continued)

(58) Field of Classification Search
CPC ......... C07C 2/82; C07C 5/327; C07C 4/025; C07C 11/04; C07C 15/46; C07C 9/04; C07C 2/00; C10G 50/00
USPC ......................................... 585/324; 518/700
See application file for complete search history.

(56) References Cited

U.S. PATENT DOCUMENTS 2,486,980 A 11/1949 Robinson
2,579,601 A 12/1951 Nelson et al.
(Continued)

FOREIGN PATENT DOCUMENTS

CA 2765769 A1 1/2011
CN 1403375 A 3/2003
(Continued)

OTHER PUBLICATIONS

"Autothermal Partial Oxidative Coupling of Methane," IP.com, Prior Art Database Technical Disclosure, Jul. 29, 2008, 5 pages.
(Continued)

*Primary Examiner* — Jafar Parsa
(74) *Attorney, Agent, or Firm* — Wilson Sonsini Goodrich & Rosati

(57) ABSTRACT

Integrated systems are provided for the production of higher hydrocarbon compositions, for example liquid hydrocarbon compositions, from methane using an oxidative coupling of methane system to convert methane to ethylene, followed by conversion of ethylene to selectable higher hydrocarbon products. Integrated systems and processes are provided that process methane through to these higher hydrocarbon products.

19 Claims, 45 Drawing Sheets

Related U.S. Application Data

(60) Provisional application No. 61/925,200, filed on Jan. 8, 2014, provisional application No. 62/010,986, filed on Jun. 11, 2014, provisional application No. 62/050,729, filed on Sep. 15, 2014.

(51) Int. Cl.

| | | |
|---|---|---|
| *C07C 2/12* | (2006.01) | |
| *B01J 19/24* | (2006.01) | |
| *C07C 1/12* | (2006.01) | |
| *C07C 1/04* | (2006.01) | |
| *C07C 2/84* | (2006.01) | |
| *C07C 5/327* | (2006.01) | |
| *C07C 5/09* | (2006.01) | |
| *C07C 5/05* | (2006.01) | |
| *C07C 4/02* | (2006.01) | |
| *C10G 50/00* | (2006.01) | |
| *C10G 57/02* | (2006.01) | |
| *C10L 3/10* | (2006.01) | |

(52) U.S. Cl.
CPC . *C07C 1/12* (2013.01); *C07C 2/84* (2013.01); *C07C 4/02* (2013.01); *C07C 5/05* (2013.01); *C07C 5/09* (2013.01); *C07C 5/327* (2013.01); *C10G 50/00* (2013.01); *C10G 57/02* (2013.01); *C10L 3/10* (2013.01); *B01J 2219/00074* (2013.01); *B01J 2219/24* (2013.01); *C07C 2529/08* (2013.01); *C07C 2529/18* (2013.01); *C07C 2529/40* (2013.01); *C07C 2529/70* (2013.01); *C07C 2529/85* (2013.01); *C10G 2400/20* (2013.01); *C10G 2400/30* (2013.01); *Y02P 20/582* (2015.11); *Y02P 30/40* (2015.11)

(56) References Cited

U.S. PATENT DOCUMENTS

| | | |
|---|---|---|
| 2,673,221 A | 3/1954 | Berntsen et al. |
| 2,943,125 A | 6/1960 | Martin et al. |
| 3,128,317 A | 4/1964 | Arkell et al. |
| 3,413,817 A | 12/1968 | Ludwig |
| 3,459,678 A | 8/1969 | Hagemeyer et al. |
| 3,584,071 A | 6/1971 | Mcnulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,862,257 A | 1/1975 | Buben et al. |
| 3,900,526 A | 8/1975 | Johnson et al. |
| 3,931,349 A | 1/1976 | Kuo |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,314,090 A | 2/1982 | Shewbart et al. |
| 4,329,530 A | 5/1982 | Irvine et al. |
| 4,367,353 A | 1/1983 | Inglis |
| 4,375,566 A | 3/1983 | Kawamata et al. |
| 4,433,185 A | 2/1984 | Tabak |
| 4,440,956 A | 4/1984 | Couvillion |
| 4,465,887 A | 8/1984 | Schammel |
| 4,481,305 A | 11/1984 | Jorn et al. |
| 4,551,438 A | 11/1985 | Miller |
| 4,552,644 A | 11/1985 | Johnson et al. |
| 4,567,307 A | 1/1986 | Jones et al. |
| 4,629,718 A | 12/1986 | Jones et al. |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,814,539 A | 3/1989 | Jezl et al. |
| 4,822,477 A | 4/1989 | Avidan et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,882,400 A | 11/1989 | Dumain et al. |
| 4,895,823 A | 1/1990 | Kolts et al. |
| 4,900,347 A | 2/1990 | McCue et al. |
| 4,935,568 A | 6/1990 | Harandi et al. |
| 4,939,312 A | 7/1990 | Baerns et al. |
| 4,966,874 A | 10/1990 | Young et al. |
| 5,012,028 A | 4/1991 | Gupta et al. |
| 5,034,565 A | 7/1991 | Harandi et al. |
| 5,057,638 A | 10/1991 | Sweeney |
| 5,080,872 A | 1/1992 | Jezl et al. |
| 5,118,898 A | 6/1992 | Tyler et al. |
| 5,132,472 A | 7/1992 | Durante et al. |
| 5,137,862 A | 8/1992 | Mackrodt et al. |
| 5,179,056 A | 1/1993 | Bartley |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,473,027 A | 12/1995 | Batchelor et al. |
| 5,523,493 A | 6/1996 | Cameron et al. |
| 5,599,510 A | 2/1997 | Kaminsky et al. |
| 5,633,422 A | 5/1997 | Murray |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | DeVries |
| 5,723,713 A | 3/1998 | Maunders |
| 5,736,107 A | 4/1998 | Inomata et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,830,822 A | 11/1998 | Euzen |
| 5,849,973 A | 12/1998 | Van der Vaart |
| 5,856,257 A | 1/1999 | Freeman et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,936,135 A | 8/1999 | Choudhary et al. |
| 6,013,851 A | 1/2000 | Verrelst et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,146,549 A | 11/2000 | Mackay et al. |
| 6,153,149 A | 11/2000 | Rabitz et al. |
| 6,221,986 B1 | 4/2001 | Commereuc et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |

(56) References Cited

U.S. PATENT DOCUMENTS

| | | |
|---|---|---|
| RE37,853 E | 9/2002 | Detering et al. |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | Kibby et al. |
| 6,713,657 B2 | 3/2004 | Miller et al. |
| 6,726,850 B1 | 4/2004 | Reyes et al. |
| 6,759,562 B2 | 7/2004 | Gartside et al. |
| 6,764,602 B2 | 7/2004 | Shutt et al. |
| 6,768,035 B2 | 7/2004 | Mathur et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,157,612 B2 | 1/2007 | Ewert et al. |
| 7,164,052 B2 | 1/2007 | Carati et al. |
| 7,183,451 B2 | 2/2007 | Gattis et al. |
| 7,196,238 B2 | 3/2007 | Nurminen et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,781,636 B2 | 8/2010 | Iaccino et al. |
| 7,795,490 B2 | 9/2010 | Iaccino et al. |
| 7,838,710 B2 | 11/2010 | Ryu |
| 7,879,119 B2 | 2/2011 | Abughazaleh et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,021,620 B2 | 9/2011 | Nicholas et al. |
| 8,080,215 B2 | 12/2011 | Taheri et al. |
| 8,119,848 B2 | 2/2012 | Cross et al. |
| 8,129,305 B2 | 3/2012 | Bagherzadeh et al. |
| 8,153,851 B2 | 4/2012 | Gartside et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,399,527 B1 | 3/2013 | Brown et al. |
| 8,399,726 B2 | 3/2013 | Chinta et al. |
| 8,552,236 B2 | 10/2013 | Iaccino |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,912,109 B2 | 12/2014 | Chinta et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 2003/0045761 A1 | 3/2003 | Kuechler et al. |
| 2003/0094398 A1 | 5/2003 | Porter et al. |
| 2003/0189202 A1 | 10/2003 | Li et al. |
| 2004/0220053 A1 | 11/2004 | Bagherzadeh et al. |
| 2005/0065391 A1 | 3/2005 | Gattis et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0283780 A1 | 12/2006 | Spivey et al. |
| 2007/0027030 A1 | 2/2007 | Cheung et al. |
| 2007/0083073 A1 | 4/2007 | Bagherzadeh et al. |
| 2008/0141713 A1 | 6/2008 | Verma |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian et al. |
| 2010/0003179 A1 | 1/2010 | Katusic et al. |
| 2010/0191031 A1 | 7/2010 | Sundaram |
| 2010/0197986 A1 | 8/2010 | Midorikawa et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0124488 A1 | 5/2011 | Neltner et al. |
| 2011/0189559 A1 | 8/2011 | Baldanza et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2012/0041246 A1 | 2/2012 | Scher et al. |
| 2012/0065412 A1 | 3/2012 | Abdallah et al. |
| 2012/0129690 A1 | 5/2012 | Larcher et al. |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2013/0023079 A1 | 1/2013 | Kang et al. |
| 2013/0023709 A1 | 1/2013 | Cizeron et al. |
| 2013/0040806 A1 | 2/2013 | Dismukes et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2014/0012053 A1 | 1/2014 | Iyer et al. |
| 2014/0018589 A1 | 1/2014 | Iyer et al. |
| 2014/0107385 A1 | 4/2014 | Schammel et al. |
| 2014/0121433 A1 | 5/2014 | Cizeron et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0235911 A1 | 8/2014 | Laha |
| 2014/0274671 A1 | 9/2014 | Schammel et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |

(56) References Cited

U.S. PATENT DOCUMENTS

| | | |
|---|---|---|
| 2015/0232395 A1 | 8/2015 | Nyce et al. |
| 2015/0329438 A1 | 11/2015 | Nyce et al. |
| 2015/0329439 A1 | 11/2015 | Nyce et al. |

FOREIGN PATENT DOCUMENTS

| | | |
|---|---|---|
| CN | 101224432 | 7/2008 |
| CN | 101387019 A | 3/2009 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| EP | 0253522 A2 | 1/1988 |
| EP | 0608447 A1 | 8/1994 |
| EP | 0634211 A1 | 1/1995 |
| EP | 0722822 A1 | 7/1996 |
| EP | 0716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| FR | 649429 A | 12/1928 |
| GB | 733336 * | 7/1955 |
| GB | 2191212 A | 12/1987 |
| JP | 2005161225 A | 6/2005 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2009071463 A2 | 6/2009 |
| WO | 2009074203 A1 | 6/2009 |
| WO | 2009115805 A1 | 9/2009 |
| WO | 2011008464 A1 | 1/2011 |
| WO | 2011041184 A2 | 4/2011 |
| WO | 2011050359 A1 | 4/2011 |
| WO | 2010069488 | 5/2011 |
| WO | 2011149996 A2 | 12/2011 |
| WO | 2012162526 A2 | 11/2012 |
| WO | 2013169462 A1 | 11/2013 |
| WO | 2013175204 A1 | 11/2013 |
| WO | 2013177461 A2 | 11/2013 |
| WO | 2014044387 A1 | 3/2014 |
| WO | 2015000061 A1 | 1/2015 |
| WO | 2015003193 A2 | 1/2015 |
| WO | 2015021177 A1 | 2/2015 |

OTHER PUBLICATIONS

Barrett, et al. "The determination of pore volume and area distributions in porous substances—Computations from nitrogen isotherms." J. Am. Chem. Soc. (1951) 73:373-380.

Bollmann, et al. "Ethylene tetramerization: a new route to produce 1-octene in exceptionally high selectivities." J Am Chem Soc. (Nov. 17, 2004) 126(45):14712-3.

Botella, et al. "Effect of Potassium Doping on the Catalytic Behavior of Mo—V—Sb Mixed Oxide Catalysts in the Oxidation of Propane to Acrylic Acid." Catalysis Letters (Sep. 2003) 89(3-4):249-253.

Carter, et al. "High activity ethylene trimerisation catalysts based on diphosphine ligands." Chem Commun (Camb). (Apr. 21, 2002) (8):858-9.

Cavani et al. "Oxidative dehydrogenation of ethane and propane: How far fro commercial implementation?" Catalysis Today (2007) 127:113-131.

Chemsystems PERP Report Ethylene Oxide/Ethylene Glycol 2005.

Chen, et al. "M2 Forming—A Process for Aromatization of Light Hydrocarbons." Ind. Eng. Chem. Process. Des. Dev. (1986) 25:151-155.

Choudhary et al. "Aromatization of dilute ethylene over Ga-modified ZSM-5 type zeolite catalysts" Microporous and Mesoporous Materials (2001) 47:253-267.

Choudhary et al. "Oxidative conversion of methane/natural gas into higher hydrocarbons" Catalysis Surveys from Asia (2004) 8(1):15-25.

Choudhary et al. "Surface basicity and acidity of alkaline earth-promoted La2O3 catalysts and their performance in oxidative coupling of methane" J Chem. Technol. Biotechnol (1998) 72:125-130.

Christopher et al. "Engineering selectivity in heterogeneous catalysis: Ag nanowires as selective ethylene epoxidation catalysts" J Am Chem Soc. (2008) 130:11264-11265.

Debart et al., "Alpha-MnO2 Nanowires: A Catalyst for the O2 Electrode in Rechargeable Lithium Batteries," Angew. Chem. Int. Ed. (2008) 47:4521-4524.

Ding, X et al. "Effect of acid density of HZSM-5 on the oligomerization of ethylene in FCC dry gas" J Nat Gas Chem (2009) 18:156-160.

Enger et al., "A review of catalytic partial oxidation of methane to synthesis gas with emphasis on reaction mechanisms over transition metal catalysts," Applied Catalysis A: General 346:1-27, Aug. 2008.

Gao et al., "A study on methanol steam reforming to CO2 and H2 over the La2CuO4 nanofiber catalyst," Journal of Solid State Chemistry 181:7-13, 2008.

Gao et al., "The direct decomposition of NO over the La2CuO4 nanofiber catalyst," Journal of Solid State Chemistry 181:2804-2807, 2008.

Guo et al. "Current Status and Some Perspectives of Rare Earth Catalytic Materials" J Chinese Rare Earth Soc (2007) 25(1):1-15.

Haag, W.O. et al. "Aromatics, Light Olefins and Gasoline from Methanol: Mechanistic Pathways with ZSM-5 Zeolite Catalyst" J Mol Catalysis (1982) 17:161-169.

Huang et al., "Exploiting Shape Effects of La2O3 Nanocatalysts for Oxidative Coupling of Methane Reaction," The Royal Society of Chemistry 2013, 5 pages.

Huang et al., "Exploiting Shape Effects of La2O3 Nanocatalysts for Oxidative Coupling of Methane Reaction," The Royal Society of Chemistry 2013, 7 pages (Electronic Supplementary Information).

International search report and written opinion dated Mar. 6, 2014 for PCT/US2013/042480.

International search report and written opinion dated Jun. 26, 2015 for PCT Application No. US2015/010525.

International search report and written opinion dated Nov. 1, 2013 for PCT/US2013/049742.

International search report dated Mar. 19, 2014 for PCT Application No. PCT/US2013/073657.

Jiangrong Niu, et al. "Preparation and Characterization of La2O2CO3 Nanowires with High Surface Areas" J Chinese Rare Earth Soc (Dec. 2005) 23:33-36.

Keller, et al. Synthesis of Ethylene via Oxidative Coupling of Methane. Journal of Catalysis 73: 9-19, 1982.

Knuuttila, et al. "Advanced Polyethylene Technologies—Controlled Material Properties. Long Term Properties of Polyolefins" Advances in Polymer Science (2004) 169:13-28.

Kuang, et al. "Grafting of PEG onto lanthanum hydroxide nanowires". Materials Letters (2008) 62:4078-4080.

Labinger, "Oxidative Coupling of Methane: An Inherent Limit to Selectivity?" Catalysis Letters (1988) 1:371-376.

Li, et al. "Combined Single-Pass Conversion of Methane Via Oxidative Coupling and Dehydroaromatization." Catalysis Letters (Sep. 2003) 89(3-4):275-279.

Li, et al. Energy and Fuels. (2008) 22: 1897-1901.

Ling et al. "Preparation of Ag_coreAu_core Nanowires and Their Surface Enhanced Raman Spectroscopic Studies" Acta Chem Sinica (2007) 65(9):779-784.

Liu, et al. A novel Na_WO4—Mn.SiC monolithic foam catalyst with improved thermal properties for the oxidative coupling of methane. Catalysis Communications 9: 1302-1306, 2008.

(56) References Cited

OTHER PUBLICATIONS

Lunsford, "The Catalytic Oxidative Coupling of Methane," Angew. Chem. Int. Ed. Engl. (1995) 34:970-980.
Lunsford, J.H. "Catalytic conversion of methane to more useful chemicals and fuels: a challenge for the 21st century" Catalysis Today (2000) 63:165-174.
Mleczko, et al. "Catalytic oxidative coupling of methane—reaction engineering aspects and process schemes" Fuel Processing Tech (1995) 42:217-248.
Morgan, C.R. et al. "Gasoline from Alcohols" Ind Eng Chem Prod Res Dev (1981) 20:185-190.
Natural Gas Spec Sheet, prepared by Florida Power and Light Company, 2003.
Neltner et al. "Production of Hydrogen Using Nanocrystalline Protein-Templated Catalysts on M13 Phage" ACS Nano (2010) 4(6): 3227-3235.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nielsen, et al. "Treat LPGs with amines." Hydrocarbon Process (1997) 79:49-59.
Notice of allowance dated Jan. 20, 2016 for U.S. Appl. No. 14/789,936.
Notice of Allowance dated Jan. 21, 2016 for U.S. Appl. No. 14/789,917.
Notice of allowance dated Dec. 30, 2015 for U.S. Appl. No. 14/789,957.
Nyce, G. et al. "Ethylene-to-Liquids Systems and Methods" U.S. Appl. No. 15/076,436, filed Mar. 23, 2016.
Office action dated Mar. 9, 2016 for U.S. Appl. No. 14/099,614.
Office action dated Sep. 11, 2015 for U.S. Appl. No. 14/789,917.
Office Action dated Sep. 23, 2015 for U.S. Appl. No. 14/789,936.
Office action dated Oct. 23, 2014 for U.S. Appl. No. 13/739,954.
Olah, G. Hydrocarbon Chemistry. 2nd Edition, John Wiley & Sons, 2003.
Pak et al., "Elementary Reactions in the Oxidative Coupling of Methane over Mn/Na2WO4/SiO2 and Mn/Na2WO4/MgO Catalysts," Journal of Catalysis (1998) 179:222-230.
Qiu et al., "Steady-state conversion of methane to aromatics in high yields using an integrated recycle reaction system," Catalysis Letters 48:11-15, 1997.
Saito, et al. "Dehydrogenation of Propane Over a Silica-Supported Gallium Oxide Catalyst." Catalysis Letters (Sep. 2003) 89(3-4):213-217.
Schweer et al., "OCM in a fixed-bed reactor: limits and perspectives," Catalysis Today 21:357-369, 1994.
Somorjai et al., "High technology catalysts towards 100% selectivity Fabrication, characterization and reaction studies," Catalysis Today 100:201-215, 2005.
Sugiyama, et al. "Redox Behaviors of Magnesium Vanadate Catalysts During the Oxidative Dehydrogenation of Propane." Catalysis Letters (Sep. 2003) 89(3-4):229-233.
Tabak, S.A. et al. "Conversion of Methanol over ZSM-5 to Fuels and Chemicals" Cat Today (1990) 307-327.
Takanabe et al., "Mechanistic Aspects and eaction Pathways for Oxidative Coupling of Methane on Mn/Na2WO4/SiO2 Catalysts," J. Phys. Chem. C (2009) 113(23):10131-10145.
Takanabe et al., "Rate and Selectivity Enhancements Mediated by OH Radicals in the Oxidative Coupling of Methane Catalyzed by Mn/Na2WO4/SiO2," Angew. Chem. Int. Ed. (2008) 47:7689-7693.
Tong et al. "Development Strategy Research of Downstream Products of Ethene in Tianjin" Tianjin Economy (1996) 37-40.
Trautmann et al., "Cyrogenic Technology for Nitrogen Rejection from Variable Content Natural Gas," XIV Convencion Internacional de Gas, Caracas, Venezuela May 10-12, 2000. (ref from client).
Wang et al., "Autothermal oxidative coupling of methane on the SrCO3/Sm2O3 catalysts," Catalysis Communications 10(6):807-810, 2009.
Wang et al., "Comparative study on oxidation of methane to ethane and ethylene over Na2WO4—Mn/SiO2 catalysts prepared by different methods," Journal of Molecular Catalysis A: Chemical (2006) 245:272-277.
Wang et al., "Low-temperature selective oxidation of methane to ethane and ethylene over BaCO3/La2O3 catalysts prepared by urea combustion method," Catalysis Communications 7(2):59-63, 2006.
Wong et al., "Oxidative Coupling of Methane Over Alkali Metal Oxide Promoted LA2O3/BACO3 Catalysts," Journal of Chemical Technology and Biotechnology 65(4):351-354, 1996.
Xu, et al. "Maximise ethylene gain and acetylene selective hydrogenation efficiency." Petroleum technology quarterly (2013) 18.3:39-42.
Yang et al., "Anisotropic syntheses of boat-shaped core-shell Au—Ag nanocrystals and nanowires," Nanotechnology 17(9): 2304-2310, 2006.
Yu, C et al. "Oxidative Coupling of Methane over Acceptor-doped SrTiO3: Corelation between p-type Conductivity an dC2 Silectivity and C2 Yield," J. Catalysis (1992) 13(5):338-344.
Zhang, Q. Journal of Natural Gas Chem., (2003) 12:81.
Zhao, X-W, "Technologies and Catalysts for Catalytic Preparation of Ethene," Industrial Catalysis (2004) 12 (Supplement):285-289.
Zhou, M et al., "Functionalization of lanthanum hydroxide nanowires by atom transfer radical polymerization," Nanotechnology (2007) 18(40): 7 pages.
Zhou. "BP-UOP Cyclar Process". Handbook of Petroleum Refining Processes, The McGraw-Hill Companies (2004), pp. 2.29-2.38.
Zimmermann et al., "Ethylene," Ullmann's Encyclopedia of Industrial Chemistry, Wiley-VCH Verlag GmbH & Co. KGaA, Weinheim, Germany, 2009, 66 pages.
International preliminary report on patentability dated Jul. 21, 2016 for PCT Application No. US2015/010525.

\* cited by examiner

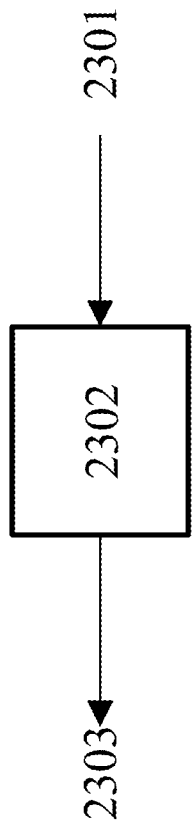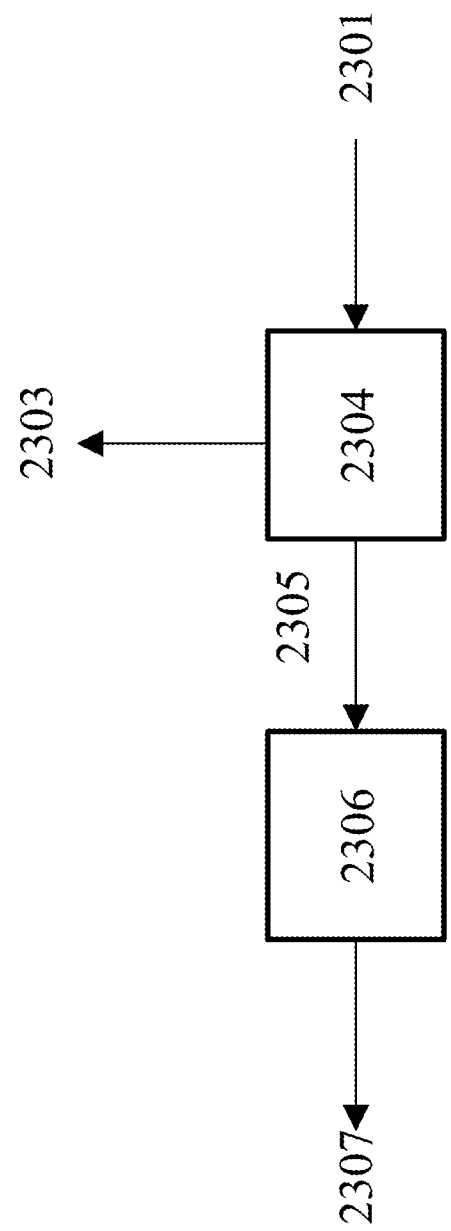
FIG. 23A
FIG. 23B

ETHYLENE-TO-LIQUIDS SYSTEMS AND METHODS

CROSS-REFERENCE

This application is a continuation application of U.S. patent application Ser. No. 14/789,917, filed Jul. 1, 2015, which application is a continuation application of U.S. patent application Ser. No. 14/591,850, filed Jan. 7, 2015, which application claims the benefit of U.S. Provisional Patent Application Ser. No. 61/925,200, filed Jan. 8, 2014, U.S. Provisional Patent Application Ser. No. 62/010,986, filed Jun. 11, 2014, and U.S. Provisional Patent Application Ser. No. 62/050,729, filed Sep. 15, 2014, each of which is entirely incorporated herein by reference in its entirety.

BACKGROUND

The modern petrochemical industry makes extensive use of cracking and fractionation technology to produce and separate various desirable compounds from crude oil. Cracking and fractionation operations are energy intensive and generate considerable quantities of greenhouse gases.

The gradual depletion of worldwide petroleum reserves and the commensurate increase in petroleum prices may place extraordinary pressure on refiners to minimize losses and improve efficiency when producing products from existing feedstocks, and also to seek viable alternative feedstocks capable of providing affordable hydrocarbon intermediates and liquid fuels to downstream consumers.

Methane may provide an attractive alternative feedstock for the production of hydrocarbon intermediates and liquid fuels due to its widespread availability and relatively low cost when compared to crude oil. Worldwide methane reserves may be in the hundreds of years at current consumption rates and new production stimulation technologies may make formerly unattractive methane deposits commercially viable.

Ethylene is an important commodity chemical intermediate. It may be used in the production of polyethylene plastics, polyvinyl chloride, ethylene oxide, ethylene chloride, ethylbenzene, alpha-olefins, linear alcohols, vinyl acetate, and fuel blendstocks such as, but not limited to, aromatics, alkanes and alkenes. With economic growth in developed and developing portions of the world, demand for ethylene and ethylene based derivatives continues to increase. Currently, ethylene is produced through the cracking of ethane derived either from crude oil distillates, called naphtha, or from the relatively minor ethane component of natural gas. Ethylene production is primarily limited to high volume production as a commodity chemical in relatively large steam crackers or other petrochemical complexes that also process the large number of other hydrocarbon byproducts generated in the crude oil cracking process. Producing ethylene from far more abundant and significantly less expensive methane in natural gas provides an attractive alternative to ethylene derived from ethane in natural gas or crude oil.

SUMMARY

Recognized herein is the need for efficient and commercially viable systems and methods for converting ethylene to higher molecular weight hydrocarbons, including gasoline, diesel fuel, jet fuel, and aromatic chemicals. In some cases, the higher molecular weight hydrocarbons can be produced from methane in an integrated process that converts methane to ethylene and the ethylene to the higher molecular weight compounds. An oxidative coupling of methane ("OCM") reaction is a process by which methane can form one or more hydrocarbon compounds with two or more carbon atoms (also "$C_{2+}$ compounds" herein), such as olefins like ethylene.

In an OCM process, methane can be oxidized to yield products comprising $C_{2+}$ compounds, including alkanes (e.g., ethane, propane, butane, pentane, etc.) and alkenes (e.g., ethylene, propylene, etc.). Such alkane (also "paraffin" herein) products may not be suitable for use in downstream processes. Unsaturated chemical compounds, such as alkenes (or olefins), may be more preferable for use in downstream processes. Such compounds may be polymerized to yield polymeric materials, which may be employed for use in various commercial settings.

Oligomerization processes can be used to further convert ethylene into longer chain hydrocarbons useful as polymer components for plastics, vinyls, and other high value polymeric products. Additionally, these oligomerization processes may be used to convert ethylene to other longer hydrocarbons, such as $C_6$, $C_7$, $C_8$ and longer hydrocarbons useful for fuels like gasoline, diesel, jet fuel and blendstocks for these fuels, as well as other high value specialty chemicals.

An aspect of the present disclosure provides an oxidative coupling of methane (OCM) system, comprising: (a) an OCM subsystem that (i) takes as input a feed stream comprising methane ($CH_4$) and a feed stream comprising an oxidizing agent, and (ii) generates from the methane and the oxidizing agent a product stream comprising $C_{2+}$ compounds and non-$C_{2+}$ impurities; (b) at least one separations subsystem downstream of, and fluidically coupled to, the OCM subsystem, wherein the separations subsystem comprises a first heat exchanger, a de-methanizer unit downstream of the first heat exchanger, and a second heat exchanger downstream of the de-methanizer unit, wherein (i) the first heat exchanger cools the product stream, (ii) the de-methanizer unit accepts the product stream from the first heat exchanger and generates an overhead stream comprising at least a portion of the non-$C_{2+}$ impurities, and (iii) at least a portion of the overhead stream is cooled in the second heat exchanger and is subsequently directed to the first heat exchanger to cool the product stream; and (c) an olefin to liquids subsystem downstream of the OCM subsystem, wherein the olefin to liquids subsystem is configured to generate higher hydrocarbon(s) from one or more olefins included in the $C_{2+}$ compounds.

In some embodiments of aspects provided herein, the oxidizing agent is $O_2$. In some embodiments of aspects provided herein, the $O_2$ is provided by air. In some embodiments of aspects provided herein, the OCM subsystem comprises at least one OCM reactor. In some embodiments of aspects provided herein, the OCM subsystem comprises at least one post-bed cracking unit downstream of the at least one OCM reactor, which post-bed cracking unit is configured to convert at least a portion of alkanes in the product stream to alkenes. In some embodiments of aspects provided herein, the system further comprises a non-OCM process upstream of the OCM subsystem. In some embodiments of aspects provided herein, the non-OCM process is a natural gas liquids process. In some embodiments of aspects provided herein, the post-bed cracking unit is configured to receive an additional stream comprising propane, separately from the product stream. In some embodiments of aspects provided herein, the non-$C_{2+}$ impurities comprise one or more of nitrogen ($N_2$), oxygen ($O_2$), water ($H_2O$), argon (Ar), carbon monoxide (CO), carbon dioxide ($CO_2$), hydrogen ($H_2$) and methane ($CH_4$). In some embodiments of aspects provided herein, the higher hydrocarbon is a higher molecular weight hydrocarbon.

An aspect of the present disclosure provides an oxidative coupling of methane (OCM) system, comprising: (a) an OCM subsystem that (i) takes as input a feed stream comprising methane ($CH_4$) and a feed stream comprising an oxidizing agent, and (ii) generates from the methane and the oxidizing agent a product stream comprising $C_{2+}$ compounds and non-$C_{2+}$ impurities; (b) at least one methanation subsystem downstream of, and fluidically coupled to, the OCM subsystem, wherein the methanation subsystem reacts CO, $CO_2$ and $H_2$ included in the non-$C_{2+}$ impurities to generate methane; and (c) an ethylene-to-liquids (ETL) subsystem downstream of the OCM subsystem, wherein the ETL subsystem is configured to generate higher hydrocarbon(s) from ethylene included in the $C_{2+}$ compounds.

In some embodiments of aspects provided herein, at least a portion of the methane generated in the methanation subsystem is recycled to the OCM subsystem. In some embodiments of aspects provided herein, the oxidizing agent is $O_2$. In some embodiments of aspects provided herein, the $O_2$ is provided by air. In some embodiments of aspects provided herein, the OCM subsystem comprises at least one OCM reactor. In some embodiments of aspects provided herein, the OCM subsystem comprises at least one post-bed cracking unit downstream of the at least one OCM reactor, which post-bed cracking unit is configured to convert at least a portion of alkanes in the product stream to alkenes. In some embodiments of aspects provided herein, the system further comprises a non-OCM process upstream of the OCM subsystem. In some embodiments of aspects provided herein, the non-OCM process is a natural gas liquids process. In some embodiments of aspects provided herein, the post-bed cracking unit is configured to receive an additional stream comprising propane, separately from the product stream. In some embodiments of aspects provided herein, the higher hydrocarbon(s) comprise aromatics. In some embodiments of aspects provided herein, the non-$C_{2+}$ impurities comprise one or more of nitrogen ($N_2$), oxygen ($O_2$), water ($H_2O$), argon (Ar), carbon monoxide (CO), carbon dioxide ($CO_2$), hydrogen ($H_2$) and methane ($CH_4$). In some embodiments of aspects provided herein, the methanation subsystem comprises at least one methanation reactor.

An aspect of the present disclosure provides a method of producing a plurality of hydrocarbon products, the method comprising: (a) introducing methane and a source of oxidant into an oxidative coupling of methane (OCM) reactor system capable of converting methane to ethylene at reactor inlet temperatures of between about 450° C. and 600° C. and reactor pressures of between about 15 psig and 125 psig, with $C_{2+}$ selectivity of at least about 50%, under conditions for the conversion of methane to ethylene; (b) converting methane to a product gas comprising ethylene; (c) introducing separate portions of the product gas into at least a first and second integrated ethylene conversion reaction systems, each integrated ethylene conversion reaction system being configured for converting ethylene into a different higher hydrocarbon product; and (d) converting the ethylene into different higher hydrocarbon products.

In some embodiments of aspects provided herein, the first and second integrated ethylene conversion systems are selected from the group consisting of selective and full range ethylene conversion systems. In some embodiments of aspects provided herein, the method further comprises introducing a portion of the product gas into a third integrated ethylene conversion system. In some embodiments of aspects provided herein, the method further comprises introducing a portion of the product gas into a fourth integrated ethylene conversion systems. In some embodiments of aspects provided herein, the at least first and second integrated ethylene conversion systems are selected from the group consisting of linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems. In some embodiments of aspects provided herein, the first and second ethylene conversion systems are selected from the group consisting of LAO systems that produce one or more of 1-butene, 1-hexene, 1-octene and 1-decene. In some embodiments of aspects provided herein, at least one of the LAO systems is configured for performing a selective LAO process. In some embodiments of aspects provided herein, the first or second integrated ethylene conversion systems comprises a full range ethylene oligomerization system configured for producing higher hydrocarbons in the range of $C_3$ to $C_{30}$. In some embodiments of aspects provided herein, the OCM reactor system comprises nanowire OCM catalyst material. In some embodiments of aspects provided herein, the product gas comprises less than 5 mol % of ethylene. In some embodiments of aspects provided herein, the product gas comprises less than 3 mol % of ethylene. In some embodiments of aspects provided herein, the product gas further comprises one or more gases selected from the group consisting of $CO_2$, CO, $H_2$, $H_2O$, $C_2H_6$, $CH_4$ and $C_{3+}$ hydrocarbons. In some embodiments of aspects provided herein, the method further comprises enriching the product gas for ethylene prior to introducing the separate portions of the product gas into the at least first and second integrated ethylene conversion reaction systems. In some embodiments of aspects provided herein, the method further comprises introducing an effluent gas from the first or second integrated ethylene conversion reaction systems into the OCM reactor system.

An aspect of the present disclosure provides a method of producing a plurality of liquid hydrocarbon products, the method comprising: (a) catalytically converting methane to a product gas comprising ethylene; and (b) processing separate portions of the product gas with at least two discrete catalytic reaction systems selected from the group consisting of linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

An aspect of the present disclosure provides a processing system, comprising: (a) an oxidative coupling of methane (OCM) reactor system comprising an OCM catalyst, the OCM reactor system being fluidly connected at an input to a source of methane and a source of oxidant, wherein the OCM reactor system (i) takes as input the methane and the oxidant and (ii) generates from the methane and the oxidant a product stream comprising $C_{2+}$ compounds; (b) at least a first catalytic ethylene conversion reactor systems and a second catalytic ethylene conversion reactor system downstream of the OCM reactor system, the first catalytic ethylene reactor system being configured to convert ethylene to a first higher hydrocarbon, and the second catalytic ethylene reactor system being configured to convert ethylene to a second higher hydrocarbon different from the first higher hydrocarbon; and (c) a selective coupling unit between the OCM reactor system and the first and second catalytic ethylene reactor systems, which selective coupling unit is configured to selectively direct at least a portion of the product gas to each of the first and second catalytic ethylene reactor systems.

In some embodiments of aspects provided herein, the first and second ethylene conversion systems are selected from the group consisting of linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, ethylene copolymerization systems, and hydrocarbon polymer systems. In some embodiments of aspects provided herein, the OCM catalyst comprises a nanowire catalyst. In some embodiments of aspects provided herein, the system further comprises an ethylene recovery system between the OCM reactor system and the first and second catalytic ethylene conversion reactor systems, the ethylene recovery system configured to enrich the product gas for ethylene.

An aspect of the present disclosure provides a chemical production system, comprising: an OCM subsystem that includes an OCM reactor, wherein the OCM reactor (i) takes as input a feed stream comprising methane ($CH_4$) and a feed stream comprising an oxidizing agent and (ii) generates from the methane and the oxidizing agent $C_{2+}$ compounds and non-$C_{2+}$ impurities; and an ethylene-to-liquids (ETL) subsystem downstream of the OCM subsystem that includes an ETL reactor, wherein the ETL reactor converts at least a portion of the $C_{2+}$ compounds to a product stream comprising $C_{3+}$ compounds, which $C_{3+}$ compounds are generated at a single pass conversion of at least about 40%.

In some embodiments of aspects provided herein, the methane is from a non-OCM process. In some embodiments of aspects provided herein, the ETL reactor operates at a pressure between about 4 bar and 50 bar. In some embodiments of aspects provided herein, the single pass conversion is at least about 40% without recycle.

An aspect of the present disclosure provides a method for generating hydrocarbons, comprising: (a) directing a feed stream comprising methane ($CH_4$) and a feed stream comprising an oxidizing agent to an OCM reactor; (b) in the OCM reactor, generating an OCM product stream comprising $C_{2+}$ compounds and non-$C_{2+}$ impurities from the methane and the oxidizing agent; (c) directing at least a portion of the $C_{2+}$ compounds to an ethylene-to-liquids (ETL) subsystem downstream of the OCM subsystem, wherein the ETL subsystem has an ETL reactor that converts at least a portion of the $C_{2+}$ compounds in the OCM product stream to an ETL product stream comprising $C_{3+}$ compounds; and (d) recycling less than 25% of ethylene in the product stream to the ETL subsystem.

In some embodiments of aspects provided herein, the OCM and ETL subsystems generate the $C_{3+}$ compounds at a single pass conversion efficiency of at least about 40%. In some embodiments of aspects provided herein, the single pass conversion efficiency is at least about 40% without recycle. In some embodiments of aspects provided herein, the methane is from a non-OCM process. In some embodiments of aspects provided herein, the ETL reactor operates at a pressure between about 10 bar and 50 bar.

An aspect of the present disclosure provides a method for generating a catalyst, comprising: (a) providing a catalyst base material having a first set of pores, wherein the base material comprises an active component that facilitates the conversion of olefins to a first set of hydrocarbons, at least some of which is in liquid form at room temperature and atmospheric pressure; (b) introducing a second set of pores into the base material having an average diameter of at least about 10 nanometers as measured by BET isotherms; and (c) providing one or more dopants on one or more surfaces of the base material, wherein the one or more dopants facilitate the conversion of olefins to a second set of hydrocarbons, at least some of which are in liquid form at room temperature and atmospheric pressure, wherein the second set of hydrocarbons has a different product distribution than the first set of hydrocarbons.

In some embodiments of aspects provided herein, the first set of pores have an average diameter from at least about 4 Angstroms to 10 Angstroms. In some embodiments of aspects provided herein, the base material comprises a zeolite. In some embodiments of aspects provided herein, (b) is subsequent to (c). In some embodiments of aspects provided herein, (b) and (c) are performed simultaneously. In some embodiments of aspects provided herein, the base material has a surface area from about 100 $m^2/g$ to 1000 $m^2/g$. In some embodiments of aspects provided herein, (c) comprises providing dopants selected from the group consisting of Ga, Zn, Al, In, Ni, Mg, B and Ag. In some embodiments of aspects provided herein, the catalyst base material is H—Al-ZSM-5, H—Ga-ZSM-5, H—Fe-ZSM-5, H—B-ZSM-5, or any combination thereof. In some embodiments of aspects provided herein, the second set of hydrocarbons has a narrower product distribution than the first set of hydrocarbons.

An aspect of the present disclosure provides a system for generating hydrocarbons, comprising: an ethylene-to-liquids (ETL) unit comprising one or more ETL reactors, wherein an individual ETL reactor accepts ethylene from a non-ETL process and generates a product stream comprising higher hydrocarbons through an oligomerization process, wherein at least some of the higher hydrocarbons are in liquid form at room temperature and atmospheric pressure; and at least one separations unit downstream of, and fluidically coupled to, the ETL unit, wherein the separations unit separates the product stream into individual streams, each comprising a subset of the higher hydrocarbons.

In some embodiments of aspects provided herein, the ETL reactor comprises a catalyst having an active material and one or more dopants on surfaces of the active material. In some embodiments of aspects provided herein, the system further comprises an oxidative coupling of methane (OCM) unit upstream of the ETL unit, wherein the OCM unit comprises one or more OCM reactors, each of which (i) takes as input a feed stream comprising methane ($CH_4$) and a feed stream comprising an oxidizing agent, (ii) generates from the methane and the oxidizing agent $C_{2+}$ compounds and non-$C_{2+}$ impurities, and (iii) directs at least a subset of ethylene in the $C_{2+}$ compounds to the ETL unit.

An aspect of the present disclosure provides a catalyst for the conversion of ethylene to liquid hydrocarbon fuels, the catalyst comprising: (a) a ZSM-5 base material; (b) a binder material; and (c) a dopant material; wherein the catalyst has a cycle lifetime of at least about 1 week when in contact with up to about 100 parts per million (ppm) acetylene, and wherein the catalyst has a replacement lifetime of at least about 1 year when in contact with up to about 100 ppm acetylene.

An aspect of the present disclosure provides a catalyst for hydrogenation of acetylene in an oxidative coupling of methane (OCM) and ethylene to liquids (ETL) process comprising at least one elemental metal, wherein the catalyst is capable of decreasing the concentration of acetylene to less than about 100 parts per million (ppm) in an OCM effluent prior to flowing the OCM effluent into an ETL process.

In some embodiments of aspects provided herein, the catalyst is capable of decreasing the concentration of acetylene to less than about 10 ppm in the OCM effluent. In some embodiments of aspects provided herein, the catalyst is capable of decreasing the concentration of acetylene to less than about 1 ppm in the OCM effluent. In some embodiments of aspects provided herein, the at least one elemental metal includes palladium. In some embodiments of aspects provided herein, the at least one elemental metal is part of a metal oxide. In some embodiments of aspects provided herein, the catalyst is capable of providing an OCM effluent that comprises at least about 0.5% carbon monoxide. In some embodiments of aspects provided herein, the catalyst is capable of providing an OCM effluent that comprises at least about 1% carbon monoxide. In some embodiments of aspects provided herein, the catalyst is capable of providing an OCM effluent that comprises at least about 3% carbon monoxide. In some embodiments of aspects provided herein, the catalyst has a lifetime of at least about 1 year. In some embodiments of aspects provided herein, the catalyst is capable of providing an OCM effluent that comprises at least about 0.1% acetylene. In some embodiments of aspects provided herein, the catalyst is capable of providing an OCM effluent that comprises at least about 0.3% acetylene. In some embodiments of aspects provided herein, the catalyst is capable of providing an OCM effluent that comprises at least about 0.5% acetylene. In some embodiments of aspects provided herein, the ETL process converts ethylene in the OCM effluent into higher hydrocarbon(s). In some embodiments of aspects provided herein, the at least one metal comprises a plurality of metals.

An aspect of the present disclosure provides a catalyst for converting carbon monoxide (CO) and/or carbon dioxide ($CO_2$) into methane ($CH_4$) in an oxidative coupling of methane (OCM) and ethylene to liquids (ETL) process, wherein the catalyst comprises at least one elemental metal, and wherein the catalyst converts CO and/or $CO_2$ into $CH_4$ at a selectivity for the formation of methane that is at least about 10-fold greater than the selectivity of the catalyst for formation of coke in an ETL effluent.

In some embodiments of aspects provided herein, the catalyst has a selectivity for the formation of methane that is at least about 100-fold greater than the selectivity of the catalyst for formation of coke. In some embodiments of aspects provided herein, the catalyst has a selectivity for the formation of methane that is at least about 1000-fold greater than the selectivity of the catalyst for formation of coke. In some embodiments of aspects provided herein, the catalyst has a selectivity for the formation of methane that is at least about 10000-fold greater than the selectivity of the catalyst for formation of coke. In some embodiments of aspects provided herein, the ETL effluent comprises at least about 3% olefin and/or acetylene compounds. In some embodiments of aspects provided herein, the ETL effluent comprises at least about 5% olefin and/or acetylene compounds. In some embodiments of aspects provided herein, the ETL effluent comprises at least about 10% olefin and/or acetylene compounds. In some embodiments of aspects provided herein, the at least one elemental metal includes nickel. In some embodiments of aspects provided herein, the at least one elemental metal is part of a metal oxide.

An aspect of the present disclosure provides a method for preventing coke formation on a methanation catalyst in an oxidative coupling of methane (OCM) and ethylene to liquids (ETL) process, the method comprising: (a) providing an ETL effluent comprising carbon monoxide (CO) and/or carbon dioxide ($CO_2$); and (b) using a methanation catalyst to perform a methanation reaction with the ETL effluent, wherein: (i) hydrogen and/or water is added to the ETL effluent prior to (b); (ii) olefins and/or acetylene in the ETL effluent is hydrogenated prior to (b); and/or (iii) olefins and/or acetylene are separated and/or condensed from the ETL effluent prior to (b).

In some embodiments of aspects provided herein, (iii) is performed using absorption or adsorption. In some embodiments of aspects provided herein, the methanation reaction forms at least about 1000-fold more methane than coke. In some embodiments of aspects provided herein, the methanation reaction forms at least about 10000-fold more methane than coke. In some embodiments of aspects provided herein, the methanation reaction forms at least about 100000-fold more methane than coke. In some embodiments of aspects provided herein, the method further comprises any two of (i), (ii) and (iii). In some embodiments of aspects provided herein, the method further comprises all of (i), (ii) and (iii). In some embodiments of aspects provided herein, $C_{5+}$ compounds are removed from the ETL effluent prior to performing the methanation reaction with the methanation catalyst. In some embodiments of aspects provided herein, $C_{4+}$ compounds are removed from the ETL effluent prior to performing the methanation reaction with the methanation catalyst. In some embodiments of aspects provided herein, $C_{3+}$ compounds are removed from the ETL effluent prior to performing the methanation reaction with the methanation catalyst.

An aspect of the present disclosure provides a method of producing a plurality of hydrocarbon products, comprising: (a) in an oxidative coupling of methane (OCM) reactor, reacting methane and an oxidant in an OCM process to yield heat and an OCM product stream comprising hydrocarbon compounds with two or more carbon atoms ($C_{2+}$ compounds), including ethylene; (b) directing the OCM product stream from the OCM reactor to a post-bed cracking (PBC) unit downstream of the OCM reactor; (c) in the PBC unit, subjecting the OCM product stream to thermal cracking under conditions that are suitable to crack ethane to ethylene, wherein the thermal cracking is conducted at least in part with the heat from (a), thereby producing a PBC product stream comprising ethylene and hydrogen ($H_2$) at concentrations that are increased relative to the respective concentrations of ethylene and $H_2$ in the OCM product stream; (d) directing the PBC product stream from the PBC unit to an ethylene-to-liquids (ETL) reactor downstream of the PBC unit, wherein the ETL reactor converts the ethylene in the PBC product stream into higher hydrocarbons.

An aspect of the present disclosure provides a method of producing a plurality of hydrocarbon products, comprising: directing ethylene and hydrogen ($H_2$) into an ethylene-to-liquids (ETL) reactor, wherein the ETL reactor is configured to convert hydrocarbon compounds with two or more carbon atoms ($C_{2+}$ compounds), including ethylene, into higher hydrocarbons; and in the ETL reactor, converting the ethylene into higher hydrocarbons in the presence of the $H_2$, wherein the converting results in less coke formation than if the converting is conducted in the absence of the $H_2$.

An aspect of the present disclosure provides a method of producing a plurality of hydrocarbon products, comprising: directing ethylene and water ($H_2O$) into an ethylene-to-liquids (ETL) reactor, wherein the ETL reactor is configured to convert hydrocarbon compounds with two or more carbon atoms ($C_{2+}$ compounds), including ethylene, into higher hydrocarbons; and in an ethylene-to-liquids (ETL) reactor, converting the ethylene into higher hydrocarbons in the presence of the $H_2O$, wherein the converting results in less coke formation than if the converting is conducted in the absence of the $H_2O$.

An aspect of the present disclosure provides a method of producing a plurality of hydrocarbon products, comprising: (a) introducing a feed stream comprising ethylene and ethane into an ethylene-to-liquids (ETL) reactor, wherein the ETL reactor is configured to convert hydrocarbon compounds with two or more carbon atoms ($C_{2+}$ compounds) into higher hydrocarbons, and wherein the ethylene to ethane molar ratio in the feed stream is at least about 3:1 and (b) in the ETL reactor, converting the ethylene into the higher hydrocarbons.

An aspect of the present disclosure provides a method of producing a plurality of hydrocarbon products, comprising: directing ethylene to an ethylene-to-liquids (ETL) reactor, wherein the ETL reactor is configured to convert hydrocarbon compounds with two or more carbon atoms ($C_{2+}$ compounds) into higher hydrocarbons; in the ETL reactor, converting the ethylene into the higher hydrocarbons; and separating the higher hydrocarbons into at least two product streams, at least one of which product streams is characterized by five or more characteristics selected from the group consisting of: (a) no more than 1.30 vol % benzene; (b) no more than 50 vol % aromatics; (c) no more than 25 vol % olefins; (d) a motor octane number (MON) of at least 82; (e) a total octane number of at least 87; (f) a Reid vapor pressure (RVP) of no more than 15 psi; (g) a 10% boiling point of no more than 70° C.; (h) a 50% boiling point of no more than 121° C.; (i) a 90% boiling point of no more than 190° C.; (j) a final boiling point (FBP) of no more than 221° C.; and (k) an oxidative induction time of at least 240 minutes.

An aspect of the present disclosure provides a method of producing a plurality of hydrocarbon products, comprising: directing ethylene into an ethylene-to-liquids (ETL) reactor, wherein the ETL reactor is configured to convert hydrocarbon compounds with two or more carbon atoms ($C_{2+}$ compounds), including ethylene, into higher hydrocarbons; and in the ETL reactor, converting ethylene into higher hydrocarbon products in an ETL product stream that comprises less than 60% water.

An aspect of the present disclosure provides a method of producing a plurality of hydrocarbon products, comprising: (a) directing ethylene into an ethylene-to-liquids (ETL) reactor, wherein the ETL reactor comprises an ETL catalyst that is configured to convert hydrocarbon compounds with two or more carbon atoms ($C_{2+}$ compounds), including ethylene, into higher hydrocarbons; (b) in the ETL reactor, converting the ethylene into higher hydrocarbons to provide an ETL product stream comprising the higher hydrocarbons, and forming coke on the ETL catalyst; (c) contacting the ETL catalyst with an oxidant to regenerate the ETL catalyst by burning the coke on the ETL catalyst; and (d) repeating (b)-(c) for at least 20 cycles, wherein a composition of the ETL product stream from a first cycle differs from a composition of the ETL product stream from a twentieth cycle by no more than 0.1%.

An aspect of the present disclosure provides a method of producing a plurality of hydrocarbon products, comprising: (a) introducing a feed stream comprising hydrocarbons into a fluid catalytic cracking (FCC) reactor comprising an FCC catalyst, wherein the FCC catalyst is configured to crack the hydrocarbons into lower molecular weight hydrocarbons; (b) in the FCC reactor, (i) cracking the hydrocarbons into the lower molecular weight hydrocarbons and (ii) generating coke on the FCC catalyst; (c) transferring at least a portion of the FCC catalyst into a regeneration unit and introducing an oxidant stream into the regeneration unit; (d) in the regeneration unit, burning the coke on the FCC catalyst in the presence of the oxidant stream, thereby regenerating the FCC catalyst and producing a flue gas stream comprising carbon monoxide and/or carbon dioxide; (e) directing the flue gas stream into a heat exchanger to transfer heat from the flue gas stream to a first stream comprising ethane or propane; and (f) subjecting the first stream to thermal cracking under conditions that (i) crack the ethane to ethylene and/or (ii) crack the propane to propene, wherein the thermal cracking is conducted at least in part with the heat from (e).

An aspect of the present disclosure provides a method of producing a plurality of hydrocarbon products, comprising: (a) in a first oxidative coupling of methane (OCM) reactor, reacting methane and a first oxidant in an OCM process to yield a first OCM product stream comprising unreacted methane and hydrocarbon compounds with two or more carbon atoms ($C_{2+}$ compounds), including ethylene; (b) introducing the first OCM product stream into an ethylene-to-liquids (ETL) reactor that is configured to convert $C_{2+}$ compounds into higher hydrocarbons; (c) in the ETL reactor, converting at least a portion of the ethylene in the first OCM product stream into higher hydrocarbons to provide an ETL product stream comprising the higher hydrocarbons and the unreacted methane; (d) introducing a second oxidant stream and at least a portion of the ETL product stream into a second OCM reactor; and (e) in the second OCM reactor, reacting the unreacted methane and the second oxidant in another OCM process to yield a second OCM product stream comprising $C_{2+}$ compounds, including ethylene.

In some embodiments of aspects provided herein, the method further comprises, prior to the introducing of (e), removing at least a portion of the higher hydrocarbons from the ETL product stream.

An aspect of the present disclosure provides a method of producing a plurality of hydrocarbon products, comprising: (a) directing a feed stream comprising ethylene to an ethylene-to-liquids (ETL) reactor, wherein the ETL reactor is configured to convert hydrocarbon compounds with two or more carbon atoms ($C_{2+}$ compounds) into higher hydrocarbons; (b) converting the ethylene to an ETL product stream comprising the higher hydrocarbons; (c) directing the ETL product stream to a separations system and, in the separations system, separating the ETL product stream into a higher hydrocarbon stream and a light olefin stream comprising propylene and butene; (d) introducing the light olefin stream into an oligomerization reactor, wherein the oligomerization reactor includes an oligomerization catalyst that oligomerizes $C_{2+}$ compounds into higher hydrocarbons; and (e) in the oligomerization reactor, oligomerizing the propylene and butene in the light olefin stream to produce an oligomerization product stream comprising oligomerization products of propylene and butene.

In some embodiments of aspects provided herein, the oligomerization product stream comprises olefins with carbon numbers from 6 to 16. In some embodiments of aspects provided herein, a temperature within the oligomerization reactor during the oligomerizing is from about 50° C. to 200° C. In some embodiments of aspects provided herein, the oligomerization catalyst comprises a solid acid catalyst. In some embodiments of aspects provided herein, the oligomerization reactor is of a form selected from the group consisting of a slurry bed reactor, a fixed bed reactor, a tubular isothermal reactor, a moving bed reactor, and a fluidized bed reactor.

An aspect of the present disclosure provides a method of producing a plurality of hydrocarbon products, comprising: (a) in an oxidative coupling of methane (OCM) reactor, reacting methane and an oxidant in an OCM process to yield an OCM product stream comprising unreacted methane and hydrocarbon compounds with two or more carbon atoms ($C_{2+}$ compounds) including ethylene, ethane, and propane; (b) introducing the OCM product stream into an ethylene-to-liquids (ETL) reactor, wherein the ETL reactor is configured to convert the unreacted methane and at least a portion of the $C_{2+}$ compounds into aromatic hydrocarbons, and wherein the ETL reactor comprises an ETL catalyst doped with one or more dopants selected from the group consisting of molybdenum (Mo), gallium (Ga), and tungsten (W); and (c) in the ETL reactor, converting the unreacted methane and the at least the portion of the $C_{2+}$ compounds into an aromatic product stream comprising the aromatic hydrocarbons.

An aspect of the present disclosure provides a method of producing a plurality of hydrocarbon products, comprising: (a) directing hydrogen ($H_2$) and a low octane stream comprising n-hexane to an isomerization reactor that is configured to isomerize n-hexane to i-hexane, wherein the low octane stream is characterized by an octane number of no more than 62; and (b) reacting the $H_2$ and the n-hexane to produce an isomerization product stream comprising i-hexane, wherein the isomerization product stream is characterized by an octane number of at least 73.

An aspect of the present disclosure provides a method of producing a plurality of hydrocarbon products, comprising: (a) in a natural gas liquids (NGL) system, producing from natural gas an NGL product stream comprising hydrocarbon compounds with four or more carbon atoms ($C_{4+}$ compounds), including butanes; (b) introducing the first NGL product stream into an isomerization reactor configured to isomerize the $C_{4+}$ compounds); and (c) in the isomerization reactor, isomerizing at least a portion of the $C_{4+}$ compounds to form isomerization products, thereby producing an isomerate stream comprising the isomerization products.

An aspect of the present disclosure provides a method of producing a plurality of hydrocarbon products, comprising: (a) in an oxidative coupling of methane (OCM) reactor, reacting methane and an oxidant in an OCM process to yield an OCM product stream comprising unreacted methane and hydrocarbon compounds comprising two or more carbon atoms ($C_{2+}$ compounds), including ethylene; (b) introducing the OCM product stream into an ethylene-to-liquids (ETL) reactor that reacts the ethylene in the OCM product stream to yield an ETL product stream higher hydrocarbons and unreacted methane; and (c) introducing the ETL product stream into at least one separation unit that separates the ETL product stream into a gas stream comprising the unreacted methane and at least one product stream comprising hydrocarbon compounds with at least 3, 4, or 5 carbon atoms.

In some embodiments of aspects provided herein, the methane is supplied at least in part from a natural gas pipeline, and wherein the method further comprises outputting the gas stream to the natural gas pipeline. In some embodiments of aspects provided herein, the methane is supplied at least in part from a cryogenic separations system, and wherein the method further comprises directing the gas stream to a re-compressor unit. In some embodiments of aspects provided herein, the methane is supplied at least in part from a cryogenic separations system, and wherein the method further comprises compressing the gas stream in a compressor to produce a compressed stream and directing the compressed stream to the cryogenic separations unit. In some embodiments of aspects provided herein, the methane is supplied at least in part from a cryogenic separations unit, and the method further comprises: compressing the gas stream in a compressor to produce a compressed stream; directing the compressed stream to the cryogenic separations unit; in the cryogenic separations unit, removing any $C_{2+}$ compounds from the gas stream along a $C_{2+}$ product stream; and optionally directing the gas stream to a re-compressor unit.

An aspect of the present disclosure provides a method of producing a plurality of hydrocarbon products including hydrocarbon compounds with two carbon atoms ($C_2$ compounds), hydrocarbon compounds with three carbon atoms ($C_3$ compounds), hydrocarbon compounds with four carbon atoms ($C_4$ compounds), and hydrocarbon compounds with five or more carbon atoms ($C_{5+}$ compounds), comprising: (a) introducing a natural gas stream comprising methane into a gas treatment system and, in the gas treatment system, removing from the natural gas stream at least one of mercury, water, and acid gases; (b) directing the natural gas stream from the gas treatment system into a natural gas liquids (NGL) extraction system that produces from the natural gas stream a first stream comprising methane and a second stream comprising $C_2$ compounds, $C_3$ compounds, $C_4$ compounds, and $C_{5+}$ compounds; (c) directing a first portion of the first stream into a liquefaction unit, and in the liquefaction unit, producing liquid natural gas from the first portion of the first stream; (d) directing the second stream into an NGL fractionation system that separates the second stream into at least (i) a $C_2$-$C_3$ stream comprising $C_2$ compounds and $C_3$ compounds, (ii) a $C_4$ stream comprising $C_4$ compounds, and (iii) a $C_{5+}$ stream comprising $C_{5+}$ compounds; (e) directing a second portion of the first stream, the $C_2$-$C_3$ stream, and an oxidant into an oxidative coupling of methane (OCM) system that converts the methane in the second portion of the first stream in an OCM process to yield an OCM product stream including ethylene; (f) directing the OCM product stream into an ethylene-to-liquids (ETL) reactor that converts the ethylene in the OCM product stream into the higher hydrocarbons, thereby forming an ETL product stream comprising $C_2$ compounds, $C_3$ compounds, $C_4$ compounds, and $C_{5+}$ compounds; and (g) directing the ETL product stream into the NGL extraction system.

In some embodiments of aspects provided herein, the method further comprises, prior to the directing of (b), directing the natural gas stream from the gas treatment system into a pre-cooling system, and, in the pre-cooling system, removing a first fuel gas stream comprising methane from the natural gas stream. In some embodiments of aspects provided herein, the method further comprises directing the liquid natural gas stream into a nitrogen rejection unit, and, in the nitrogen rejection unit, removing a stream comprising nitrogen from the liquid natural gas stream.

An aspect of the present disclosure provides a method of producing a plurality of hydrocarbon products including hydrocarbon compounds with two carbon atoms ($C_2$ compounds), hydrocarbon compounds with three carbon atoms ($C_3$ compounds), hydrocarbon compounds with four carbon atoms ($C_4$ compounds), and hydrocarbon compounds with five or more carbon atoms ($C_{5+}$ compounds), comprising: (a) directing a natural gas stream into a natural gas liquids (NGL) extraction system that produces from the natural gas stream a first stream comprising methane and a second stream comprising $C_2$ compounds, $C_3$ compounds, $C_4$ compounds, and $C_{5+}$ compounds; (b) removing a first portion of the first stream as a pipeline gas product stream; (c) directing the second stream into an NGL fractionation system that separates the second stream into at least (i) a $C_2$-$C_3$ stream comprising $C_2$ compounds and $C_3$ compounds, (ii) a $C_4$ stream comprising $C_4$ compounds, and (iii) a $C_{5+}$ stream comprising $C_{5+}$ compounds; (d) directing a second portion of the first stream, the $C_2$-$C_3$ stream, and an oxidant into an oxidative coupling of methane (OCM) system that converts the methane in the second portion of the first stream in an OCM process to yield an OCM product stream including ethylene; (e) directing the OCM product stream into an ethylene-to-liquids (ETL) reactor that converts the ethylene in the OCM product stream into an ETL product stream comprising $C_2$ compounds, $C_3$ compounds, $C_4$ compounds, and $C_{5+}$ compounds; and (f) directing the ETL product stream into the NGL extraction system.

An aspect of the present disclosure provides a method of producing a plurality of hydrocarbon products including hydrocarbon compounds with two carbon atoms ($C_2$ compounds"), hydrocarbon compounds with three carbon atoms ($C_3$ compounds), hydrocarbon compounds with four carbon atoms ($C_4$ compounds), and hydrocarbon compounds with five or more carbon atoms ($C_{5+}$ compounds), comprising: (a) introducing a first natural gas stream comprising methane into a gas treatment system that removes from the first natural gas stream at least one of mercury, water, and acid gases; (b) introducing a second natural gas stream comprising methane into a gas conditioning system that removes from the second natural gas stream at least one sulfur compound; (c) directing the first natural gas stream from the gas treatment system and a first portion of the second natural gas stream from the gas conditioning system into a natural gas liquids (NGL) extraction system that produces from the first natural gas stream and the first portion of the second natural gas stream (i) a first stream comprising methane, (ii) a second stream comprising $C_2$ compounds, and (iii) a third stream comprising $C_2$ compounds, $C_3$ compounds, $C_4$ compounds, and $C_{5+}$ compounds, wherein a portion of the first stream is removed as a pipeline gas product stream; (d) directing the third stream into an NGL fractionation system that separates the third stream into at least (i) a $C_2$ stream comprising $C_2$ compounds, (ii) a $C_3$-$C_4$ stream comprising $C_3$ compounds and $C_4$ compounds, and (iii) a $C_{5+}$ stream comprising $C_{5+}$ compounds; (e) directing a second portion of the second natural gas stream from the gas conditioning system, the second stream from the NGL extraction system, the $C_2$ stream from the NGL fractionation system, and an oxidant into an oxidative coupling of methane (OCM) reactor that converts methane at least some of the streams in an OCM process to yield an OCM product stream including ethylene; (f) directing the OCM product stream into an ethylene-to-liquids (ETL) reactor that converts the ethylene in the OCM product stream into an ETL product stream comprising $C_2$ compounds, $C_3$ compounds, $C_4$ compounds, and $C_{5+}$ compounds; and (g) directing the ETL product stream into the NGL extraction system.

An aspect of the present disclosure provides a method of producing a plurality of hydrocarbon products including hydrocarbon compounds with two carbon atoms ($C_2$ compounds), hydrocarbon compounds with three carbon atoms ($C_3$ compounds), hydrocarbon compounds with four carbon atoms ($C_4$ compounds), and hydrocarbon compounds with five or more carbon atoms ($C_{5+}$ compounds), comprising: (a) directing a first stream including ethylene from a refinery gas plant into an ethylene-to-liquids (ETL) reactor that converts the ethylene into an ETL product stream comprising $C_2$ compounds, $C_3$ compounds, $C_4$ compounds, and $C_{5+}$ compounds; (b) directing the ETL product stream into a separations system that separates the ETL product stream into at least (i) a fuel gas stream comprising methane, (ii) a $C_2$ stream comprising $C_2$ compounds, and (iii) a $C_3$ stream comprising $C_3$ compounds; (c) using a heat exchanger, transferring heat from the $C_2$ stream to a first stream comprising ethane and/or propane; and (d) subjecting the first stream to thermal cracking under conditions that crack the ethane to ethylene and/or the propane to propene, wherein the thermal cracking is conducted at least in part with the heat from (c).

In some embodiments of aspects provided herein, the method further comprises directing the $C_2$ stream from the heat exchanger to the ETL reactor.

An aspect of the present disclosure provides a method of producing a plurality of hydrocarbon products including hydrocarbon compounds with two carbon atoms ($C_2$ compounds), hydrocarbon compounds with three carbon atoms ($C_3$ compounds), hydrocarbon compounds with four carbon atoms ($C_4$ compounds), and hydrocarbon compounds with five or more carbon atoms ($C_{5+}$ compounds), comprising: (a) directing a first stream including ethylene from a refinery gas plant into a demethanizer that removes a first methane stream including methane from the first stream, wherein the first stream is subjected to sulfur removal prior to being directed to the demethanizer; (b) directing the first methane stream, a second methane stream comprising methane, and an oxidant into an oxidative coupling of methane (OCM) system that converts methane in the in an OCM process to yield an OCM product stream including ethylene; (c) directing the first stream and the OCM product stream into an ethylene-to-liquids (ETL) that converts the ethylene in the OCM product stream into an ETL product stream comprising $C_2$ compounds, $C_3$ compounds, $C_4$ compounds, and $C_{5+}$ compounds; (d) directing the ETL product stream into a separations system that separates the ETL product stream into at least streams comprising a $C_2$-$C_3$ stream comprising $C_2$ compounds and $C_3$ compounds; and (e) using a heat exchanger, transferring heat from the $C_2$-$C_3$ stream to a second stream comprising ethane and/or propane; and (f) subjecting the second stream to thermal cracking under conditions that crack the ethane to ethylene and/or the propane to propene, wherein the thermal cracking is conducted at least in part with the heat from (e).

In some embodiments of aspects provided herein, the method further comprises directing at least a portion of the $C_2$-$C_3$ stream from the heat exchanger to the OCM reactor system. In some embodiments of aspects provided herein, the method further comprises directing at least a portion of the $C_2$-$C_3$ stream from the heat exchanger to the ETL reactor.

An aspect of the present disclosure provides a method of producing a plurality of hydrocarbon products including hydrocarbon compounds with two or more carbon atoms ($C_{2+}$ compounds), comprising: (a) directing methane and an oxidant to an oxidative coupling of methane (OCM) reactor that is upstream of a post-bed cracking (PBC) unit, wherein the OCM reactor is configured to facilitate an OCM reaction using the methane and the oxidant to generate the $C_{2+}$ compounds including ethylene and one or more alkanes, and wherein the PBC unit is configured to convert the one or more alkanes, including ethane, to one or more alkenes, including ethylene; (b) in the OCM reactor, reacting the methane and the oxidant in the OCM reaction to generate an OCM product stream and heat, wherein the OCM product stream comprises ethylene and one or more alkanes; (c) directing the OCM product stream to the PBC unit; (d) in the PBC unit, subjecting the OCM product stream to thermal cracking under conditions that crack ethane to ethylene, wherein the thermal cracking is conducted at least in part with the heat from (c), thereby producing a PBC product stream comprising ethylene; (e) directing the PBC product stream to a separations module, and, in the separations module, separating ethane from the PBC product stream to generate an ethane stream; and (f) directing the ethane stream to the PBC unit.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

FIG. 23A schematically illustrates a natural gas liquids (NGL) system; FIG. 23B schematically illustrates the NGL process of FIG. 23A retrofitted with an OCM and ethylene to liquids system;

FIG. 36A shows a graph of ETL product with ethylene feedstock; FIG. 36B shows a graph of ETL product with propylene feedstock; FIG. 36C shows a graph of ETL product with butylene feedstock; FIG. 36D shows a graph of ETL product with 50:50 ethylene/propylene feedstock; and FIG. 36E shows a graph of ETL product with 50:50 ethylene/butylene feedstock;

DETAILED DESCRIPTION

Figure 1:
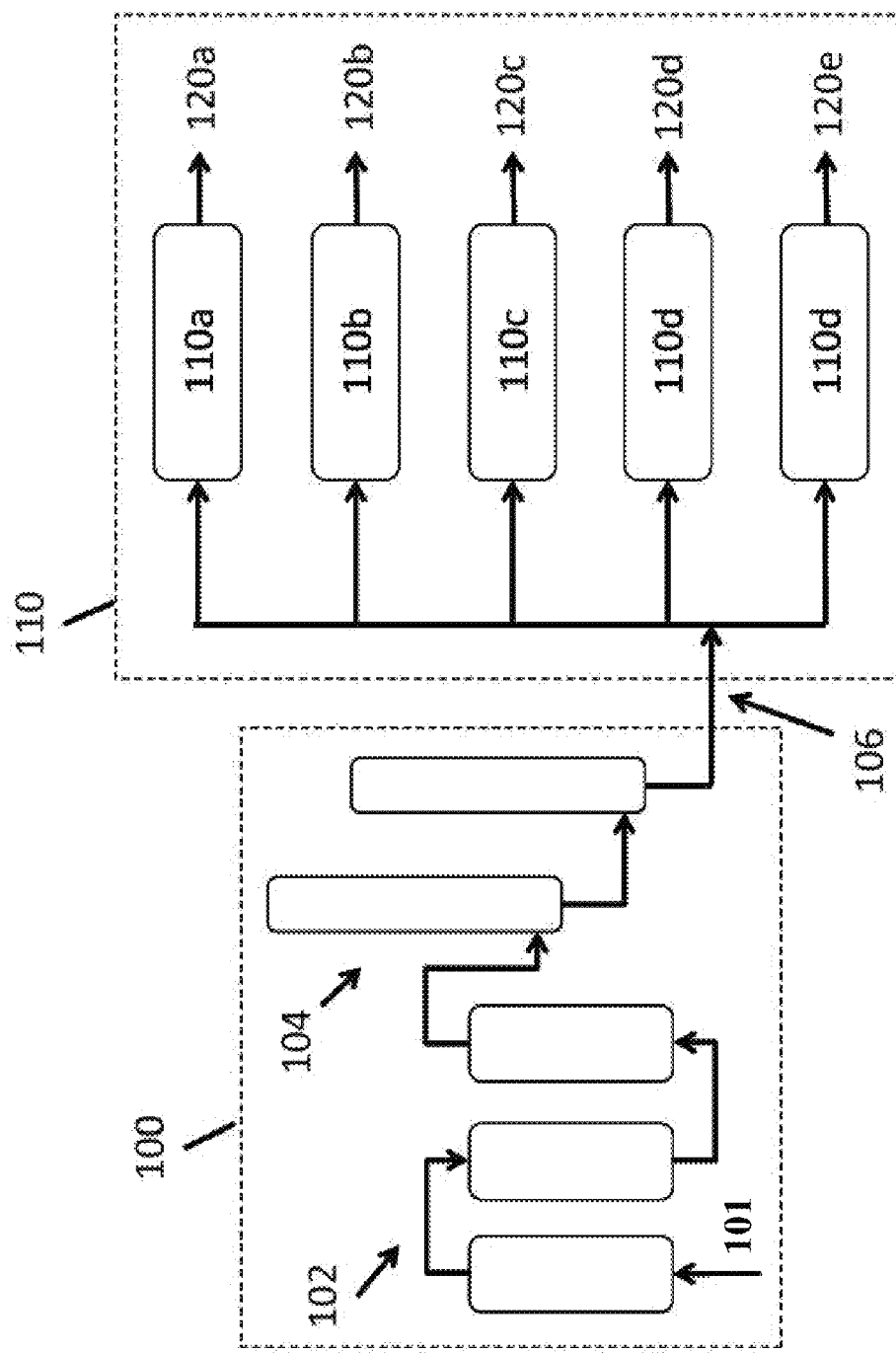
FIG. 1 shows an oxidative coupling of methane (OCM) reactor system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "OCM process," as used herein, generally refers to a process that employs or substantially employs an oxidative coupling of methane (OCM) reaction. An OCM reaction can include the oxidation of methane to a higher hydrocarbon (e.g., higher molecular weight hydrocarbon or higher chain hydrocarbon) and water, and involves an exothermic reaction. In an OCM reaction, methane can be partially oxidized to one or more $C_{2+}$ compounds, such as ethylene, propylene, butylenes, etc. In an example, an OCM reaction is $2CH_4+O_2 \rightarrow C_2H_4+2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The term "ethylene-to-liquids" (ETL), as used herein, generally refers to any device, system, method (or process) that can convert an olefin (e.g., ethylene) to higher molecular weight hydrocarbons, which can be in liquid form.

The term "non-ETL process," as used herein, generally refers to a process that does not employ or substantially employ the conversion of an olefin to a higher molecular weight hydrocarbon through oligomerization. Examples of processes that may be non-ETL processes include processes employed in hydrocarbon processing in oil refineries, a natural gas liquids separations processes, steam cracking of ethane, steam cracking or naphtha, Fischer-Tropsch processes, and the like.

The terms "$C_{2+}$," and "$C_{2+}$ compound," as used herein, generally refer to a compound comprising two or more carbon atoms, e.g., $C_2$, $C_3$ etc. $C_{2+}$ compounds include, without limitation, alkanes, alkenes, alkynes and aromatics containing two or more carbon atoms. In some cases, $C_{2+}$ compounds include aldehydes, ketones, esters and carboxylic acids. Examples of $C_{2+}$ compounds include ethane, ethene, acetylene, propane, propene, butane, butene, etc.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "weight hourly space velocity" (WHSV), as used herein, generally refers to the mass flow rate of olefins in a feed divided by the mass of a catalyst, which can have units of inverse time (e.g., $hr^{-1}$).

The term "slate," as used herein, generally refers to distribution, such as product distribution.

The term "oligomerization," as used herein, generally refers to a reaction in which hydrocarbons are combined to form larger chain hydrocarbons.

The term "greenfield," as used herein, generally refers to an investment in a manufacturing, office, industrial or other physical commerce-related structure or group of structures in an area where no previous facilities exist or have existed.

The term "brownfield," as used herein, generally refers to an investment at a site that was previously used for business purposes, such as a steel mill or an oil refinery, but is subsequently expanded or upgraded to achieve a return.

The term "catalyst," as used herein, generally refers to a substance that alters the rate of a chemical reaction. A catalyst may either increase the chemical reaction rate (i.e. a "positive catalyst") or decrease the reaction rate (i.e. a "negative catalyst"). A catalyst can be a heterogeneous catalyst. Catalysts can participate in a reaction in a cyclic fashion such that the catalyst is cyclically regenerated. "Catalytic" generally means having the properties of a catalyst.

The term "nanowire," as used herein, generally refers to a nanowire structure having at least one diameter on the order of nanometers (e.g. between about 1 and 100 nanometers) and an aspect ratio greater than 10:1. The "aspect ratio" of a nanowire is the ratio of the actual length (L) of the nanowire to the diameter (D) of the nanowire. Aspect ratio is expressed as L:D.

The term "polycrystalline nanowire," as used herein, generally refers to a nanowire having multiple crystal domains. Polycrystalline nanowires generally have different morphologies (e.g. bent vs. straight) as compared to the corresponding "single-crystalline" nanowires.

The term "effective length" of a nanowire, as used herein, generally refers to the shortest distance between the two distal ends of a nanowire as measured by transmission electron microscopy (TEM) in bright field mode at 5 kilo electron volt (keV). "Average effective length" refers to the average of the effective lengths of individual nanowires within a plurality of nanowires.

The term "actual length" of a nanowire, as used herein, generally refers to the distance between the two distal ends of a nanowire as traced through the backbone of the nanowire as measured by TEM in bright field mode at 5 keV. "Average actual length" refers to the average of the actual lengths of individual nanowires within a plurality of nanowires.

A "diameter" of a nanowire can be measured in an axis perpendicular to the axis of the nanowire's actual length (i.e. perpendicular to the nanowires backbone). The diameter of a nanowire will vary from narrow to wide as measured at different points along the nanowire backbone. As used herein, the diameter of a nanowire is the most prevalent (i.e. the mode) diameter.

A "ratio of effective length to actual length" can be determined by dividing the effective length by the actual length. A nanowire having a "bent morphology" can have a ratio of effective length to actual length of less than one as described in more detail herein. A straight nanowire will have a ratio of effective length to actual length equal to one.

The term "inorganic," as used herein, generally refers to a substance comprising a metal element or semi-metal element. In certain embodiments, inorganic refers to a substance comprising a metal element. An inorganic compound can contain one or more metals in its elemental state, or more typically, a compound formed by a metal ion ($M^{n+}$, wherein n 1, 2, 3, 4, 5, 6 or 7) and an anion ($X^{m-}$, m is 1, 2, 3 or 4), which balance and neutralize the positive charges of the metal ion through electrostatic interactions. Non-limiting examples of inorganic compounds include oxides, hydroxides, halides, nitrates, sulfates, carbonates, phosphates, acetates, oxalates, and combinations thereof, of metal elements. Other non-limiting examples of inorganic compounds include $Li_2CO_3$, $Li_2PO_4$, LiOH, $Li_2O$, LiCl, LiBr, LiI, $Li_2C_2O_4$, $Li_2SO_4$, $Na_2CO_3$, $Na_2PO_4$, NaOH, $Na_2O$, NaCl, NaBr, NaI, $Na_2C_2O_4$, $Na_2SO_4$, $K_2CO_3$, $K_2PO_4$, KOH, $K_2O$, KCl, KBr, KI, $K_2C_2O_4$, $K_2SO_4$, $Cs_2CO_3$, $CsPO_4$, CsOH, $Cs_2O$, CsCl, CsBr, CsI, $CsC_2O_4$, $CsSO_4$, $Be(OH)_2$, $BeCO_3$, $BePO_4$, BeO, $BeCl_2$, $BeBr_2$, $BeI_2$, $BeC_2O_4$, $BeSO_4$, $Mg(OH)_2$, $MgCO_3$, $MgPO_4$, MgO, $MgCl_2$, $MgBr_2$, $MgI_2$, $MgC_2O_4$, $MgSO_4$, $Ca(OH)_2$, CaO, $CaCO_3$, $CaPO_4$, $CaCl_2$, $CaBr_2$, $CaI_2$, $Ca(OH)_2$, $CaC_2O_4$, $CaSO_4$, $Y_2O_3$, $Y_2(CO_3)_3$, $Y_2(PO_4)_3$, $Y(OH)_3$, $YCl_3$, $YBr_3$, $YI_3$, $Y_2(C_2O4)_3$, $Y_2(SO4)_3$, $Zr(OH)_4$, $Zr(CO_3)_2$, $Zr(PO_4)_2$, $ZrO(OH)_2$, ZrO2, $ZrCl_4$, $ZrBr_4$, $ZrI_4$, $Zr(C_2O_4)_2$, $Zr(SO_4)_2$, $Ti(OH)_4$, $TiO(OH)_2$, $Ti(CO_3)_2$, $Ti(PO_4)_2$, $TiO_2$, $TiCl_4$, $TiBr_4$, $TiI_4$, $Ti(C_2O_4)_2$, $Ti(SO_4)_2$, BaO, $Ba(OH)_2$, $BaCO_3$, $BaPO_4$, $BaCl_2$, $BaBr_2$, $BaI_2$, $BaC_2O_4$, $BaSO_4$, $La(OH)_3$, $La_2(CO_3)_3$, $La_2(PO_4)_3$, $La_2O_3$, $LaCl_3$, $LaBr_3$, $LaI_3$, $La_2(C_2O_4)_3$, $La_2(SO_4)_3$, $Ce(OH)_4$, $Ce(CO_3)_2$, $Ce(PO_4)_2$, $CeO_2$, $Ce_2O_3$, $CeCl_4$, $CeBr_4$, $CeI_4$, $Ce(C_2O_4)_2$, $Ce(SO_4)_2$, $ThO_2$, $Th(CO_3)_2$, $Th(PO_4)_2$, $ThCl_4$, $ThBr_4$, $ThI_4$, $Th(OH)_4$, $Th(C_2O_4)_2$, $Th(SO_4)_2$, $Sr(OH)_2$, $SrCO_3$, $SrPO_4$, SrO, $SrCl_2$, $SrBr_2$, $SrI_2$, $SrC_2O_4$, $SrSO_4$, $Sm_2O_3$, $Sm_2(CO_3)_3$, $Sm_2(PO_4)_3$, $SmCl_3$, $SmBr_3$, $SmI_3$, $Sm(OH)_3$, $Sm_2(CO3)_3$, $Sm_2(C_2O_3)_3$, $Sm_2(SO_4)_3$, $LiCa_2Bi_3O_4Cl_6$, $Na_2WO_4$, K/Sr-$CoO_3$, K/Na/$SrCoO_3$, Li/$SrCoO_3$, $SrCoO_3$, molybdenum oxides, molybdenum hydroxides, molybdenum carbonates, molybdenum phosphates, molybdenum chlorides, molybdenum bromides, molybdenum iodides, molybdenum oxalates, molybdenum sulfates, manganese oxides, manganese chlorides, manganese bromides, manganese iodides, manganese hydroxides, manganese oxalates, manganese sulfates, manganese tungstates, vanadium oxides, vanadium carbonates, vanadium phosphates, vanadium chlorides, vanadium bromides, vanadium iodides, vanadium hydroxides, vanadium oxalates, vanadium sulfates, tungsten oxides, tungsten carbonates, tungsten phosphates, tungsten chlorides, tungsten bromides, tungsten iodides, tungsten hydroxides, tungsten oxalates, tungsten sulfates, neodymium oxides, neodymium carbonates, neodymium phosphates, neodymium chlorides, neodymium bromides, neodymium iodides, neodymium hydroxides, neodymium oxalates, neodymium sulfates, europium oxides, europium carbonates, europium phosphates, europium chlorides, europium bromides, europium iodides, europium hydroxides, europium oxalates, europium sulfates rhenium oxides, rhenium carbonates, rhenium phosphates, rhenium chlorides, rhenium bromides, rhenium iodides, rhenium hydroxides, rhenium oxalates, rhenium sulfates, chromium oxides, chromium carbonates, chromium phosphates, chromium chlorides, chromium bromides, chromium iodides, chromium hydroxides, chromium oxalates, chromium sulfates, potassium molybdenum oxides and the like.

The term "salt," as used herein, generally refers to a compound comprising negative and positive ions. Salts are generally comprised of cations and counter ions. Under appropriate conditions, e.g., the solution also comprises a template, the metal ion ($M^{n+}$) and the anion ($X^{m-}$) bind to the template to induce nucleation and growth of a nanowire of $M_mX_n$ on the template. "Anion precursor" thus is a compound that comprises an anion and a cationic counter ion, which allows the anion ($X^{m-}$) to dissociate from the cationic counter ion in a solution. Specific examples of the metal salt and anion precursors are described in further detail herein.

The term "oxide," as used herein, generally refers to a metal or semiconductor compound comprising oxygen. Examples of oxides include, but are not limited to, metal oxides ($M_xO_y$), metal oxyhalides ($M_xO_yX_z$), metal hydroxyhalides ($M_xOH_yX_z$), metal oxynitrates ($M_xO_y(NO_3)_z$), metal phosphates ($M_x(PO_4)_y$), metal oxycarbonates ($M_xO_y(CO_3)_z$), metal carbonates ($M_x(CO_3)_z$), metal sulfates ($M_x(SO_4)_z$), metal oxysulfates ($M_xO_y(SO_4)_z$), metal phosphates ($M_x(PO_4)_z$), metal acetates ($M_x(CH_3CO_2)_z$), metal oxalates ($M_x(C_2O_4)_z$), metal oxyhydroxides ($M_xO_y(OH)_z$), metal hydroxides ($M_x(OH)_z$), hydrated metal oxides ($M_xO_y$). ($H_2O)_z$ and the like, wherein X is independently, at each occurrence, fluoro, chloro, bromo or iodo, and x, y and z are independently numbers from 1 to 100.

The term "mixed oxide" or "mixed metal oxide," as used herein, generally refers to a compound comprising two or more metals and oxygen (i.e., $M1_xM2_yO_z$, wherein M1 and M2 are the same or different metal elements, O is oxygen and x, y and z are numbers from 1 to 100). A mixed oxide may comprise metal elements in various oxidation states and may comprise more than one type of metal element. For example, a mixed oxide of manganese and magnesium comprises oxidized forms of magnesium and manganese. Each individual manganese and magnesium atom may or may not have the same oxidation state. Mixed oxides comprising 2, 3, 4, 5, 6 or more metal elements can be represented in an analogous manner. Mixed oxides also include oxy-hydroxides (e.g., $M_xO_yOH_z$, wherein M is a metal element, O is oxygen, x, y and z are numbers from 1 to 100 and OH is hydroxy). Mixed oxides may be represented herein as M1-M2, wherein M1 and M2 are each independently a metal element.

The term "crystal domain," as used herein, generally refers to a continuous region over which a substance is crystalline.

The term "single-crystalline" or "mono-crystalline," as used herein, generally refers to a material (e.g., nanowire) having a single crystal domain.

The term "dopant" or "doping agent," as used herein, generally refers to a material (e.g., impurity) added to or incorporated within a catalyst to alter (e.g., optimize) catalytic performance (e.g. increase or decrease catalytic activity). As compared to the undoped catalyst, a doped catalyst may increase or decrease the selectivity, conversion, and/or yield of a reaction catalyzed by the catalyst.

The term "OCM catalyst," as used herein, generally refers to a catalyst capable of catalyzing an OCM reaction.

"Group 1" elements include lithium (Li), sodium (Na), potassium (K), rubidium (Rb), cesium (Cs), and francium (Fr).

"Group 2" elements include beryllium (Be), magnesium (Mg), calcium (Ca), strontium (Sr), barium (Ba), and radium (Ra).

"Group 3" elements include scandium (Sc) and yttrium (Y).

"Group 4" elements include titanium (Ti), zirconium (Zr), halfnium (Hf), and rutherfordium (Rf).

"Group 5" elements include vanadium (V), niobium (Nb), tantalum (Ta), and dubnium (Db).

"Group 6" elements include chromium (Cr), molybdenum (Mo), tungsten (W), and seaborgium (Sg).

"Group 7" elements include manganese (Mn), technetium (Tc), rhenium (Re), and bohrium (Bh).

"Group 8" elements include iron (Fe), ruthenium (Ru), osmium (Os), and hassium (Hs).

"Group 9" elements include cobalt (Co), rhodium (Rh), iridium (Ir), and meitnerium (Mt).

"Group 10" elements include nickel (Ni), palladium (Pd), platinum (Pt) and darmistadium (Ds).

"Group 11" elements include copper (Cu), silver (Ag), gold (Au), and roentgenium (Rg).

"Group 12" elements include zinc (Zn), cadmium (Cd), mercury (Hg), and copernicium (Cn).

"Lanthanides" include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), yitterbium (Yb), and lutetium (Lu).

"Actinides" include actinium (Ac), thorium (Th), protactinium (Pa), uranium (U), neptunium (Np), plutonium (Pu), americium (Am), curium (Cm), berklelium (Bk), californium (Cf), einsteinium (Es), fermium (Fm), mendelevium (Md), nobelium (No), and lawrencium (Lr).

"Rare earth" elements include Group 3, lanthanides and actinides.

"Metal element" or "metal" is any element, except hydrogen, selected from Groups 1 through 12, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, as well as various polymorphs thereof, and the like.

The term "semi-metal element," as used herein, generally refers to an element selected from boron (B), silicon (Si), germanium (Ge), arsenic (As), antimony (Sb), tellurium (Te), and polonium (Po).

The term "non-metal element," as used herein, generally refers to an element selected from carbon (C), nitrogen (N), oxygen (O), fluorine (F), phosphorus (P), sulfur (S), chlorine (Cl), selenium (Se), bromine (Br), iodine (I), and astatine (At).

The term "higher hydrocarbon," as used herein, generally refers to a higher molecular weight and/or higher chain hydrocarbon. A higher hydrocarbon can have a higher molecular weight and/or carbon content that is higher or larger relative to starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The present disclosure is generally directed to processes and systems for use in the production of hydrocarbon compositions. These processes and systems may be characterized in that they derive the hydrocarbon compositions from ethylene that is, in turn, derived from methane, for example as is present in natural gas. The disclosed processes and systems are typically further characterized in that the process for conversion of methane to ethylene is integrated with one or more processes or systems for converting ethylene to one or more higher hydrocarbon products, which, in some embodiments, comprise liquid hydrocarbon compositions. By converting the methane present in natural gas to a liquid material, one can eliminate one of the key hurdles involved in exploitation of the world's vast natural gas reserves, namely transportation. In particular, exploitation of natural gas resources traditionally has required extensive, and costly pipeline infrastructures for movement of gas from the wellhead to its ultimate destination. By converting that gas to a liquid material, more conventional transportation systems become available, such as truck, rail car, tanker ship, and the like.

In some embodiments, processes and systems provided herein include multiple (i.e., two or more) ethylene conversion process paths integrated into the overall processes or systems, in order to produce multiple different higher hydrocarbon compositions from the single original methane source. Further advantages are gained by providing the integration of these multiple conversion processes or systems in a switchable or selectable architecture whereby a portion or all of the ethylene containing product of the methane to ethylene conversion system is selectively directed to one or more different process paths, for example two, three, four, five or more different process paths to yield as many different products. This overall process flow is schematically illustrated in FIG. 1. As shown, an oxidative coupling of methane ("OCM") reactor system 100 is schematically illustrated that includes an OCM reactor train 102 coupled to a OCM product gas separation train 104, such as a cryogenic separation system. The ethylene rich effluent (shown as arrow 106) from the separation train 104 is shown being routed to multiple different ethylene conversion reactor systems and processes 110, e.g., ethylene conversion systems 110a-110e, which each produce different hydrocarbon products, e.g., products 120a-120e.

As noted, the fluid connection between the OCM reactor system 100 and each of the different ethylene conversion systems 110a-110e, can be a controllable and selective connection in some embodiments, e.g., a valve and control system, that can apportion the output of the OCM reactor system to one, two, three, four, five or more different ethylene conversion systems. Valve and piping systems for accomplishing this may take a variety of different forms, including valves at each piping junction, multiport valves, multi-valve manifold assemblies, and the like.

Ethylene-to-Liquids (ETL) Systems

Ethylene-to-liquids (ETL) systems and methods of the present disclosure can be used to form various products, including hydrocarbon products. Products and product distributions can be tailored to a given application, such as products for use as fuel (e.g., jet fuel or automobile fuels such as diesel or gasoline).

The present disclosure provides reactors for the conversion of olefins to higher molecular weight hydrocarbons, which can be in liquid form. Such reactors can be ETL reactors, which can be used to convert ethylene and/or other olefins to higher molecular weight hydrocarbons.

An ETL system (or sub-system) can include one or more reactors. An ETL system can include at least 1, 2, 3, 4, 5, 6, 7, 8, 9, 10, 11, 12, 13, 14, 15, 16, 17, 18, 19, or 20 ETL reactors, which can be in a parallel, serial, or a combination of parallel and serial configuration.

An ETL reactor can be in the form of a tube, packed bed, moving bed or fluidized bed. An ETL reactor can include a single tube or multiple tubes, such as a tube in a shell. A multi-tubular reactor can be used for highly exothermic conversions, such as the conversion of ethylene to other hydrocarbons. Such a design can allow for an efficient management of thermal fluxes and the control of reactor and catalyst bed temperatures.

An ETL reactor can be an isothermal or adiabatic reactor. An ETL reactor can have one or more of the following: 1) multiple cooling zones and arrangements within the reactor shell in which the temperature within each cooling zone may be independently set and controlled; 2) multiple residence times of the reactants as they traverse the tubular reactor from the inlet of the individual tubes to the outlet; and 3) multiple pass design in which the reactants may make several passes within the reactor shell from the inlet of the reactor to the outlet.

Multi-tubular reactors of the present disclosure can be used to convert ethylene to liquid hydrocarbons in a variety of ways. In some cases, the disclosed multi-tubular ETL reactors can result in smaller reactors and gas compressors compared to adiabatic ETL designs. The ETL hydrocarbon reaction is exothermic and thus reaction heat management may be important for reaction control and improved product selectivity. In adiabatic ETL reactor designs, there is an upper limit to the ethylene concentration that is flowed through reactor due to the amount of heat released and subsequent temperature rise inside the reactor. To control the heat of reaction, adiabatic reactors can use a large amount of diluent gas to mitigate the temperature rise in the reactor bed. In some cases, the heat of reaction can be managed using multiple reactors with cooling between reactors and limited conversion between reactors (i.e., about 20%, about 30%, about 40%, about 50%, about 60%, or about 70% conversion in one reactor), cooling of the product effluent, and converting the remaining feedstock in one or more subsequent reactors. The use of diluent gas can result in larger catalyst beds, reactors, and gas compressors. The multi-tubular reactors described herein can allow for significantly greater ethylene concentrations while controlling the reactor bed temperature, since heat can be removed at the reactor wall. As a consequence, for a targeted rate of production, smaller catalyst beds, reactors, and gas compressors may be used.

In addition to smaller ETL reactors, the disclosed multi-tubular ETL reactors can result in smaller downstream liquid-gas product separation equipment due to less diluent gas needed to cool the reactor.

Multi-tubular ETL reactors of the present disclosure can result in more favorable process conditions toward higher carbon number hydrocarbon liquids compared to an adiabatic ETL design. Relative to adiabatic reactors where ethylene feed can be diluted to control reaction temperature, the disclosed multi-tubular designs can allow for more concentrated ethylene feed into the reactor while maintaining good reactor temperature control. Higher ethylene concentration in the reactor can facilitate the formation for higher hydrocarbon liquids such as jet and/or diesel fuel since reactant concentration is important process parameter to yield higher hydrocarbon oligomers. In some cases, olefinic liquids of specific carbon number range and types can also be recycled into the reactor bed to further generate higher carbon number liquids (e.g., jet/diesel).

Multi-tubular reactors can have multiple temperature zones and offer multiple residence times. This can allow a wide range of process flexibility to target a particular product slate. As an example, a reactor can have multiple temperature zones and/or residence times. One use of this design can be to make jet and/or diesel fuel from ethylene. Ethylene oligomerization can require a relatively high reaction temperature. The temperature required to react ethylene, to start the oligomerization process may not be compatible with jet or diesel products, due to the rapid cracking and/or disproportionation of these jet/diesel products at elevated temperatures. Multiple reactor temperature zones can allow for a separate and higher temperature zone to start ethylene oligomerization while having another lower temperature zone to facilitate further oligomerization into jet/diesel fuel while discouraging cracking and disproportionation side reactions.

The use of multiple temperature zones may require different residence times within a reactor bed. In the jet/diesel example, the residence time for the ethylene reaction can be different than the residence time for a lower temperature finishing step to form jet/diesel. To maximize jet/diesel liquid yield, the ethylene oligomerization reaction bed temperature may need to be higher but with a lower residence time than the step to make jet/diesel which can require a lower temperature but higher residence time. In adiabatic ETL reactors, multi-temperature processes may occur over multiple reactor beds with a different temperature associated with each reactor. The multi-temperature zone approach disclosed herein can obviate the need for multiple reactors, as in the adiabatic ETL case, since multiple temperature zones can be achieved within a single reactor and thus lower capital outlay for reactor deployment.

Catalyst aging can be an important design constraint in ETL reaction engineering. ETL catalysts can deactivate over time until the catalyst bed is no longer able to sustain high ethylene conversion. A slower catalyst deactivation rate may be desired since more ethylene can be converted per catalyst bed before the catalyst bed can need to be taken off-line and regenerated. Typically, the catalyst deactivates due to "coke", deposits of carbonaceous material, which results in decreasing catalyst performance upon coke build-up. The rate of "coke" build-up is attributable to many different parameters. In ETL adiabatic reactors, the formation of catalyst bed "hot-spots" can play an important role in causing catalyst coking. "Hot-spots" favor aromatic compound formation, which are precursors to coke formation. "Hot-spots" are a result of temperature non-uniformities within the catalyst bed due to inadequate heat transfer. The localized "hot-spots" increase the rate of catalyst coking/deactivation. The disclosed multi-tubular design can decrease localized "hot-spots" due to better heat transfer properties of the multi-tubular design relative to the adiabatic design. It is anticipated that the decrease in catalyst "hot-spots" can slow catalyst deactivation.

The product slate of the ETL slate is a result of many factors. An important factor is the catalyst bed temperature. For example, higher temperatures catalyst bed temperatures can skew the product slate, for some catalysts, to aromatic products. In large adiabatic reactors, controlling "hot spot" formation is challenging and inhomogeneities in the catalyst bed temperature profiles lead a wider distribution of products. The proposed multi-tubular design can significantly reduce catalyst bed temperature inhomogeneities/"hot spots" due to better heat transfer characteristics relative to the adiabatic design. As a result, a narrower product distribution can be more readily achieved than with adiabatic reactor design. While the multi-tubular design provides excellent catalyst bed temperature uniformity, catalyst bed temperature bed uniformity can be further enhanced by injection of "trim gas" and/or "trim liquid."

The heat capacity of "trim gas" can be used to fine-tune the catalyst bed to a target temperature. Trim gas composition can be inert/high heat capacity gas for example: ethane, propane, butane, and other high heat capacity hydrocarbons.

In some cases, liquid hydrocarbons can be injected into the ETL reactors to take advantage of the heat of vaporization to further regulate and cool the reactor bed in order to achieve the desired temperature. Also, one can use both of them (gases and liquids) as "trim" agents in this design for ETL.

ETL catalysts may need to be regenerated from a state of low ethylene conversion (e.g., 20% or less) to high ethylene conversion, such as, e.g., greater than 20%, 30%, 40%, 50%, 60%, or 70%. Regeneration can occur by heating the catalyst bed to an appropriate temperature while introducing a portion of diluted air. The oxygen in air can be used to remove coke by combustion and thus renew catalyst activity. Too much oxygen can cause uncontrolled combustion, a highly exothermic process, and the resultant catalyst bed temperature rise may cause irreversible catalyst damage. As a consequence, the amount of air that is permitted during adiabatic reactor regeneration is limited and monitored.

The catalyst regeneration time for an adiabatic reactor can be largely dictated by the amount of oxygen that can be permitted in the reactor. The greater heat transfer properties of the disclosed multi-tubular reactors can permit greater concentrations of oxygen during catalyst regeneration to hasten catalyst regeneration while ensuring that the catalyst bed temperature does not reach the point of irreversible catalyst deactivation.

The present disclosure also provides reactor systems for carrying out ethylene conversion processes. A number of ethylene conversion processes can involve exothermic catalytic reactions where substantial heat is generated by the process. Likewise, for a number of these catalytic systems, the regeneration processes for the catalyst materials likewise involve exothermic reactions. As such, reactor systems for use in these processes can generally be configured to effectively manage excess thermal energy produced by the reactions, in order to control the reactor bed temperatures to most efficiently control the reaction, prevent deleterious reactions, and prevent catalyst or reactor damage or destruction.

Tubular reactor configurations that may present high wall surface area per unit volume of catalyst bed may be used for reactions where thermal control is desirable or otherwise required, as they can permit greater thermal transfer out of the reactor. Reactor systems that include multiple parallel tubular reactors may be used in carrying out the ethylene conversion processes described herein. In particular, arrays of parallel tubular reactors each containing the appropriate catalyst for one or more ethylene conversion reaction processes may be arrayed with space between them to allow for the presence of a cooling medium between them. Such cooling medium may include any cooling medium appropriate for the given process. For example, the cooling medium may be air, water or other aqueous coolant formulations, steam, oil, upstream of reaction feed or for very high temperature reactor systems, molten salt coolants.

In some cases, reactor systems are provided that include multiple tubular reactors segmented into one, two, three, four or more different discrete cooling zones, where each zone is segregated to contain its own, separately controlled cooling medium. The temperature of each different cooling zone may be independently regulated through its respective cooling medium and an associated temperature control system, e.g., thermally connected heat exchangers, etc. Such differential control of temperature in different reactors can be used to differentially control different catalytic reactions, or reactions that have catalysts of different age. Likewise, it allows for the real time control of reaction progress in each reactor, in order to maintain a more uniform temperature profile across all reactors, and therefore synchronize catalyst lifetimes, regeneration cycles and replacement cycles.

Figure 2:
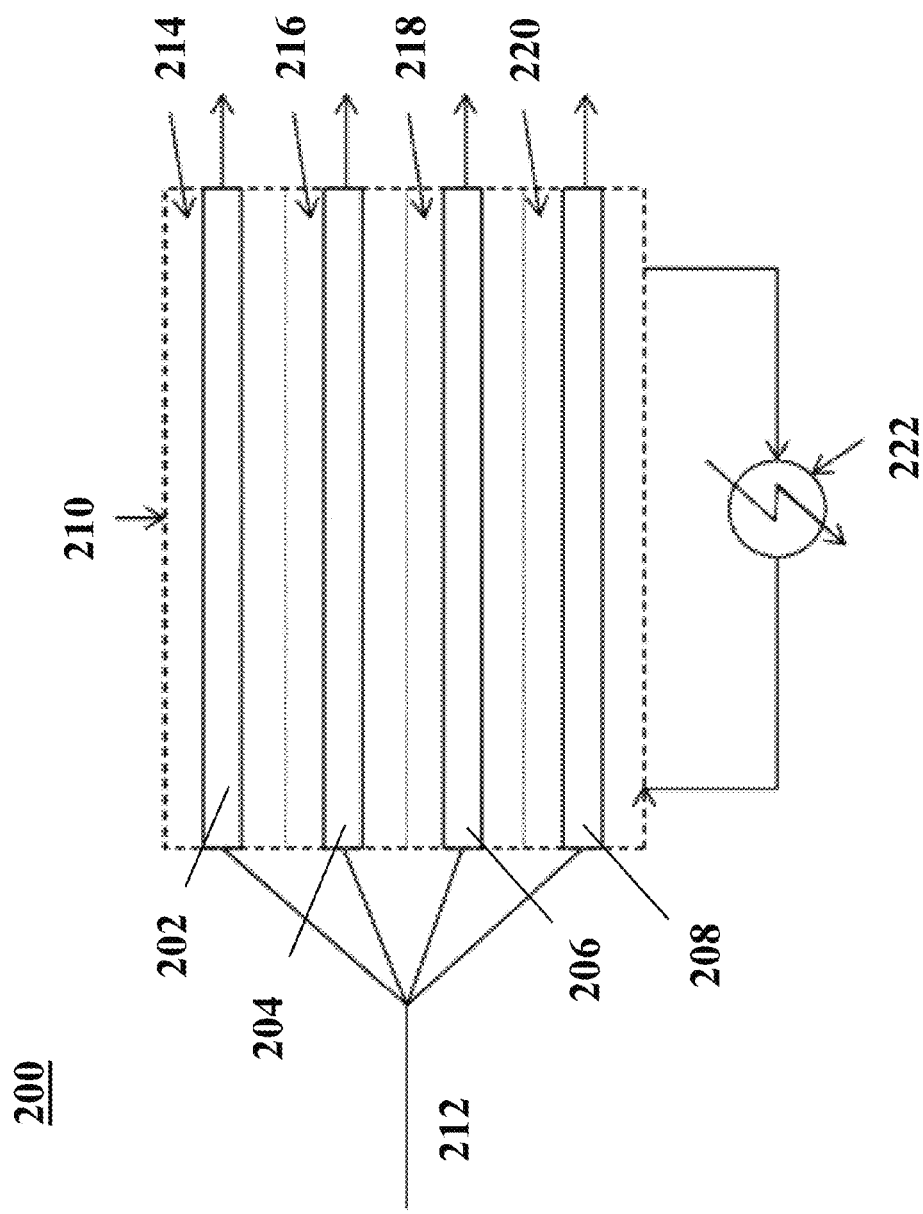
FIG. 2 schematically illustrates differentially cooled tubular reactor systems.

Differentially cooled tubular reactor systems are schematically illustrated in FIG. 2. As shown, an overall reactor system 200 includes multiple discrete tubular reactors 202, 204, 206 and 208 contained within a larger reactor housing 210. Within each tubular reactor is disposed a catalyst bed for carrying out a given catalytic reaction. The catalyst bed in each tubular reactor may be the same or it may be different from the catalyst in the other tubular reactors, e.g., optimized for catalyzing a different reaction, or for catalyzing the same reaction under different conditions. As shown, the multiple tubular reactors 202, 206, 208 and 210 share a common manifold 212 for the delivery of reactants to the reactors. However, each individual tubular reactor or subset of the tubular reactors may alternatively include a single reactant delivery conduit or manifold for delivering reactants to that tubular reactor or subset of reactors, while a separate delivery conduit or manifold is provided for delivery of the same or different reactants to the other tubular reactors or subsets of tubular reactors.

As an alternative or in addition to, the reactor systems used in conjunction with the olefin (e.g., ethylene) conversion processes described herein can provide for variability in residence time for reactants within the catalytic portion of the reactor. Residence time within a reactor can be varied through the variation of any of a number of different applied parameters, e.g., increasing or decreasing flow rates, pressures, catalyst bed lengths, etc. However, a single reactor system may be provided with variable residence times, despite sharing a single reactor inlet, by varying the volume of different reactor tubes or reactor tube portions within a single reactor unit ("catalyst bed length"). As a result of varied volumes among reactor tubes or reactor tube portions into which reactants are being introduced at a given flow rate, residence times for those reactants within those varied volume reactor tubes or reactor tube portions, can be consequently varied.

Variation of reactor volumes may be accomplished through a number of approaches. By way of example, varied volume may be provided by including two or more different reactor tubes into which reactants are introduced at a given flow rate, where the two or more reactor tubes each have different volumes, e.g., by providing varied diameters. As can be appreciated, the residence time of gases being introduced at the same flow rate into two or more different reactors having different volumes can be different. In particular, the residence time can be greater in the higher volume reactors and shorter in the smaller volume reactors. The higher volume within two different reactors may be provided by providing each reactor with different diameters. Likewise, one can vary the length of the reactors catalyst bed, in order to vary the volume of the catalytic portion.

Alternatively, or additionally, the volume of an individual reactor tube can be varied by varying the diameter of the reactor along its length, effectively altering the volume of different segments of the reactor. Again, in the wider reactor segments, the residence time of gas being introduced into the reactor tube can be longer in the wider reactor segments than in the narrower reactor segments.

Varied volumes can also be provided by routing different inlet reactant streams to different numbers of similarly sized reactor conduits or tubes. In particular, reactants, e.g., gases, may be introduced into a single reactor tube at a given flow rate to yield a particular residence time within the reactor. In contrast, reactants introduced at the same flow rate into two or more parallel reactor tubes can have a much longer residence time within those reactors.

Figure 3:
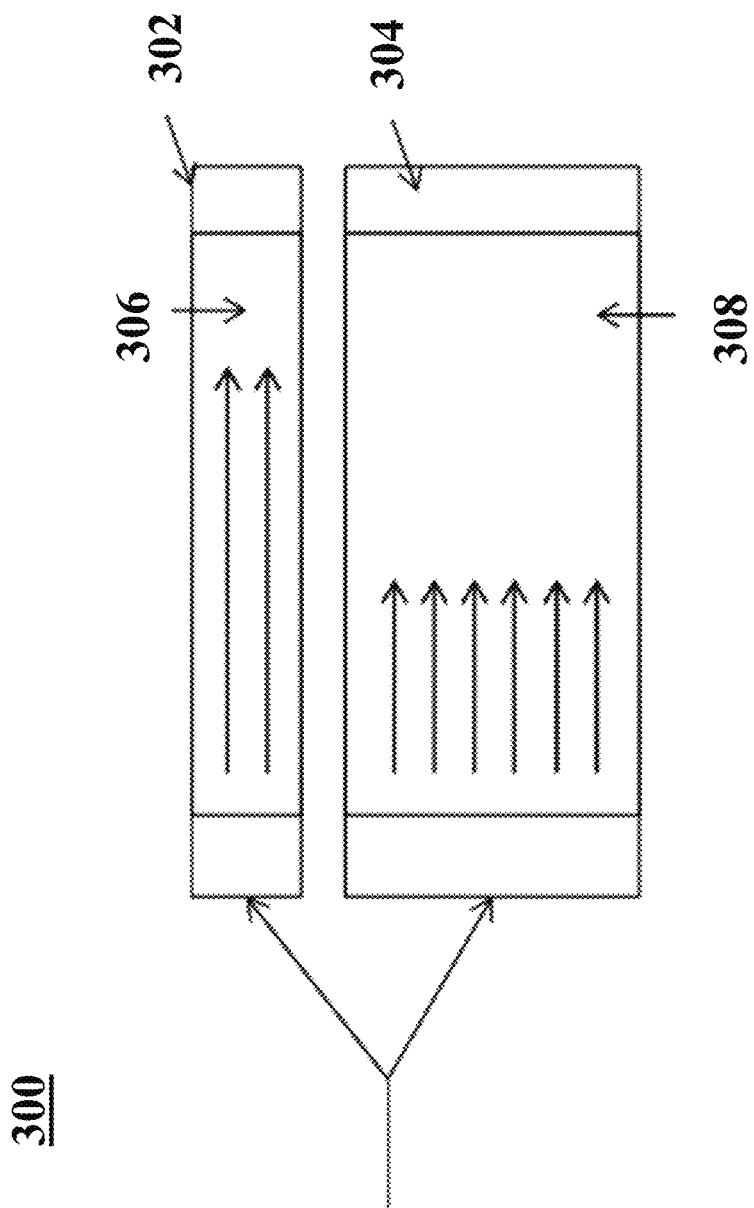
FIG. 3 schematically illustrates a reactor system with two or more tubular reactors.
Figure 4A:
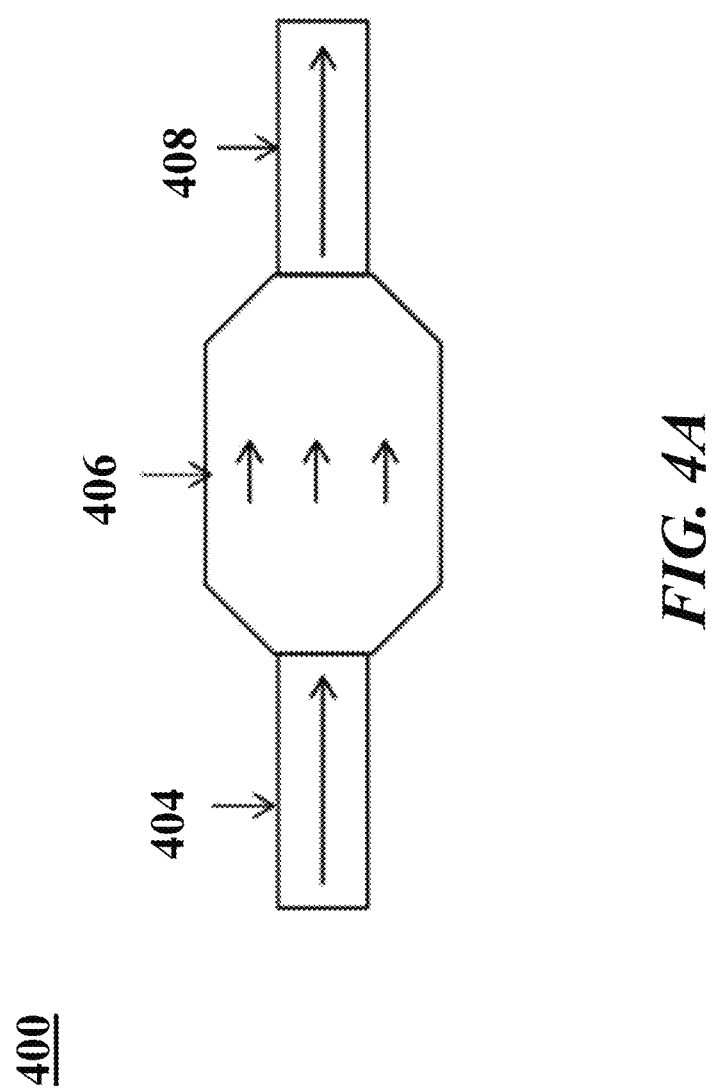
FIG. 4A schematically illustrates an alternative approach for varying reactor volumes in order to vary residence time of reactants in a catalyst bed.

The above-described approaches to varying residence time within reactor catalyst beds are illustrated with reference to FIGS. 3-4. FIG. 3 schematically illustrates a reactor system 300 in which two or more tubular reactors 302 and 304 are disposed, each having its own catalyst bed, 306 and 308, respectively, disposed therein. The two reactors are connected to the same inlet manifold such that the flow rate of reactants being introduced into each of reactors 302 and 304 are the same. Because reactor 304 has a larger volume (shown as a wider diameter), the reactants can be retained within catalyst bed 308 for a longer period. In particular, as shown, reactor 304 has a larger diameter, resulting in a slower linear velocity of reactants through the catalyst bed 308, than the reactants passing through catalyst bed 306. As noted above, one can similarly increase residence time within the catalyst bed of reactor 304 by providing a longer reactor. However, such longer reactor bed may be required to have similar back pressure as a shorter reactor to ensure reactants are introduced at the same flow rate as the shorter reactor FIG. 4 schematically illustrates an alternative approach for varying reactor volumes in order to vary residence times of reactants in the catalyst bed. As shown, an individual reactor unit, e.g., reactor tube 400, can be configured to provide for differing residence times within different portions of the reactor tube by varying the diameter of the reactor between reactor segment 404, 406 and 408. In particular, by providing a larger diameter of the reactor tube in segment 404 and 406, respectively, one can increase the residence time of reactants moving through these segments, as the linear velocity of the reactants through such segments decreases.

The residence time of reactants within reactor systems can be controlled by varying the diameter of the ETL reactor along the path of fluid flow. In some cases, the reactor system can include multiple different reactor tubes, where each reactor tube includes a catalyst bed disposed therein. Differing residence times may be employed in catalyzing different catalytic reactions, or catalyzing the same reactions under differing conditions. In particular, one may wish to vary residence time of a given set of reactants over a single catalyst system, in order to catalyze a reaction more completely, catalyze a different or further reaction, or the like. Likewise, different reactors within the system may be provided with different catalyst systems that may benefit from differing residence times of the reactants within the catalyst bed to catalyze the same or different reactions from each other.

Alternatively or additionally, residence times of reactants within catalyst beds may be configured to optimize thermal control within the overall reactor system. In particular, residence times may be longer at a zone in the reactor system in which removal of excess thermal energy is less critical or more easily managed, e.g., because the overall reaction has not yet begun generating excessive heat. In contrast, in other zones of the reactor, e.g., where removal of excess thermal energy is more difficult due to rapid exothermic reactivity, the reactor portion may only maintain the reactants for a much shorter time, by providing a narrower reactor diameter. As can be appreciated, thermal management becomes easier due to the shorter period of time that the reactants are present and reacting to produce heat. Likewise, the reduced volume of a tubular reactor within a reactor housing also provides for a greater volume of cooling media, to more efficiently remove thermal energy.

Systems and methods of the present disclosure can employ fixed bed reactors. Fixed bed reactors can be adiabatic reactors. Fixed bed adiabatic ETL reactors can provide for simplicity of the reactor design. No active external cooling mechanism of the reactor may be necessary. To control the reactor temperature, profile dilution of the reactive olefin or other feedstocks (e.g., ethylene, propylene, butenes, pentenes, etc.) may be necessary. The diluent gas can be any material that is non-reactive or non-poisonous to the ETL catalyst but preferably has a high heat capacity to moderate the temperature rise within the catalyst bed. Examples of diluent gases include nitrogen ($N_2$), argon, methane, ethane, propane and helium. The reactive part of the feedstock can be diluted directly or diluted indirectly in the reactor by recycling process gas to dilute the feedstock to an acceptable concentration. Temperature profile can also be controlled by internal reactor heat exchangers that can actively control the heat within the catalyst bed. Catalyst bed temperature control can also be achieved by limiting feedstock conversion within the catalyst bed. To achieve full feedstock conversion in this scenario, fixed bed adiabatic reactors are placed in series with heat exchangers between reactors to moderate temperature rise reactor over reactor. Partial conversion occurs in each reactor with inter-stage cooling to achieve the desired conversion and selectivity for the ETL process.

Since ETL catalysts can deactivate over time through coke deposition, the fixed bed reactors can be taken off-line and regenerated, such as by an oxidative or non-oxidative process, as described elsewhere herein. Once regenerated to full activity the ETL reactors can be put back on-line to process more feedstock.

Systems and methods of the present disclosure can employ the use of ETL continuous catalyst regeneration reactors. Continuous catalyst regeneration reactors (CCRR) can be attractive for processes where the catalyst deactivates over time and need to be taken off-line to be regenerated. By regenerating the catalyst in a continuous fashion less catalyst, fewer reactors for the process as well as fewer required operations are to regenerate the catalyst. There are two classes of deployments for CCRR reactors: (1) moving bed reactors and (2) fluidized bed reactors. In moving bed CCRR design, the pelletized catalyst bed moves along the reactor length and is removed and regenerated in a separate vessel. Once the catalyst is regenerated the catalyst pellets are put back in the ETL conversion reactor to process more feedstock. The online/regeneration process can be continuous and can maintain a constant flow of active catalyst in the ETL reactor. In fluidized bed ETL reactors, ETL catalyst particles are "fluidized" by a combination of ETL process gas velocity and catalyst particle weight. During bed fluidization, the bed expands, swirls, and agitates during reactor operation. The advantages of an ETL fluidized bed reactor are excellent mixing of process gas within the reactor, uniform temperature within the reactor, and the ability to continuously regenerate the coked ETL catalyst.

Figure 4B:
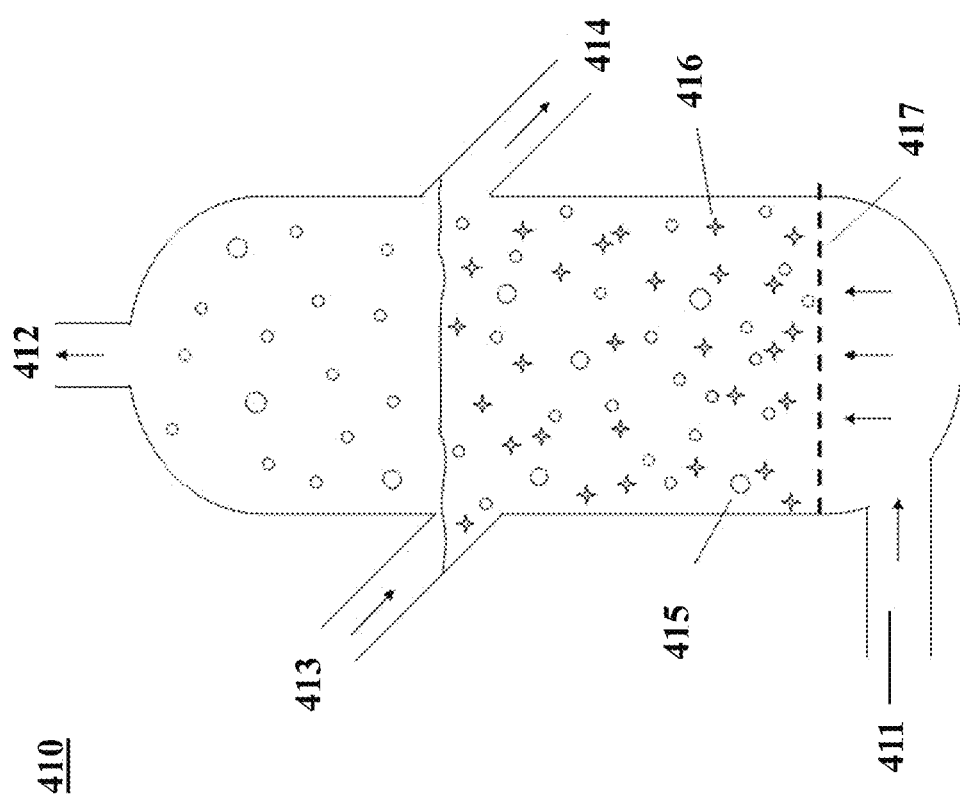
FIG. 4B schematically illustrates an exemplary fluidized bed reactor.
Figure 4C:
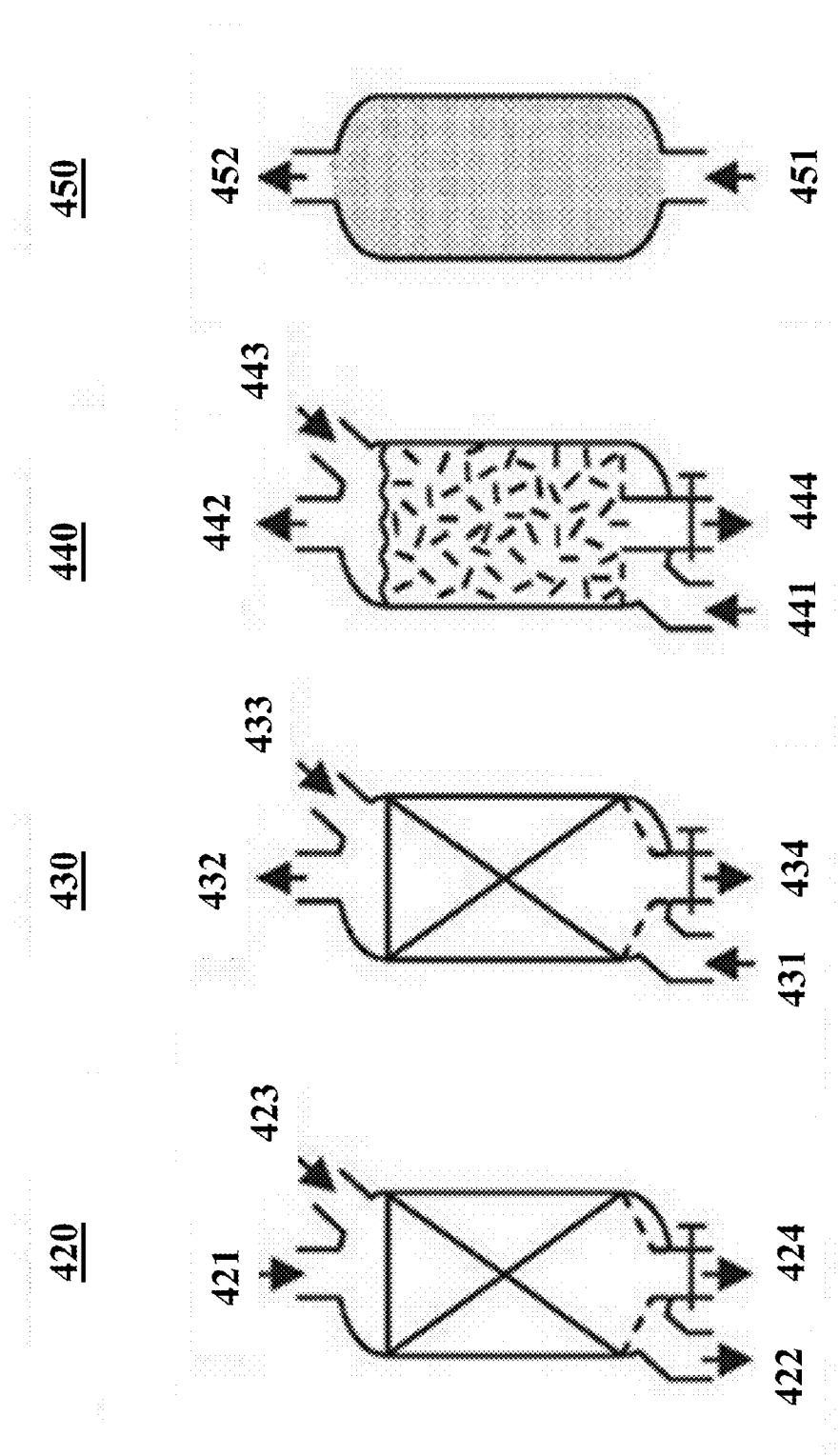
FIG. 4C schematically illustrates exemplary moving bed, fluidized bed, and slurry bed reactors.

Other reactor designs, such as moving bed (MBR), fluidized bed, and slurry bed reactors can also be employed. An exemplary fluidized bed reactor 410 is shown in FIG. 4B. A gas inlet stream 411 enters at the bottom of the reactor and a gas outlet stream 412 exits from the top of the reactor. Solid particles (e.g., catalyst) enter 413 at one side and exit 414 at another. Within the fluidized bed, gas bubbles 415 can encounter solid particles 416. The reactor can comprise a distributor 417 for distributing the gas flow. FIG. 4C shows additional schematics of exemplary reactor configurations for co-current moving bed reactors (420), counter-current moving bed reactors (430), fluidized bed reactors (440), and slurry bed reactors (450). The moving bed and fluidized bed reactors have separate gas inlet (421, 431, 434), gas outlet (422, 432, 442), catalyst inlet (423, 433, 443), and catalyst outlet (424, 434, 444) configurations. The slurry bed reactor has a combined gas/catalyst inlet 451 and gas/catalyst outlet 452.

The ETL catalyst can be regenerated with methane or natural gas. The regeneration stream can have oxygen ($O_2$) or other oxidizing agent. The concentration of oxygen in the regeneration stream can be below the limiting oxygen concentration (LOC), such that the mixture is not flammable. In some embodiments, the concentration of $O_2$ in the regeneration stream is less than about 6%, less than about 5%, less than about 4%, less than about 3%, less than about 2%, or less than about 1%. In some cases, the concentration of $O_2$ in the regeneration stream is between 0% and about 3%. An advantage of regenerating the ETL catalyst with methane or natural gas is that, following flowing over the ETL catalyst for regeneration, the stream can be used in the OCM and/or ETL process (e.g., the stream can be combusted to provide energy). The use of methane and/or natural gas to regenerate the ETL catalyst may not introduce any new components into the process to achieve catalyst regeneration, which can lead to an efficient use of materials. In some cases, the use of methane and/or natural gas makes the economics of the process insensitive, or less dependent on, the period of time that the ETL catalyst can operate between regeneration cycles.

Catalysts for the Conversion of Olefins to Liquids

The present invention also provides catalysts and catalyst compositions for ethylene conversion processes, in accordance with the processes described herein. In some embodiments, the disclosure provides modified zeolite catalysts and catalyst compositions for carrying out a number of desired ethylene conversion reaction processes. In some cases, provided are impregnated or ion exchanged zeolite catalysts useful in conversion of ethylene to higher hydrocarbons, such as gasoline or gasoline blendstocks, diesel and/or jet fuels, as well as a variety of different aromatic compounds. For example, where one is using ethylene conversion processes to convert OCM product gases to gasoline or gasoline feedstock products or aromatic mixtures, one may employ modified ZSM catalysts, such as ZSM-5 catalysts modified with Ga, Zn, Al, or mixtures thereof. In some cases, Ga, Zn and/or Al modified ZSM-5 catalysts are preferred for use in converting ethylene to gasoline or gasoline feedstocks. Modified catalyst base materials other than ZSM-5 may also be employed in conjunction with the invention, including, e.g., Y, ferrierite, mordenite, and additional catalyst base materials described herein.

In some cases, ZSM catalysts, such as ZSM-5 are modified with Co, Fe, Ce, or mixtures of these and are used in ethylene conversion processes using dilute ethylene streams that include both carbon monoxide and hydrogen components (See, e.g., Choudhary, et al., Microporous and Mesoporous Materials 2001, 253-267, which is incorporated herein by reference). In particular, these catalysts can be capable of co-oligomerizing the ethylene and $H_2$ and CO components into higher hydrocarbons, and mixtures useful as gasoline, diesel or jet fuel or blendstocks of these. In such embodiments, a mixed stream that includes dilute or non-dilute ethylene concentrations along with $CO/H_2$ gases can be passed over the catalyst under conditions that cause the co-oligomerization of both sets of feed components. Use of ZSM catalysts for conversion of syngas to higher hydrocarbons can be described in, for example, Li, et al., Energy and Fuels 2008, 22:1897-1901, which is incorporated herein by reference in its entirety.

The present disclosure provides various catalysts for use in converting olefins to liquids. Such catalysts can include an active material on a solid support. The active material can be configured to catalyze an ETL process to convert olefins to higher molecular weight hydrocarbons.

ETL reactors of the present disclosure can include various types of ETL catalysts. In some cases, such catalysts are zeolite and/or amorphous catalysts. Examples of zeolite catalysts include ZSM-5, Zeolite Y, Beta zeolite and Mordenite. Examples of amorphous catalysts include solid phosphoric acid and amorphous aluminum silicate. Such catalysts can be doped, such as using metallic and/or semiconductor dopants. Examples of dopants include, without limitation, Ni, Pd, Pt, Zn, B, Al, Ga, In, Be, Mg, Ca and Sr. Such dopants can be situated at the surfaces, in the pore structure of the catalyst and/or bulk regions of such catalysts.

Catalyst can be doped with materials that are selected to effect a given or predetermined product distribution. For example, a catalyst doped with Mg or Ca can provide selectivity towards olefins for use in gasoline. As another example, a catalyst doped with Zn or Ga (e.g., Zn-doped ZSM-5 or Ga-doped ZSM-5) can provide selectivity towards aromatics. As another example, a catalyst doped with Ni (e.g., Ni-doped zeolite Y) can provide selectivity towards diesel or jet fuel.

Catalysts can be situated on solid supports. Solid supports can be formed of insulating materials, such as TiOx or AlOx, wherein 'x' is a number greater than zero, or ceramic materials.

Catalyst of the present disclosure can have various cycle lifetimes (e.g., the average period of time between catalyst regeneration cycles). In some cases, ETL catalysts can have lifetimes of at least about 50 hours, 100 hours, 110 hours, 120 hours, 130 hours, 140 hours, 150 hours, 160 hours, 170 hours, 180 hours, 190 hours, 200 hours, 210 hours, 220 hours, 230 hours, 240 hours, 250 hours, 300 hours, 350 hours, or 400 hours. At such cycle lifetimes, olefin conversion efficiencies less than about 90%, 85%, 80%, 75%, 70%, 65%, or 60% may be observed.

Catalysts of the present disclosure can be regenerated through various regeneration procedures, as described elsewhere herein. Such procedures can increase the total lifetimes of catalysts (e.g., length of time before the catalyst is disposed of). An example of a catalyst regeneration process is provided in Lubo Zhou, "BP-UOP Cyclar Process," Handbook of Petroleum Refining Processes, The McGraw-Hill Companies (2004), pages 2.29-2.38, which is entirely incorporated herein by reference.

In some embodiments, ETL catalysts can be comprised of base materials (first active components) and dopants (second active components). The dopants can be introduced to the base materials through appropriate methods and procedures, such as vapor or liquid phase deposition. Dopants can be selected from a variety of elements, including metallic, non-metallic or amphoteric in forms of elementary substance, ions or compounds. A few representative doping elements are Ga, Zn, Al, In, Ni, Mg, B and Ag. Such dopants can be provided by dopant sources. For example, silver can be provided by way of AgCl or sputtering. The selection of doping materials can depend on the target product nature, such as product distribution. For example, Ga is favorable for aromatics-rich liquid production while Mg is favorable for aromatics-poor liquid production.

Base materials can be selected from crystalline zeolite materials, such as ZSM-5, ZSM-11, ZSM-22, Y, beta, mordenite, L, ferrierite, MCM-41, SAPO-34, SAPO-11, TS-1, SBA 15 or amorphous porous materials, such as amorphous silicoaluminate (ASA) and solid phosphoric acid catalysts. The cations of these materials can be $NH_4^+$, $H^+$ or others. The surface areas of these materials can be in a range of 1 $m^2/g$ to 10000 $m^2/g$, 10 $m^2/g$ to 5000 $m^2/g$, or 100 $m^2/g$ to 1000 $m^2/g$. The base materials can be directly used for synthesis or undergo some chemical treatment, such as desilication (de-Si) or dealumination (de-Al) to further modify the functionalities of these materials.

The base materials can be directly used for synthesis or undergo chemical treatment, such as desilication (de-Si) or dealumination (de-Al), to get derivatives of the base materials. Such treatment can improve the catalyst lifetime performance by creating larger pore volumes, such as pores having diameters greater than or equal to about 1 nanometer (nm), 2 nm, 3 nm, 4, nm, 5 nm, 10 nm, 20 nm, 30 nm, 40 nm, 50 nm, or 100 nm. In some cases, mesopores having diameters between about 1 nm and 100 nm, or 2 nm and 50 nm are created. In some examples, silica or alumina, or a combination of silica and alumina, can be etched from the base material to make a larger pore structure in the base catalyst that can enhance diffusion of reactants and products into the catalyst material. Pore diameter(s) and volume, in addition to porosity, can be as determined by adsorption or desorption isotherms (e.g., Brunauer-Emmett-Teller (BET) isotherm), such as using the method of Barrett-Joyner-Halenda (BJH). See Barrett E. P. et al., "The determination of pore volume and area distributions in porous substances. I. Computations from nitrogen isotherms," J. Am. Chem. Soc. 1951. V. 73. P. 373-380. Such method can be used to calculate material porosity and mesopore volumes, in some cases volumes that are 3-7 times larger than their original materials. In general, any changes in catalyst structure, composition and morphology can be measured by technologies of BET, SEM and TEM, etc.

There are various approaches for doping catalysts. In an example, the doping components can be added to the base materials and their derivatives through impregnation, in some cases using incipient wetness impregnation (IWI), ion exchange or framework substitution in a zeolite synthesis operation. In some cases, IWI can include i) mixing a salt solution of the doping component with base material, for which the amount of salt is calculated based on doping level, ii) drying the mixture in an oven, and iii) calcining the product at a certain temperature for a certain time, typically 550-650° C., 6-10 hrs. Ion exchange catalyst synthesis can include i) mixing a salt solution, which can contain at least 1.5, 2, 3, 4, 5, 6, 7, 8, 9, or 10 times excess amount of the doping component, with base material, ii) heating the mixture, such as, for example, at a temperature from about 50° C. to 100° C., 60° C. to 90° C., or 70° C. to 80° C. for a time period of at least about 10 minutes, 30 minutes, 1 hour, 2 hours, 3 hours, 4 hours, 5 hours, 6 hours, 7 hours, 8 hours, 9 hours, 10 hours, 11 hours, or 12 hours, to conduct a first ion exchange, iii) separating the first ion exchange mother solution, iv) adding a new salt solution and repeating ii) and iii) to conduct a second ion exchange, v) washing the wet solid with deionized water to remove or lower the concentration of soluble components, vi) drying the raw product, such as air drying or in an oven, and vii) calcining the raw product at a temperature from about 450° C. to 800° C., 500° C. to 750° C., or 550° C. to 650° C. for a time period from about 1 hour to 24 hours, 4 hours to 12 hours, or 6 hours to 10 hours.

In some situations, powder catalysts prepared according to methods of the present disclosure may need to be formed prior to prepared in predetermined forms (or form factors) prior to use. In some examples, the forms can be selected from cylinder extrudates, rings, trilobe, and pellets. The sizes of the forms can be determined by reactor size. For example, for a 1"-2" internal diameter (ID) reactor, 1.7 mm to 3.0 mm extrudates or equivalent size for other forms can be used. Larger forms can be used for different commercial scales (such as 5 mm forms). The ETL reactor inner diameter (ID) can be any diameter, including ranging from 2 inches to 10 feet, from 1 foot to 6 feet, and from 3 feet to 4 feet. In commercial reactors, the diameters of the catalyst (e.g., extrudate) can be greater than about 3 mm, greater than about 4 mm, greater than about 5 mm, greater than about 7 mm, greater than about 10 mm, greater than about 15 mm, or greater than about 20 mm. Binding materials (binder) can be used for forming the catalysts and improving catalyst particle strength. Various solid materials that are inert towards olefins (e.g., ethylene), such as Boehmite, alumina, silicate, Bentonite, or kaolin, can be used as binders.

A wide range of catalyst:binder ratio can be used, such as, from about 95:5 to 30:70, or 90:10 to 50:50. In some cases, a ratio of 80:20 is used for bench scale and pilot reactor catalyst synthesis. For formed catalysts, the crush strengths can be in the range of about 1 N/mm to 60 N/mm, 5 N/mm to 30 N/mm, or 7 N/mm to 15 N/mm.

Catalysts prepared according to methods of the present disclosure can be tested for the production of various hydrocarbon products, such as gasoline and/or aromatics production. In some cases, such catalysts are tested for the production of both gasoline and aromatics.

In an example, a short-term test condition for gasoline production is 300° C., atmospheric pressure, WHSV=0.65 $hr^{-1}$, $N_2$ 50% and $C_2H_4$ 50%, two hour runs. In another example, a short-term test condition for aromatics production is 450° C., atmospheric pressure, WHSV=1.31 $hr^{-1}$, $N_2$ 50% and $C_2H_4$ 50%, two hour runs. In addition to conducting the two hour short-term test to obtain the initial catalytic activity data, for some selected catalysts, the long-term test (lifetime test) are also performed to obtain data of catalyst lifetime, catalyst capacity as well as average product composition over the lifetime runs.

In an example, the results on an initial catalytic activity test at gasoline production conditions is $C_2H_4$ conversion greater than about 99%, $C_{5+}$ C mole selectivity greater than about 65% (e.g., 65%-70%), and $C_{5+}$ C mole yield greater than about 65% (e.g., 65%-70%). Catalyst lifetime performance in one cycle run at gasoline conditions can be at least about 189 hours, cut at conversion down to 80%; catalyst capacity is about 182 g-$C_2H_4$ converted per g-catalyst with C mole yield of $C_{5+}+C_{3=}$ $C_{4-}$ greater than about 70%. With recycling, $C_{3=}$ and $C_{4=}$ can be accounted as liquid products.

In another example, the results on an initial catalytic activity at aromatics production conditions is $C_2H_4$ conversion greater than about 99%, $C_5^+$ C mole selectivity greater than about 75% (e.g., 75-80%), $C_{5+}$ C mole yield greater than about 75% (e.g., 75-80%) and aromatics in $C_{5+}$ greater than about 90%. Catalyst lifetime performance in one cycle run at aromatics production conditions can be at least about 228 hours, cut at conversion down to 82%, catalyst capacity 143 g-$C_2H_4$ converted/g-catalyst with average $C_{5+}$ yield around 72% and aromatics yield around 62%.

An ETL catalysts can have a porosity that is selected to optimize catalyst performance, including selectivity, lifetime, and product output. The porosity of an ETL catalyst can be between about 4 Angstroms to about 1 micrometer, from 0.01 nm to 500 nm, from 0.1 nm to 100 nm, or from 1 nm to 10 nm as measured by pore symmetry (e.g., nitrogen porosimetry). An ETL catalyst can have a base material with a set of pores that have an average pore size (e.g., diameter) from about 4 Angstroms to 100 nm, or 4 Angstroms to 10 nm, or 4 Angstroms to 10 Angstroms.

The catalytic materials may also be employed in any number of forms. In this regard, the physical form of the catalytic materials may contribute to their performance in various catalytic reactions. In particular, the performance of a number of operating parameters for a catalytic reactor that impact its performance can be significantly impacted by the form in which the catalyst is disposed within the reactor. The catalyst may be provided in the form of discrete particles, e.g., pellets, extrudates or other formed aggregate particles, or it may be provided in one or more monolithic forms, e.g., blocks, honeycombs, foils, lattices, etc. These operating parameters include, for example, thermal transfer, flow rate and pressure drop through a reactor bed, catalyst accessibility, catalyst lifetime, aggregate strength, performance, and manageability.

In some cases, it is also desirable that the catalyst forms used will have crush strengths that meet the operating parameters of the reactor systems. In particular, a catalyst particle crush strength should generally support both the pressure applied to that particle from the operating conditions, e.g., gas inlet pressure, as well as the weight of the catalyst bed. In general, it is desirable that a catalyst particle have a crush strength that is greater than about 1 $N/mm^2$, and preferably greater than about 10 $N/mm^2$, for example greater than 1 $N/mm^2$, and preferably greater than 10 $N/mm^2$. As will be appreciated, crush strength may be increased through the use of catalyst forms that are more compact, e.g., having lower surface to volume ratios. However, adopting such forms may adversely impact performance. Accordingly, forms are chosen that provide the above described crush strengths within the desired activity ranges, pressure drops, etc. Crush strength is also impacted though use of binder and preparation methods (e.g., extrusion or pelleting).

For example, in some embodiments the catalytic materials are in the form of an extrudate or pellet. Extrudates may be prepared by passing a semi-solid composition comprising the catalytic materials through an appropriate orifice or using molding or other appropriate techniques. Pellets may be prepared by pressing a solid composition comprising the catalytic materials under pressure in the die of a tablet press. Other catalytic forms include catalysts supported or impregnated on a support material or structure. In general, any support material or structure may be used to support the active catalyst. The support material or structure may be inert or have catalytic activity in the reaction of interest. For example, catalysts may be supported or impregnated on a monolith support. In some particular embodiments, the active catalyst is actually supported on the walls of the reactor itself, which may serve to minimize oxygen concentration at the inner wall or to promote heat exchange by generating heat of reaction at the reactor wall exclusively (e.g., an annular reactor in this case and higher space velocities).

The stability of the catalytic materials is defined as the length of time a catalytic material will maintain its catalytic performance without a significant decrease in performance (e.g., a decrease >20%, >15%, >10%, >5%, or greater than 1% in hydrocarbon or soot combustion activity). In some embodiments, the catalytic materials have stability under conditions required for the hydrocarbon combustion reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

Catalyst Poisoning

Catalysts of the present disclosure can be poisoned during the course of catalytically generating a given product. ETL catalysts, for instance, can be poisoned upon generating higher molecular weight hydrocarbons from olefins (e.g., ethylene). The present disclosure provides various approaches for avoiding such poisons.

Alkynes can be oligomerized over ETL catalysts, such as zeolites or acid catalysts. During alkyne oligomerization, the alkynes can be rapidly transformed into polyaromatic molecules, precursors to coke, which can deactivate the catalyst. The selectivity for acetylene to make coke can deactivate the ETL catalyst at a faster rate than an alkene and the catalyst may need to be taken off line to be regenerated. Any molecule containing an alkyne functional group can deactivate the ETL catalyst at a faster rate than an alkene group. One example is acetylene, an alkyne produced in small quantities within the OCM process.

An approach for eliminating alkynes from feedstock to an ETL catalyst is to convert the alkynes to other material that may not poison the ETL catalyst. For example, alkynes can be selectively hydrogenated to make olefins using a variety of transition metal catalysts without hydrogenating the olefins into alkanes. Examples of these catalysts are Pd, Fe, Co, Ni, Zn, and Cu containing catalysts. Such catalysts can be incorporated in or more reactors upstream of ETL catalysts.

Dienes can be oligomerized over ETL catalysts, such as zeolites or acid catalysts. However during diene oligomerization, dienes can be rapidly transformed into polydienes molecules, precursors to coke, which can deactivate the ETL catalyst. The selectivity for dienes to make coke can rapidly deactivate the ETL catalyst and the catalyst may need to be taken off line to be regenerated. Any molecule containing a diene functional group can rapidly deactivate the ETL catalyst. An example is butadiene, a diene produced in small quantities within the OCM process.

An approach for eliminating dienes from feedstock to an ETL catalyst is to convert the dienes to other material that may not poison the ETL catalyst. For example, dienes can be selectively hydrogenated to make olefins using a variety of transition metal catalysts without hydrogenating the olefins into alkanes. Examples of these catalysts are Pd, Fe, Co, Ni, Zn, and Cu containing catalysts.

Bases can react to neutralize the acid functionality that catalyzes ETL reactions. If enough base reacts with the ETL catalyst, the catalyst may no longer be active toward oligomerization and may need to be regenerated. Bases include nitrogen containing compounds, particularly ammonia, amines, pyridines, pyroles, and other organic nitrogen containing compounds. Metal hydroxide compounds such as lithium, sodium, potassium, cesium hydroxides and group IIA metal hydroxides may deactivate the catalyst as well as carbonates of group IA and IIA metals.

Bases can be removed from feedstock to an ETL reactor by, for example, contacting the feedstock stream with water. This can remove or decrease the concentration of bases, such as amines, carbonates, and hydroxides.

Sulfur-containing compounds can deactivate ETL catalysts, particularly if the catalysts are doped with transition metal compounds. Sulfur can irreversible bind to the catalyst or metal dopant to deactivate the catalyst toward oligomerization. Organic sulfur compounds such as thiols, disulfides, thiolethers, thiophenes and others mercaptan compounds can be detrimental to the ETL catalyst.

Sulfur-containing compounds can be removed from feedstock to an ETL reactor by gas scrubbing, such as, for example, amine gas scrubbing. Amines can react with sulfur compounds (e.g., $H_2S$) to remove such compounds from gas streams. Other ways of removing sulfur compounds are by molecular sieves or hydrotreating. Examples of approaches for removing sulfur-containing compounds from a gas stream are provided in Nielsen, Richard B., et al. "Treat LPGs with amines," Hydrocarbon Process 79 (1997): 49-59, which is entirely incorporated herein by reference.

The impact that certain non-ethylene gases can have on ETL catalysts is summarized in Table 1.

TABLE 1

Impact of non-ethylene gases on ETL catalyst

| Feedstock | General Catalyst Impact |
|---|---|
| $N_2$ | Inert |
| Methane | Inert |
| $CO_2$ | Inert |
| $H_2$ | Coke suppressant |
| $H_2O$ | Coke suppressant but will deactivate catalyst in large quantities |
| ethane | Inert |
| propylene | Oligomerizes to gasoline |
| butylene | Oligomerizes to gasoline |
| acetylene | Coke accelerator |
| Dienes | Coke accelerator |
| CO | Inert |

Catalyst Regeneration

During the life cycle of a catalyst (e.g., ETL catalyst), carbon-containing material (e.g., petroleum coke) can deposit and accumulate on the catalyst. Over time, such carbon-containing material can decrease the activity of the catalyst, and can even render the catalyst incapable of converting a feedstock to a product. The catalyst may need to be changed or regenerated. There are various approaches for regenerating an ETL catalyst, such as oxidative regeneration and non-oxidative regeneration.

In oxidative regeneration, an oxidizing agent (e.g., $O_2$) can be directed over the ETL catalyst at elevated temperatures to remove or decrease the concentration of the carbon-containing material deposited on or over the catalyst. This can occur by combusting the carbon-containing material. In some cases, prior to subjecting the catalyst to the oxidizing agent, the catalyst can be purged with and inert gas (e.g., He, Ar or $N_2$) to remove any volatile or residual hydrocarbon product on the catalyst surface. The catalyst can be subsequently exposed to the oxidizing agent. In some cases, the oxidizing agent is $O_2$ that can be provided by air.

In an example oxidative regeneration process, the process conditions and amount of air (or oxygen) can be predetermined to limit or control the amount of heat and water generated during the combustion process of removing the coke. The amount of $O_2$ can be limited to no more than 50%, 40%, 30%, 20%, 10%, or 5% concentration. Air can be diluted with $N_2$ or another gas that is inert toward combustion to dilute the concentration to less than or equal to about 50%, 40%, 30%, 20%, 10% or 5%. Process conditions can be selected to keep the increase in temperature of the ETL catalyst less than or equal to about 700° C., 650° C., 600° C., 550° C., or 500° C. during the regeneration. This can help prevent catalyst damage during the regeneration process. Oxidative regeneration reactor inlet temperatures can range from about 100° C. to 800° C., 150° C. to 700° C., or 200° C. to 600° C. Inlet gas temperatures can be ramped from low to high temperatures to safely control the regeneration process. During oxidative regeneration, process gas pressures can range from about 1 bar (gauge, or "barg") to 100 barg, 1 barg to 80 barg, or 1 barg to 50 barg.

In non-oxidative regeneration, hydrogen ($H_2$) and/or hydrocarbons can be used to regenerate the catalyst bed to improve catalyst activity of the ETL catalyst. Hydrogen or hydrocarbon gases can be directed over the catalyst bed at a temperature from about 100° C. to 800° C., 150° C. to 600° C., or 200° C. to 500° C. This can aid in removing or decreasing the concentration of carbon-containing material from the catalyst.

There are other approaches for reducing the concentration of catalyst poisons. Acetylene can be a poison at low levels. The acetylene and, in some cases, methyl acetylene, butadiene, propadiene and benzene, may need to be removed to some permissible levels. An approach for decreasing the concentration of acetylene is to direct the acetylene to a hydrogenation reactor that hydrogenates the acetylene and butadiene to a mixture of ethylene and ethane as well as butane and/or butene.

The acetylene can be hydrogenated, for example, prior to being contacted with the ETL catalyst. The acetylene hydrogenation reaction can be practiced over a palladium-based catalyst, such as those used to convert acetylene to ethylene in conventional steam cracking (e.g., the PRICAT™ series including models PD 301/1, PD 308/4, PD 308/6, PD 508/1, PD 408/5, PD 408/7 and PD 608/1, which are commercially available as tablets or spheres supported on alumina). A palladium-based catalyst can include one or more metals, including palladium. In some cases, the acetylene hydrogenation catalyst is a doped or modified version of a commercially available catalyst.

However, in some cases, applying an acetylene hydrogenation catalyst to the OCM process that has been developed or optimized for another process (e.g., steam cracking separations and purification processes) can result in operational issues and/or non-optimized performance. For example, in steam cracking, the acetylene conversion reactor can either be located on the front end (prior to cryogenic separations) or back end (after cryogenic separations) of the process. In steam cracking, these differences in running front end and back end typically have to do with the ratio of hydrogen to acetylene present, the ethylene to acetylene ratio, and the non-ethylene olefin (e.g., butadiene) to acetylene ratio. All of these factors can impact the catalyst selectivity for forming ethylene from acetylene, the lifetime and regeneration of the catalyst, green oil formation, specific process conditions for the reactor, and additional hydrogen required for the reaction. These factors are also different between steam cracking versus OCM and/or ETL processes, therefore, provided herein is an acetylene hydrogenation catalyst that is designed to be used in an OCM process.

In OCM and/or ETL implementations, the chemical components going into the acetylene reactor can be different than for steam cracking. For example, OCM effluent can include carbon monoxide and hydrogen. Carbon monoxide can be undesirable because it can compete with the acetylene for the active sites on the hydrogenation catalyst and lead to lower activity of the catalyst (i.e., by occupying those active sites). Hydrogen can be desirable because it is needed for the hydrogenation reaction, however that hydrogen is present in the OCM effluent in a certain ratio and adjusting that ratio can be difficult. Therefore, the catalyst described herein provides the desired outlet concentrations of acetylene, desired selectivity of acetylene conversion to ethylene, desired conversion of acetylene, desired lifetime and desired activity in OCM effluent gas. As used herein, "OCM effluent gas" generally refers to the effluent taken directly from an OCM reactor, or having first undergone any number of further unit operations such as changing the temperature, the pressure, or performing separations on the OCM reactor effluent. The OCM effluent gas can have CO, $H_2$ and butadiene.

In some embodiments, the catalyst decreases the acetylene concentration below about 100 parts per million (ppm), below about 80 ppm, below about 60 ppm, below about 40 ppm, below about 20 ppm, below about 10 ppm, below about 5 ppm, below about 3 ppm, below about 2 ppm, below about 1 ppm, below about 0.5 ppm, below about 0.3 ppm, below about 0.1 ppm, or below about 0.05 ppm.

The concentration of acetylene can be reached in the presence of carbon monoxide (CO). In some embodiments, the feed stream entering the acetylene hydrogenation reactor contains at least about 10%, at least about 9%, at least about 8%, at least about 7%, at least about 6%, at least about 5%, at least about 4%, at least about 3%, at least about 2%, or at least about 1% carbon monoxide.

When used in an OCM and/or ETL process, the acetylene hydrogenation catalyst can have a lifetime of at least about 6 months, at least about 1 year, at least about 2 years, at least about 3 years, at least about 4 years, at least about 5 years, at least about 6 years, at least about 7 years, at least about 8 years, at least about 9 years, or at least about 10 years.

Another option can be to employ the use of a guard bed in front of the ETL reactor (or reactor train comprising multiple ETL reactors). The guard bed can enable the ETL reactor to preferentially coke out the acetylene. Can guard bed can coke relatively quickly and may need to be placed in a lead-lag configuration so that one bed can be regenerated while the other bed is being operated. The guard bed can contain a catalyst, and in some cases spent ETL catalyst, to perform preferential coking. The inlet temperature of guard bed can be lower than the inlet temperature for ETL, and the space velocity can be higher.

In an example, two guard beds are placed upstream of four or five parallel ETL reactor beds. The two guard beds are designed in a lead-lag configuration. The inlet temperature of the guard bed is about 40° C., about 60° C., about 80° C., or about 100° C. lower than the inlet to the ETL reactors and the space velocity is at least about 5×, at least about 10×, at least about 20× or at least about 50× greater than the space velocity of the ETL reactors. The ETL reactors are on a schedule where each parallel reactor is regenerated and decoked every three weeks. But the guard bed is regenerated and decoked every 36 hours.

Catalyst Activators

The lifetime of a catalyst can be increased using activators. Activators can be used with catalysts of the present disclosure, such as ETL catalysts. With the aid of activators of the present disclosure, the lifetime of a catalyst can be increased by at least about 10 hours, 20 hours, 30 hours, 40 hours, 50 hours, 100 hours, 110 hours, 120 hours, 130 hours, 140 hours, 150 hours, 160 hours, 170 hours, 180 hours, 190 hours, 200 hours, 210 hours, 220 hours, 230 hours, 240 hours, 250 hours, 300 hours, 350 hours, or 400 hours. Activators of the present disclosure can be used to increase the lifetime of a catalyst by a factor of at least about 1.1, 1.2, 1.3, 1.4, 1.5, 1.6, 1.7, 1.8, 1.9, 2, 3, 4, 5, 6, 7, 8, 9, or 10 in relation to situations in which activators are not used. Activators can be molecules included in the process flow that contacts the catalyst and/or molecules or elements contained in the catalyst itself (e.g., dopants). For example, Ga-doped ZSM-5 has an increased lifetime (cycle lifetime and/or replacement lifetime) relative to non-doped ZSM-5 (e.g., because the doped catalyst has a lower selectivity for coke formation).

For example, the addition of water can enhance ETL catalyst lifetime by suppressing coke formation. Coke formation can be suppressed by water by reacting with coke to form carbon monoxide and hydrogen. One of the attractive features from the OCM-ETL process is that water addition can be optimized to have the maximum benefit for reducing coke formation in the reactor. Water can be supplied in a concentration of at least about 1%, 2%, 3%, 4%, 5%, 10%, 15%, 20%, 25%, or 30%. In some situations, the concentration of water in feedstock into an ETL reactor is from 0% to 30%, or 1% to 25%.

The addition of hydrogen in a feedstock stream into an ETL reactor can enhance ETL catalyst lifetime. Hydrogen gas ($H_2$) can be directed into an ETL reactor and over an ETL catalyst, which can reduce the concentration of carbon-containing material (e.g., coke) that may be present on the catalyst and prohibit the deposition of carbon-containing material by hydrocracking reactions, for example, by breaking up larger molecules that may be eventually turned into coke and decrease catalyst activity.

ETL Processes and Operating Conditions

The present disclosure provides methods for operating ETL reactors to effect a given or predetermined product distribution or selectivity. The process conditions can be applied across a single or plurality of ETL reactors in series and/or parallel.

Hydrocarbon streams into or out of an ETL reactor can include various other non-hydrocarbon material. In some cases, hydrocarbon streams can include one or more elements leached from an OCM catalyst (e.g., La, Nd, Sr, W) or ETL catalyst (e.g., Ga dopant)

Reactor conditions can be selected to provide a given selectivity and product distribution. In some cases, for catalyst selectivity towards aromatics, an ETL reactor can be operated at a temperature greater than or equal to about 300° C., 350° C., 400° C., 410° C., 420° C., 430° C., 440° C., 450° C., or 500° C., and a pressure greater than or equal to about 250 pounds per square inch (PSI) (absolute), 200 PSI, 250 PSI, 300 PSI, 350 PSI or 400 PSI. For catalyst selectivity towards jet or diesel fuel, an ETL reactor can be operated at a temperature greater than or equal to about 100° C., 150° C., 200° C., 210° C., 220° C., 230° C., 240° C., 250° C., or 300° C., and a pressure greater than or equal to about 350 PSI, 400 PSI, 450 PSI, or 500 PSI. For catalyst selectivity towards gasoline, an ETL reactor can be operated at a temperature greater than or equal to about 200° C., 250° C., 300° C., 310° C., 320° C., 330° C., 340° C., 350° C., or 400° C., and a pressure greater than or equal to about 250 PSI, 300 PSI, 350 PSI, or 400 PSI.

In some cases, the operating conditions of an ETL process are substantially determined by one or more of the following parameters: process temperature range, weight-hourly space velocity (mass flow rate of reactant per mass of solid catalyst), partial pressure of a reactant at the reactor inlet, concentration of a reactant at the reactor inlet, and recycle ratio and recycle split. The reactant can be a (light) olefin— e.g., an olefin that has a carbon number in the range C2-C7, C2-C6, or C2-C5.

Temperatures used in a gasoline process can be from about 150 to 600° C., 220° C. to 520° C., or 270° C. to 450° C. Lower temperature can result in insufficient conversion while higher temperatures can result in excessive coking and cracking of product. In an example, the WHSV can be between about 0.5 hr$^{-1}$ and 3 hr$^{-1}$, partial pressures can be between about 0.5 bar (absolute) and 3 bar, and concentrations at the reactor inlet can be between about 2% and 30%. Higher concentrations can yield difficult-to-manage temperature excursions, while lower concentrations can make it difficult to achieve sufficiently high partial pressures and separation of the products. A process can achieve longer catalyst lifetime and higher average yields when a portion of the effluent is recycled. The recycle can be determined by a recycle ratio (e.g., volume of recycle gas/volume of make-up feed) and the post-reactor vapor-liquid split which determines the composition of the recycle stream. There may be several degrees of freedom to the recycle split, but in some cases the composition of the recycle stream may be important, which is achieved by post-reactor separation (i.e., typical carbon number/boiling point range that is recycled vs. the carbon number/boiling point ranges that are removed by product and/or secondary process streams.

To achieve longer average chain lengths and to avoid cracking of elongated chains such as those found in jet fuel and distillates, ETL can be performed at reactor operating temperatures from about 150° C. to 500° C., 180° C. to 400° C., or 200° C. to 350° C. The slower kinetics may suggest a lower minimum WHSV of about 0.1 hr$^{-1}$. Longer chain lengths may be favored by high partial pressures, so the upper end for jet/distillates may be higher than for gasoline, in some cases as high as about 30 bar (absolute), 20 bar, 15 bar, or 10 bar.

More consistent production of aromatics can be achieved at high temperature ranges, such as a temperature up to about 200° C., 250° C., 300° C., 350° C., 400° C., 450° C., or 500° C. In an adiabatic or even in a pseudo-isothermal reactor, the ethylene/olefin feed can be diluted by an inert gas (e.g., $N_2$, Ar, methane, ethane, propane, butane or He). The inert gas can serve to moderate the temperature increase in the reactor bed, and maintain and stabilize contact time. The olefin concentration at the reactor inlet can be less than about 50%, 40%, 30%, 20%, or 10%. In some cases, the higher the molar heat capacity of the diluent, the higher the inlet concentration of olefins can be to achieve the same temperature rise.

The following is a list of suitable compounds that may be found in significant quantities in the process. Such compounds are listed in the order of increasing heat capacity: nitrogen, carbon dioxide, methane, ethane, propane, n-butane, iso-butane.

In some cases, a continuous process for making mixtures of hydrocarbons from (light) olefins by oligomerization comprises feeding olefinic compounds to a reaction zone of an ETL reactor. The reactor zone can contain a heterogeneous catalyst. One or more inert gases can be co-fed to the reactor inlet, making up from about 50% (volume %) to 99%, 60% to 98%, or 70% to 98% of the feedstock. The mixture can be comprised at least one of the following compounds: nitrogen, carbon dioxide, methane, ethane, propane, n-butane, iso-butane. The process (e.g., ETL reactor) temperature can be between about 150° C. and 600° C., 180° C. and 550° C., or 200° C. and 500° C. The partial pressure of olefins in the feed can be between about 0.1 bar (absolute) to 30 bar, 0.1 bar to 15 bar, or 0.2 bar to 10 bar. The total pressure can be between about 1 bar (absolute) to 100 bar, 5 bar to 50 bar, or 10 bar to 50 bar. The weight hourly space velocity can be between about 0.05 hr$^{-1}$ to 20 hr$^{-1}$, 0.1 hr$^{-1}$ to 10 hr$^{-1}$, or 0.1 hr$^{-1}$ to 5 hr$^{-1}$.

An effluent or product stream from an ETL reactor can be characterized by low water content. For example, an ETL product stream can comprise less than 60 wt %, 56 wt %, 55 wt %, 50 wt %, 45 wt %, 40 wt %, 39 wt %, 35 wt %, 30 wt %, 25 wt %, 20 wt %, 15 wt %, 10 wt %, 5 wt %, 3 wt %, or 1 wt % water.

In some cases, at least a portion of the reactor effluent is recycled to the reactor inlet. As an alternative, at most a portion of the reactor effluent is recycled to the reactor inlet. The volumetric recycle ratio (i.e., flow rate of the recycle gas stream divided by flow rate of the make-up gas stream (i.e., fresh feed)) can be between about 0.1 and 30, 0.3 and 20, or 0.5 and 10.

A continuous process for making mixtures of hydrocarbons for use as gasoline can comprise feeding olefinic compounds to a reaction zone of an ETL reactor. The ETL reactor can include a catalyst that is selected for gasoline production, as described elsewhere herein. The process temperature can be between about 200° C. and 600° C., 250° C. and 500° C., or 300° C. and 450° C. The partial pressure of olefins in the feed can be between about 0.1 bar (absolute) to 10 bar, 0.3 bar to 5 bar, or 0.5 bar to 3 bar. The total pressure can be between about 1 bar (absolute) to 100 bar, 5 bar to 50 bar, or 10 bar to 50 bar. The weight hourly space velocity can be between about 0.1 $hr^{-1}$ to 20 $hr^{-1}$, 0.3 $hr^{-1}$ to 10 $hr^{-1}$, or 0.5 $hr^{-1}$ to 3 $hr^{-1}$.

For products in the distillate range (e.g., $C_{10+}$ molecules, which can exclude gasoline in some cases), the catalyst composition can be selected as described elsewhere herein. The process temperature can be between about 100° C. and 600° C., 150° C. and 500° C., or 200° C. and 375° C. The partial pressure of olefins in the feed can be between about 0.5 bar (absolute) to 30 bar, 1 bar to 20 bar, or 1.5 bar to 10 bar. The total pressure can be between about 1 bar (absolute) to 100 bar, 5 bar to 50 bar, or 10 bar to 50 bar. The weight hourly space velocity can be between about 0.05 $hr^{-1}$ to 20 $hr^{-1}$, 0.1 $hr^{-1}$ to 10 $hr^{-1}$, or 0.1 $hr^{-1}$ to 1 $hr^{-1}$.

For products comprising mixtures of hydrocarbons substantially comprised of aromatics, the catalyst composition can be selected as described elsewhere herein. The process temperature can be between about 200° C. and 800° C., 300° C. and 600° C., or 400° C. and 500° C. The partial pressure of olefins in the feed can be between about 0.1 bar (absolute) to 10 bar, 0.3 bar to 5 bar, or 0.5 bar to 3 bar. The total pressure can be between about 1 bar (absolute) to 100 bar, 5 bar to 50 bar, or 10 bar to 50 bar. The weight hourly space velocity can be between about 0.05 $hr^{-1}$ to 20 $hr^{-1}$, 0.1 $hr^{-1}$ to 10 $hr^{-1}$, or 0.2 $hr^{-1}$ to 1 $hr^{-1}$.

The ETL process can generate a variety of long-chain hydrocarbons, including normal and isoparaffins, napthenes, aromatics and olefins, which may not be present in the feed to the ETL reactor. The catalyst can deactivate due to the deposition of carbonaceous deposits ("coke") on the surfaces of the catalyst. As the deactivation progresses, the conversion of the process changes until a point is reached when the catalyst can be regenerated.

Figure 5:
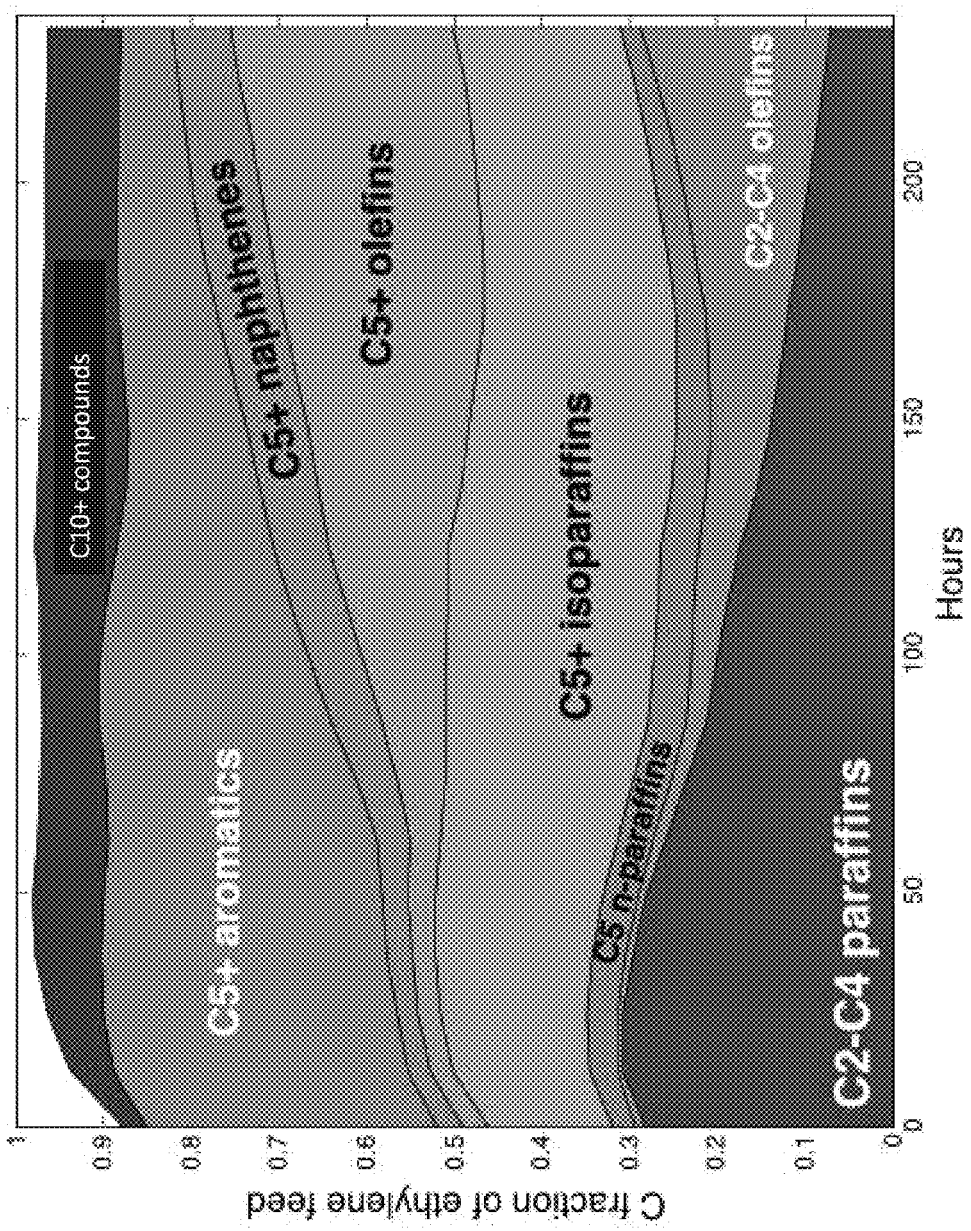
FIG. 5 is an example of the manner in which product distribution can change over time for an ETL catalyst.

In some cases, in the early stages of a reaction cycle, the product distribution can contain large fractions of aromatics and short-chained alkanes. Later stages can feature increased fractions of olefins. All stages can feature various amounts isoparaffins, n-paraffins, naphthenes, aromatics, and olefins, including olefins other than feed olefins. The change in selectivity with time can be exploited by separating products. For example, the aromatics-rich effluent characteristic of the early stages of a reaction cycle may be readily separated from the effluent of a catalyst bed in a later stage of its cycle. This can result in high selectivities of individual products. An example of how the product distribution can change over time is given in FIG. 5, which is for a Ga-ZSM-5 catalyst.

The ETL process can generate various byproducts, such as carbon-containing byproducts (e.g., coke) and hydrogen. The selectivity for coke can be on the order of at least about 1%, 2%, 3%, 4%, or 5% over the course of an ETL process. Hydrogen production can vary with time, and the amount of hydrogen generated can be correlated with aromatics production.

In some cases, the time-averaged product of the process can yield a liquid with a composition that meets the specification of reformulated gasoline blendstock for oxygen blending (RBOB). In some cases, RBOB has at least about an 93 octane rating using the (RON+MON)/2 method, has less than about 1.3 vol % benzene as measured by ASTM D3606, has less than about 50 vol % aromatics as measured by ASTM D5769, has less than about 25 vol % olefins as measured by ASTM D1319 and/or D6550, has less than 80 ppm (wt) sulfur as measured by ASTM D2622, or any combination thereof. Such liquid can be employed for use as fuel or other combustion settings. This liquid can be partially characterized by the content of aromatics. In some cases, this liquid has an aromatics content from 10% to 80%, 20% to 70%, or 30% to 60%, and an olefins content from 1% to 60%, 5% to 40%, or 10% to 30%. Gasoline can comprise about 60% to 95%, 70% to 90%, or 80-90% of such liquid, with the remainder in some cases being an alcohol, such as ethanol.

In some situations, an ETL process is used to generate a mixture of hydrocarbons from light olefin compounds (e.g., ethylene). The mixture can be liquid at room temperature and atmospheric pressure. The process can be used to form a mixture of hydrocarbons having a hydrocarbon content that can be tailored for various uses. For example, mixtures typically characterized as gasoline or distillate (e.g., kerosene, diesel) blend stock, or aromatic compounds, can contribute at least 30%, 40%, 50%, 60%, or 70% by weight to the final fuel product.

The product selectivity of the ETL process can change with time. With such changes in selectivity, the product can include varying distributions of hydrocarbons. Separations units can be used to generate a product distribution which can be suitable for given end uses, such as gasoline.

Products of ETL processes of the present disclosure can include other elements or compounds that may be leached from reactors or catalysts of the system (e.g., OCM and/or ETL reactors). Examples of OCM catalysts and the elements comprising the catalyst that can be leached into the product can be found in U.S. patent application Ser. No. 13/689,611 or U.S. Provisional Patent Application 61/988,063, each of which is incorporated by reference in its entirety. Such elements can include transition metals and lanthanides. Examples include, but are not limited to Mg, La, Nd, Sr, W, Ga, Al, Ni, Co, Ga, Zn, In, B, Ag, Pd, Pt, Be, Ca, and Sr. The concentration of such elements or compounds can be at least about 0.01 parts per billion (ppb), 0.05 ppb, 0.1 ppb, 0.2 ppb, 0.3 ppb, 0.4 ppb, 0.5 ppb, 0.6 ppb, 0.7 ppb, 0.8 ppb, 0.9 ppb, 1 ppb, 5 ppb, 10 ppb, 50 ppb, 100 ppb, 500 ppb, 1 part per million (ppm), 5 ppm, 10 ppm, or 50 ppm as measured by inductively coupled plasma mass spectrometry (ICPMS).

The composition of ETL products from a system can be consistent over several cycles of catalyst use and regeneration. A reactor system can be used and regenerated for at least about 10, 20, 30, 40, 50, 60, 70, 80, 90, or 100 cycles. After a number of regeneration cycles, the composition of the ETL product stream can differ from the composition of the first cycle ETL product stream by no more than about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20%.

ETL Process Design

Figure 6:
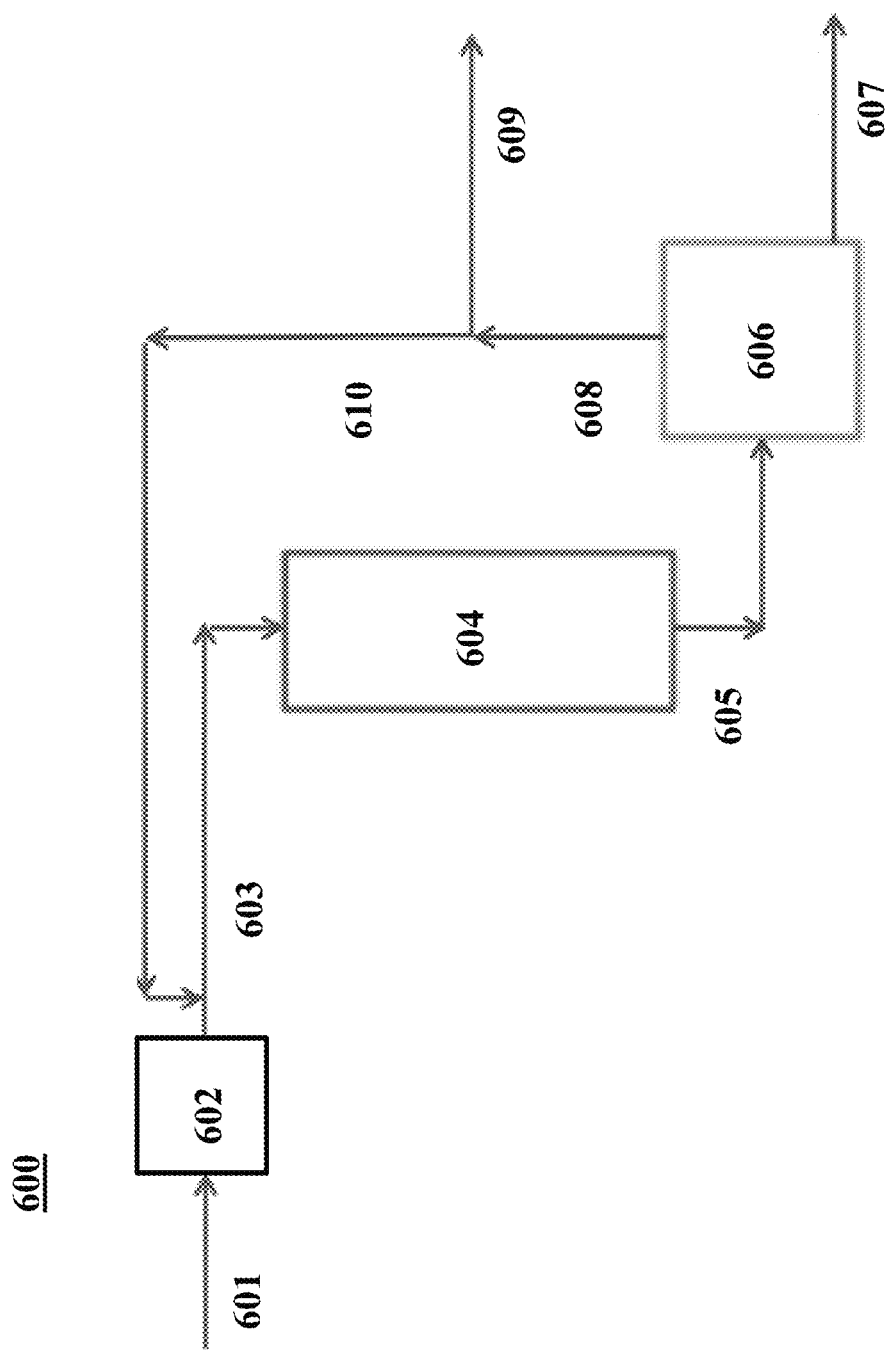
FIG. 6 schematically illustrates an ethylene-to-liquids (ETL) reactor system with process inlet and recycle stream combining to form a reactor inlet process stream.

The present disclosure provides various approaches for designing an ETL process. In the oligomerization of $C_2H_4$, a range of hydrocarbons can be formed, including $C_2H_6$ and $CH_4$, as well as $H_2$. The shorter chain hydrocarbons (e.g., C1-C4) and hydrogen in the product stream can be separated from the $C_{5+}$ liquid fraction. A fraction of the process stream containing these lighter molecular weight products can be combined, or recycled, with incoming $C_2H_4$ feed stream, as shown in FIG. 6. In this figure, product stream 605 can be separated, for instance by a condenser/phase separator 606.

The gas stream 608 from the condenser/phase separator can be partially recovered 609 and partially recycled 610 back into the reactor 604 for further contacting with the catalyst. The OCM reactor effluent 601, which can have been treated and/or compressed, is then routed to the treatment unit 602 which may comprise of a water removal unit, or any other purification unit. The treated ETL feed 603 reacts in the ETL reactor 604 to generate net liquid product 607 from the condenser and phase separator unit. The condenser and phase separator unit also sends a recycle 608 back to the ETL reactor inlet.

Recycling can have various benefits, such as: 1) further reaction of shorter chain hydrocarbon products to form higher molecular weight products, 2) increasing catalyst lifetime, and 3) diluting the $C_2H_4$ feed stream to control the reactor process conditions of reactant concentration and adiabatic temperature rise.

Figure 7A:
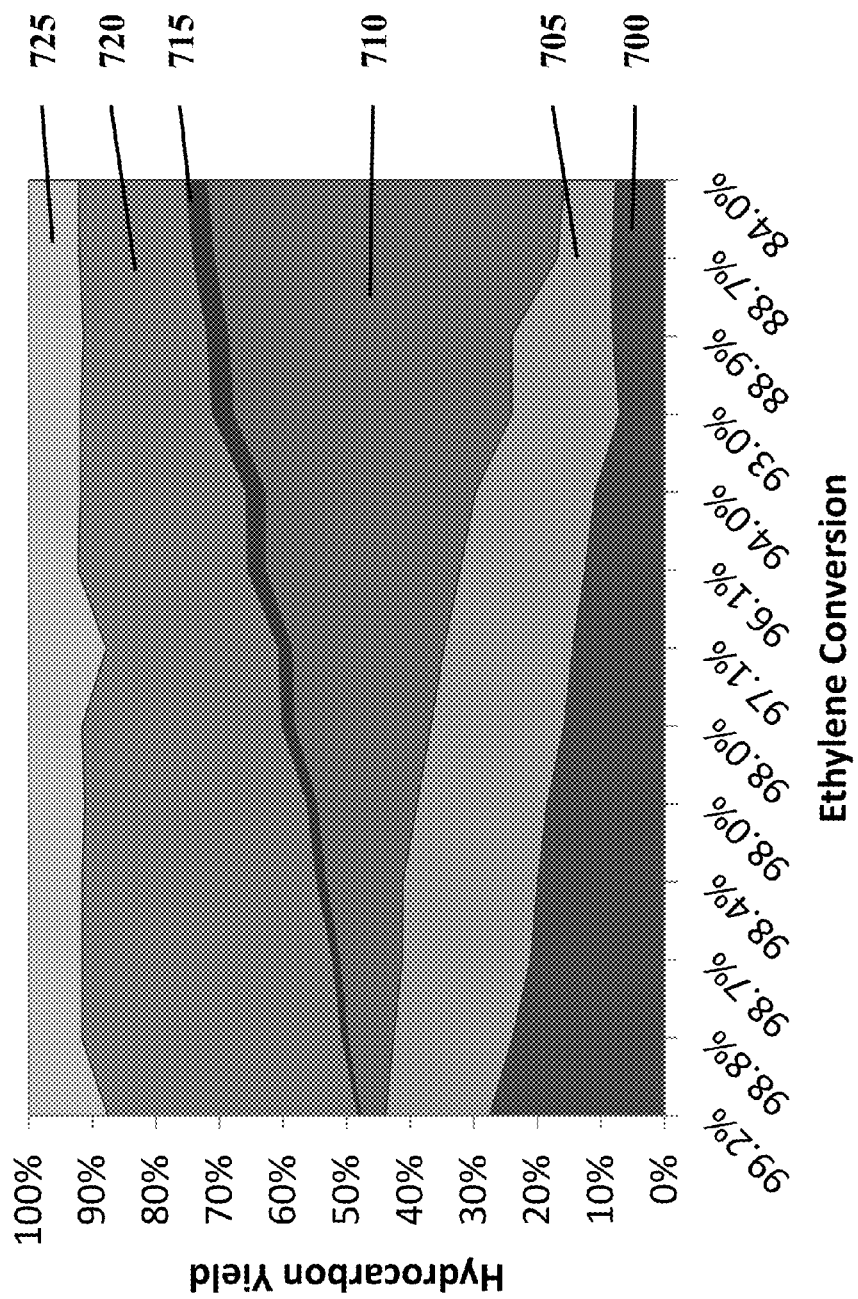
FIG. 7A shows liquid phase hydrocarbon yield as a function of $C_2H_4$ conversion by using a single pass reactor.
Figure 7B:
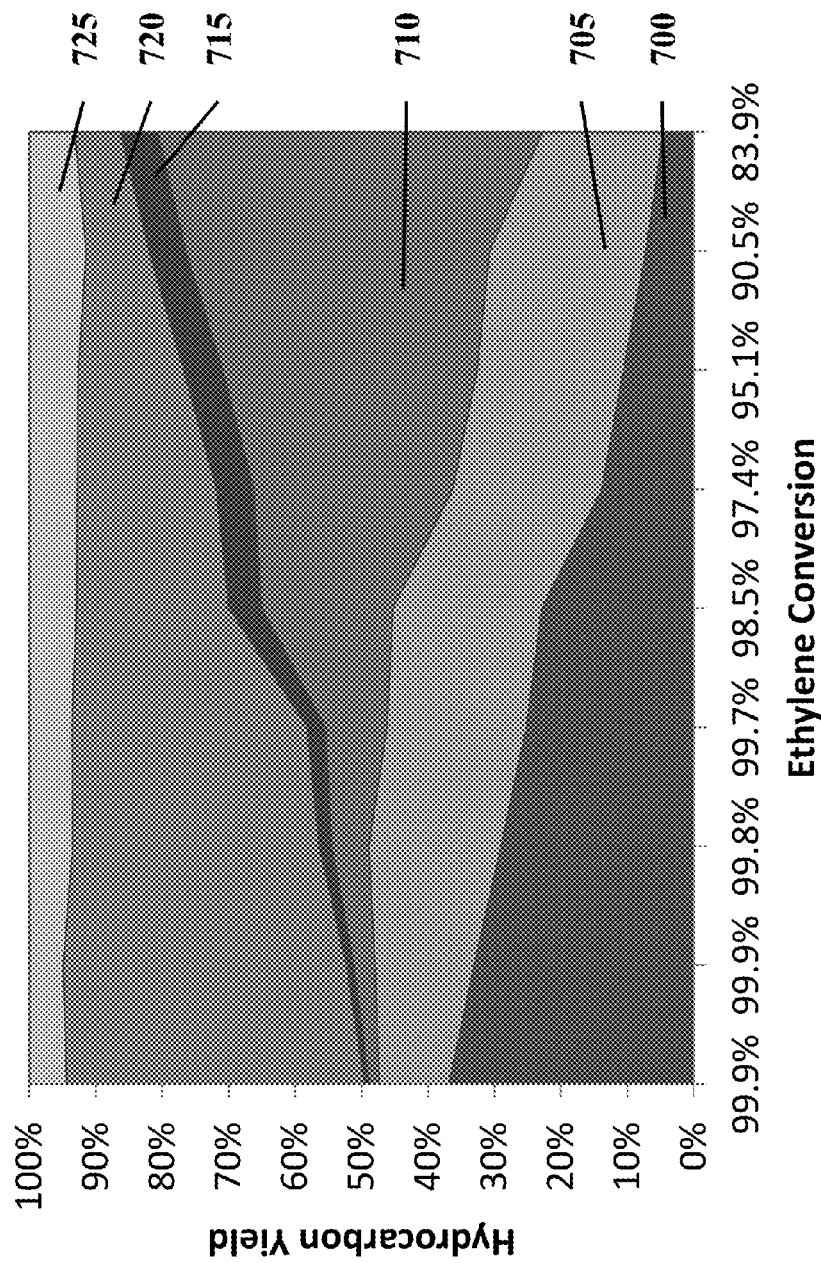
FIG. 7B shows liquid phase hydrocarbon yield as a function of $C_2H_4$ conversion by using a reactor with 5:1 recycle:fresh ratio.
Figure 8:
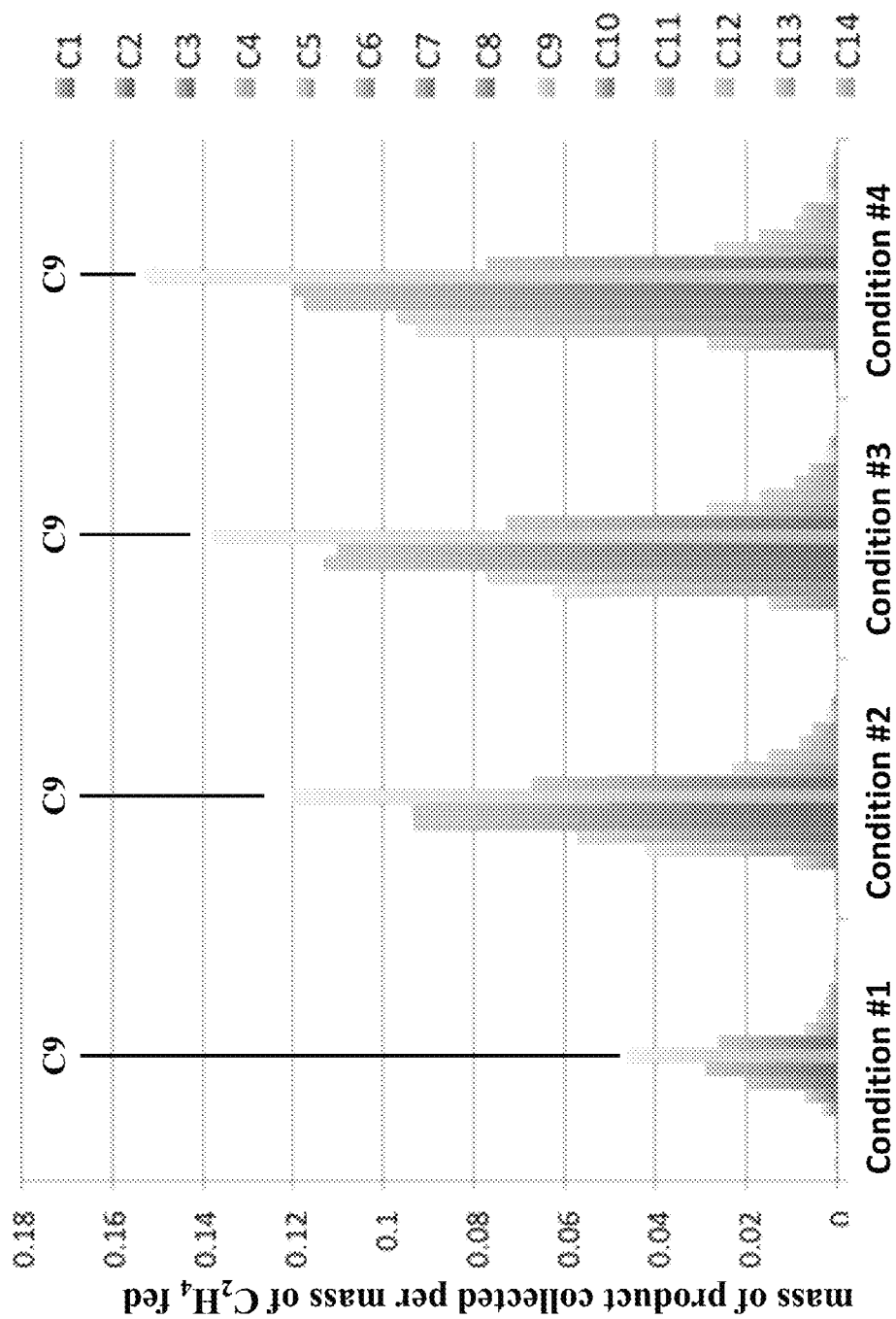
FIG. 8 is a plot showing increasing $C_{5+}$ yield (liquid condensed at about 0° C.) with increasing recycle reaction conditions.

At the same $C_2H_4$ WHSV, the conversion of a reactor inlet stream containing recycle can have a higher yield of liquids production ($C_{5+}$), particularly $C_{5+}$ condensable at a temperature of around 0° C., than that of a reactor inlet stream without recycle products (see FIGS. 7 and 8). The use of recycle can also increase catalyst lifetime, as measured by time-on-stream and grams $C_2H_4$ converted per grams of catalyst. Recycle ratios and g liquid condensed at about 0° C. are shown in Table 2.

FIG. 7A shows liquid phase mass balance for $C_2H_4$ conversion by using single pass reactor. FIG. 7B shows liquid phase mass balance for $C_2H_4$ conversion by using a reactor with 5:1 recycle. The reactors are operated at a pressure of about 30 bar, a weight hourly space velocity (WHSV) of about 0.7 $h^{-1}$, and an inlet temperature of about 350° C. The amounts of various hydrocarbons produced ranges from 0% to 100% for various ethylene conversions with paraffins 700, isoparaffins 705, olefins 710, napthenes 715, aromatics 720 and $C_{12+}$ compounds 725 being shown. FIG. 8 is a plot showing increasing $C_{5+}$ yield (liquid condensed at about 0° C.) with increasing recycle. The reaction conditions included a WHSV=0.27 $h^{-1}$; reactor inlet $C_2H_4$ mol %=2; $T_{peakbed}$=315° C.; total pressure 300 psi (gauge);

TABLE 2

Reactor conditions characterized by product stream data shown in FIG. 8, including recycle ratios, process inlet $C_2H_4$ mol %, reactor inlet $C_2H_4$ mol % and grams of liquid condensed per grams of $C_2H_4$ fed.

| Recycle ratio | Process inlet $C_2H_4$ mol % | Reactor inlet $C_2H_4$ mol % | g liquid condensed per g $C_2H_4$ fed |
|---|---|---|---|
| 9:1 | 20 | 2 | 0.76 |
| 4:1 | 10 | 2 | 0.66 |
| 2:1 | 6 | 2 | 0.54 |
| 0:1 (no recycle) | 2 | 2 | 0.15 |

In some cases, an inlet feed stream that is diluted with recycle product stream allows for a smaller adiabatic temperature rise in the reactor and reduced $C_2H_4$ concentration into the reactor. A lower adiabatic temperature rise, and therefore peak reactor temperature, can alter the effluent product stream composition. Higher peak reactor temperatures, for instance, can increase the yield and selectivity of aromatic products.

Different amounts of ethylene in an ETL product stream can be recycled. In some cases, at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99%, or 100% of ethylene in an ETL product stream is recycled. In some cases, at most about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99%, or 100% of ethylene in an ETL product stream is recycled.

An ETL process can be characterized by a single pass conversion or single pass conversion of $C_{2+}$ compounds to $C_{3+}$ compounds of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, or 99.99%.

ETL Process Feedstock

The feedstock to an ETL reactor can have an effect on the product distribution out of the ETL reactor. The product distribution can be related to the concentration of olefins into the ETL reactor, such as ethylene, propylene, butene(s) and pentene(s). The feedstock concentration can impact ETL catalyst efficiency. A feedstock having an olefin concentration that is greater than or equal to about 5%, 10%, 15%, 20%, 25%, 30%, or 40% can be efficient at generating higher molecular weight hydrocarbons. In some cases, the optimum olefin concentration can be less than about 80%, 85%, 75%, 70% or 60%. The ETL feedstock can be characterized based on the ethylene to ethane molar ratio of the feedstock, which can be at least about 2:1, 3:1, 4:1, 5:1, 6:1, 7:1, or 8:1.

The presence of other $C_{2+}$ compounds and non-$C_{2+}$ impurities (e.g., CO, $CO_2$, $H_2O$ and $H_2$) can have an impact on ETL selectivity and/or product distribution. For instance, the presence of acetylene and/or dienes in a feedstock to an ETL reactor can have a significant impact on ETL selectivity and/or product distribution, since acetylene may be a deactivator and coke accelerator.

Separations for ETL

Separations for ETL processes of the present disclosure can be carried out in three places within the ETL scheme: before the ETL reactor, within the ETL reactor and downstream of the ETL reactor. In each of these three places, different separations technologies can be employed.

To process the ETL reactor feed, traditional gas separations equipment can be used. These separations may include pressure swing adsorption, temperature swing adsorption and membrane-based separation. The reactor feed could also be augmented by utilizing cryogenic separations equipment found in a traditional midstream gas plant.

To make changes to the composition within the reactor, different types of catalyst can be co-mixed or layered within the catalyst bed or reactor vessel. Different types of zeolite catalysts (for example a ZSM-5 and a SAPO 34 in a 60%/40% mixture or in a 50%/50% mixture) could create different hydrocarbon profiles at the reactor vessel outlet. Also within this vessel, there could be a combination of multiple beds with appropriate quenches built in to affect the final product composition.

To separate the reactor outlet mixtures, a combination of flash separation, hydrogenation, isomerization and distillation can be used. Flash separation will remove most of the light fractions of the hydrocarbon liquid product. This can affect product qualities like Reid Vapor Pressure. Hydrogenation, isomerization and distillation can then be used, much like traditional refining processes, to create a fungible product.

ETL separation can be implemented upstream of an ETL reactor. Membranes used in conjunction with the ETL process can be used on the process feedstock to enrich components prior to directing the feedstock to the ETL reactor. Ethylene may be a component that can be enriched. Other components of the feedstock may also be enriched, such as $H_2$ and/or $CO_2$. In some cases, CO may be rejected.

For example, CO in the feedstock may be a catalyst poison. CO can be removed prior to directing the feedstock to the ETL reactor. Hydrogen may be an advantageous species to have in the feedstock because it can reduce coking rates, thus lengthening on-stream time between de-coke cycles.

In some cases, a membrane separation unit upstream of an ETL reactor may be employed. The membrane unit can remove at least about 20%, 30%, 40%, 50% or 60% of one component, or increase the amount of ethylene from at least about 1%, 2%, 3%, 4% or 5% to at least about 10%, 15%, 20%, 30%, or 40%.

As another example, ethylene can be enriched using a membrane that has a certain chemical affinity to ethylene. For oxygen separations membranes, cobalt can be used within the membranes to chemically pull oxygen through the membranes. Chemically-modified membranes can be used to effect such separation.

Figure 9:
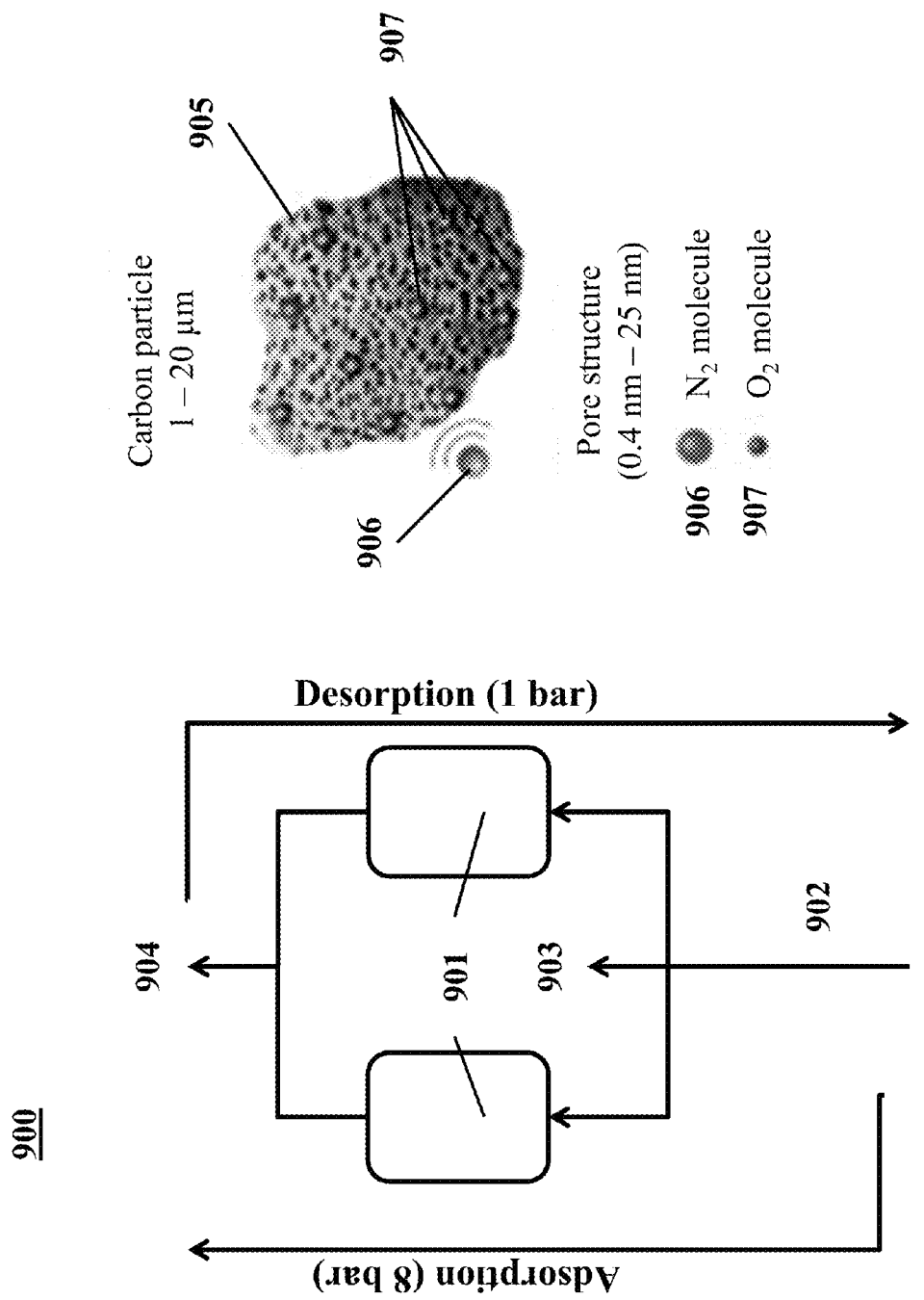
FIG. 9 shows an example of a pressure swing adsorption (PSA) unit.

Another technique that can be employed for upstream separation is pressure swing adsorption (PSA). Pressure swing adsorption can be used to remove substantially all of a certain poison, or enrich ethylene to near purity. In some cases, PSA may be used in place of, or in addition, membrane. The PSA unit can include at least 2, 3, 4, 5, 6, 7, 8, 9, or 10 vessels that contain an adsorbent. This adsorbent may be a combination of zeolites, molecular sieves or activated carbon, for example. Each vessel can contain one or more adsorbents co-mixed or layered within the vessel. An example of a PSA unit is shown in FIG. 9. The system shown in FIG. 9 is an activated carbon based system 900 to separate oxygen from nitrogen. The system comprises carbon molecular sieves 901 which receive gas streams 902 to be treated. Part of the gas streams can be released as off gas 903. Treated gas 904 can comprise produced nitrogen. The activated carbon system can comprise carbon particles 905, which can interact with $N_2$ molecules 906 and $O_2$ molecules 907. The carbon particles can have sizes for example from about 1 to about 20 micrometers, with a pore size from about 0.4 nanometers to about 25 nanometers.

The PSA units can operate at ETL reactor pressures (e.g., 5-50 bar) and blow down to atmospheric pressure. Activated carbon, 3A, 4A, 5A molecular sieves and zeolites can be used in these beds. The vessels can be operated such that the wanted gases (e.g., ethylene) pass through the beds at high pressure, and unwanted gases (e.g., CO, $CO_2$ or methane) are blown down out of the bed at low pressure.

As an example, the specific choice of sorbent can determine the species that passes through at high pressure or is exhausted at low pressure. In some cases, a PSA can use layered sorbents, such as to effect methane and nitrogen separation. Such layering within the bed allows methane to be the blow down gas, rather than nitrogen.

PSA technology can also be used in other situations. Multiple beds can be used in series to further enrich the wanted process gases. PSA units with at least 2, 3, 4, 5, 6, 7, 8, 9, 10, 20, or 30 vessels may be employed. The PSA can be operated at high frequencies, which can further promote better separation.

Another separation technique that can be employed for use with ETL is temperature swing adsorption (TSA). In TSA, temperature changes are used to effect separation. TSA can be used to separation hydrocarbons mixtures after the ETL reactor. When gas mixtures are close to changing phases, TSA can be helpful in removing the heavy fraction from the light fraction.

The present disclosure also provides in-reactor separations (product augmentation) approaches. Some of the separations goals can be achieved within the catalyst bed, or within the reactor vessel itself, using reactive separations, for example. In reactive separation, a first molecule can be reacted to form a larger or smaller molecule that may be separated from a given stream.

In some cases, gas phase ethylene can be condensed to a liquid via reaction. This augmentation can take two forms within the catalyst bed: it can augment the product to bring it to within a given specification, or it can augment the product to remove downstream equipment. As an example of bringing products into specification, a hydrogenation catalyst can be co-mixed or layered within the bed, or as a second bed within a reactor vessel. This catalyst can utilize the available hydrogen to decrease the olefin content of the final product. Since fungible gasoline (and many other products) can have an olefin specification to prevent gumming, this in situ separation can remove a large amount of olefin content from the resulting liquid, bringing it to within a given specification.

A co-mixed bed with multiple types of different zeolite can affect the overall product composition. For example, a low-aromatic producing catalyst can be added in an 80%/20% mixture to a typical ETL catalyst. The resulting product stream can be lower in aromatics, and can bring an off-spec product to within a given specification.

As another approach, a downstream (in vessel) isomerization bed can be used to remove unwanted isomers, like durene. Hydrocarbon compounds of any appropriate carbon number, such as hydrocarbon compounds with four or more carbon atoms ($C_{4+}$ compounds), can be isomerized. If a downstream unit is necessary to isomerize components like durene, or remove components, such as high boiling point components, an in-bed reactor approach can be employed.

In some situations, a mixture of zeolites that have been augmented via a process may also provide for a desirable separation. Such mixture can be used to provide for product augmentation.

The present disclosure also provides separations approaches downstream of an ETL reactor. Downstream separations equipment for an ETL process can be similar to equipment employed for use in refineries. In some cases, downstream unit operations can include flash separation, isomerization, hydrogenation and distillation, which can aid in bringing the final product to within a given specification.

Isomerization equipment can convert unwanted iso-durene into a more volatile form. Hydrogenation equipment can reduce the amount of olefins/aromatics in the final product. Distillation can separate material on the basis of boiling point. These units can be readily used to create a product having a product distribution as desired.

Isomerization equipment can be used to upgrade the octane rating of a hydrocarbon product composition. For example, n-hexane can be isomerized to i-hexane. N-pentane (62 octane) can be isomerized to 2-methyl-butane (93 octane). Hexane (25 octane) can be isomerized to 2-methyl-pentane (73 octane).

Alkylation and dimerization units can upgrade lighter fractions, such as butanes, into more valuable, higher octane products. If the ETL reactor produces a large amount of butenes compared to butanes, then dimerization can be used to convert the butene into isooctene/isooctane.

A catalytic reformer unit can upgrade light naphtha fraction to a reformate. This unit works by combining molecules and producing hydrogen. If well-placed, the hydrogen produced in this unit can be utilized in a downstream unit.

Depending on the size and scale of the ETL reactor, vacuum distillation can be employed to further refine the hydrocarbon product outputted by the ETL reactor. If such products are valuable as lubricants, oils and waxes, then the extra step to vacuum distill these products can be advantageous. In some cases, the amount of heavy components produced in the ETL reactor is less than 20%, 15%, 10%, 5% or 1%, but the value generated out of those products can be substantial.

Another approach for separating hydrocarbons is cryogenic separation. Such separation can be used to capture C4 and $C_{5+}$ compounds from an ETL reactor effluent product stream. In some cases, a cryogenic separation unit can include a cold box that may not use traditional deep cryogenic temperatures and may not require traditional unit operations of demethanizer and deethanizer. Such cryogenic separation unit may not produce high purity methane, ethane, or propane products. However, it may produce a mixed (in some cases primarily methane) stream with impurity ethane, propane, other light hydrocarbons and inert gases that are acceptable for use in other settings, such as reinjection to pipeline gas, as residue gas, or used to meet fuel requirements for power plants or feedstocks for syngas plants for the production of methanol or ammonia.

In some examples, a cryogenic separation unit can operate at a temperature from about −100° C. to −20° C., −90° C. to −40° C., or −80° C. to −50° C. Such temperatures can be obtained through methods that use the turboexpansion of high pressure pipeline natural gas or turboexpansion of moderate pressure high methane content feedstock gas, which may be typical of OCM reactor inlet requirements where additional cooling may be accomplished using traditional process plant refrigeration loops, including propane refrigeration or other mixed refrigerants.

In some cases, there may be substantial recovery of pressure-reduced power by coupling of turboexpander and residue gas compressors depending on final destination and usage of lighter nonreacted and unrecoverable hydrocarbons and other components.

In an example OCM-ETL system, gas is expanded and/or additional refrigeration cooled and fed to a cryogenic cold box unit, where heat is exchanged with multiple downstream product streams. It can then be fed to an OCM reaction and heat recovery section. Pressure can be increased through multiple process gas compressors, then heated for ETL and then ETL reaction section. Unrefrigerated liquids recovery can be accomplished using air and cooling water utilities before the product gas enters the cryogenic cold box unit, where it is cooled, pressure reduced for cooling effects, and additional condensed liquids removed via a liquid-liquid separator. Separated liquids can reenter the cryogenic cold box unit, where they are heat exchanged prior to being fed to a depropanizer unit which removes impurity propane and other light compounds from final $C_{4+}$ product. Separated gas from the liquid-liquid separator also renter the cryogenic cold box unit where they are heat exchanged prior to being mixed with depropanizer overhead product gas and then fed to residue gas compressors based on final residue gas users. The depropanizer reflux condensation is also provided by sending this gas stream through the cryogenic cold box unit.

In some cases, a debutanizer column can be installed with bottoms product from depropanizer as feed. Its use can be to provide RVP control of final $C_{4+}$ product. In some cases, RVP control may be precluded, other purifications or chemical conversions may be employed.

ETL Reactor Feedstock

Olefin-to-liquids (e.g., ETL) processes of the present disclosure can be performed using feedstocks comprising one or more olefins, such as pure ethylene or diluted ethylene. Ethylene can be mixed with non-hydrocarbon molecules or other hydrocarbons, including olefins, paraffins, naphthenes, and aromatics. When a feedstock comprising these materials is directed over an ETL catalyst, such as a zeolite catalyst bed at temperatures of at least about 150° C., 200° C., 250° C., or 300° C., the reactants can oligomerize to form a combination of longer chain isomers of olefins and paraffins, naphthenes, and aromatics. The product slate can include hydrocarbons with carbon numbers between 1 and 19 (i.e., $C_1$-$C_{19}$).

The concentration of ethylene (or other olefin(s)) can be changed by adjusting the partial pressure of ethylene (or other olefin(s)) at constant total pressure by dilution with an inert gas, such as nitrogen or methane, or by adding an inert gas to increase the total pressure while keeping the partial pressure of ethylene constant. A change in concentration due to changes in the total pressure may not lead to significant variations in the process unless the system is operated in an adiabatic mode, in which temperature spikes introduce additional variability.

In an isothermal reactor operation, a change in concentration via adjustments in the partial pressure of ethylene can prompt increases in liquid content and reduction of olefins at the benefit of paraffins and aromatics. The changes observed in product slate and liquid formation can depend on the temperature regime and the class of molecules formed in that regime (i.e., isoparaffins and aromatics at temperatures below or above about 400° C., respectively). For example, increasing the concentration of ethylene from 5% to 15% at a constant total pressure of 1 bar and a WHSV of 1 g ethylene/g catalyst/hour can result in a change from 15% to 45% liquids at 300° C.

As the temperature increases, the starting liquid percent increases, yet the net change upon an increase in concentration diminishes. For example, at 390° C., increasing the concentration of ethylene from 5% to 15% at a constant total pressure of 1 bar can result in a change of 45% to 65% liquids. The composition of the product can also change with increasing concentration of ethylene. The trend is uniform with temperature: as the concentration increases, the content of olefins decreases at the benefit of paraffin isomers, naphthenes, and aromatics. As the temperature is increased to at least about 300° C., 350° C., 400° C. or 450° C. and the product slate is heavily aromatic, changes in the partial pressure of ethylene may not change the product slate but can cause a decrease in the liquid content.

In an adiabatic operation, the concentration of ethylene may result in a change in the liquid and product slate, which is coupled to the variations in temperature zones across the reactor bed. In this mode, the rate of heat transfer from a differential volume unit of the reactor bed is a function of the heat capacity of the catalyst and gaseous molecules in the stream—in particular the inert species. Thus, decreasing the concentration of ethylene helps increase the heat dissipation and the temperature in the volume unit. In general, as the concentration of ethylene is increased, the temperature in the bed can increase and the content of aromatics and net liquids can also increase at the expense of paraffins, isoparaffins, olefins, and naphthenes. When the temperature reaches at least about 300° C., 350° C., 400° C. or 450° C., the net amount of liquid can decrease as cracking of the liquid molecules becomes more prevalent.

In some cases, the addition of other hydrocarbons from a recycle, refinery or midstream operation combined with the ethylene feedstock may have a positive effect on the formation of liquids. The ETL process is an oligomerization reaction, in which hydrocarbons are combined to form longer chain hydrocarbons. Thus, introducing hydrocarbons with $C_{3+}$ olefin chain length in addition to the $C_2$ ethylene promotes the formation of liquid. As long as the reaction conditions or inherent nature of the catalyst itself precludes cracking (β-scission) of the hydrocarbon, the addition of longer chain hydrocarbons in the feed may yield an oligomerized product that is the sum of the two molecules. In other words, the barrier to producing longer chain molecules is reduced by minimizing the number of molecular units at the start of the reactor ($C_2+C_2+C_2+C_2=C_8$ vs. $C_2+C_6=C_8$).

Gas molecules that can be co-fed with ethylene can come from a recycle stream, natural gas liquids, midstream operations, or refinery effluents comprising ethane, propylene, propane, butene isomers, and butane isomers, and other $C_{4+}$ olefins. The general product slate can be more or less unchanged by introducing propylene, isobutene, and trans-2-butene (with similar expectations for other butene isomers). At a constant volumetric flowrate of hydrocarbon species, substitution of a longer chain hydrocarbon for a shorter chain hydrocarbon (e.g., propylene replacing ethylene) can result in a higher content of liquid formed.

For example, at T=300° C. with 0.15 bar partial pressure of hydrocarbon, 1 bar total pressure, a 50:50 mixture of propylene or isobutene with ethylene increases the liquid yield by 10%-20% in comparison to a pure ethylene feedstock (an increase in liquids can be due to an increase in liquid ($C_{5+}$) isoparaffins). When the temperature is 390° C. or higher and aromatic molecules are the dominant product species, the impact of hydrocarbon length has less effect on the liquid formation. Regardless, we have found that the presence of propylene or isobutene in the feed promotes the formation of liquids (aromatics) to an extent (a few percentage points) that is greater than using an isolated pure feeds.

Additional paraffins (e.g., ethane, propane, and butane) can influence may impact an ETL reaction and product distribution. The introduction of n-paraffins may yield an increase in isoparaffin content due to isomerization of the molecules on the acid zeolite catalyst. As the temperature and rate of dehydrogenation increases, the impact of introduced paraffins may mirror the behavior observed by adding olefins. Co-feeding $C_{5+}$ hydrocarbons with ethylene may also improve the liquid conversion performance of the ETL process due to the nature of the oligomerization process.

Oxidative Coupling of Methane (OCM) Processes

In an OCM process, methane ($CH_4$) reacts with an oxidizing agent over a catalyst bed to generate $C_{2+}$ compounds. For example, methane can react with oxygen over a suitable catalyst to generate ethylene, e.g., $2\ CH_4+O_2 \rightarrow C_2H_4+2\ H_2O$ (See, e.g., Zhang, Q., *Journal of Natural Gas Chem.*, 12:81, 2003; Olah, G. "Hydrocarbon Chemistry", Ed. 2, John Wiley & Sons (2003)). This reaction is exothermic (ΔH=−67 kcals/mole) and has typically been shown to occur at very high temperatures (>700° C.). Experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couples in the gas phase to form ethane ($C_2H_6$), followed by dehydrogenation to ethylene ($C_2H_4$). Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e. ethane and ethylene), and more importantly, all such reported yields operate at extremely high temperatures (>800° C.). Catalysts and processes have been described for use in performing OCM in the production of ethylene from methane at substantially more practicable temperatures, pressures and catalyst activities. These are described in U.S. Patent Publication Nos. 2012/0041246, 2013/0023079, and 2013/165728, and U.S. patent application Ser. Nos. 13/936,783 and 13/936,870 (both filed Jul. 8, 2013), the full disclosures of each of which is incorporated herein by reference in its entirety for all purposes.

An OCM reactor can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed. In some embodiments, at least a portion of the OCM catalyst in at least a portion of the OCM reactor can include one or more OCM catalysts and/or nanostructure-based OCM catalyst compositions, forms and formulations described in, for example, U.S. Patent Publication Nos. 2012/0041246, 2013/0023709, 2013/0158322, 2013/0165728, and pending U.S. application Ser. No. 13/901,309 (filed May 23, 2013) and Ser. No. 14/212,435 (filed Mar. 14, 2014), each of which is entirely incorporated herein by reference. Using one or more nanostructure-based OCM catalysts within the OCM reactor, the selectivity of the catalyst in converting methane to desirable $C_{2+}$ compounds can be about 10% or greater; about 20% or greater; about 30% or greater; about 40% or greater; about 50% or greater; about 60% or greater; about 65% or greater; about 70% or greater; about 75% or greater; about 80% or greater; or about 90% or greater.

An OCM reactor can be sized, shaped, configured, and/or selected based upon the need to dissipate the heat generated by the OCM reaction. In some embodiments, multiple, tubular, fixed bed reactors can be arranged in parallel to facilitate heat removal. At least a portion of the heat generated within the OCM reactor can be recovered, for example the heat can be used to generate high temperature and/or pressure steam. Where co-located with processes requiring a heat input, at least a portion of the heat generated within the OCM reactor may be transferred, for example, using a heat transfer fluid, to the co-located processes. Where no additional use exists for the heat generated within the OCM reactor, the heat can be released to the environment, for example, using a cooling tower or similar evaporative cooling device. In some embodiments, an adiabatic fixed bed reactor system can be used and the subsequent heat can be utilized directly to convert or crack alkanes into olefins. In some embodiments, a fluidized bed reactor system can be utilized. OCM reactor systems useful in the context of the present invention may include those described in, for example, U.S. patent application Ser. No. 13/900,898 (filed May 23, 2013), which is incorporated herein by reference in its entirety for all purposes.

The methane feedstock for an OCM reactor can be provided from various sources, such as non-OCM processes. In an example, methane is provided through natural gas, such as methane generated in a natural gas liquids (NGL) system.

Methane can be combined with a recycle stream from downstream separation units prior to or during introduction into an OCM reactor. In the OCM reactor, methane can catalytically react with an oxidizing agent to yield $C_{2+}$ compounds. The oxidizing agent can be oxygen ($O_2$), which may be provided by way of air or enriched air. Oxygen can be extracted from air, for example, in a cryogenic air separation unit.

To carry out an OCM reaction in conjunction with preferable catalytic systems, the methane and oxygen containing gases generally need to be brought up to appropriate reaction temperatures, e.g., typically in excess of 450° C. for preferred catalytic OCM processes, before being introduced to the catalyst, in order to allow initiation of the OCM reaction. Once that reaction begins or "lights off," then the heat of the reaction is typically sufficient to maintain the reactor temperature at appropriate levels. Additionally, these processes may operate at a pressure above atmospheric pressure, such as in the range of about 1 to 30 bars (absolute).

In some cases, the oxidizing agent and/or methane are pre-conditioned prior to, or during, the OCM process. The reactant gases can be pre-conditioned prior to their introduction into a catalytic reactor or reactor bed, in a safe and efficient manner. Such pre-conditioning can include (i) mixing of reactant streams, such as a methane-containing stream and a stream of an oxidizing agent (e.g., oxygen) in an OCM reactor or prior to directing the streams to the OCM reactor, (ii) heating or pre-heating the methane-containing stream and/or the stream of the oxidizing agent using, for example, heat from the OCM reactor, or (iii) a combination of mixing and pre-heating. Such pre-conditioning can minimize, if not eliminate auto-ignition of methane and the oxidizing agent. Systems and methods for pre-conditioning reactant gases are described in, for example, U.S. patent application Ser. No. 14/553,795, filed Nov. 25, 2014, which is entirely incorporated herein by reference.

A wide set of competitive reactions can occur simultaneously or substantially simultaneously with the OCM reaction, including total combustion of both methane and other partial oxidation products. An OCM process can yield $C_{2+}$ compounds as well as non-$C_{2+}$ impurities. The $C_{2+}$ compounds can include a variety of hydrocarbons, such as hydrocarbons with saturated or unsaturated carbon-carbon bonds. Saturated hydrocarbons can include alkanes, such as ethane, propane, butane, pentane and hexane. Unsaturated hydrocarbons may be more suitable for use in downstream non-OCM processes, such as the manufacture of polymeric materials (e.g., polyethylene). Accordingly, it may be preferable to convert at least some, all or substantially all of the alkanes in the $C_{2+}$ compounds to compounds with unsaturated moieties, such as alkenes, alkynes, alkoxides, ketones, including aromatic variants thereof.

Figure 42:
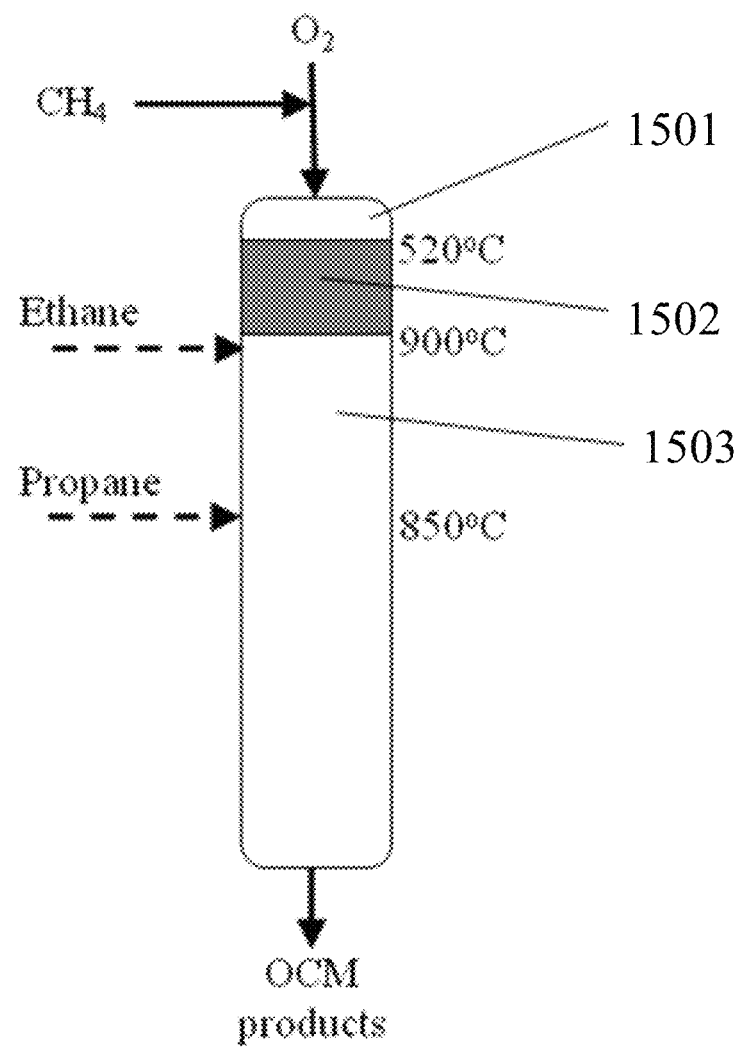
FIG. 42 shows an OCM reactor comprising an integrated catalyst unit and cracking unit.

Once formed, $C_{2+}$ compounds can be subjected to further processing to generate desired or otherwise predetermined chemicals. In some situations, the alkane components of the $C_{2+}$ compounds are subjected to cracking in an OCM reactor or a reactor downstream of the OCM reactor to yield other compounds, such as alkenes (or olefins). See, e.g., U.S. patent application Ser. No. 14/553,795, filed Nov. 25, 2014, now published as U.S. Patent Publication No. 2015/0152025, which is entirely incorporated herein by reference. FIG. 42 shows an OCM reactor 1501 comprising a catalyst unit 1502 and a cracking unit 1503. The catalyst unit 1502 can be, for example, a packed bed reactor comprising a heterogeneous catalyst. The catalyst unit 1502 can be configured to perform an OCM process using natural gas and $O_2$ inputted into the reactor 1501. The cracking unit 1503 is configured to perform crack alkanes (e.g., ethane) to other types of hydrocarbons, such as alkenes (e.g., ethylene). The cracking unit 1503 can be configured to operate adiabatically using heat liberated in the catalyst unit 1502 in the OCM process, which heat can be conveyed by way of steam generated in the OCM process, for example.

In some situations, an OCM system generates ethylene that can be subjected to further processing to generate different hydrocarbons with the aid of conversion processes (or systems). Such a process can be part of an ethylene to liquids (ETL) or ethylene, propene, butene gases to liquids. The ETL process includes OCM olefins gases, ethylene, propene, butene, or other OCM gaseous products to produce liquids. OCM-ETL process flow comprising one or more OCM reactors, separations units, and one or more conversion processes for generating higher molecular weight hydrocarbons. The conversion processes can be integrated in a switchable or selectable manner in which at least a portion or all of the ethylene containing product can be selectively directed to 1, 2, 3, 4, 5, 6, 7, 8, 9, 10, or more different process paths to yield as many different hydrocarbon products. An example OCM and ETL (collectively "OCM-ETL" herein) process is schematically illustrated in FIG. 1, which shows an OCM reactor system 100 that includes an OCM reactor train 102 coupled to an OCM product gas separation train 104. The OCM product gas separation train 104 can include various separation unit operations ("units"), such as a distillation unit and/or a cryogenic separation unit. The ethylene rich effluent (shown as arrow 106) from the separation train 104 is routed to multiple different ethylene conversion reactor systems and processes 110, e.g., ethylene conversion systems 110a-110e, which each produce different hydrocarbon products, e.g., products 120a-120e. Products 120a-120e can include, for example, hydrocarbons having between three and twelve carbon atoms per molecule (C3-C12 hydrocarbons). Such hydrocarbons may be suitable for use as fuels for various machines, such as automobiles.

The fluid connection between the OCM reactor system 100 and each of the different ethylene conversion systems 110a-110e can be controllable and selective, e.g., with the aid of a valve and control system, which can apportion the output of the OCM reactor system 100 to 1, 2, 3, 4, 5, 6, 7, 8, 9, 10, or more different ethylene conversion systems. The conversions systems 110a-110e can be ETL or gas to liquids (GTL) reactors. Valve and piping systems for accomplishing this may take a variety of different forms, including valves at each piping junction, multiport valves, multi-valve manifold assemblies, and the like. Other details of the OCM-ETL process of FIG. 1 are provided in, for example, U.S. patent application Ser. No. 14/099,614, filed on Dec. 6, 2013, which is entirely incorporated herein by reference.

As noted, the present disclosure includes processes and systems for production of various higher hydrocarbons (i.e., $C_{3+}$) from ethylene, and particularly liquid hydrocarbon compositions. In some aspects, the ethylene is itself derived from methane in a methane containing feedstock, such as natural gas. Production of ethylene from methane can be accomplished through a number of different catalytic pathways, for example in some embodiments, the processes and systems of the disclosure convert methane to ethylene through OCM in an OCM reactor system. In some embodiments, the ethylene produced in the OCM reactor system is charged to one or more ethylene conversion reactor systems where it can be converted to a higher hydrocarbon, for example a different higher hydrocarbon in each of the ethylene conversion reactor systems.

OCM reactions, processes and systems can operate within economic and reasonable process windows. In some cases, catalysts, processes and reactor systems have been able to carry out OCM reactions at temperatures, pressures, selectivities and yields that are commercially attractive. See, e.g., U.S. patent application Ser. Nos. 13/115,082, 13/479,767, 13/689,611, 13/739,954, 13/900,898, 13/901,319, 13/936,783, and 14/212,435, the full disclosures of which are incorporated herein by reference in their entirety for all purposes.

As used herein, an OCM process or system typically employs one or more reactor vessels that contain an appropriate OCM catalyst material, typically in conjunction with additional system components. A variety of OCM catalysts have been described previously. See, e.g., U.S. Pat. Nos. 5,712,217, 6,403,523, and 6,576,803, the full disclosures of which are incorporated herein by reference in their entirety for all purposes. Some catalysts have been developed that yield conversion and selectivity that enable economic methane conversion under practical operating conditions. These are described in, for example, Published U.S. Patent Application No. 2012-0041246, as well as patent application Ser. No. 13/479,767, filed May 24, 2012, and Ser. No. 13/689,611, filed Nov. 29, 2012, the full disclosures of each of which are incorporated herein by reference in their entirety for all purposes.

Accordingly, in some embodiments, the disclosure provides a method of producing a hydrocarbon product, the method comprising: (a) introducing methane and a source of oxidant into an OCM reactor system capable of converting methane to ethylene at reactor inlet temperatures of between about 450° C. and 600° C. and reactor pressures of between about 15 psig and 125 psig, with $C_{2+}$ selectivity of at least 50%, under conditions for the conversion of methane to ethylene; (b) converting methane to a product gas comprising ethylene; (c) introducing at least a portion of the product gas into an integrated ethylene conversion reaction systems, the integrated ethylene conversion reaction system being configured for converting ethylene into a higher hydrocarbon product; and (d) converting the ethylene into a higher hydrocarbon product.

In some embodiments, the method is for producing a plurality of hydrocarbon products. Accordingly, in some embodiments, the invention provides a method of producing a plurality of hydrocarbon products, the method comprising: (a) introducing methane and a source of oxidant into an OCM reactor system capable of converting methane to ethylene at reactor inlet temperatures of between about 450° C. and 600° C. and reactor pressures of between about 15 psig and 125 psig, with $C_{2+}$ selectivity of at least 50%, under conditions for the conversion of methane to ethylene; (b) converting methane to a product gas comprising ethylene; (c) introducing separate portions of the product gas into at least first and second integrated ethylene conversion reaction systems, each integrated ethylene conversion reaction system being configured for converting ethylene into a different higher hydrocarbon product; and (d) converting the ethylene into different higher hydrocarbon products. In some embodiments, the integrated ethylene conversion systems are selected from selective and full range ethylene conversion systems.

In some embodiments the methods further comprise introducing a portion of the product gas into at least a third integrated ethylene conversion system. Some embodiments further comprise introducing a portion of the product gas into at least first, second, third and fourth integrated ethylene conversion systems.

In any of the methods described herein, the integrated ethylene conversion systems can be selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

In some embodiments, the integrated ethylene conversion systems can be selected from LAO systems that produce one or more of 1-butene, 1-hexene, 1-octene and 1-decene. For example, in certain embodiments at least one of the LAO systems is configured for performing a selective LAO process.

In some embodiments, at least one of the integrated ethylene conversion systems comprises a full range ethylene oligomerization system configured for producing higher hydrocarbons in the range of $C_4$ to $C_{30}$.

In some embodiments, the OCM reactor system comprises nanowire OCM catalyst material. In some embodiments, the product gas comprises less than 5 mol % of ethylene. For example, in certain embodiments, the product gas comprises less than 3 mol % of ethylene. In some embodiments, the product gas can further comprise one or more gases selected from $CO_2$, CO, $H_2$, $H_2O$, $C_2H_6$, $CH_4$ and $C_{3+}$ hydrocarbons.

In some embodiments, the method further comprises enriching the product gas for ethylene prior to introducing the separate portions of the product gas into the at least first and second integrated ethylene conversion reaction systems.

In some embodiments, the method further comprises introducing an effluent gas from the first or second integrated ethylene conversion reaction systems into the OCM reactor system. For example, in some of these embodiments the method further comprises converting methane present in the effluent gas to ethylene and charging the ethylene to one or more of the integrated ethylene conversion systems.

In various embodiments, the disclosure is directed to a method of producing a plurality of hydrocarbon products, the method comprising: (a) introducing methane and a source of oxidant into an OCM reactor system capable of converting methane to ethylene at reactor inlet temperatures of between about 450° C. and 600° C. and reactor pressures of between about 15 psig and 125 psig, with $C_{2+}$ selectivity of at least 50%, under conditions for the conversion of methane to ethylene; (b) recovering ethylene from the OCM reactor system; and (c) introducing separate portions of the ethylene recovered from the OCM reactor system into at least two integrated, but discrete and different catalytic ethylene conversion reaction systems for converting ethylene into at least two different higher hydrocarbon products.

In some embodiments, the at least two ethylene conversion systems are selected from selective and full range ethylene conversion systems. In some embodiments, the at least two ethylene conversion systems comprise at least three ethylene conversion systems. For example, in some embodiments the at least two ethylene conversion systems comprise at least four ethylene conversion systems.

In yet more embodiments, the at least two ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

In some cases, the at least two ethylene conversion systems are selected from LAO systems that produce one or more of 1-butene, 1-hexene, 1-octene and 1-decene. For example, in some embodiments at least one of the at least two LAO processes comprises a selective LAO process, and in other exemplary embodiments at least one of the at least two ethylene conversion systems comprises a full range ethylene oligomerization system for producing higher hydrocarbons in the range of $C_4$ to $C_{30}$. In some instances, the OCM reactor system comprises nanowire OCM catalyst material.

In some embodiments, the disclosure provides a method of producing a plurality of liquid hydrocarbon products, comprising: (a) converting methane to a product gas comprising ethylene using a catalytic reactor process; and (b) contacting separate portions of the product gas with at least two discrete catalytic reaction systems selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

In some cases, a method of producing a plurality of liquid hydrocarbon products is provided. The method comprises: (a) converting methane to ethylene using a catalytic reactor process; (b) recovering ethylene from the catalytic reactor process; and (c) contacting separate portions of the ethylene recovered from the OCM reactor system with at least two discrete catalytic reaction systems selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, and hydrocarbon polymer systems.

Some embodiments of the present disclosure are directed to a processing system for preparation of $C_{2+}$ hydrocarbon products from methane. For example, in some embodiments the invention provides a processing system comprising: (a) an OCM reactor system comprising an OCM catalyst, the OCM reactor system being fluidly connected at an input, to a source of methane and a source of oxidant; (b) an integrated ethylene conversion reactor system, the ethylene reactor system being configured to convert ethylene to a higher hydrocarbon; and (c) a selective coupling between the OCM reactor system and the ethylene reactor system, the selective coupling configured to selectively direct a portion or all of the product gas to the ethylene conversion reactor system.

In some instances, the disclosure provides a processing system comprising: (a) an OCM reactor system comprising an OCM catalyst, the OCM reactor system being fluidly connected at an input, to a source of methane and a source of oxidant; (b) at least first and second catalytic ethylene conversion reactor systems, the first catalytic ethylene reactor system being configured to convert ethylene to a first higher hydrocarbon, and the second catalytic ethylene reactor system being configured to convert ethylene to a second higher hydrocarbon different from the first higher hydrocarbon; and (c) a selective coupling between the OCM reactor system and the first and second catalytic ethylene reactor systems configured to selectively direct a portion or all of the product gas to each of the first and second catalytic ethylene reactor systems.

In some embodiments, the ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, ethylene copolymerization systems, and hydrocarbon polymer systems.

In some instances, the OCM catalyst comprises a nanowire catalyst. In some embodiments, the system further comprises an ethylene recovery system fluidly coupled between the OCM reactor system and the at least first and second catalytic ethylene conversion reactor systems, the ethylene recovery system configured for enriching the product gas for ethylene.

In some cases, the disclosure is directed to a processing system, the processing system comprising: (a) an OCM reactor system comprising an OCM catalyst, the OCM reactor system being fluidly connected at an input, to a source of methane and a source of oxidant; (b) an ethylene recovery system fluidly coupled to the OCM reactor system at an outlet, for recovering ethylene from an OCM product gas; (c) at least first and second catalytic ethylene conversion reactor systems, the first catalytic ethylene reactor system being configured to convert ethylene to a first higher hydrocarbon composition, and the second catalytic ethylene reactor system being configured to convert ethylene to a second higher hydrocarbon composition different from the first higher hydrocarbon composition; and (d) a selective coupling between the outlet of the ethylene recovery system and the first and second catalytic ethylene reactor systems to selectively direct a portion or all of the ethylene recovered from the OCM product gas to each of the first and second catalytic ethylene reactor systems.

In some cases, two or more of the at least two ethylene conversion systems are selected from linear alpha olefin (LAO) systems, linear olefin systems, branched olefin systems, saturated linear hydrocarbon systems, branched hydrocarbon systems, saturated cyclic hydrocarbon systems, olefinic cyclic hydrocarbon systems, aromatic hydrocarbon systems, oxygenated hydrocarbon systems, halogenated hydrocarbon systems, alkylated aromatic systems, ethylene copolymerization systems, and hydrocarbon polymer systems. In other embodiments, the OCM catalyst comprises a nanowire catalyst.

In some embodiments, the catalyst systems used in any of the above described OCM reaction comprise nanowire catalysts. Such nanowire catalysts can include substantially straight nanowires or nanowires having a curved, twisted or bent morphology. The actual lengths of the nanowire catalysts may vary. For example in some embodiments, the nanowires have an actual length of between 100 nm and 100 µm. In other embodiments, the nanowires have an actual length of between 100 nm and 10 µm. In other embodiments, the nanowires have an actual length of between 200 nm and 10 µm. In other embodiments, the nanowires have an actual length of between 500 nm and 5 µm. In other embodiments, the actual length is greater than 5 µm. In other embodiments, the nanowires have an actual length of between 800 nm and 1000 nm. In other further embodiments, the nanowires have an actual length of 900 nm. As noted below, the actual length of the nanowires may be determined by TEM, for example, in bright field mode at 5 keV.

The diameter of the nanowires may be different at different points along the nanowire backbone. However, the nanowires comprise a mode diameter (i.e., the most frequently occurring diameter). As used herein, the diameter of a nanowire refers to the mode diameter. In some embodiments, the nanowires have a diameter of between 1 nm and 10 μm, between 1 nm and 1 μm, between 1 nm and 500 nm, between 1 nm and 100 nm, between 7 nm and 100 nm, between 7 nm and 50 nm, between 7 nm and 25 nm, or between 7 nm and 15 nm. On other embodiments, the diameter is greater than 500 nm. As noted below, the diameter of the nanowires may be determined by TEM, for example, in bright field mode at 5 keV.

The nanowire catalysts may have different aspect ratios. In some embodiments, the nanowires have an aspect ratio of greater than 10:1. In other embodiments, the nanowires have an aspect ratio greater than 20:1. In other embodiments, the nanowires have an aspect ratio greater than 50:1. In other embodiments, the nanowires have an aspect ratio greater than 100:1.

In some embodiments, the nanowires comprise a solid core while in other embodiments, the nanowires comprise a hollow core. In general, the morphology of a nanowire (including length, diameter, and other parameters) can be determined by transmission electron microscopy (TEM). Transmission electron microscopy (TEM) is a technique whereby a beam of electrons is transmitted through an ultra-thin specimen, interacting with the specimen as it passes through. An image is formed from the interaction of the electrons transmitted through the specimen. The image is magnified and focused onto an imaging device, such as a fluorescent screen, on a layer of photographic film or detected by a sensor such as a CCD camera.

In some embodiments, the nanowire catalysts comprise one or multiple crystal domains, e.g., monocrystalline or polycrystalline, respectively. In some other embodiments, the average crystal domain of the nanowires is less than 100 nm, less than 50 nm, less than 30 nm, less than 20 nm, less than 10 nm, less than 5 nm, or less than 2 nm. Crystal structure, composition, and phase, including the crystal domain size of the nanowires, can be determined by XRD.

Typically, the nanowire catalytic material comprises a plurality of nanowires. In certain embodiments, the plurality of nanowires form a mesh of randomly distributed and, to various degrees, interconnected nanowires, that presents a porous matrix.

The total surface area per gram of a nanowire or plurality of nanowires may have an effect on the catalytic performance. Pore size distribution may affect the nanowires catalytic performance as well. Surface area and pore size distribution of the nanowires or plurality of nanowires can be determined by BET (Brunauer, Emmett, Teller) measurements. BET techniques utilize nitrogen adsorption at various temperatures and partial pressures to determine the surface area and pore sizes of catalysts. There are BET techniques for determining surface area and pore size distribution currently available. In some embodiments the nanowires have a surface area of between 0.0001 and 3000 m$^2$/g, between 0.0001 and 2000 m$^2$/g, between 0.0001 and 1000 m$^2$/g, between 0.0001 and 500 m$^2$/g, between 0.0001 and 100 m$^2$/g, between 0.0001 and 50 m$^2$/g, between 0.0001 and 20 m$^2$/g, between 0.0001 and 10 m$^2$/g or between 0.0001 and 5 m$^2$/g. In some embodiments the nanowires have a surface area of between 0.001 and 3000 m$^2$/g, between 0.001 and 2000 m$^2$/g, between 0.001 and 1000 m$^2$/g, between 0.001 and 500 m$^2$/g, between 0.001 and 100 m$^2$/g, between 0.001 and 50 m$^2$/g, between 0.001 and 20 m$^2$/g, between 0.001 and 10 m$^2$/g or between 0.001 and 5 m$^2$/g. In some other embodiments the nanowires have a surface area of between 2000 and 3000 m$^2$/g, between 1000 and 2000 m$^2$/g, between 500 and 1000 m$^2$/g, between 100 and 500 m$^2$/g, between 10 and 100 m$^2$/g, between 5 and 50 m$^2$/g, between 2 and 20 m$^2$/g or between 0.0001 and 10 m$^2$/g. In other embodiments, the nanowires have a surface area of greater than about 2000 m$^2$/g, greater than about 1000 m$^2$/g, greater than about 500 m$^2$/g, greater than about 100 m$^2$/g, greater than about 50 m$^2$/g, greater than about 20 m$^2$/g, greater than about 10 m$^2$/g, greater than about 5 m$^2$/g, greater than about 1 m$^2$/g, greater than about 0.0001 m$^2$/g.

The nanowire catalysts and catalyst compositions used in conjunction with the processes and systems of some embodiments of the invention may have any number of compositions and/or morphologies. These nanowire catalysts may be inorganic and either polycrystalline or monocrystalline. In some other embodiments, the nanowires are inorganic and polycrystalline. In certain examples, the nanowire catalysts comprise one or more elements from any of Groups 1 through 7, lanthanides, actinides or combinations thereof. Thus in certain aspects, the catalysts comprise an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof.

In still other cases, the nanowire catalysts comprise one or more metal elements from any of Groups 1-7, lanthanides, actinides or combinations thereof, for example, the nanowires may be mono-metallic, bi-metallic, tri-metallic, etc. (i.e., contain one, two, three, etc. metal elements), where the metal elements may be present in the nanowires in elemental or oxidized form, or in the form of a compound comprising a metal element. The metal element or compound comprising the metal element may be in the form of oxides, hydroxides, oxyhydroxides, salts, hydrated oxides, carbonates, oxy-carbonates, sulfates, phosphates, acetates, oxalates and the like. The metal element or compound comprising the metal element may also be in the form of any of a number of different polymorphs or crystal structures.

In some examples, metal oxides may be hygroscopic and may change forms once exposed to air, may absorb carbon dioxide, may be subjected to incomplete calcination or any combination thereof. Accordingly, although the nanowires are often referred to as metal oxides, in some embodiments the nanowires also comprise hydrated oxides, oxyhydroxides, hydroxides, oxycarbonates (or oxide carbonates), carbonates or combinations thereof.

In some cases, the nanowires comprise one or more metal elements from Group 1, Group 2, Group 3, Group 4, Group 5, Group 6, Group 7, lanthanides, and/or actinides, or combinations of these, as well as oxides of these metals. In other cases, the nanowires comprise hydroxides, sulfates, carbonates, oxide carbonates, acetates, oxalates, phosphates (including hydrogen phosphates and dihydrogenphosphates), oxy-carbonates, oxyhalides, hydroxyhalides, oxyhydroxides, oxysulfates, mixed oxides or combinations thereof of one or more metal elements from any of Groups 1-7, lanthanides, actinides or combinations thereof. Examples of such nanowire materials include, but are not limited to nanowires comprising, e.g., $Li_2CO_3$, LiOH, $Li_2O$, $Li_2C_2O_4$, $Li_2SO_4$, $Na_2CO_3$, NaOH, $Na_2O$, $Na_2C_2O_4$, $Na_2SO_4$, $K_2CO_3$, KOH, $K_2O$, $K_2C_2O_4$, $K_2SO_4$, $Cs_2CO_3$, CsOH, $Cs_2O$, $CsC_2O_4$, $CsSO_4$, $Be(OH)_2$, $BeCO_3$, BeO, $BeC_2O_4$. $BeSO_4$, $Mg(OH)_2$, $MgCO_3$, MgO, $MgC_2O_4$. $MgSO_4$, $Ca(OH)_2$, CaO, $CaCO_3$, $CaC_2O_4$, $CaSO_4$, $Y_2O_3$, $Y_2(CO_3)_3$, $Y(OH)_3$, $Y_2(C_2O4)_3$, $Y_2(SO_4)_3$, $Zr(OH)_4$, ZrO $(OH)_2$, ZrO2, $Zr(C_2O_4)_2$, $Zr(SO_4)_2$, $Ti(OH)_4$, $TiO(OH)_2$, $TiO_2$, $Ti(C_2O_4)_2$, $Ti(SO_4)_2$, BaO, $Ba(OH)_2$, $BaCO_3$, $BaC_2O_4$, $BaSO_4$, $La(OH)_3$, $La_2O_3$, $La_2(C_2O_4)_3$, $La_2(SO_4)_3$, $La_2(CO_3)_3$, $Ce(OH)_4$, $CeO_2$, $Ce_2O_3$, $Ce(C_2O_4)_2$, $Ce(SO_4)_2$, $Ce(CO_3)_2$, $ThO_2$, $Th(OH)_4$, $Th(C_2O_4)_2$, $Th(SO_4)_2$, $Th(CO_3)_2$, $Sr(OH)_2$, $SrCO_3$, SrO, $SrC_2O_4$, $SrSO_4$, $Sm_2O_3$, $Sm(OH)_3$, $Sm_2(CO_3)_3$, $Sm_2(C_2O_4)_3$, $Sm_2(SO_4)_3$, $LiCa_2Bi_3O_4Cl_6$, $NaMnO_4$, $Na_2WO_4$, $NaMn/WO_4$, $CoWO_4$, $CuWO_4$, $K/SrCoO_3$, $K/Na/SrCoO_3$, $Na/SrCoO_3$, $Li/SrCoO_3$, $SrCoO_3$, $Mg_6MnO_8$, $LiMn_2O_4$, $Li/Mg_6MnO_8$, $Na_{10}Mn/W_5O_{17}$, $Mg_3Mn_3B_2O_{10}$, $Mg_3(BO_3)_2$, molybdenum oxides, molybdenum hydroxides, molybdenum oxalates, molybdenum sulfates, $Mn_2O_3$, $Mn_3O_4$, manganese oxides, manganese hydroxides, manganese oxalates, manganese sulfates, manganese tungstates, manganese carbonates, vanadium oxides, vanadium hydroxides, vanadium oxalates, vanadium sulfates, tungsten oxides, tungsten hydroxides, tungsten oxalates, tungsten sulfates, neodymium oxides, neodymium hydroxides, neodymium carbonates, neodymium oxalates, neodymium sulfates, europium oxides, europium hydroxides, europium carbonates, europium oxalates, europium sulfates, praseodymium oxides, praseodymium hydroxides, praseodymium carbonates, praseodymium oxalates, praseodymium sulfates, rhenium oxides, rhenium hydroxides, rhenium oxalates, rhenium sulfates, chromium oxides, chromium hydroxides, chromium oxalates, chromium sulfates, potassium molybdenum oxides/silicon oxide or combinations thereof.

Still other examples of these nanowire materials include, but are not limited to, nanowires comprising, e.g., $Li_2O$, $Na_2O$, $K_2O$, $Cs_2O$, BeO MgO, CaO, $ZrO(OH)_2$, $ZrO_2$, $TiO_2$, $TiO(OH)_2$, BaO, $Y_2O_3$, $La_2O_3$, $CeO_2$, $Ce_2O3$, $ThO_2$, SrO, $Sm_2O_3$, $Nd_2O_3$, $Eu_2O_3$, $Pr_2O_3$, $LiCa_2Bi_3O_4C_{16}$, $NaMnO_4$, $Na_2WO_4$, $Na/Mn/WO_4$, $Na/MnWO_4$, $Mn/WO_4$, $K/SrCoO_3$, $K/Na/SrCoO_3$, $K/SrCoO_3$, $Na/SrCoO_3$, $Li/SrCoO_3$, $SrCoO_3$, $Mg_6MnO_8$, $Na/B/Mg_6MnO_8$, $Li/B/Mg_6MnO_8$, $Zr_2Mo_2O_8$, molybdenum oxides, $Mn_2O_3$, $Mn_3O_4$, manganese oxides, vanadium oxides, tungsten oxides, neodymium oxides, rhenium oxides, chromium oxides, or combinations thereof. A variety of different nanowire compositions have been described in, e.g., Published U.S. Patent Application No. 2012-0041246 and U.S. patent application Ser. No. 13/689,611, filed Nov. 29, 2012 (the full disclosures of which are incorporated herein in their entirety for all purposes), and are envisioned for use in conjunction with the present invention.

Products produced from these catalytic reactions typically include CO, $CO_2$, $H_2O$, $C_{2+}$ hydrocarbons, such as ethylene, ethane, and larger alkanes and alkenes, such as propane and propylene. In some embodiments, the OCM reactor systems operate to convert methane into desired higher hydrocarbon products (ethane, ethylene, propane, propylene, butanes, pentanes, etc.), collectively referred to as $C_{2+}$ compounds, with high yield. In particular, the progress of the OCM reaction is generally discussed in terms of methane conversion, $C_{2+}$ selectivity, and $C_{2+}$ yield. As used herein, methane conversion generally refers to the percentage or fraction of methane introduced into the reaction that is converted to a product other than methane. $C_{2+}$ selectivity generally refers to the percentage of all non-methane, carbon containing products of the OCM reaction that are the desired $C_{2+}$ products, e.g., ethane, ethylene, propane, propylene, etc. Although primarily stated as $C_{2+}$ selectivity, it will be appreciated that selectivity may be stated in terms of any of the desired products, e.g., just C2, or just C2 and C3. Finally, $C_{2+}$ yield generally refers to the amount of carbon that is incorporated into a $C_{2+}$ product as a percentage of the amount of carbon introduced into a reactor in the form of methane. This may generally be calculated as the product of the conversion and the selectivity divided by the number of carbon atoms in the desired product. $C_{2+}$ yield is typically additive of the yield of the different $C_{2+}$ components included in the $C_{2+}$ components identified, e.g., ethane yield+ethylene yield+propane yield+propylene yield etc.).

Exemplary OCM processes and systems typically provide a methane conversion of at least 10% per process pass in a single integrated reactor system (e.g., single isothermal reactor system or integrated multistage adiabatic reactor system), with a $C_{2+}$ selectivity of at least 50%, but at reactor inlet temperatures of between 400 and 600° C. and at reactor inlet pressures of between about 15 psig and about 150 psig. Thus, the catalysts employed within these reactor systems are capable of providing the described conversion and selectivity under the described reactor conditions of temperature and pressure. In the context of some OCM catalysts and system embodiments, it will be appreciated that the reactor inlet or feed temperatures typically substantially correspond to the minimum "light-off" or reaction initiation temperature for the catalyst or system. Restated, the feed gases are contacted with the catalyst at a temperature at which the OCM reaction is able to be initiated upon introduction to the reactor. Because the OCM reaction is exothermic, once light-off is achieved, the heat of the reaction can be expected to maintain the reaction at suitable catalytic temperatures, and even generate excess heat.

In some aspects, the OCM reactors and reactor systems, when carrying out the OCM reaction, operate at pressures of between about 15 psig and about 125 psig at the above described temperatures, while providing the conversion and selectivity described herein, and in even more embodiments, at pressures less than 100 psig, e.g., between about 15 psig and about 100 psig.

Examples of particularly useful catalyst materials are described in, for example, Published U.S. Patent Application No. 2012-0041246, as well as patent application Ser. No. 13/479,767, filed May 24, 2012, and Ser. No. 13/689,611, filed Nov. 29, 2012, which are incorporated herein by reference in their entirety for all purposes. In some embodiments, the catalysts comprise bulk catalyst materials, e.g., having relatively undefined morphology or, in certain embodiments, the catalyst material comprises, at least in part, nanowire containing catalytic materials. In either form, the catalysts used in accordance with the present invention may be employed under the full range of reaction conditions described above, or in any narrower described range of conditions. Similarly, the catalyst materials may be provided in a range of different larger scale forms and formulations, e.g., as mixtures of materials having different catalytic activities, mixtures of catalysts and relatively inert or diluent materials, incorporated into extrudates, pellets, or monolithic forms, or the like. Ranges of exemplary catalyst forms and formulations are described in, for example, U.S. patent application Ser. No. 13/901,319 and U.S. Provisional Patent Application No. 62/051,779, the full disclosures of which are incorporated herein by reference in their entireties for all purposes.

The reactor vessels used for carrying out the OCM reaction in the OCM reactor systems of the invention may include one or more discrete reactor vessels each containing OCM catalyst material, fluidly coupled to a methane source and a source of oxidant as further discussed elsewhere herein. Feed gas containing methane (e.g., natural gas) is contacted with the catalyst material under conditions suitable for initiation and progression of the reaction within the reactor to catalyze the conversion of methane to ethylene and other products.

For example, in some embodiments the OCM reactor system comprises one or more staged reactor vessels operating under isothermal or adiabatic conditions, for carrying out OCM reactions. For adiabatic reactor systems, the reactor systems may include one, two, three, four, five or more staged reactor vessels arranged in series, which are fluidly connected such that the effluent or "product gas" of one reactor is directed, at least in part, to the inlet of a subsequent reactor. Such staged serial reactors provide higher yield for the overall process, by allowing catalytic conversion of previously unreacted methane. These adiabatic reactors are generally characterized by the lack of an integrated thermal control system used to maintain little or no temperature gradient across the reactor. With no integrated temperature control system, the exothermic nature of the OCM reaction results in a temperature gradient across the reactor indicative of the progress of the reaction, where the inlet temperature can range from about 450° C. to about 600° C., while the outlet temperature ranges from about 700° C. to about 900° C. Typically, such temperature gradients can range from about 100° C. to about 450° C. By staging adiabatic reactors, with interstage cooling systems, one can step through a more complete catalytic reaction without generating extreme temperatures, e.g., in excess of 900° C.

In operation of certain embodiments, methane-containing feed gas is introduced into the inlet side of a reactor vessel, e.g., the first reactor in a staged reactor system. Within this reactor, the methane is converted into $C_{2+}$ hydrocarbons, as well as other products, as discussed above. At least a portion of the product gas stream is then cooled to an appropriate temperature and introduced into a subsequent reactor stage for continuation of the catalytic reaction. In particular, the effluent from a preceding reactor, which in some cases may include unreacted methane, can provide at least a portion of the methane source for a subsequent reactor. An oxidant source and a methane source, separate from the unreacted methane from the first reactor stage, are also typically coupled to the inlet of each subsequent reactor.

In some aspects, the reactor systems include one or more 'isothermal' reactors, that maintain a relatively low temperature gradient across the overall reactor bed, e.g., between the inlet gas and outlet or product gas, through the inclusion of integrated temperature control elements, such as coolant systems that contact heat exchange surfaces on the reactor to remove excess heat, and maintain a flat or insignificant temperature gradient between the inlet and outlet of the reactor. Typically, such reactors utilize molten salt or other coolant systems that operate at temperatures below 593° C. As with adiabatic systems, isothermal reactor systems may include one, two, three or more reactors that may be configured in serial or parallel orientation. Reactor systems for carrying out these catalytic reactions are also described in U.S. U.S. patent application Ser. No. 13/900,898, the full disclosure of which is incorporated herein by reference in its entirety for all purposes.

The OCM reactor systems used in certain embodiments of the present invention also typically include thermal control systems that are configured to maintain a desired thermal or temperature profile across the overall reactor system, or individual reactor vessels. In the context of adiabatic reactor systems, it will be appreciated that the thermal control systems include, for example, heat exchangers disposed upstream, downstream or between serial reactors within the overall system in order to maintain the desired temperature profile across the one or more reactors. In the context of reactors carrying out exothermic reactions, like OCM, such thermal control systems also optionally include control systems for modulating flow of reactants, e.g., methane containing feed gases and oxidant, into the reactor vessels in response to temperature information feedback, in order to modulate the reactions to achieve the thermal profiles of the reactors within the desired temperature ranges. These systems are also described in U.S. patent application Ser. No. 13/900,898, previously incorporated herein by reference.

For isothermal reactors, such thermal control systems include the foregoing, as well as integrated heat exchange components, such as integrated heat exchangers built into the reactors, such as tube/shell reactor/heat exchangers, where a void space is provided surrounding a reactor vessel or through which one or more reactor vessels or tubes pass. A heat exchange medium is then passed through the void to remove heat from the individual reactor tubes. The heat exchange medium is then routed to an external heat exchanger to cool the medium prior to recirculation into the reactor.

Following the OCM process, ethylene optionally may be recovered from the OCM product gas using an ethylene recovery process that separates ethylene present in the product gas from other components, such as residual, i.e., unreacted methane, ethane, and higher hydrocarbons, such as propane, butanes, pentanes and the like. Alternatively, the OCM product gas is used in subsequent reactions, as described below, without further purification or separation of the ethylene. In various other embodiments, the OCM product gas is enriched for ethylene before being used in subsequent reactions. In this respect, "enriched" includes, but is not limited to, operations which increases the overall mol % of ethylene in the product gas.

In accordance with the present disclosure, ethylene derived from methane, e.g., using the OCM processes and systems, is further processed into higher hydrocarbon compositions, and particularly liquid hydrocarbon compositions. For ease of discussion, reference to OCM processes and systems, when referring to their inclusion in an overall process flow, from methane to higher hydrocarbon compositions, also optionally includes intermediate process steps involved in purification of ethylene from an OCM product gas, e.g., recycling of product gases through the OCM reactor system, separations of methane and higher hydrocarbons, e.g., NGLs and other $C_{2+}$ compounds, from the OCM product gas, and the like. Examples of such intermediate processes include, for example, cryogenic or lean oil separation systems, temperature swing adsorption (TSA), pressure swing adsorption (PSA), and membrane separations, for separation of different hydrocarbon and other components from ethylene, e.g., CO, $CO_2$, water, nitrogen, residual methane, ethane, propane, and other higher hydrocarbon compounds, potentially present in the OCM product gas. Examples of such systems are described in, e.g., U.S. patent application Ser. Nos. 13/739,954, 13/936,783, and 13/936,870, the full disclosures of which are incorporated herein by reference in their entirety for all purposes.

Figure 10:
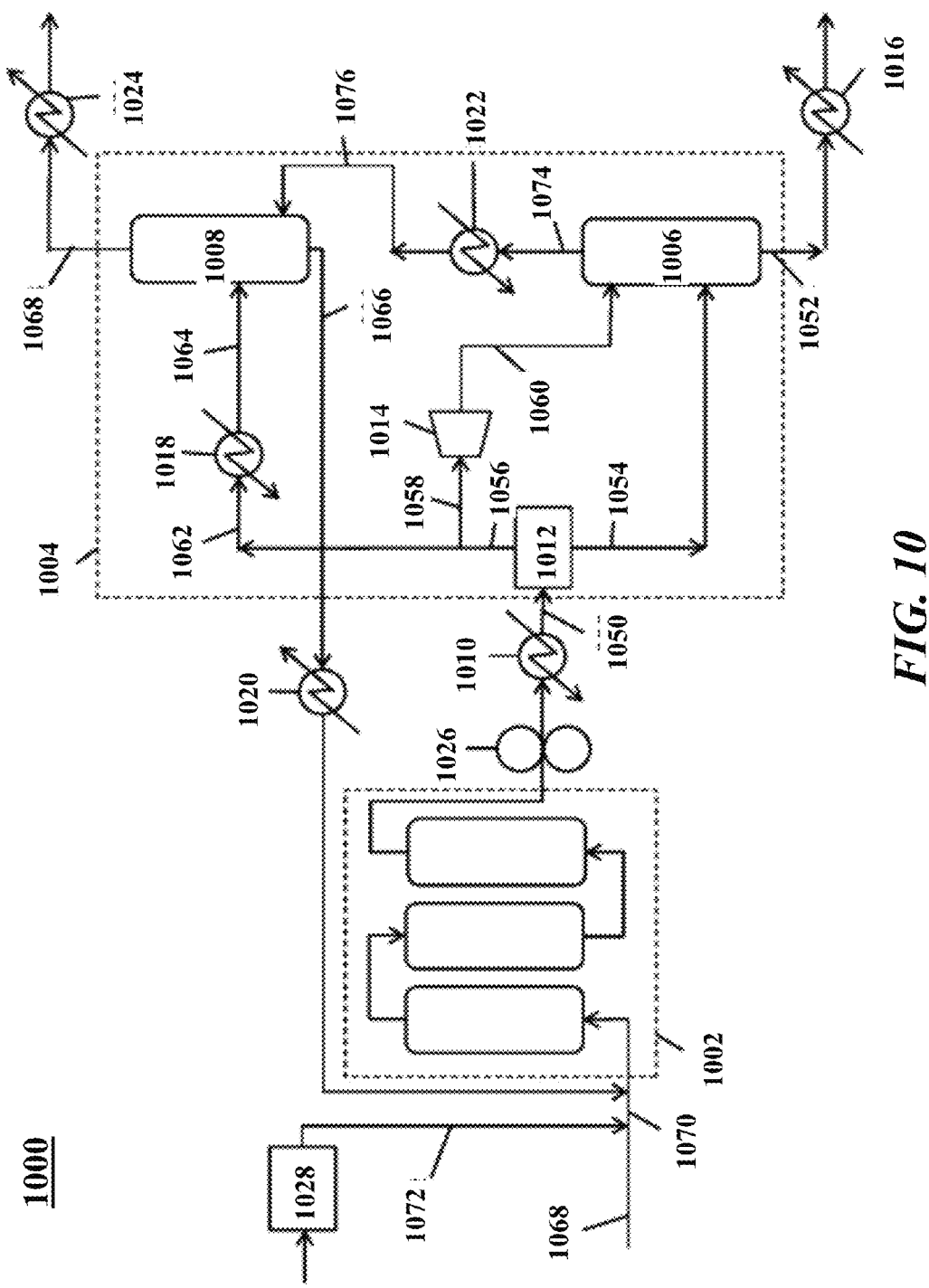
FIG. 10 schematically illustrates an integrated OCM system with integrated separations system.

FIG. 10 schematically illustrates an exemplary OCM system with integrated separations system component or components. In particular, shown in FIG. 10 is an exemplary process flow diagram depicting a process 1000 for methane based $C_2$ production, in a product gas from an OCM reactor or reactors 1002, and separation process 1004, that includes a first separator 1006 providing the C₂-rich effluent 1052 and a methane/nitrogen-rich effluent 1074. In the embodiment illustrated in FIG. 10, the OCM product gas from the OCM reactor(s) 1002 is compressed through compressor 1026. The temperature of the compressed OCM product gas 1050 is reduced using one or more heat exchangers 1010. The temperature of the compressed OCM product gas 1050 may be reduced through the use of an external provided cooling media, introduction of or thermal exchange with a cool process stream, or combinations of these. Reducing the temperature of the OCM product gas 1050 will typically condense at least a portion of the higher boiling point components in the compressed OCM product gas 1050, including at least a portion of the C₂ and heavier hydrocarbon components present in the compressed OCM product gas 1050.

At least a portion of the condensed high boiling point components can be separated from the compressed OCM product gas 1050 using one or more liquid gas separators, such as knockout drums 1012 to provide an OCM product gas condensate 1054 and a compressed OCM product gas 1056. The OCM product gas condensate 1054 is introduced to the first separator 1006 and at least a portion 1058 of the compressed OCM product gas 1056 can be introduced to one or more turboexpanders 1014. The isentropic expansion of the compressed OCM product gas 1058 within the turboexpanders 1014 can produce shaft work useful for driving one or more compressors or other devices in the separation unit 1004. The isentropic expansion of the compressed OCM product gas 1058 with the turboexpanders reduces the temperature of the compressed OCM product gas 1060 that exits from the one or more turboexpanders. The compressed OCM product gas 1060 from the one or more turboexpanders 1014 is introduced to the first separator 1006.

The first separator 1006 can be any system, device or combination of systems and devices suitable for promoting the separation of C₂ and heavier hydrocarbons from a gas stream that includes methane and nitrogen. For example, cryogenic distillation at a relatively high temperature may be used to promote separation of the C₂ and heavier hydrocarbons from the methane and nitrogen components in the gas stream. The C₂-rich effluent 1052 is withdrawn from the first separator 1006 and a mixed nitrogen and methane containing gas mixture 1074 is also withdrawn from the first separator 1054. The nitrogen content of the nitrogen/methane containing gas mixture 1074 withdrawn from the first separator 1006 can be about 95 mol % or less; about 85 mol % or less; about 75 mol % or less; about 55 mol % or less; about 30 mol % or less. The balance of the nitrogen/methane gas mixture 1054 comprises principally methane with small quantities of hydrogen, carbon monoxide, and inert gases such as argon. The nitrogen/methane rich gas 1074 is then further cooled using heat exchanger(s) 1022, and the cooled nitrogen/methane containing gas 1076 is then introduced into second separator 1008, described in more detail, below.

In at least some embodiments, the first separator functions as a "demethanizer" based upon its ability to separate methane from the C₂ and heavier hydrocarbon components. An exemplary first separator 1006 includes a vertical distillation column operating at below ambient temperature and above ambient pressure. In particular, the operating temperature and pressure within the first separator 1006 can be established to improve the recovery of the desired C₂ hydrocarbons in the C₂-rich effluent 1052. In exemplary embodiments, the first separator 1006 can have an overhead operating temperature of from about −260° F. (−162° C.) to about −180° F. (−118° C.); about −250° F. (−157° C.) to about −190° F. (−123° C.); about −240° F. (−151° C.) to about −200° F. (−129° C.; or even from about −235° F. (−148° C.) to about −210° F. (−134° C.) and a bottom operating temperature of from about −150° F. (−101° C.) to about −50° F. (−46° C.); about −135° F. (−93° C.) to about −60° F. (−51° C.); from about −115° F. (−82° C.) to about −70° F. (−57° C.); or about −100° F. (−73° C.) to about −80° F. (−62° C.). In an exemplary aspect, the first separator 1006 may operate at pressures of from about 30 psig (205 kPa) to about 130 psig (900 kPa); about 40 psig (275 kPa) to about 115 psig (790 kPa); about 50 psig (345 kPa) to about 95 psig (655 kPa); or about 60 psig (415 kPa) to about 80 psig (550 kPa).

The temperature of at least a portion of the C₂-rich effluent 1052 from the first separator 1006 can be increased in one or more heat exchangers 1016, again using an externally supplied heat transfer medium, introduction of, or thermal contact, with a warmer process flow stream, or a combination of these, or other heating systems. The one or more heat exchanger devices 1016 may include any type of heat exchange device or system, including but not limited to one or more plate and frame, shell and tube or similar heat exchanger system. After exiting the one or more heat exchangers 1016, the heated C₂-rich effluent 1052 may be at temperatures of 50° F. (10° C.) or less; 25° F. (−4° C.) or less; about 0° F. (−18° C.) or less; about −25° F. (−32° C.) or less; or about −50° F. (−46° C.) or less. Furthermore, the pressure may be about 130 psig (900 kPa) or less; about 115 psig (790 kPa or less; about 100 psig (690 kPa) or less; or about 80 psig (550 kPa) or less.

In some embodiments, a portion 1062 of the OCM product gas 1056 removed from the knockout drum 1012 and not introduced into the one or more turboexpanders 1014 can be cooled using one or more heat exchangers 1018. As noted previously, the heat exchangers may include any type of heat exchanger suitable for the operation. The temperature of the portion 1062 of the OCM product gas 1056 can be decreased using one or more refrigerants, one or more relatively cool process flows, or combinations of these. The cooled portion 1064 of the OCM product gas 1056 containing a mixture of nitrogen and methane is introduced into the second separator 1008.

The second separator 1008 may include any system, device or combination of systems and devices suitable for separating methane from nitrogen. For example, cryogenic distillation at a relatively low temperature can be used to promote the separation of liquid methane from gaseous nitrogen within the second separator 1008. An exemplary second separator 1008 may include another vertical distillation column operating significantly below ambient temperature and above ambient pressure, and also generally below the temperature of a cryogenic distillation column operating as the first separator, e.g., as described above. For example, the second separator 1008 may have an overhead operating temperature of from about −340° F. (−210° C.) to about −240° F. (−151° C.); from about −330° F. (−201° C.) to about −250° F. (−157° C.); about −320° F. (−196° C.) to about −260° F. (−162° C.); about −310° F. (−190° C.) to about −270° F. (−168° C.); or about 300° F. (−184° C.) to about −280° F. (−173° C.); and a bottom operating temperature of from about −280° F. (−173° C.) to about −170° F. (112° C.); about −270° F. (−168° C.) to about −180° F. (−118° C.); about −260° F. (−162° C.) to about −190° F. (−123° C.); about −250° F. (−159° C.) to about −200° F. (−129° C.); or about −240° F. (−151° C. to about −210° F.

(−134° C.). In exemplary embodiments, the second separator 1008 will typically operate at pressures of from about 85 psig (585 kPa) or less; about 70 psig (480 kPa) or less; about 55 psig (380 kPa) or less; or about 40 psig (275 kPa) or less.

The temperature of at least a portion of the methane-rich effluent 1066 from the second separator 1008 can be increased using one or more heat exchangers 1020, as described above. After exiting the one or more heat exchangers 1020, in exemplary embodiments the temperature of the methane-rich effluent 1066 may be about 125° F. (52° C.) or less; about 100° F. (38° C.) or less; or about 90° F. (32° C.) or less, while the pressure of the effluent 1066 may be about 150 psig (1035 kPa) or less; about 100 psig (690 kPa) or less, or about 50 psig (345 kPa) or less. In an embodiment, e.g., schematically illustrated in FIG. 10, at least a portion of the methane-rich effluent 1066 may be recycled back into the feedstock gas 1068 for the OCM reactor(s) 1002, the feedstock gas/oxygen mixture 1070 the compressed oxygen containing gas 1072 (from compressor 1028) or directly to the one or more OCM reactors 1002.

The temperature of at least a portion of the nitrogen-rich effluent 1068 from second separator 1008 can be increased using one or more heat exchangers 1024 like those described above, such that the temperature may be raised to about 125° F. (52° C.) or less; 100° F. (38° C.) or less; or about 90° F. (32° C.) or less, with a pressure of about 150 psig (1035 kPa) or less; about 100 psig (690 kPa) or less; or about 50 psig (345 kPa) or less.

As will be appreciated, in integrating overall systems, while the one or more heat exchangers 1010, 1016, 1018, 1020, 1022 and 1024 are illustrated as separate heat exchange devices, such heat exchangers may be integrated into one or more integrated systems, where the different temperature process flows may be provided in thermal contact, e.g., as heat exchange media for each other, with in the heat exchange device or system. In particular, a cooled process flow that is desired to be heated may be passed through an opposing portion of a heat exchanger from a heated process flow that is desired to be cooled, such that the heat from the heated flow heats the cooler flow, and is, as a result, itself cooled.

Ethylene products of these processes, e.g., in $C_2$-rich effluent 1052, are then subjected to additional processing to yield the desired higher hydrocarbon compositions. For ease of discussion, the processes and systems for converting ethylene into higher hydrocarbons are referred to generally as ethylene conversion processes and systems. A number of exemplary processes for ethylene conversion are described in greater detail herein.

ETL Integration with Hydrocarbon Processes

The conversion of methane to ethylene, as well as the conversion of ethylene to higher hydrocarbon compositions, can be carried out in integrated processes. In some cases, conversion of ethylene to higher hydrocarbons is performed without conversion of methane to ethylene. As used herein, integrated processes refers to two or more processes or systems that are fluidly integrated or coupled together. Thus, the process for conversion of methane to ethylene can be fluidly connected to one or more processes for ethylene conversion to one or more higher hydrocarbon compounds. Fluid integration or fluid coupling generally refers to a persistent fluid connection or fluid coupling between two systems within an overall system or facility. Such persistent fluid communication typically refers to an interconnected pipeline network coupling one system to another. Such interconnected pipelines may also include additional elements between two systems, such as control elements, e.g., heat exchangers, pumps, valves, compressors, turbo-expanders, sensors, as well as other fluid or gas transport and/or storage systems, e.g., piping, manifolds, storage vessels, and the like, but are generally entirely closed systems, as distinguished from two systems where materials are conveyed from one to another through any non-integrated component, e.g., railcar or truck transport, or systems that are not co-located in the same facility or immediately adjacent facilities. As used herein, fluid connection and/or fluid coupling includes complete fluid coupling, e.g., where all effluent from a given point such as an outlet of a reactor, is directed to the inlet of another unit with which the reactor is fluidly connected. Also included within such fluid connections or couplings are partial connections, e.g., where only a portion of the effluent from a given first unit is routed to a fluidly connected second unit. Further, although stated in terms of fluid connections, it will be appreciated that such connections include connections for conveying either or both of liquids and/or gas.

In some instances, a methane to ethylene conversion process is not just integrated with a single ethylene conversion process, but instead, is integrated with multiple (i.e., two or more) different ethylene conversion processes or systems. In particular, ethylene produced from a single methane feed stream may be converted to multiple different products using multiple different ethylene conversion processes. For example, in some embodiments a single OCM reactor system is fluidly connected to one, two, three, four, five or more different catalytic or other reactor systems for further conversion of the ethylene containing product of the OCM reactor system (also referred to herein as the "ethylene product") to multiple different higher hydrocarbon compositions.

In some aspects, the ethylene product is selectively directed in whole or in part to any one or more of the various ethylene conversion processes or systems integrated with the OCM reactor system. For example, at any given time, all of the ethylene product produced through an OCM reactor system may be routed through a single process. Alternatively, a portion of the ethylene product may be routed through a first ethylene conversion process or system, while some or all of the remaining ethylene product is routed through one, two, three, four or more different ethylene conversion systems.

Although described in terms of directing ethylene streams to a single or multiple different ethylene conversion processes, in some aspects, those ethylene streams may be relatively dilute ethylene streams, e.g., that contain other components in addition to ethylene, such as other products of the OCM reaction, unreacted feed gases, or other by products. Typically, such other components may include additional reaction products, unreacted feedgases, or other reactor effluents from an ethylene production process, e.g., OCM, such as methane, ethane, propane, propylene, CO, $CO_2$, $O_2$, $N_2$, $H_2$, and/or water. The use of dilute ethylene streams, and particularly those containing other hydrocarbon components can be particularly advantageous in the ethylene conversion processes. In particular, because these ethylene conversion processes can utilize more dilute and less pure streams, the incoming ethylene streams may not be required to go through as stringent a separations process or processes as may be required for other processes intended to produce higher purity ethylene, e.g., cryogenic separations systems, lean oil separators, TSA and PSA based separations processes. These separations processes typically have relatively high capital costs that scale, at least in part, based upon the volume of incoming gases. As such, separation processes for highly dilute ethylene streams can have substantially high capital and operating costs associated with them. By providing less stringent separations requirements on these ethylene streams, one can substantially reduce the capital costs. Further, because the ethylene conversion processes used in conjunction with the invention typically result in the production of desired liquid hydrocarbons, subsequent separation of gas co-products, or unreacted feed gases is made much simpler.

In addition to reducing capital and operating costs, the use of ethylene streams that comprise additional hydrocarbon components can enhance the product slate emanating from the ethylene conversion processes through which those ethylene streams are routed. In particular, the presence of higher order hydrocarbons, $C_3$, $C_4$, $C_5$, etc. in the ethylene streams entering into the ethylene conversion processes can improve the overall efficiency of those processes, by providing enriched starting materials, and also affects the overall carbon efficiency of the OCM and ethylene conversion processes, by ensuring that a greater fraction of the carbon input is converted to higher hydrocarbon products.

While ethylene streams being routed to the ethylene conversion processes of the invention may range anywhere from trace concentrations of ethylene to pure or substantially pure ethylene, e.g., approaching 100% ethylene, the dilute ethylene streams described herein may generally be characterized as having anywhere from about 1% to about 50% ethylene, preferably, between about 5% and about 25% ethylene, and in further preferred aspects, between about 10% and about 25% ethylene, in addition to other components. In other embodiments, the ethylene feed gas comprises less than about 5% ethylene, for example less than about 4%, less than about 3%, less than about 2% or even less than about 1% ethylene. In some embodiments, the dilute ethylene product gases employed in the ethylene conversion processes further comprise one or more gases which are either produced during the OCM reaction or are unreacted during the OCM process. For example, in some embodiments the product gas comprises ethylene at any of the foregoing concentrations and one or more gas selected from $CO_2$, CO, $H_2$, $H_2O$, $C_2H_6$, $CH_4$ and $C_{3+}$ hydrocarbons. In some embodiments, such dilute ethylene feed gasses, which optionally include one or more of the foregoing gases are advantageous for use in reactions comprising conversion of ethylene to higher olefins and/or saturated hydrocarbons, for example conversion of ethylene to liquid fuels such as gasoline diesel or jet fuel at higher efficiencies (e.g., from methane) than previously attainable.

By utilizing dilute ethylene streams to feed into one or more ethylene conversion processes, one eliminates the need to separate or purify the ethylene coming into the process, e.g., as a product of an OCM reaction process. The elimination of additional costly process steps is particularly useful where the ethylene conversion processes are used to produce lower margin products, such as gasoline, diesel or jet fuel or blendstocks for these fuels. In particular, where the desired product is a lower value product, one may pass the OCM feed gases directly into one or more ethylene conversion processes that produce hydrocarbon mixtures that can be used as gasoline, diesel fuel or jet fuel or their blendstocks. Such direct passage may be in the absence of any intermediate purification steps, such as any processes used for the removal of the above described impurities. Alternatively, it may include certain purification steps to separate out some or all of the non-hydrocarbon impurities, e.g., $N_2$, $CO_2$, CO, $H_2$, etc. The direct passage may avoid any hydrocarbon fractionation, including removal of any of $C_1$, $C_2$, $C_3$, $C_4$ compounds, or it may include some fractionation, e.g., to enhance carbon efficiency. For example, such included fractionation may include separation of methane and or ethane from the OCM effluent gas to recycle back to the OCM process. In addition to the foregoing, the presence of additional components such as $CO_2$, $H_2O$ and $H_2$ in the feed streams may also be expected to improve catalyst lifetime in the ethylene conversion processes by reducing deactivation, thereby requiring fewer catalyst regeneration cycles.

In contrast, where one desires to produce more selectively pure compounds, e.g., aromatic compounds, one may need to pretreat the feed gases to remove many of the non-ethylene impurities.

Other components of these dilute ethylene streams may include co-products of the ethylene production processes, e.g., OCM reactions, such as other $C_{2+}$ hydrocarbons, like ethane, propane, propylene, butane, pentane, and larger hydrocarbons, as well as other products such as CO, $CO_2$, $H_2$, $H_2O$, $N_2$, and the like.

A variety of different ethylene conversion processes may be employed in the various aspects of the present invention to produce higher hydrocarbon materials for use in, e.g., chemical manufacturing, polymer production, fuel production, as well as a variety of other products. In particular, the ethylene produced using the OCM processes may be oligomerized and/or reacted by a variety of different processes and reactor systems for producing linear alpha-olefins (LAOs), olefinic linear and/or olefinic branched hydrocarbons, saturated linear and/or branched hydrocarbons, saturated and/or olefinic cyclic hydrocarbons, aromatic hydrocarbons, oxygenated hydrocarbons, halogenated hydrocarbons, alkylated aromatics, and/or hydrocarbon polymers.

In some cases, an ETL sub-system configured to perform an ethylene conversion process (e.g., oligomerization) can be located between two OCM sub-systems. A first OCM sub-system produces a first OCM effluent comprising ethylene and other olefins (e.g., propylene). This first OCM effluent can be fed into the ETL sub-system, wherein olefins (e.g., ethylene, propylene) are oligomerized and converted into higher hydrocarbon products. These higher hydrocarbon oligomerization products can be recovered from the ETL effluent. The ETL effluent can be fed into a second OCM sub-system, where unreacted methane can be converted into ethylene and other olefins (e.g., propylene) in a second OCM process. The reduced content of $C_2$ and $C_3$ compounds in the second OCM feed stream (due to the consumption of $C_2$ and $C_3$ compounds in the ETL or oligomerization process) can result in decreased OCM side reactions and increased $C_2$ selectivity in the second OCM sub-system. The effluent from the second OCM sub-system can be processed in a variety of ways, including by separation in a separations system (e.g., a 3-way cryogenic separations system). A separations system can be used to recover methane, which can be recycled to the first or second OCM system, olefin products (e.g., ethylene, propylene), and gases such as $N_2$, CO, and $H_2$.

ETL processes can result in products such as $C_3$ and $C_4$ products, including olefins. Rather than being flared or used for fuel value, these light olefins can be oligomerized into higher-value products. $C_3$ olefins, $C_4$ olefins, or a combination thereof can be recovered from an ETL product stream as a light olefin fraction. This light olefin fraction can be reacted in a separate oligomerization reactor to produce higher molecular weight olefins, such as those in the $C_6$ to $C_{16}$ range. The molecular weight range of the oligomerization products can be tuned by appropriate choice of catalyst and process parameters. This approach provides the benefit of increased yield of higher molecular weight products, including products that are non-aromatic and mostly olefinic. This oligomerization process can result in little or no coke formation or other deactivation mechanisms. This oligomerization process can operate at a temperature of at least about 50° C. This oligomerization process can operate at a temperature of at most about 200° C. This oligomerization process can operate at a temperature from about 50° C. to about 200° C. Oligomerization catalysts useful for this process include strong Lewis acid catalysts, $AlCl_3$/water solutions, solid superacids, and other solid acid catalysts capable of oligomerizing C3 and C4 olefins. C4 olefins in this process can also be used with an alkylation process to generate iso-octane. Reactor configurations useful for this process include slurry bed, fixed bed, tubular/isothermal, moving bed, and fluidized bed reactors, including those disclosed herein (e.g., FIG. 4).

OCM processes, ETL processes, and combinations thereof (e.g., OCM-ETL) can result in methane (e.g., unreacted methane), ethane, and $C_{3+}$ non-olefinic hydrocarbon compounds. These compounds (e.g., methane, ethane, propane, and combinations thereof) can be converted into aromatic hydrocarbons. For example, excess methane and ethane from an OCM process can be converted into aromatics with the use of a catalyst appropriate for ETL, such as those discussed in this disclosure. Such catalysts can be doped with compounds including but not limited to molybdenum (Mo), gallium (Ga), tungsten (W), and combinations thereof. These conversions to aromatic products can occur in an ETL reactor, as described, and can also involve the conversion of ethylene to aromatic products.

Integration of ETL and/or OCM-ETL with Hydrocarbon Processes

The present disclosure provides methods for integrating ETL sub-systems (or modules) with OCM sub-systems. Such integration can advantageously enable the formation of products that can be tailored for various uses, such as, for example fuel. Such integration can enable the conversion of ethylene in a $C_{2+}$ product stream from an OCM reactor to be converted to higher molecular weight hydrocarbons.

OCM, ETL and OCM-ETL methods and systems of the present disclosure can be used in greenfield and brownfield contexts. For example, in a brownfield investment initiative, an OCM-ETL system can be installed in an old oil refinery. As another example, in a greenfield investment initiative, an OCM-ETL system can be installed in a new parcel of round that has access to natural gas. Brownfield and greenfield initiatives of OCM can be used to meet world scale production of ethylene.

The present disclosure can be used to form ethylene for various uses, such as liquefied natural gas (LNG) integration. Liquefied natural gas (LNG) can be used to enable simplified transport of natural gas with its volume reduced by at least about 100×, 200×, 300×, 400×, 500×, or 600× as enabled by cooling from a vapor to a liquid. LNG facilities can include several main process areas—gas treatment area where natural gas has acid gases, water, and mercury removed; NGL extraction area; NGL fractionation area; and LNG liquefaction and storage areas. $C_{4+}$ products from raw natural gas are typically recovered in the fractionation area.

Substantial capital reduction and improved mixed $C_4$ and $C_{5+}$ yields can be realized by integrating an OCM/ETL process train into the traditional LNG facility. An OCM-ETL process may be added to LNG facility such that it utilizes a portion of the main gas stream that has passed through gas treatment and NGL extraction. Additional feedstock to the post-bed reactor section of the OCM may include ethane and propane both fed from high purity streams generated in the NGL fractionation area. The generated additional mixed $C_4$ and $C_{5+}$ products can be recovered though using available capacity in the NGL fractionation process area. The $C_4$ and $C_{5+}$ products can be referred to as "SBOB," which may be any composition similar to RBOB but not meeting one or more ASTM standards.

Alternatively, the process may utilizes the above gas streams (main gas stream, ethane and propane from fractionation area) in addition to a dilute methane containing stream produced by the nitrogen rejection unit in the LNG liquification area. LNG plants can utilize this stream as low BTU fuel gas for internal energy generation. The product gas from the OCM-ETL process area can be fed back into precool portion of the NGL extraction thus enabling proper extraction of the $C_{3+}$ components as well as generation of a similar low BTU fuel gas. The mixed $C_4$ and $C_{5+}$ (SBOB) products can be recovered though using available capacity in the NGL fraction process area.

In an example, an OCM-ETL process area can include OCM reaction and heat recovery areas, process gas compression, ETL guard bed and reaction section. Steam generated in the OCM heat recovery area can be effectively used in a refrigerant compressor area to reduce external power usage.

Figure 11:
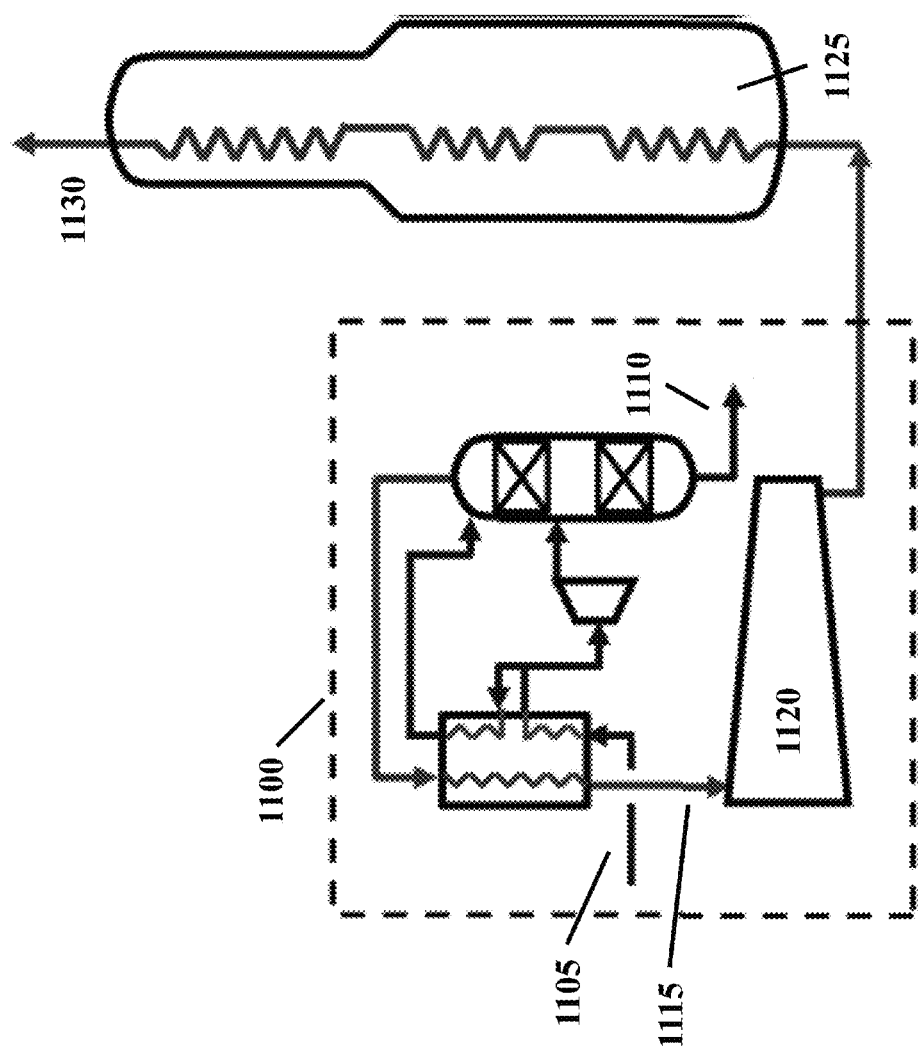
FIG. 11 shows an example of NGL extraction in a liquefied natural gas (LNG) facility.

An OCM-ETL system can be integrated with an LNG facility. To meet the LNG specification any heavy hydrocarbon (HHC) (e.g., butanes, pentanes and higher molecular weight) in the natural gas stream may be removed. However, with the natural gas being dry, it may be difficult to remove the HHC. Hence an LNG plant may require some HHC removal process. In some examples, liquids from an ETL system can be extracted in the pre-cooling process section of the LNG plant, requiring little to no additional investment. This may eliminate any additional NGL recovery system that may be required in a standalone OCM/ETL facility. In addition, a large amount of steam can be produced in the OCM/ETL system which can be effectively utilized as shaft power for the refrigerant compressors. FIG. 11 shows an example of NGL extraction in an LNG facility. The front-end NGL extraction unit 1100 can take natural gas 1105 and separate out the natural gas liquids (NGLs) 1110. The remaining methane 1115 can be compressed 1120 and cooled 1125 to provide liquified natural gas (LNG) 1130.

Figure 12:
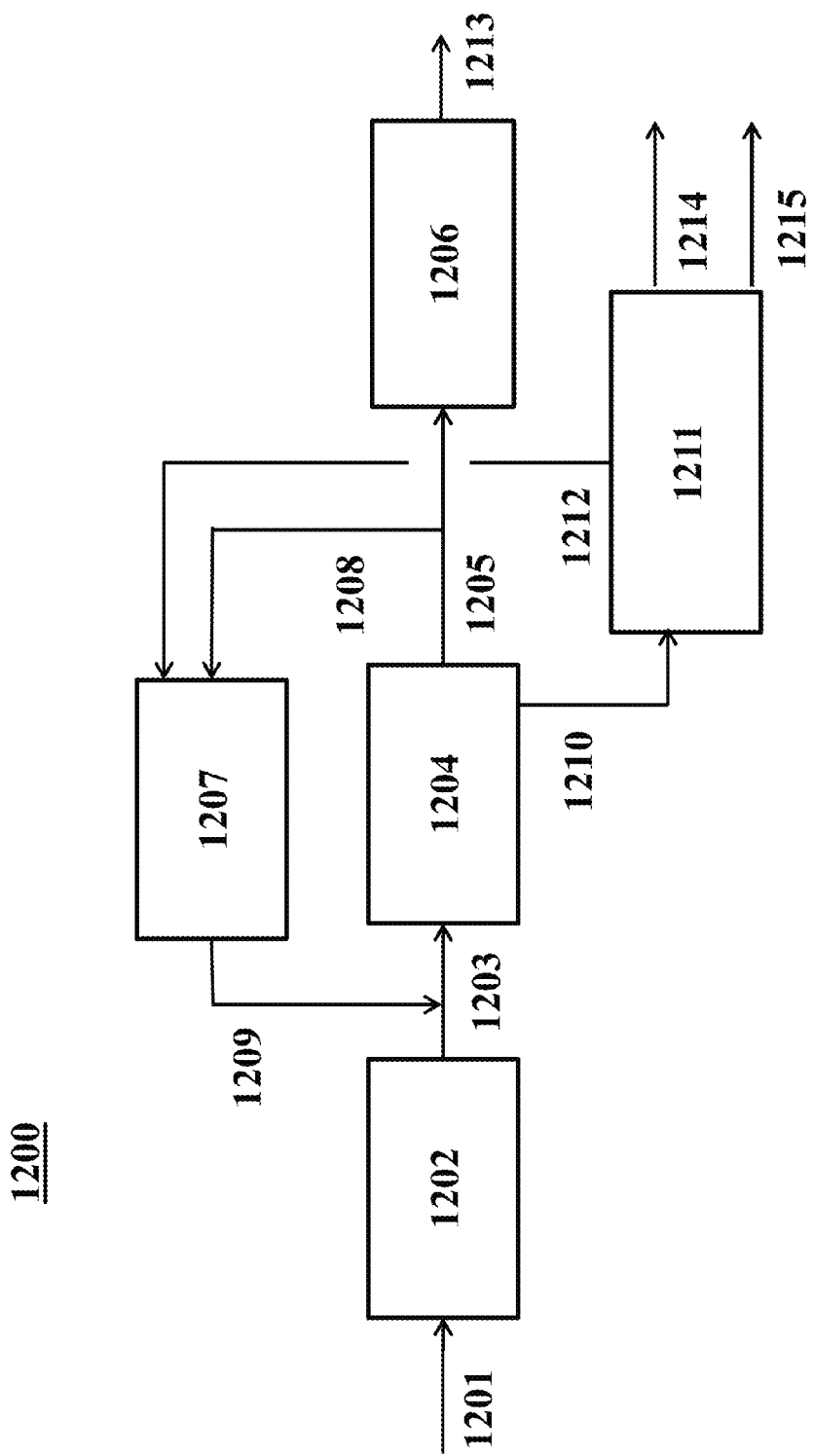
FIG. 12 shows an integrated OCM-ETL system for use in LNG production.

FIG. 12 shows an integrated OCM-ETL system for use in LNG production. The system includes a gas treatment unit, a downstream NGL extraction unit, a liquefaction unit, and an OCM/ETL sub-system that generates olefins, such as ethylene. The direction of fluid flow is indicated by the arrows. The system of FIG. 12 can provide increased $C_{5+}$ and mixed $C_4$ production. The system of FIG. 12 is exemplary of a typical gas processing plant 1200, with an OCM-ETL integration. The system contains a gas treatment unit 1202 which takes the incoming natural gas feed stream 1201. The gas treatment unit can comprise one or more of an acid gas removal unit, a dehydration unit, mercury removal unit, sulfur removal unit, or other treatment units. In some cases the acid gas removal unit is an amine unit, a pressure swing adsorption (PSA) unit, or another $CO_2$ removal system. In some cases, the dehydration unit can be a glycol based water removal unit, a pressure swing adsorption (PSA) unit and may include a series of separators. A mercury removal unit can comprise a molecular sieve or an activated carbon based system. The gas treatment unit can also comprise a nitrogen removal unit (NRU). An NRU can employ a cryogenic process or an absorption or an adsorption based process. The treated natural gas feed 1203 is fed to the NGL extraction unit 1204, which separates the NGL stream 1205 and a condensate stream containing heavier hydrocarbons 1210. The heavier hydrocarbons may be $C_{4+}$ hydrocarbons. The NGL extraction unit can comprise an adsorption process unit, a cooling unit (cooling achieved, for example, either by Joule Thompson expansion, methanol or glycol refrigeration, or a turboexpander), or a lean oil absorption unit. A part of the stream 1205 is fed to the OCM-ETL reactor system 1207 as stream 1208, where the methane contained in the stream 1208 is converted to heavier liquid hydrocarbons via OCM and subsequent ETL conversion in the reactor system 1207. The liquid hydrocarbons are fed along stream 1209 back to the NGL extraction unit to recover the unconverted methane, and separate the heavier condensates and route them along stream 1210 to NGL ETL fractionation unit 1211. The NGL ETL fractionation unit can comprise a series of fractionation tower units, including but not limited to a depropanizer and a debutanizer to generate a mixed $C_4$ product 1214, a $C_{5+}$ product 1215. The liquefaction unit 1206 produces LNG product 1213. The advantage of integrating an OCM-ETL reactor system with an existing natural gas processing plant is envisaged in this case to generate much more valuable mixed $C_4$ and $C_{5+}$ products. In addition, the $C_2$ and $C_3$ lighter hydrocarbons from the fractionation unit 1211 can be recycled to the post bed cracking (PBC) section of the OCM reactor.

Figure 13:
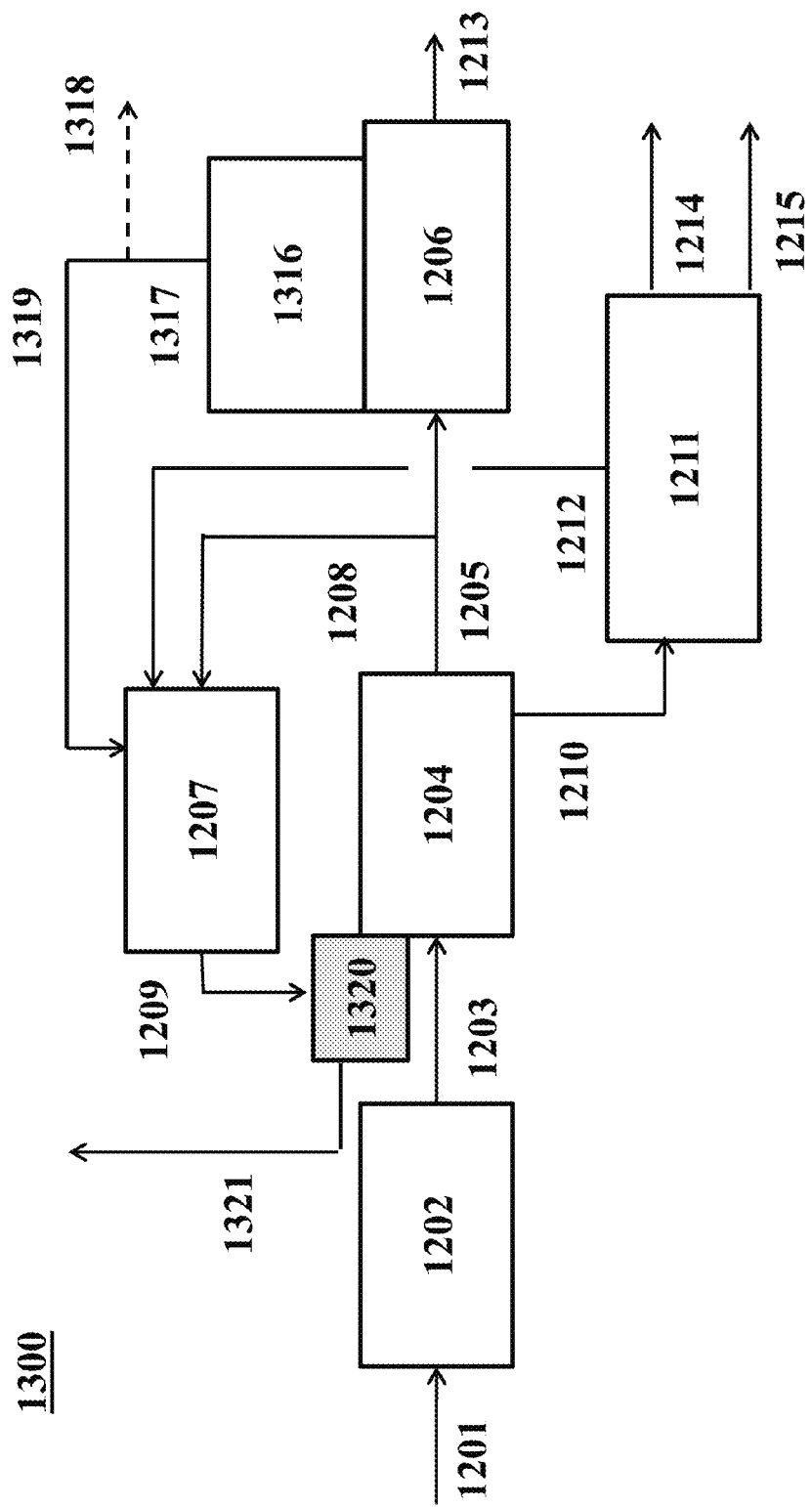
FIG. 13 shows the system of FIG. 12 that has been modified for use with a diluted C1 (methane) fuel gas stream.

The system of FIG. 12 can be modified for use with a diluted $C_1$ (methane) fuel gas stream, as shown in FIG. 13. The system 1300 of FIG. 13 includes a pre-cooling system 1320 upstream of the NGL extraction unit to extract $C_{3+}$ compounds, as well as a nitrogen rejection unit 1316 downstream of the liquefaction unit. In addition to the system of FIG. 12, the system in FIG. 13 recycles a stream 1319 to the OCM-ETL reactor system to utilize more of the methane contained in the natural gas feed. The stream 1319 can comprise a high level of methane and inerts such as nitrogen. A fuel gas stream 1321 is purged from the precooling section to avoid the buildup of inerts in the system. The nitrogen rejection unit can comprise a cryogenic based, absorption based or adsorption based system.

Figure 14:
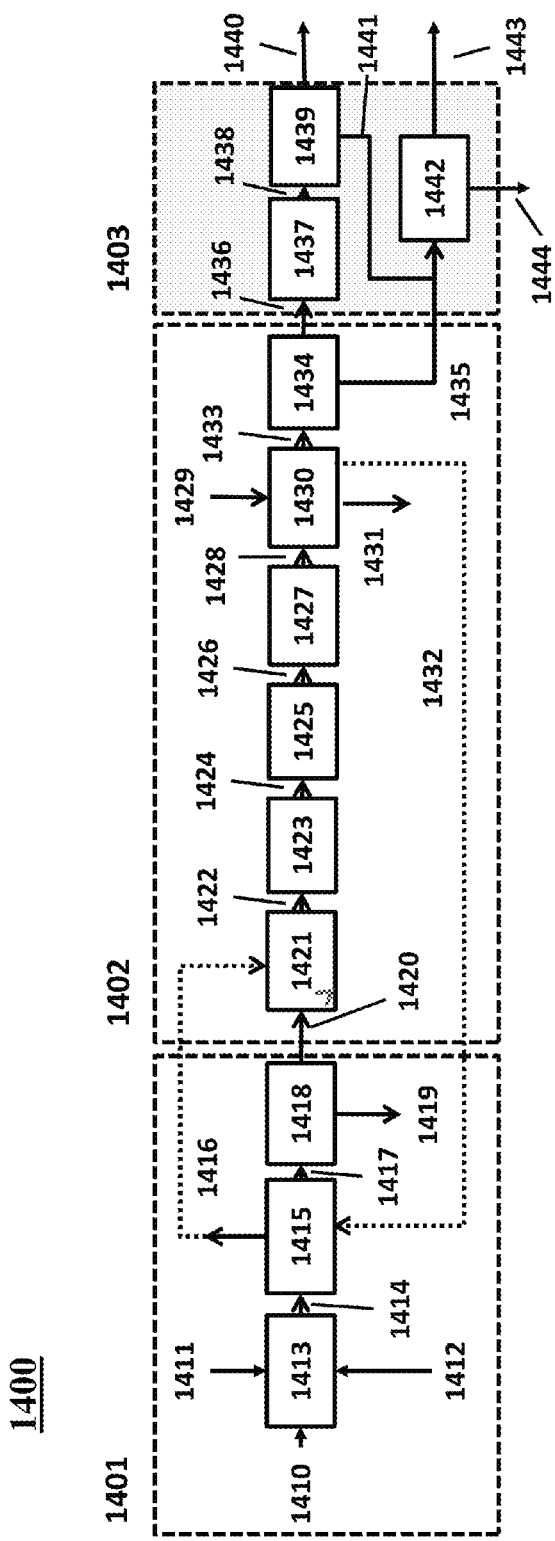
FIG. 14 shows an example OCM-ETL system comprising OCM and ETL sub-systems, and a separations sub-system downstream of the ETL sub-system.

FIG. 14 shows an example OCM-ETL system comprising OCM and ETL sub-systems, and a separations sub-system downstream of the ETL sub-system, where 1418 is a condensed water knockout, 1421 is a process gas compressor, 1423 is a guard bed to remove impurities such as acetylene and butadiene, 1415 and 1430 are heat recovery, 1437 is a secondary gas compressor, and 1439 is a low temperature separator. The system in FIG. 14 takes in a treated natural gas feed stream 1410 and oxygen 1411 from an air separation unit (ASU) or pipeline, and reacts them in the OCM reactor 1413 to generate an olefin rich stream 1414 which is then sent to an ETL reactor 1425 to be converted to higher hydrocarbons. The system shows the various subsystems as the compressors, heat recovery systems utilizing the high heat of reaction to generate steam and run the compressors on the steam produced. The system can comprise a methanation reactor 1427 to convert any CO and $CO_2$ produced back to methane, hence adding to the methane content of the sales gas. The separation subsystem 1403 can comprise a low temperature separator 1439 to generate lighter methane rich components. The debutanizer 1442 separates the heavy hydrocarbon condensate to a $C_4$ and $C_{5+}$ product.

Figure 15:
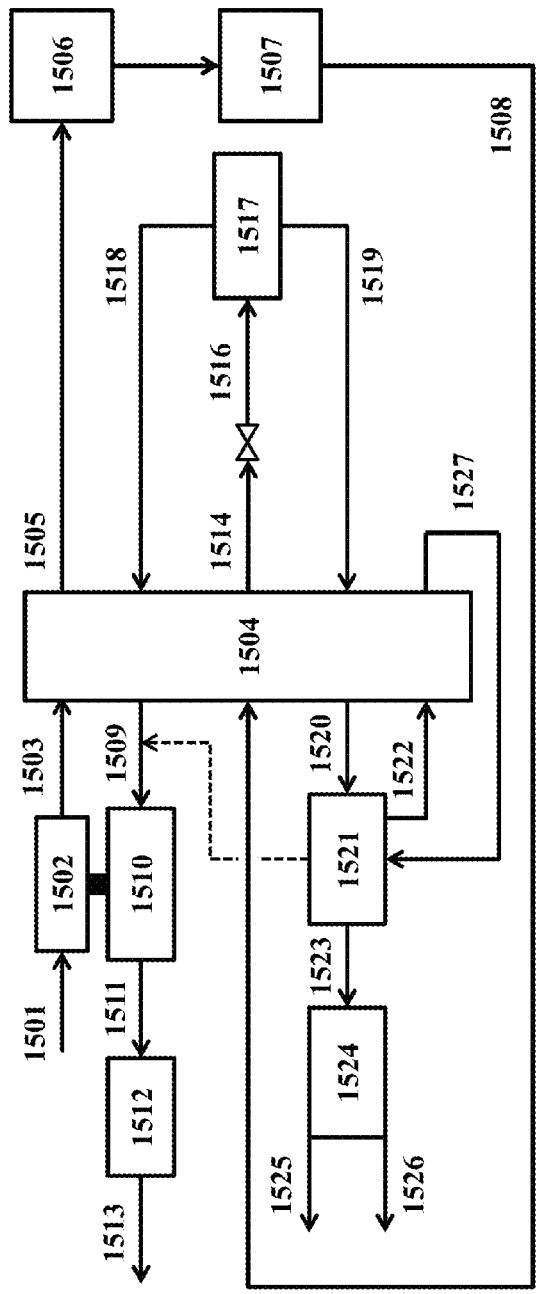
FIG. 15 shows an OCM-ETL system comprising OCM and ETL sub-systems, and a cryogenic cold box downstream of the ETL sub-system.

FIG. 15 shows an OCM-ETL system comprising OCM 1906 and ETL 1907 sub-systems, and a cryogenic cold box 1504 downstream of the ETL sub-system. The OCM-ETL system includes various separations units for separating $C_3$ 1521 and $C_4$ 1524 components from an ETL product out of the ETL sub-system. The depropanizer 1521 generates a $C_2$-rich stream which is recycled back to the sales gas export 1509. The $C_2$ recycle may also be added to the OCM-ETL reactor subsystem via a recycle stream 1522. The debutanizer produces a $C_4$ product 1525 and a $C_{5+}$ product 1526. Refrigeration for the cryogenic cold box can be provided by natural gas expansion 1502 from at least about 500 PSI, 600 PSI, 700 PSI, 800 PSI, 900 PSI, 1000 PSI, 1500 PSI, or 2000 PSI. The system can also have a methanation reactor (not shown) to further increase the methane concentration of the sales gas product. FIG. 15 indicates an approach to thermally integrate the different streams in the unit. The system can have an external refrigeration system to provide for the cryogenic requirements of the unit.

Figure 16:
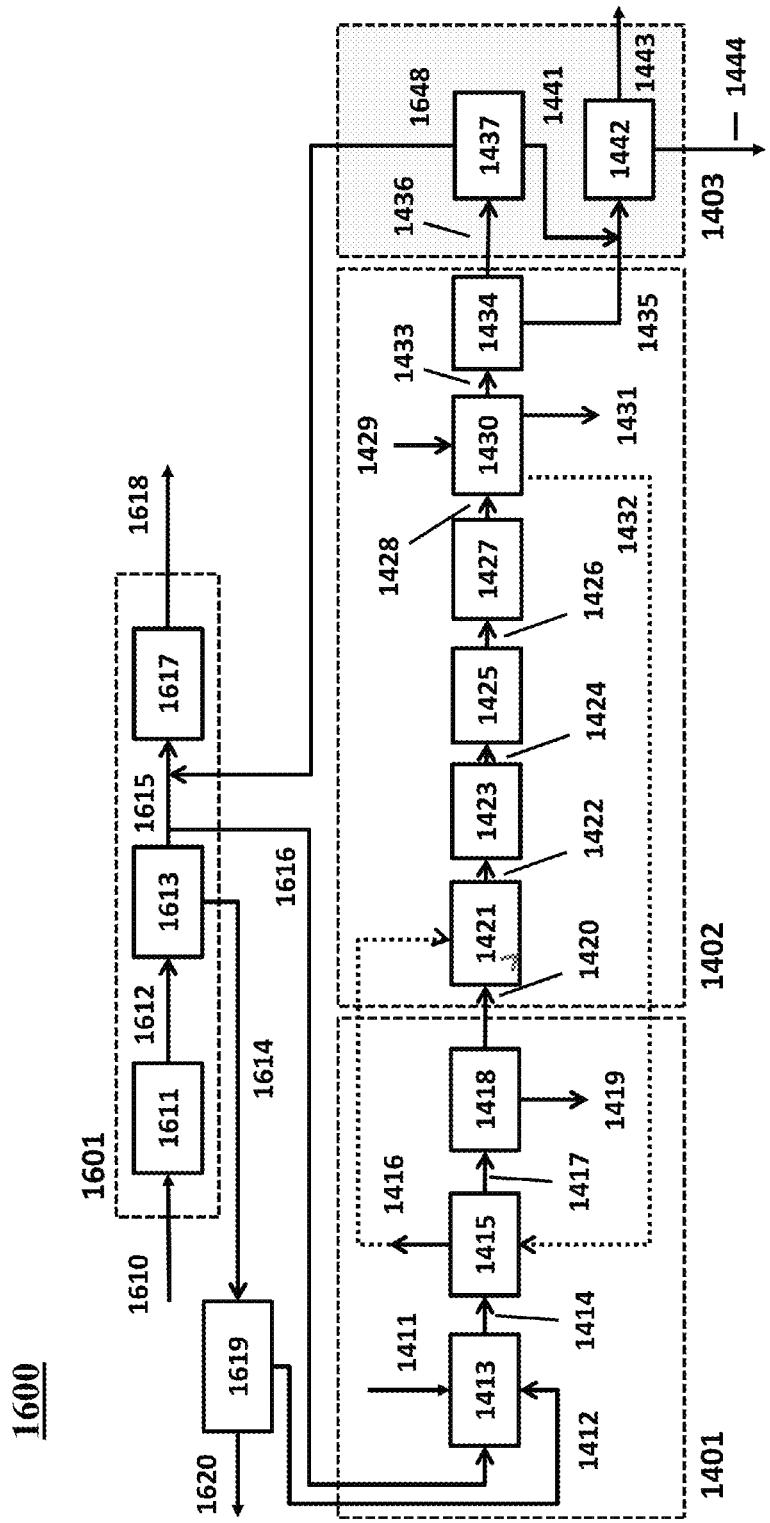
FIG. 16 shows another OCM-ETL in an alternative configuration to that shown in FIG. 14.

FIG. 16 shows another OCM-ETL in an alternative configuration to that shown in FIG. 14. The system allows for the recycle of various streams to the OCM reactor to improve the overall conversion. The methane rich stream 1648 from the low temperature separation unit 1437 and a $C_2$ rich stream 1412 from the deethanizer 1619 are recycled to the sales gas compressor 1617 and the OCM reactor 1413 respectively. The incoming natural gas feed 1610 is treated (to remove one or more of sulfur, mercury, water, or other components) in a treatment unit 1611 and then sent to the cryogenic unit 1613 to separate the heavier NGL liquids 1614 which are fed to the deethanizer 1619. The deethanizer 1619 separates the lighter LNG product 1620 from heavier $C_{2+}$ stream 1412. Feed to OCM is drawn after the cryogenic unit. As in the systems of FIG. 14 and FIG. 15, the separations subsystem generates a $C_4$ and $C_{5+}$ product.

It may be noted that the systems of FIG. 14, FIG. 15, and FIG. 16 can be integrated with an existing gas processing plant where one or more of the existing subsystems can be utilized. The utilization may arise from the fact that the existing subsystems are no longer used, or have an additional capacity available to allow for the integration.

OCM-ETL systems of the present disclosure can be integrated into and combined into conventional NGL extraction and NGL fractionation sections of a midstream gas plant. Where NGLs in the gas stream are declining (or gas is dry), the deployment of OCM-ETL can utilize an existing facility to produce additional liquid streams. The implementation of OCM-ETL can allow for the generation of on specification "pipeline gas." The products from the facility can be suitable for use (or on specification or "spec") as pipeline gas, gasoline product, hydrocarbon (HC) stream with high aromatic content and mixed $C_4$ product.

An OCM-ETL integrated facility can reduce ethane and propane product quantities to alleviate pipeline (sales-gas) specification and liquid handling constraints. Utilities and off-sites facilities can be effectively utilized. For example steam produced in the process can offset other shaft power requirements. The capacity of the OCM-ETL Facility can be varied and can be selected to best fit specific requirements.

Figure 17:
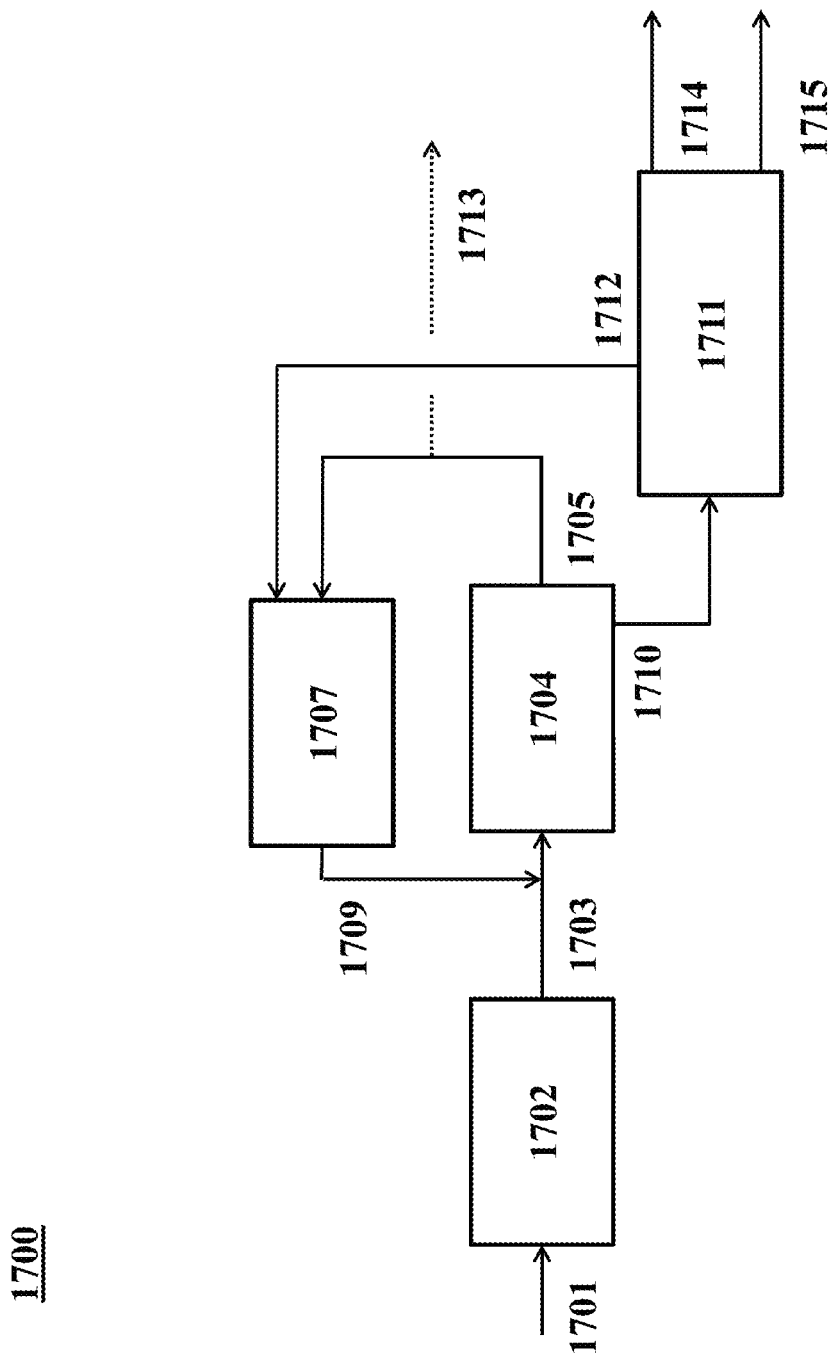
FIG. 17 show examples of OCM-ETL midstream integration.
Figure 18:
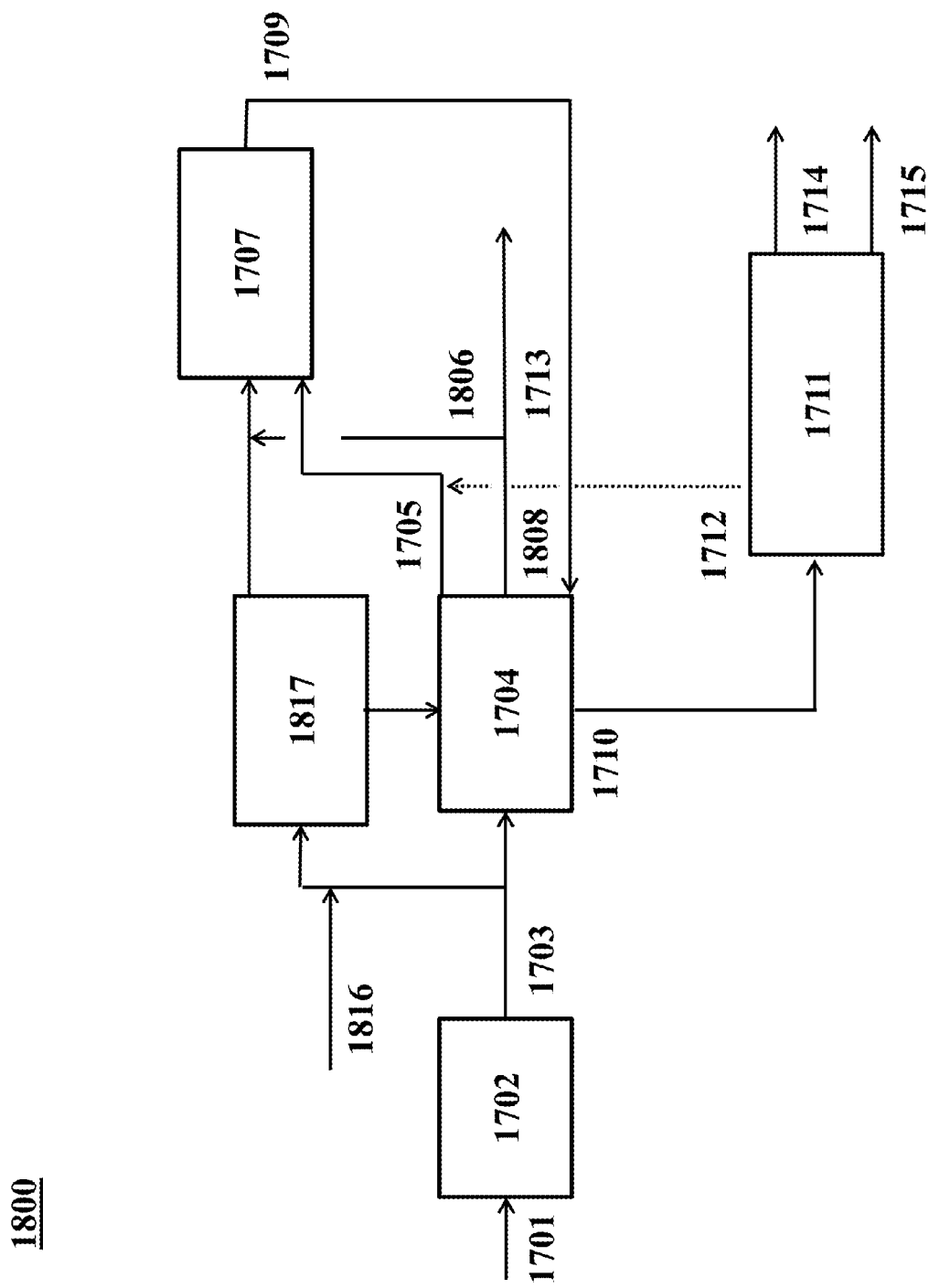
FIG. 18 show examples of OCM-ETL midstream integration.

FIGS. 17-18 show examples of OCM-ETL midstream integration. Natural gas 1701 from upstream can be fed to a gas treatment system 1702 and the treated natural gas can be fed to an NGL extraction unit 1704. In FIG. 17, $C_2$ and $C_3$ products 1705 from the NGL extraction unit 1704 can be directed to an OCM-ETL system 1707 to generate olefins (e.g., ethylene) and liquids 1709 from the olefins. Any excess or extracted methane can be directed for use as pipeline gas 1713. $C_{4+}$ hydrocarbons 1710 from the NGL extraction unit can be directed to an NGL product fractionation unit for separation in a separations system 1711 into mixed $C_4$ 1714 and $C_{5+}$ 1715 product streams, with light hydrocarbons 1712 recycled to the OCM-ETL system 1707. In the system 1800 of FIG. 18, methane from other natural gas sources 1816 is directed to a gas conditioning unit 1817 (e.g., to remove sulfur compounds) and subsequently directed to the OCM-ETL system 1707. Excess methane 1808 can be used as pipeline gas 1713, as an additional feed 1806 into the OCM-ETL system, or both.

Oxygen feed for an OCM unit in the OCM-ETL system can be provided from air, such as using an air separation unit (e.g., cryogenic air separation unit), or from an oxygen source, such as pipeline oxygen.

OCM-ETL systems provided herein can be integrated into a pipeline NG source, or as part of a new gas processing plant installation that may provide a source of NG. NG can be provided from a NG pipeline and/or from a non-OCM process.

In some cases, gas that has been depleted of recoverable hydrocarbon liquids can be recompressed to a pressure from about 700 PSI to 1500 PSI, or 800 PSI to 1300 PSI, or 900 PSI to 1200 PSI and returned to the pipeline from which it was initially skimmed. As an alternative or in addition to, gas that has been depleted of recoverable hydrocarbon liquids can be recompressed as needed and piped to downstream of cryogenic gas processing plant. As another alternative or in addition to, gas that has been depleted of recoverable hydrocarbon liquids may not be recompressed and is piped to power plant. As another alternative or in addition to, gas that has been depleted of recoverable hydrocarbon liquids can be recompressed as needed and is piped to ammonia plant for use as synthesis gas blending feedstock. As another alternative or in addition to, gas that has been depleted of recoverable hydrocarbon liquids can be recompressed as needed and piped to a methanol plant for use as synthesis gas feedstock blending.

Figure 19:
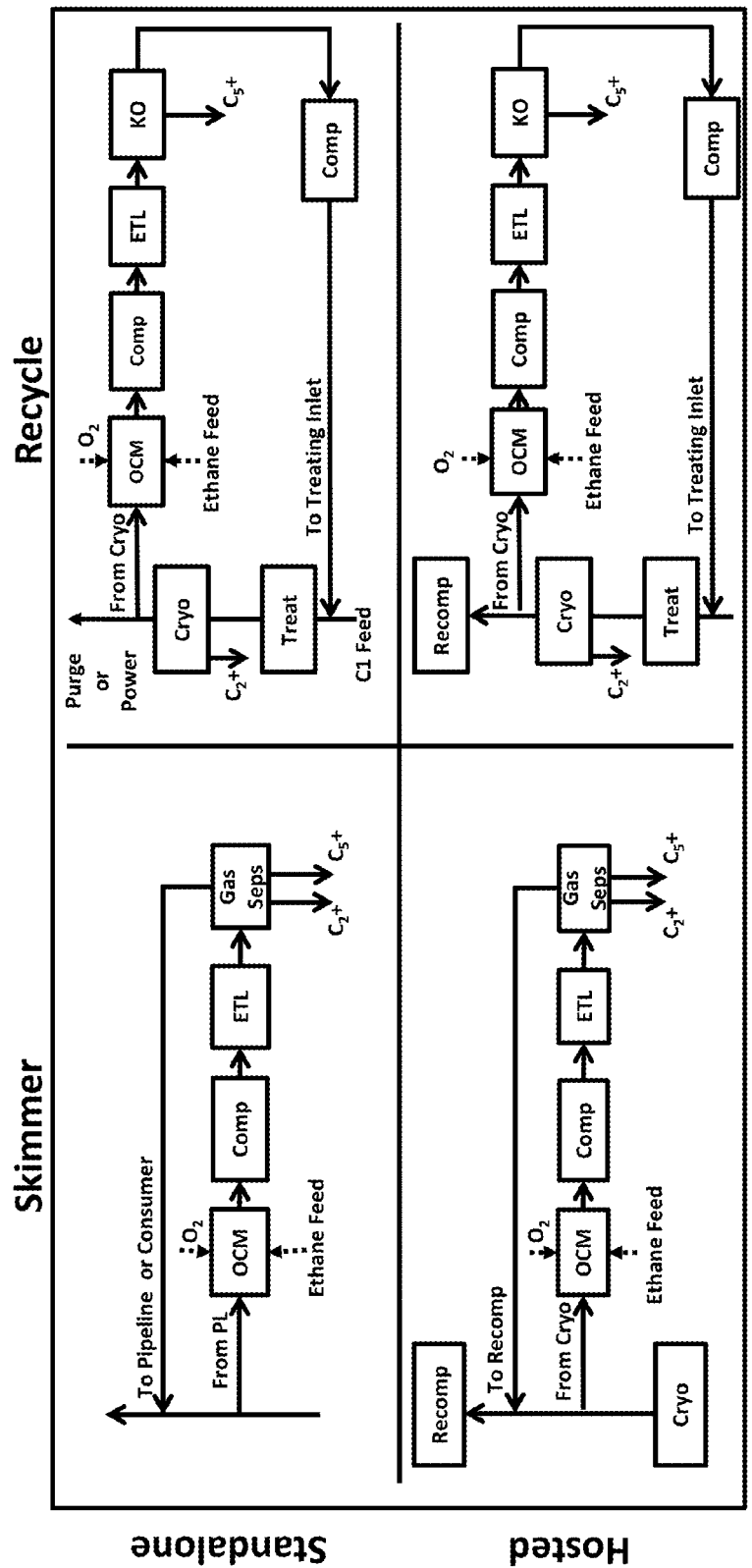
FIG. 19 shows OCM-ETL systems with various skimmer and recycle configurations.

FIG. 19 shows OCM-ETL systems with various skimmer and recycle configurations, including a standalone skimmer (top left), a hosted skimmer (bottom left), a standalone recycle (top right), and a hosted recycle (bottom right). Under the skimmer configurations, operation is a once-through process (feed moves forward) where all feed streams exit the system as product or effluent without recycle. Under the recycle configurations, some or all of the NG feed stream is exposed to the OCM catalyst multiple times (feed moves backward). Such configurations can be employed in stand-alone settings, in which all or substantially all unit operations are for OCM/ETL purposes, or hosted settings, in which the unit operations of an existing non-OCM system at least partially support the OCM-ETL system. The configurations of FIG. 19 can be used to with a NG feed of at least about 10 millions of cubic feet per day (mmcfd), 20 mmcfd, 30 mmcfd, 40 mmcfd, 50 mmcfd, 100 mmcfd, 200 mmcfd, 300 mmcfd, 400 mmcfd, 500 mmcfd, or 1000 mmcfd.

In some cases, depending on economic considerations, various separations intensities may be utilized for additional liquid product recovery. In an example, process gas that remains after a primary liquid recovery section is not further processed and is returned. In another example, process gas that remains after primary liquid recovery is fed to a Low Temperature Separator (LTS) unit where additional hydrocarbon liquids are recovered, such as $C_{4+}$. Effluent gas from this LTS is then returned, such recycled as described elsewhere herein.

In some cases, process gas that remains after primary liquid recovery can be fed to a coldbox-based cryogenic unit where additional hydrocarbon liquids are recovered, such as $C_{4+}$. This coldbox-based cryogenic unit may not utilize deep cryogenic temperatures and may not require traditional unit operations of demethanizer and deethanizer. Effluent gas from this unit may then be returned as described elsewhere herein. In some situations, a debutanizer column may be installed to provide RVP control of final $C_{4+}$ product and the additional $C_4$ stream.

There are a number of scenarios where it may be necessary to flare gas from a midstream gas gathering and or gas processing facility. In some cases, gas from a midstream system can be burned due to operating constraints, production gas fluctuations that may result in capacity limitations of gas gathering and processing facilities, feed gas conditions that may prevent the gas being processed and meet the gas specifications, and/or process gas conditions that may not allow co-processing in a gas facility.

ETL systems of the present disclosure can be integrated in various existing systems, such as petroleum refineries and/or petrochemical complexes. Such integration can be with or without OCM systems.

Petroleum refineries and petrochemical complexes may generate a significant amount and number of purge and other waste gas streams that may be burned for power generation at fuel value due to their inability to further process or recover the hydrocarbons. These waste gas streams may contain a mixture of inert gases and hydrocarbons, such as olefinic species. An ETL process can be integrated into a refinery or petrochemical complex such that it consumes one or several of these olefinic streams and chemically converts them to higher value oligomers, such as mixed C4 and $C_{5+}$ mixtures. A wide range of these ETL feedstocks can be generated within a refinery complex.

Several examples of waste gas streams with suitable olefins include, without limitation, absorber tower overhead product gas stream containing ethylene and propylene at moderate levels generated in the light ends recovery process area or the deethanizer overhead stream containing similar olefins. Streams can be reacted individually or blended as desired to meet ETL reactor inlet gas requirements.

An ETL process can include feedstock gas treatment, process gas compression, ETL reaction and heat recovery sections and units. The ETL reactor effluent can be returned to the refinery separations units if existing unit operations and capacity are available. If no such capacity is available, a small ETL separations sub-system may be provided to recover the effluent $C_4$ and $C_{5+}$ product streams using a range of process intensity separations methods—cooling water or refrigerated condensation recovery, sponge oil systems, and shallow-grade cryogenic units for the deepest recovery. Additional process units may be added for further chemical recovery benefits, including membrane separations to recovered hydrogen from the ETL reactor effluent post hydrocarbon recovery.

Figure 20:
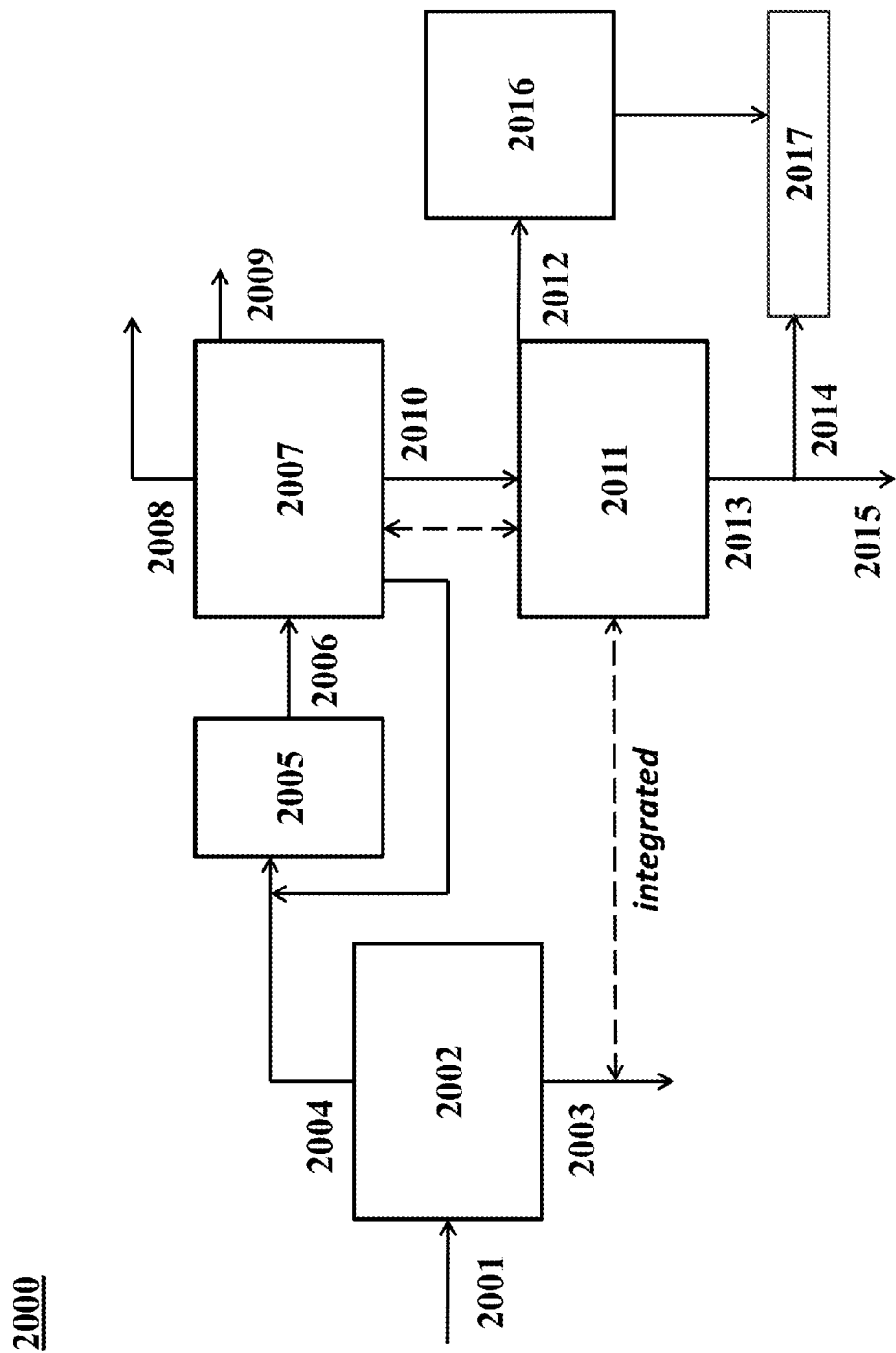
FIG. 20 shows an example of ETL integration in a refinery.
Figure 21:
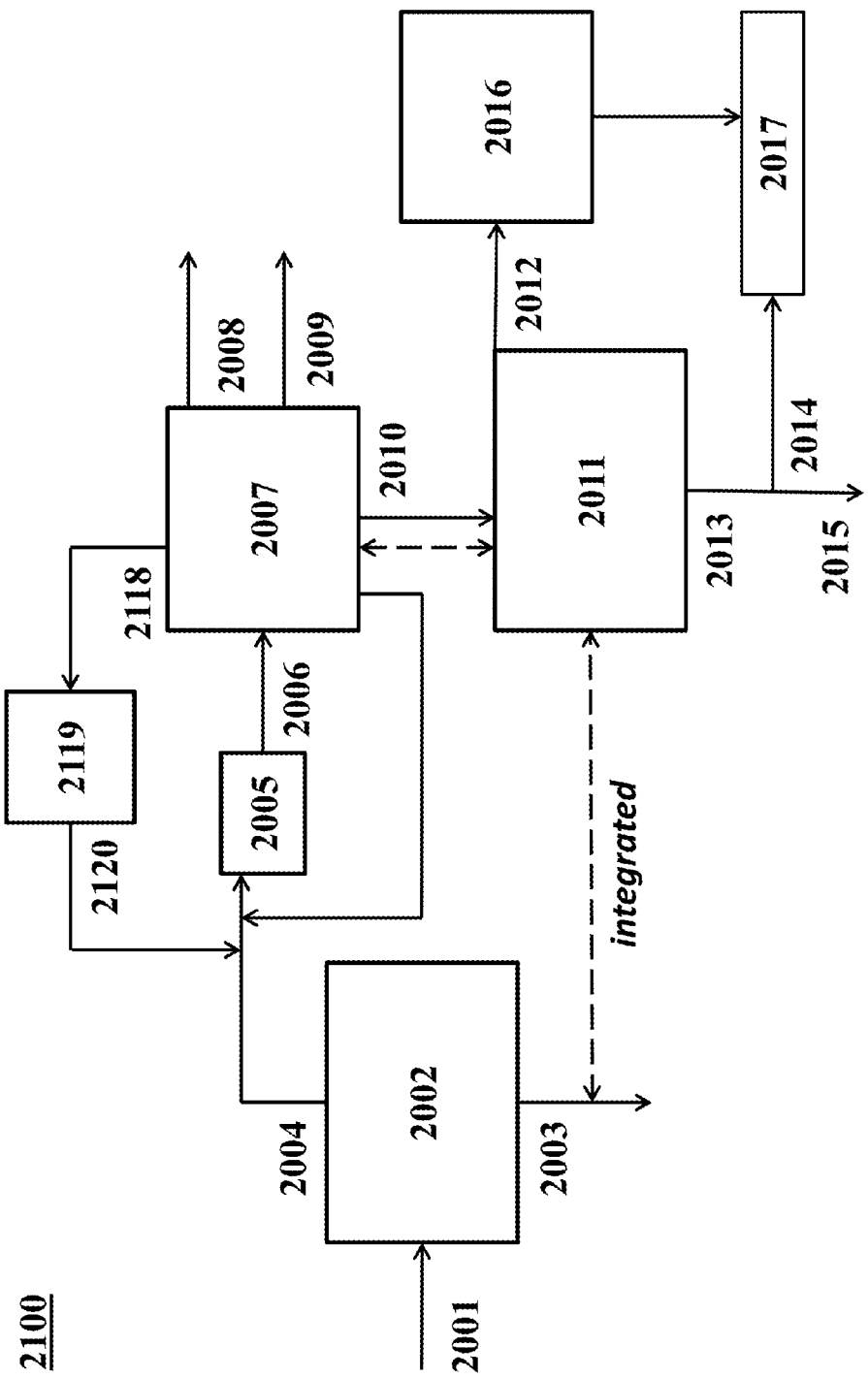
FIG. 21 shows another example of ETL integration in a refinery.
Figure 22:
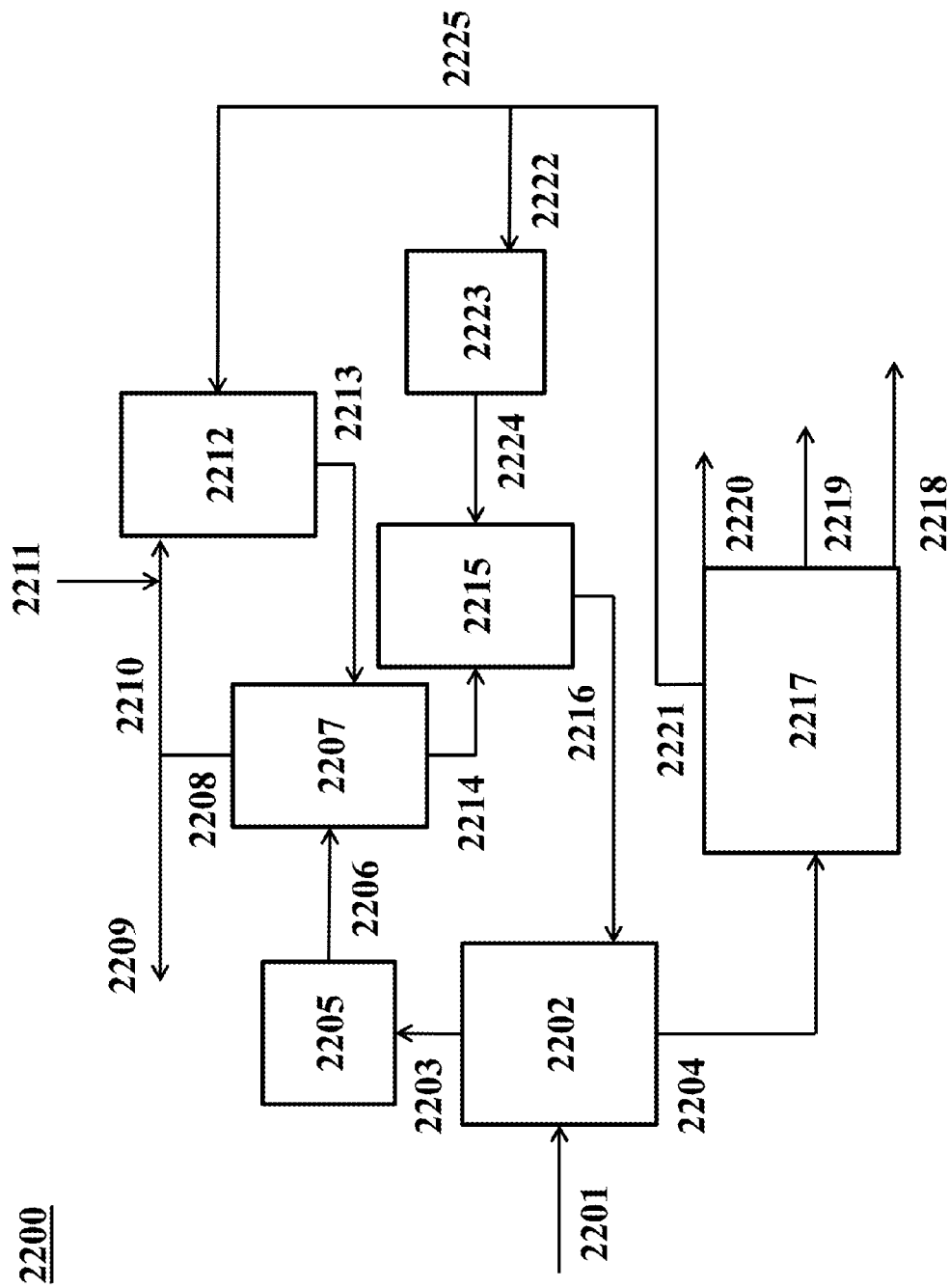
FIG. 22 shows another example of ETL integration in a refinery.

FIGS. 20-22 show various examples of ETL integration in refineries. Such systems can employ existing fractionation systems of refineries to effect product separation.

With reference to FIG. 20, gas from cracking or other units 2001 is, in a refinery gas plant 2002, generated into $C_3$ and $C_4$ products 2004 that are directed to an ETL system 2005, which generates higher molecular weight hydrocarbons 2006 that are directed to a product separation system 2007. The product separation system 2007 can employ an existing separation system of the refinery. The direction of fluid flow and separations systems can be selected to effect a given product distribution, such as a $C_{2-}$ fuel gas 2008, a $C_3$ product 2009, and a $C_{4+}$ stream 2010. The products 2013 from the fractionation unit 2011 can be treated to produce a gasoline blend component 2017 and the heavier products 2012 can be sent to the refinery aromatics separation unit 2016. Ample integration/blending opportunities exist in a typical refinery complex.

The systems of FIG. 20 can include a heat exchange ethane cracker (HXEC) 2119, as shown in FIG. 21. The HXEC can use heat from flue-gas 2118 to crack ethane to ethylene. The HXEC can utilize one or more waste heat stream (as during FCC regeneration stage) to thermally crack the ethane to generate an additional olefin rich stream as a feed to the ETL reactor. In some cases, the concept can be used to crack propane feed to produce an olefin rich stream. For example, removal of coke from catalyst by combustion can generate a hot flue gas, in some cases with the use of a co-boiler. Flue gas can reach temperatures of 1600° F. (~870° C.), 1800° F. (~980° C.), or higher. Heat can be transferred to a stream comprising ethane, propane, or a combination thereof, for example in a heat exchanger. This heat can be used to crack the ethane to ethylene or the propane to propylene. These olefin products can be used in other processes, such as in ETL.

A refinery gas plant 2202, receiving gas 2201 from cracking or other units, can be retrofitted with an OCM-ETL system, as shown in FIG. 22. The OCM reactor 2212 includes a post-bed cracking (PBC) unit. The OCM reactor 2212 accepts methane through a natural gas feed 2211 and generates a product stream 2213 that is directed to a $C_1$ separator 2207 that removes methane ($C_1$) 2208 from the product stream to provide $C_{2+}$ compounds 2214. The methane can be recycled to the OCM reactor 2210 or directed for use as refinery fuel 2209. $C_{2+}$ compounds 2214 directed to the ETL reactor 2215 are used to generate higher molecular weight hydrocarbons 2216, which are directed to the refinery gas plant 2202. $C_{3+}$ compounds 2204 from the refinery gas plant are directed to a production fractionation system 2217 for separation. The system of FIG. 22 can include an HXEC 2223 coupled with the ETL reactor 2215. The HXEC can ethane 2222 to ethylene 2224, which can then be directed to the ETL reactor 2215. In some situations, the HXEC is precluded.

The integration of an ETL system into a refinery or petrochemical facility can include a cracker and in some cases be performed without OCM. This can enable polymer grade ethylene to be turned into gasoline, for example.

It is to be noted with respect to the disclosures above pertaining to systems described in FIG. 17, FIG. 18, FIG. 19, FIG. 20, FIG. 21, and FIG. 22 that the descriptions are indicative and not limited to the concepts and configurations represented. One or more of the following can be additionally integrated into systems such as those described: a methanation reactor, an ethane skimmer, and various heat integration configurations and optimizations based on the refinery configuration, product demand and economics. An ETL reactor system, including an OCM-ETL reactor system, can be a versatile system with a wide range of configurations to achieve economic value from the refinery off gases, waste gases and additional natural gas feed(s).

Ethylene-to-Liquids (ETL) Integration with Natural Gas Processing

An aspect of the present disclosure provides olefin-to-liquids systems and methods. An olefin-to-liquids process can be integrated in a non-OCM process, such as a natural gas liquids (NGL) system. The olefin-to-liquids process can be an ethylene-to-liquids (ETL) process. The ETL process can be part of an OCM system, which can generate olefins (e.g., ethylene) from methane and an oxidizing agent (e.g., $O_2$), as described elsewhere herein. The olefins can be used as feedstock to one or more ETL reactors for the conversion of olefins to higher molecular weight hydrocarbons, which can be in liquid form.

Natural-gas processing is typically a complex industrial process for cleaning raw natural gas by separating impurities and various non-methane hydrocarbons and fluids to produce pipeline quality dry natural gas. Most extracted natural gas can contain, to varying degrees, low molecular weight hydrocarbon compounds. Examples of such compounds include methane ($CH_4$), ethane ($C_2H_6$), propane ($C_3H_8$) and butane ($C_4H_{10}$). When brought to the surface and processed into purified, finished by-products, all of these are collectively referred to as NGL.

Natural-gas processing plants may purify raw natural gas from (a) underground gas fields and/or (b) from well heads with associated gas by removing common contaminates, such as water, carbon dioxide ($CO_2$) and hydrogen sulfide ($H_2S$). Some of the substances which contaminate natural gas have economic value and are further processed or sold. A fully operational plant can deliver pipeline-quality dry natural gas that can be used as fuel by residential, commercial and industrial consumers.

In some embodiments, existing NGL processing and/or fractionation systems can be integrated with OCM and ETL processes to produce various hydrocarbons (which may be liquids), such as alkanes, alkenes, alkynes, alkoxides, aldehydes, ketones, acids (e.g., carboxylic acids), aromatics, paraffins, iso-paraffins, higher olefins, oligomers or polymers. In some examples, such hydrocarbons include liquefied petroleum gas (LPG), reformulated gasoline blendstock for oxygen blending (RBOB), and/or gasoline (e.g., natural gasoline or premium gasoline), and/or other hydrocarbon blendstocks commonly fed to refineries or blending terminals (e.g., condensate or diluent). LPG can include propane and butane, and can be employed as fuel in heating appliances and vehicles.

ETL can be used to generate hydrocarbons for various end uses, such as gasoline for use in machinery (e.g., automobiles and aircraft). Products of ETL processes of the present disclosure can be employed for use as gasoline or jet fuel blend stock, for example. In some examples, ETL can be used to generate benzene, toluene, ethylbenzene, and xylenes (BTEX).

An ETL-gasoline process can have a heat of reaction from about 80 KJ/mole to 100 KJ/mol. An adiabatic ETL reactor can have an inlet temperature of at least about 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., or 500° C. In the reactor, temperature can increase by at least about 50° C. to 150° C., 60° C. to 120° C., or 75° C. to 100° C., and process pressure can increase by at least about 1 bar, 2 bars, 3 bars, 4 bars, 5 bars, 6 bars, 7 bars, 8 bars, 9 bars, 10 bars, 20 bars, 30 bars, 40 bars or 50 bars (absolute).

In some cases, the primary products out of an ETL reactor are olefins, such as a pentene, hexene or heptene. However, other secondary products are possible, such as aromatics and paraffins. In an example, an ETL product has a liquids distribution that is selective towards C5-C10 hydrocarbons with a substantially low content of benzene and durene. Such a product may be employed for use as gasoline. In another example, an ETL product has a liquids distribution that is selective towards BTEX.

In some examples, a raw natural gas (NG) feed stock can be directed to an OCM-ETL system to generate $C_{2+}$ compounds for use in generating higher molecular weight hydrocarbons, such as hydrocarbon products described in the context of FIG. 1. Such hydrocarbons products can be further processed for various end uses. For example, the hydrocarbon products can include the constituents of gasoline, and can be combined with ethanol for use as automobile fuel.

OCM-ETL systems of the present disclosure can be integrated with NGL systems to produce NGLs and premium quality gasoline, as well as NGL associated with natural gas feed or any other hydrocarbon gas feed stocks. In some examples, NGL processing and/or fractionation or midstream gas facilities or systems can be integrated with an OCM reactor system, an ETL reactor system, separations units, compression units, methanation units and or other processing units, such as those described in U.S. patent application Ser. No. 14/099,614, filed on Dec. 6, 2013, which is entirely incorporated herein by reference.

OCM-ETL systems of the present disclosure can advantageously enable existing NGL processing systems to be retrofitted for use in producing various hydrocarbons in an efficient and economical fashion as compared to other systems presently available. In some examples, existing NGL processing and/or fractionation plants are integrated with OCM-ETL systems provided herein, in addition to other systems that may be required for further processing. OCM-ETL Integration with NGL processing may include a retrofit of recycle split vapor (RSV), gas sub-cooled process (GSP) processes or any gas processing technology. The OCM-ETL plant can include other systems that may be required for further processing. Existing NGL systems can be retrofitted with OCM-ETL systems provided herein and configured, for example, to yield a given product distribution and/or yield. Such integration may consider the spare or full capacity of an existing NGL processing plant to reduce the retrofit capital investments and operating expenses. The OCM-ETL system can be designed to accommodate any spare capacity of the NGL processing plant, or to accommodate the NGL plant operating as an OCM/ETL plant at maximum capacity. The feed (or input) to the OCM-ETL may be a quantity of fresh natural gas, residue gas, or sales gas (sales gas and pipeline gas are referring to the same natural gas which means pipeline specification) that meets the OCM inlet gas specifications and the spare capacity of the NGL plant. A requisite amount of an oxidizing agent (e.g., air or oxygen) can be used in the OCM reactor(s) of the OCM-ETL system.

In some examples, the quantity of the NGL products from OCM-ETL systems of the present disclosure is at least about 0.3, 0.5, 0.1, 1, 1.5, 2, 3, 4, 5, 6, 7, 8, 9, or 10 gallons per 1000 standard cubic feet (SCF) of inlet natural gas of inlet gas. In some cases, the quantity of the NGL products from OCM-ETL systems of the present disclosure is at least about 0.3, at least about 0.5, at least about 0.1, at least about 1, at least about 1.5, at least about 2, at least about 3, at least about 4, at least about 5, at least about 6, at least about 7, at least about 8, at least about 9, or at least about 10 gallons per 1000 standard cubic feet (SCF) of inlet natural gas of inlet gas. In some cases, the quantity of the NGL products from OCM-ETL systems of the present disclosure is at most about 0.3, at most about 0.5, at most about 0.1, at most about 1, at most about 1.5, at most about 2, at most about 3, at most about 4, at most about 5, at most about 6, at most about 7, at most about 8, at most about 9, or at most about 10 gallons per 1000 standard cubic feet (SCF) of inlet natural gas of inlet gas. In some cases, the quantity of the NGL products from OCM-ETL systems of the present disclosure is in the range of 0.8 gallons to 1.5 gallons per 1000 standard cubic feet (SCF) of inlet natural gas of inlet gas.

FIG. 23A shows an NGL process. The NGL system comprises a raw natural gas feed stream 2301, an NGL system 2302 and a product stream 2303. The raw natural gas feed stream 2301 comprises methane ($CH_4$) in addition to other chemicals (e.g., $H_2O$, $CO_2$ and $H_2S$). The NGL system 2302 can comprise various processing equipment for refining the feed stream 2301 to generate the product stream 2303 comprising one or more hydrocarbon products, such as methane, ethane, propane and/or butane. Such processing equipment can include separations units, such as distillation columns. In some examples, the product stream 2303 comprises methane at a concentration (or purity) that is higher as compared to the feed stream 2301. The product stream 2303 can be directed to a natural gas pipeline for distribution of natural gas to end users.

In FIG. 23B, the NGL process of FIG. 23A has been retrofitted with an OCM-ETL system of the present disclosure. FIG. 23B shows the feed stream 2301 directed into NGL system 2304. The NGL system 2304 can include at least a subset or all of the equipment of the NGL system 2302 described in the context of FIG. 23A. In an example, the NGL system 2304 is the NGL system 2302. The NGL system 2304 yields the product stream 2303 and an additional product stream 2305. The additional product stream 2305 is directed to an OCM-ETL system 2306. The OCM-ETL system 2306 generates product stream 2307, which can include $C_{2+}$ compounds. In some examples, the product stream comprises $C_3$-$C_{12}$ hydrocarbons.

Although FIG. 23B shows an NGL process retrofitted with an OCM-ETL system, other non-OCM processes may be retrofitted with the OCM-ETL system. For example, the OCM-ETL system can be integrated in an oil refinery, and products from crude oil refining may be directed to the OCM-ETL system for further processing.

Figure 24:
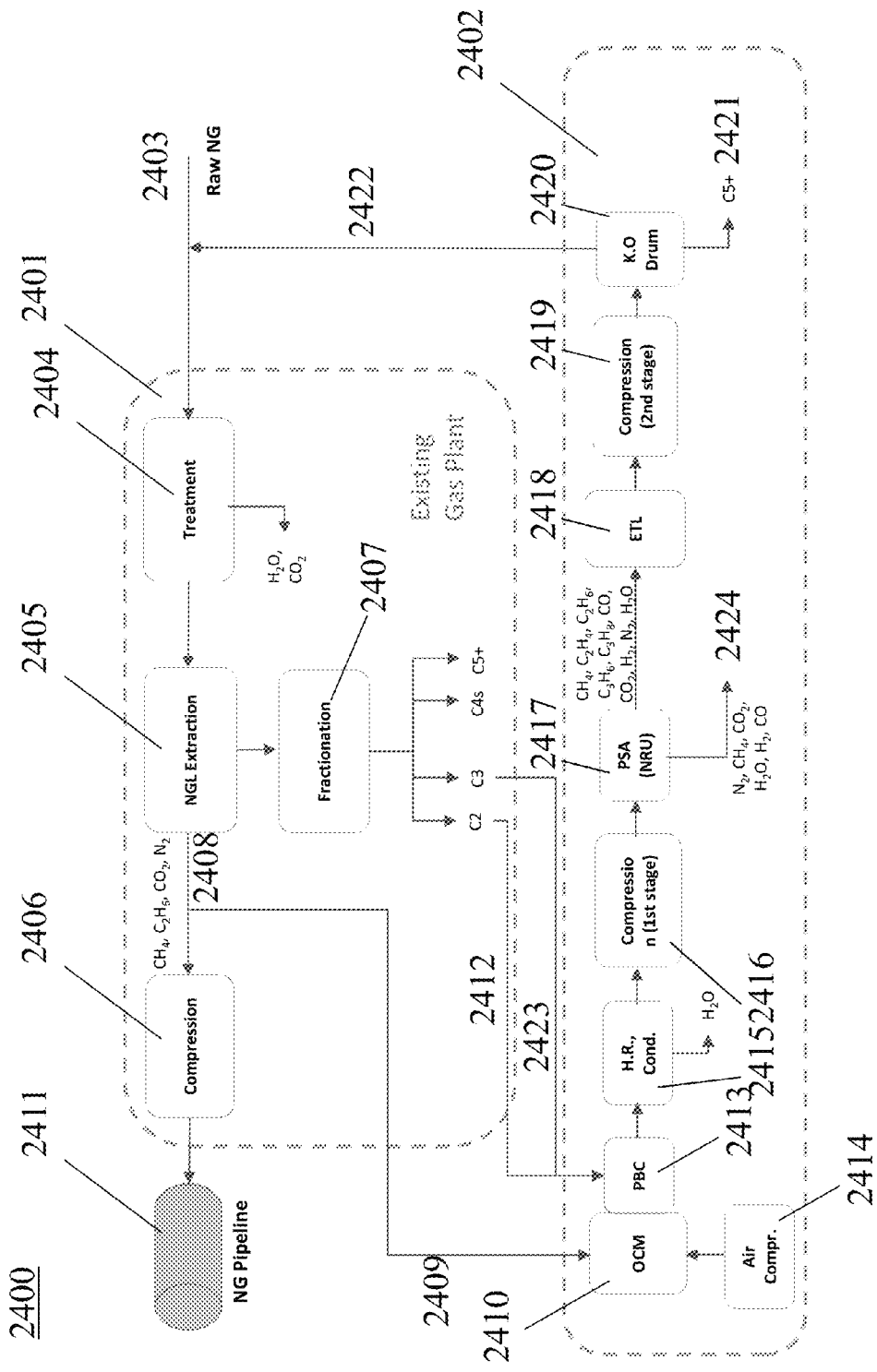
FIG. 24 schematically illustrates an oxidative coupling of methane (OCM) olefins to liquids process integrated in an NGL system, employing air in an OCM process.

FIG. 24 shows a system 2400 comprising an existing gas plant 2401 that has been retrofitted with an OCM-ETL system 2402. The OCM-ETL system 2402 may be used with ethylene or other olefins. A raw natural gas (NG) feed 2403 is directed into the existing gas plant 2401, which comprises a treatment unit 2404, NGL extraction unit 2405, compression unit 2406 and fractionation unit 2407. The NGL extraction unit 2405 can be a demethanizer unit, optionally a demethanizer unit incorporated with a recycle split vapor (RSV) retrofit or stand-alone unit. The treatment unit 2404 removes water and $CO_2$ from the NG feed 2403 and directs natural gas to the NGL extraction unit 2405. In some cases, the treatment unit removes sulfur from the NG feed. The NGL extraction unit 2405 removes methane, ethane, $CO_2$ and $N_2$ from the NG feed 2403, and directs methane, ethane, $CO_2$ and $N_2$ to the compression unit 2406 along fluid stream 2408. At least a portion of the methane from the fluid stream 2408 is directed along stream 2409 to an OCM reactor 2410 of the OCM-ETL system 2402. The compression unit 2406 compresses methane in the fluid stream 2408 and directs compressed methane to a natural gas pipeline 2411 for distribution of methane to end users.

With continued reference to FIG. 24, $C_{2+}$ compounds from the NGL extraction unit 2405 are directed to the fractionation unit 2407, which can be a distillation column. The fractionation unit 2407 splits the $C_{2+}$ compounds into streams comprising various $C_{2+}$ compounds, such as a $C_2$ stream 2412 along with $C_3$ 2423, $C_4$ and $C_5$ streams. The $C_2$ stream 2412 and/or $C_3$ stream 2423 can be directed to a post-bed cracking (PBC) unit 2413 of the OCM-ETL system 2402. In some cases, $C_3$, $C_4$ and/or $C_{4+}$ compounds are directed to the PBC unit. Examples of post-bed cracking is described in U.S. patent application Ser. No. 14/553,795, filed Nov. 25, 2014, which is entirely incorporated herein by reference.

In the OCM-ETL system 2402, methane from the stream 2409 and air 2414 are directed to the OCM reactor 2410. The OCM reactor 2410 generates an OCM product stream comprising $C_{2+}$ compounds in an OCM process, as discussed elsewhere herein. $C_{2+}$ alkanes (e.g., ethane) in the product stream, as well as $C_2$ alkanes in the $C_2$ stream 2412, may be cracked to $C_{2+}$ alkenes (e.g., ethylene) in the post-bed cracking (PBC) unit 2413 (which can be a downstream component of the OCM reactor 2410). The product stream is then directed to a condenser 2415, which removes water from the product stream. The product stream is then directed to a compression unit 2416 and subsequently a pressure swing absorption (PSA) unit 2417. The PSA separates $N_2$, CO, $CO_2$, $H_2O$, $H_2$ and some methane from $C_{2+}$ compounds in the product stream, and directs the $C_{2+}$ compounds to one or more ETL reactors 2418 of the OCM-ETL system 2402. The stream comprising nitrogen 2424 (and in some cases $CH_4$, $CO_2$, $H_2O$, $H_2$ and/or CO) can be fed into a fuel gas stream for use in generating power, burning, use as a thermal oxidizer. The $C_{2+}$ compounds directed into the ETL reactor 2418 can include ethane, ethylene, propane, propylene, along with methane, CO, $CO_2$, $H_2$, $N_2$ and water. The ETL reactor 2418 generates higher molecular weight hydrocarbons, such as $C_4$-$C_{12}$ (e.g., $C_{4+}$ or $C_{5+}$) compounds (e.g., butane, butylenes, pentane, hexane, etc.). A product stream from the ETL reactor 2418 is directed to another compression unit 2419 and subsequently a vapor-liquid separator (or knock-out drum) 2420, which separates liquids (e.g., the $C_{5+}$ compounds) from vapors (e.g., methane) in the product stream and provides a product stream 2421 comprising the $C_{5+}$ compounds. Remaining compounds, including vapors (e.g., methane), are recycled to the feed stream 2403 along recycle stream 2422. Methane directed along stream 2422 can be directed to the OCM reactor 2410 for further $C_{2+}$ product generation.

The OCM-ETL 2402 system can include one or more OCM reactor 2410. For example, the OCM reactor 2410 can be an OCM reactor train comprising multiple OCM reactors. In addition to, or as an alternative, the OCM-ETL system 2402 can include one or more ETL reactor 2418. For example, the ETL reactor 2418 can be multiple ETL reactors in parallel, with each ETL reactor configured to generate a given hydrocarbon (see, e.g., FIG. 1). In some cases, $C_3$ and/or $C_4$ compounds can be taken from the fractionators and fed into a further downstream region of a post-bed cracking (PBC) reactor for olefin production.

The compression units 2406, 2416 and 2419 can each be a multistage gas compression unit. Each stage of such multistage gas compression unit can be followed by cooling and liquid hydrocarbon and water removal.

Figure 25:
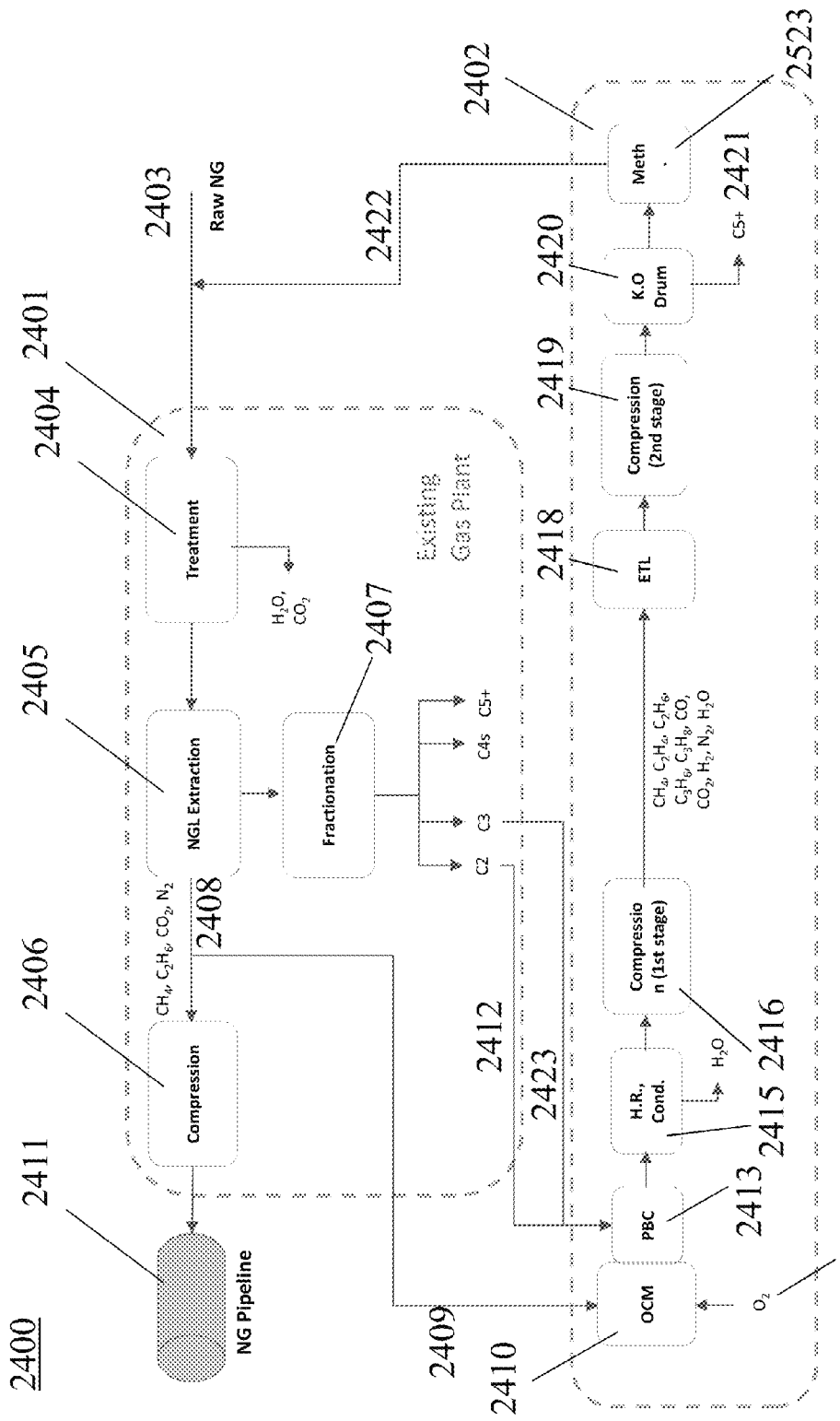
FIG. 25 schematically illustrates an OCM-ETL integration with an existing NGL system, employing oxygen ($O_2$) in an OCM process.

The OCM-ETL system 2402 can be operated with other oxidizing agents, such as previously separated $O_2$ such as $O_2$ from a pipeline or as a product from an air separation unit (ASU). In the alternative configuration of FIG. 25, an $O_2$ feed stream 414 is directed to the OCM reactor 2410. The $O_2$ feed stream 2514 can be generated, for example, using a cryogenic air separation unit (not shown), which separates air into individual streams comprising $O_2$ and $N_2$. The system of FIG. 25 further includes a methanation system 2523 (see below) that converts CO, $CO_2$ and $H_2$ from the vapor-liquid separator to methane, which can be recycled along stream 2422.

In the figures, the direction of fluid flow between units is indicated by arrows. Fluid may be directed from one unit to another with the aid of valves and a fluid flow system. In some examples, a fluid flow system can include compressors and/or pumps, as well as a control system for regulating fluid flow, as described elsewhere herein.

Methanation Systems

Oxidative Coupling of Methane (OCM) is a process that may convert natural gas (or methane) to ethylene and other longer hydrocarbon molecules via reaction of methane with oxygen. Given the operating conditions of OCM, side reactions can include reforming and combustion, which can lead to the presence of significant amounts of $H_2$, CO and $CO_2$ in the effluent stream. Typical $H_2$ content in the effluent stream can range between about 5% and about 15%, between about 1% and about 15%, between about 5% and about 10%, or between about 1% and about 5% (molar basis). CO and $CO_2$ can each range between about 1% and about 5%, between about 1% and about 3%, or between about 3% and about 5% (molar basis). In some cases, the ethylene and all the other longer hydrocarbon molecules contained in the effluent stream are separated and purified to yield the final products of the process. This can leave an effluent stream containing the unconverted methane, hydrogen, CO and $CO_2$ and several other compounds, including low amounts of the product themselves depending on their recovery rates.

In some cases, this effluent stream needs to be recycled to the OCM reactor. However, if CO and $H_2$ are recycled to the OCM reactor along with methane, they can react with oxygen to produce $CO_2$ and $H_2O$, causing various negative consequences to the process including, but not limited to: (a) an increase of the natural gas feed consumption (e.g., because a larger portion of it can result in $CO_2$ generation instead of product generation); (b) a decrease of the OCM per-pass methane conversion (e.g., because a portion of the allowable adiabatic temperature increase can be exploited by the $H_2$ and CO combustion reactions instead of the OCM reactions); and an increase of the oxygen consumption (e.g., because some of the oxygen feed can react with CO and $H_2$ instead of methane).

In some instances, the effluent stream is exported to a natural gas pipeline (i.e., to be sold as sales gas into the natural gas infrastructure). Given that specifications can be in place for natural gas pipelines, the concentrations of CO, $CO_2$ and $H_2$ in the effluent can need to be reduced to meet the pipeline requirements.

In some embodiments, the effluent stream may also be used as a feedstock for certain processes that may require lower concentrations of $H_2$, CO and $CO_2$.

Therefore, it can be desirable to reduce the concentration of $H_2$, CO and $CO_2$ in the OCM effluent stream, upstream or downstream of the separation and recovery of the final products. This can be accomplished using methanation systems and/or by separating $H_2$ and CO from the effluent stream (e.g., using cryogenic separations or adsorption processes). The disclosure also includes separating $CO_2$ from the effluent stream using $CO_2$ removal processes, such as chemical or physical absorption or adsorption or membranes. However, these separation processes can require significant capital investments and can consume considerable amounts of energy, in some cases making an OCM-based process less economically attractive.

Described herein are systems and methods for reducing CO, $CO_2$ and $H_2$ concentration in a methane stream. The method comprises reacting these compounds to form methane in a reaction called methanation.

$CO_2$ and/or sulfur-containing compounds (e.g., $H_2S$) can be separated via a $CO_2$ removal unit, such as, for example, an amine-based system, a caustic system or any other physical or chemical absorption or adsorption unit. CO and $H_2$ can be separated together with the methane in a cryogenic separator. If CO and $H_2$ are recycled to an OCM reactor along with methane, they can react with oxygen (e.g., pure $O_2$ or $O_2$ in air) to produce $CO_2$ and $H_2O$, causing various negative consequences to the process, including, without limitation: (i) increase in natural gas feed consumption and a decrease in $C_{2+}$ product generation; (ii) decrease of the OCM per-pass methane conversion; and (iii) increase in oxygen consumption. Given the potential negative effects of the presence of CO and $H_2$ in a stream comprising methane, it may be preferable to minimize the concentration of CO and $H_2$. In addition, by converting the CO and $H_2$ back into methane, the carbon efficiency of the process can be increased by recycling the methane to the OCM reactor or to the natural gas pipeline.

An aspect of the present disclosure provides a methanation system that can be employed to reduce the concentration of CO, $CO_2$ and $H_2$ in a given stream, such as an OCM product stream as well as improve carbon efficiency. This can advantageously minimize the concentration of CO, $CO_2$ and $H_2$ in any stream that may be ultimately recycled to an OCM reactor. The methanation system can be employed for use with any system of the present disclosure, such as the OCM-ETL system 302 described above.

In a methanation system, CO reacts with $H_2$ to yield methane via $CO+3H_2 \rightarrow CH_4+H_2O$. In the methanation system, $CO_2$ can react with $H_2$ to yield methane via $CO_2+4H_2 \rightarrow CH_4+2 H_2O$. Such processes are exothermic and generate heat that may be used as heat input to other process units, such as heating an OCM reactor of a PBC reactor, or pre-heating reactants, such as methane and/or an oxidizing agent (e.g., $O_2$) prior to an OCM reaction.

In some cases, to limit the heat release per unit of flow of reactants, methanation can be conducted on streams that contain CO, $CO_2$, $H_2$ and a suitable carrier gas. The carrier gas can include an inert gas, such as, e.g., $N_2$, He or Ar, or an alkane (e.g., methane, ethane, propane and/or butane). The carrier gas can add thermal heat capacity and significantly reduce the adiabatic temperature increase resulting from the methanation reactions.

In some examples, methane and higher carbon alkanes (e.g., ethane, propane and butane) and nitrogen are employed as carrier gases in a methanation process. These molecules can be present in an OCM process, such as in an OCM product stream comprising $C_{2+}$ compounds. Downstream separation units, such as a cryogenic separation unit, can be configured to produce a stream that contains any (or none) of these compounds in combination with CO and $H_2$. This stream can then be directed to the methanation system.

A methanation system can include one or more methanation reactors and heat exchangers. CO, $CO_2$ and $H_2$ can be added along various streams to the one or more methanation reactors. A compressor can be used to increase the $CO_2$ stream pressure up to the methanation operating pressure, which can be from about 2 bar (absolute) to 60 bar, or 3 bar to 30 bar. $CO_2$ can be added to the inlet of the system in order to create an excess of $CO_2$ compared to the amount stoichiometrically required to consume all the available $H_2$. This is done in order to minimize $H_2$ recycled to OCM, which may not be preferable.

Given the exothermicity of the methanation reactions, a methanation system can include various methanation reactors for performing methanation. In some cases, a methanation reactor is an adiabatic reactor, such as an adiabatic fixed bed reactor. The adiabatic reactor can be in one stage or multiple stages, depending, for example, on the concentration of CO, $CO_2$ and $H_2$ in the feed stream to the methanation system. If multiple stages are used, inter-stage cooling can be performed by either heat exchangers (e.g., a stage effluent can be cooled against the feed stream or any other colder stream available in the plant, such as boiler feed water) or quenching via cold shots, i.e. the feed stream is divided into multiple streams, with one stream being directed to the first stage while each of the other feed streams being mixed with each stage effluent for cooling purposes. As an alternative, or in addition to, a methanation reactor can be an isothermal reactor. In such a case, reaction heat can be removed by the isothermal reactor by, for example, generating steam, which can enable a higher concentration of CO, $CO_2$ and $H_2$ to be used with the isothermal reactor. Apart from adiabatic and isothermal reactors, other types of reactors may be used for methanation.

Figure 26:
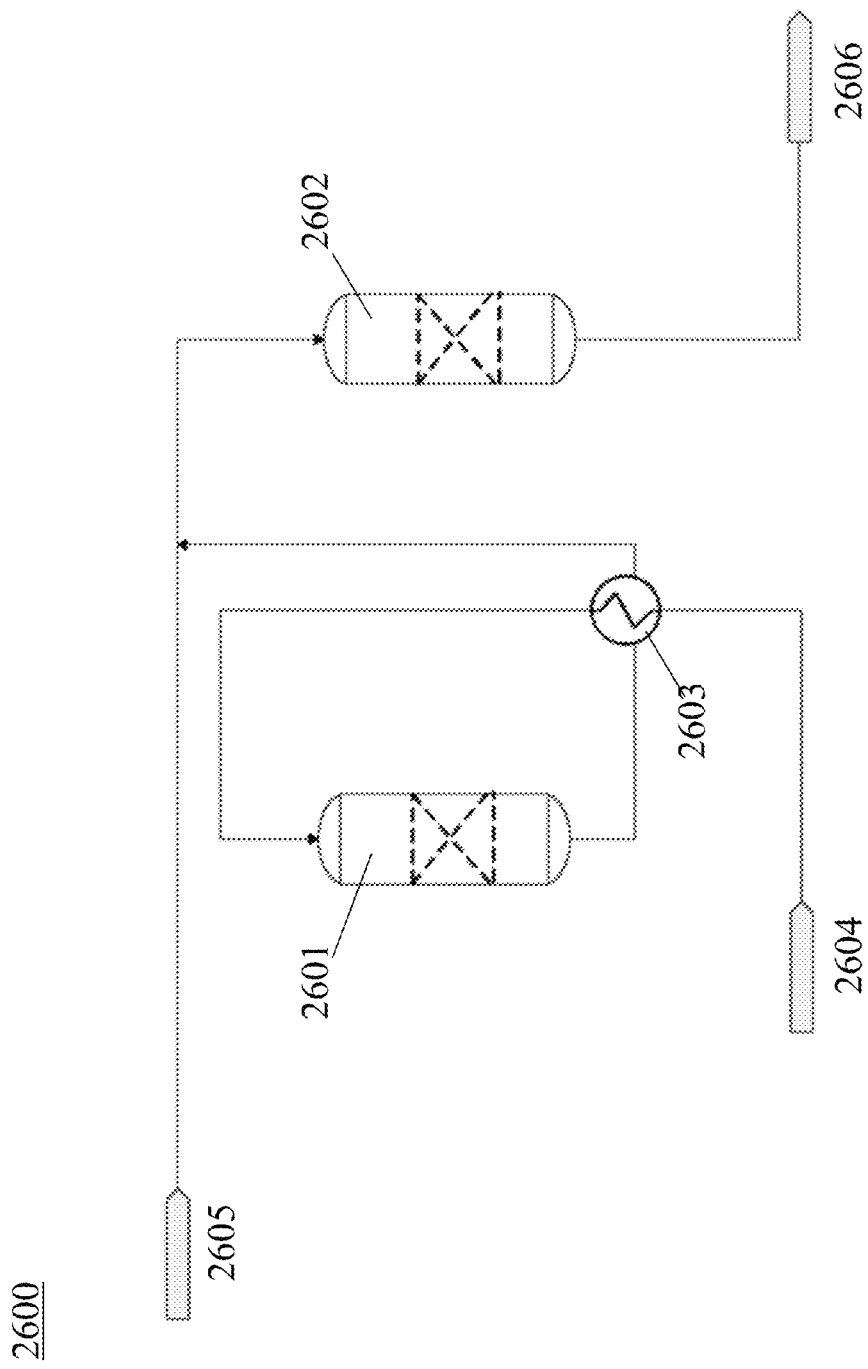
FIG. 26 schematically illustrates a methanation system.

FIG. 26 shows an example methanation system 2600. The system 2600 comprises a first reactor 2601, second reactor 2602 and a heat exchanger 2603. The first reactor 2601 and second reactor 2602 can be adiabatic reactors. During use, a recycle stream 2604 comprising methane, CO and $H_2$ (e.g., from a cryogenic separation unit) is directed to the heat exchanger 2603. In an example, the recycle stream 2604 comprises between about 65% and 90% (molar basis) methane, between about 5% and 15% $H_2$, between 1% and 5% CO, between about 0% and 0.5% ethylene, and the balance inert gases (e.g., $N_2$, Ar and He). The recycle stream 2604 can have a temperature from about 20° C. to 30° C., and a pressure from about 2 bar to 60 bar (absolute), or 3 bar to 30 bar. The recycle stream 2604 can be generated by a separation unit downstream of an OCM reactor, such as a cryogenic separation unit.

In the heat exchanger 2603, the temperature of the recycle stream 2604 is increased to about 100° C. to 400° C., or 200° C. to 300° C. The heated recycle stream 2604 is then directed to the first reactor 2601. In the first reactor 2601, CO and $H_2$ in the recycle stream 2604 react to yield methane. This reaction can progress until all of the $H_2$ is depleted and/or a temperature approach to equilibrium of about 0 to 30° C., or 0 to 15° C. is achieved. The methanation reaction in the first reactor 2601 can result in an adiabatic temperature increase of about 20° C. to 300° C., or 50° C. to 150° C.

Next, products from the first reactor, including methane and unreacted CO and/or $H_2$, can be directed along a first product stream to the heat exchanger 2603, where they are cooled to a temperature of about 100° C. to 400° C., or 200° C. to 300° C. In the heat exchanger 2603, heat from the first product stream 2603 is removed and directed to the recycle stream 2604, prior to the recycle stream 2604 being directed to the first reactor 2601.

Next, a portion of the heated first product stream is mixed with a $CO_2$ stream 2605 to yield a mixed stream that is directed to the second reactor 2602. The $CO_2$ stream 2605 can be generated by a separation unit downstream of an OCM reactor, such as a cryogenic separation unit. This can be the same separation unit that generated the recycle stream 2604. In some cases, the methods described herein increase carbon efficiency compared to methods that do not use methanation. For example, the amount of CO and/or $CO_2$ can be reduced by at least about 5%, at least about 10%, at least about 20%, at least about 50%, at least about 75% or at least about 80%.

In the second reactor 2602, CO and $CO_2$ react with $H_2$ to yield a second product stream 2606 comprising methane. The reaction(s) in the second reactor 2602 can progress until substantially all of the $H_2$ is depleted and/or a temperature approach to equilibrium of about 0 to 30° C., or 0 to 15° C. is achieved. The proportions of CO, $CO_2$ and $H_2$ in the mixed stream can be selected such that the second product stream 2606 is substantially depleted in CO and $H_2$. In some cases, the second product stream 2606 is fed back into the natural gas feed of a natural gas to liquids facility.

The first reactor 2601 and the second reactor 2602 can be two catalytic stages in the same reactor vessel or can be arranged as two separate vessels. The first reactor 2601 and second reactor 2602 can each include a catalyst, such as a catalyst comprising one or more of ruthenium, cobalt, nickel and iron. The first reactor 2601 and second reactor 2602 can be fluidized bed or packed bed reactors. Further, although the system 2600 comprises two reactors 2601 and 2602, the system 2600 can include any number of reactors in series and/or in parallel, such as at least 1, 2, 3, 4, 5, 6, 7, 8, 9, 10, 20, 30, 40, or 50 reactors.

Although the $CO_2$ stream 2605 is shown to be directed to the second reactor 2602 and not the first reactor 2601, in an alternative configuration, at least a portion or the entire $CO_2$ stream 2605 can be directed to the first reactor 2601. The proportions of CO, $CO_2$ and $H_2$ can be selected such that the methanation product stream is substantially depleted in CO and $H_2$.

Methane generated in the system 2600 can be employed for various uses. In an example, at least a portion of the methane can be recycled to an OCM reactor (e.g., as part of an OCM-ETL system) to generate $C_{2+}$ compounds, including alkenes (e.g., ethylene). As an alternative, or in addition to, at least a portion of the methane can be directed to a non-OCM process, such as a natural gas stream of a natural gas plant (see, e.g., FIGS. 3 and 4). As an alternative, or in addition to, at least a portion of the methane can be directed to end users, such as along a natural gas pipeline.

The methanation reaction can be practiced over a nickel-based catalyst, such as those used to produce SNG (Substitute Natural Gas or Synthetic Natural Gas) from syngas or used to purify streams containing CO and $CO_2$ (e.g., to remove CO and $CO_2$ present in the make-up feed to an ammonia synthesis unit). Examples of such catalysts include the KATALCO™ series (including models 11-4, 11-4R, 11-4M and 11-4MR) that are include nickel supported on refractory oxides; the HTC series (including NI 500 RP 1.2) having nickel supported on alumina; and Type 146 having ruthenium supported on alumina. Additional methanation catalysts include models PK-7R and METH-134. The methanation catalyst can be tableted or an extrudate. The shapes of such catalysts can be, for example, cylindrical, spherical, or ring structures, or partial shapes and/or combinations thereof. In some cases, ring structures are advantageous due to their reduced pressure drop across the reactor bed relative to cylindrical and spherical commercial forms. In some cases, the methanation catalyst is a doped or modified version of a commercially available catalyst.

In some cases, merely applying a methanation catalyst to the OCM and/or ETL process that has been developed or optimized for another process (e.g., SNG production or gas purification) can result in operational problems and/or non-optimal performance, including carbon formation (or coking) over the methanation catalyst. Coking can lead to de-activation of the catalyst and, eventually, to loss of conversion through the methanation reactor, thus making the methanation process ineffective, severely limiting the performances of the overall OCM and/or ETL-based process and, possibly, preventing the final products from achieving the required specifications.

The selectivity and/or conversion produced by an existing and/or commercially available methanation catalyst at a given process condition (e.g., gas-hourly space velocity, molar composition, temperature, pressure) may not be ideal for OCM and/or ETL implementations. For example, ammonia plants can have between about 100 ppm and 1% CO with a molar excess of $H_2$ (e.g., 2, 5, 10, 50, 100-fold or more excess) that drives equilibrium in favor of complete methanation. Methanation systems in ammonia plants have a small temperature difference between inlet and outlet of the adiabatic methanation reactor (e.g., 20 to 30° C.) and can be sized for catalyst lifetime. SNG production does not have a vast molar excess of $H_2$ in some cases. Methanation in SNG processes can have an inlet versus outlet temperature difference of greater than 100° C. and be performed in multiple stages. Furthermore, the purpose of methanation can be different for OCM and/or ETL. Ammonia and SNG processes typically perform methanation primarily to eliminate CO and/or $CO_2$ (although $H_2$ can also be eliminated or substantially reduced in concentration), while methanation is performed in OCM and/or ETL processes primarily to eliminate $H_2$ (although CO and/or $CO_2$ can also be eliminated or substantially reduced in concentration).

A methanation catalyst and/or catalytic process is described herein that can prevent or reduce carbon formation in the methanation reactor or other operational inefficiencies. The catalyst and/or catalytic process can be achieved through any combination of: (a) removing chemical species that can contribute to coke formation from the methanation inlet feed; (b) introducing chemical species into the methanation feed that eliminate or reduce the rate of coke formation; and (c) using the methanation catalyst described herein that reduces or eliminates coke formation and/or is designed to operate at the process conditions of OCM and/or ETL effluent or OCM and/or ETL process streams (e.g., gas-hourly space velocity, molar composition, temperature, pressure).

In some instances, the species present in the OCM and/or ETL effluent stream that can lead to carbon formation in the methanation reactor are removed or reduced in concentration using a separations or reactive process. The typical operating conditions of a methanation reactor can be between about 3 and about 50 bar pressure and between about 150 and about 400° C. temperature. Any hydrocarbon species containing carbon-carbon double or triple bonds is sufficiently reactive to form carbon deposits (i.e., coke). Examples of these species are acetylene, all olefins and aromatic compounds. Removal or significant reduction of these species can be achieved via different methods including, but not limited to: (a) hydrogenation (i.e., reaction of these species with the hydrogen present in the effluent stream itself to produce alkanes) over suitable catalysts prior to the methanation reactor; (b) condensation and separation of these species from methane prior to the methanation reactor; (c) absorption or adsorption of these species; (d) by utilizing suitable membranes; or (d) any combination thereof.

In embodiments of the present disclosure, new species are introduced into the methanation inlet stream that eliminate or reduce the rate of carbon formation. Molecular species that can create a reducing atmosphere can be used to counteract an oxidation reaction and can therefore reduce the rate of carbon formation. Hydrogen and water are examples of these particular compounds and can be added to the OCM and/or ETL effluent stream prior to methanation to increase their concentration in the methanation reactor.

An aspect of the present disclosure provides a methanation catalyst for an OCM and/or ETL process. Coke formation is typically the product of surface driven reactions. Therefore, the methanation catalyst for OCM and/or ETL alters the local electronic environment around the active site of the catalyst. This can be done by changing the elemental composition (for example via post-impregnation doping, or creating a new mixed metal of nickel and another transition metal), morphology and structure (for example via synthesizing the metal in a non-bulk form factor). Examples of such syntheses include; nanowires of the same material, nanoparticles coated on a support, and vapor deposition of the active material on a support material. Additional modifications to the surface may result from post synthetic processing steps, such as etching of the surface, oxidizing and reducing the metal to create a different surface reconstruction, calcination steps under different atmospheres (e.g., oxidizing or reducing), heating to achieve different crystal phases, and inducing defect formation. The end result of said modifications of the methanation catalyst is specifically designed to minimize carbon (coke) formation, while still effectively at conducting the methanation reactions.

The methanation process and/or methanation catalyst operates with OCM and/or ETL product gas, either directly or after one or more heat exchangers or separation operations. For example, the methanation feed stream can have the following composition on a molar basis: $CH_4$ between about 65% and about 90%; $H_2$ between about 5% and about 15%; CO between about 1% and about 5% (molar basis); $C_2H_4$ between about 0% and about 0.5%; and $C_2H_2$ between about 0% and about 0.1%. As described herein, the ETL effluent can contain $C_{2+}$ compounds including propane, propylene, butane, butylene, and $C_{5+}$ compounds. These $C_{2+}$ compounds can be present in the stream entering the methanation reactor in any concentration. The balance of the feed stream can be inert gases such as $N_2$, Ar and He. The methanation feed stream typically has a temperature close to ambient temperature and a pressure ranging between about 3 and about 50 bar.

In some cases, the entire ETL product stream and/or all of the $C_{2+}$ compounds present in the ETL effluent and/or any or all of the olefins present in the ETL effluent are fed into the methanation reactor (i.e., methanation feed). In some cases, the temperature of the ETL effluent is not reduced, or not substantially reduced before being fed into the methanation reactor such that all or most (at least about 70%, at least about 80%, at least about 90%, at least about 95%, or at least about 99%) of the $C_{2+}$ compounds and/or olefins remain in the methanation feed. In some cases, the temperature of the ETL effluent is reduced to separate some of the $C_{2+}$ compounds and/or olefins from the stream before being fed into the methanator. The temperature can be reduced to a temperature sufficiently low to remove most (at least about 70%, at least about 80%, at least about 90%, at least about 95%, or at least about 99%) of the $C_{5+}$ compounds (e.g., about 40° C.), to remove most (at least about 70%, at least about 80%, at least about 90%, at least about 95%, or at least about 99%) of the $C_{4+}$ compounds (e.g., about 10° C.), or to remove most (at least about 70%, at least about 80%, at least about 90%, at least about 95%, or at least about 99%) of the $C_{3+}$ compounds (e.g., about −40° C.).

The methanation reaction can produce water and/or have water in the methanation effluent. In some cases, it can be desirable to remove this water prior to recycling the methanation effluent to the OCM reactor. This can be accomplished by lowering the temperature of the methanation effluent or performing any separation procedure that removes the water. In some embodiments, at least about 70%, at least about 80%, at least about 70%, at least about 90%, at least about 95%, or at least about 99% of the water is removed from the methanation effluent prior to the OCM reactor. Removing the water can increase the lifetime and/or performance of the OCM catalyst.

In some cases, the ETL process can be designed to use a methanation catalyst that is not optimized for the ETL process. The OCM or OCM-ETL process can be designed to produce gasoline or distillates or aromatics (or any combination thereof) from natural gas. In this case, the effluent of the OCM reactor is fed to an ETL reactor where all short olefins (e.g., ethylene and propylene) are converted to longer chain hydrocarbons over a suitable oligomerization catalyst. An example of such a catalyst is the zeolite ZSM-5. The product stream that contains unconverted methane, unconverted olefins, CO, $CO_2$, $H_2$, water, inert species and all oligomerization products (paraffins, isoparaffins, olefins and aromatics) is fed to the methanation module. The concentration of the oligomerization products in the methanation feed stream can vary depending on the type and extent of separation conducted prior to the methanation step. The methanation feed stream typically has a temperature close to or below ambient temperature and a pressure ranging between 3 and 50 bar.

Figure 27:
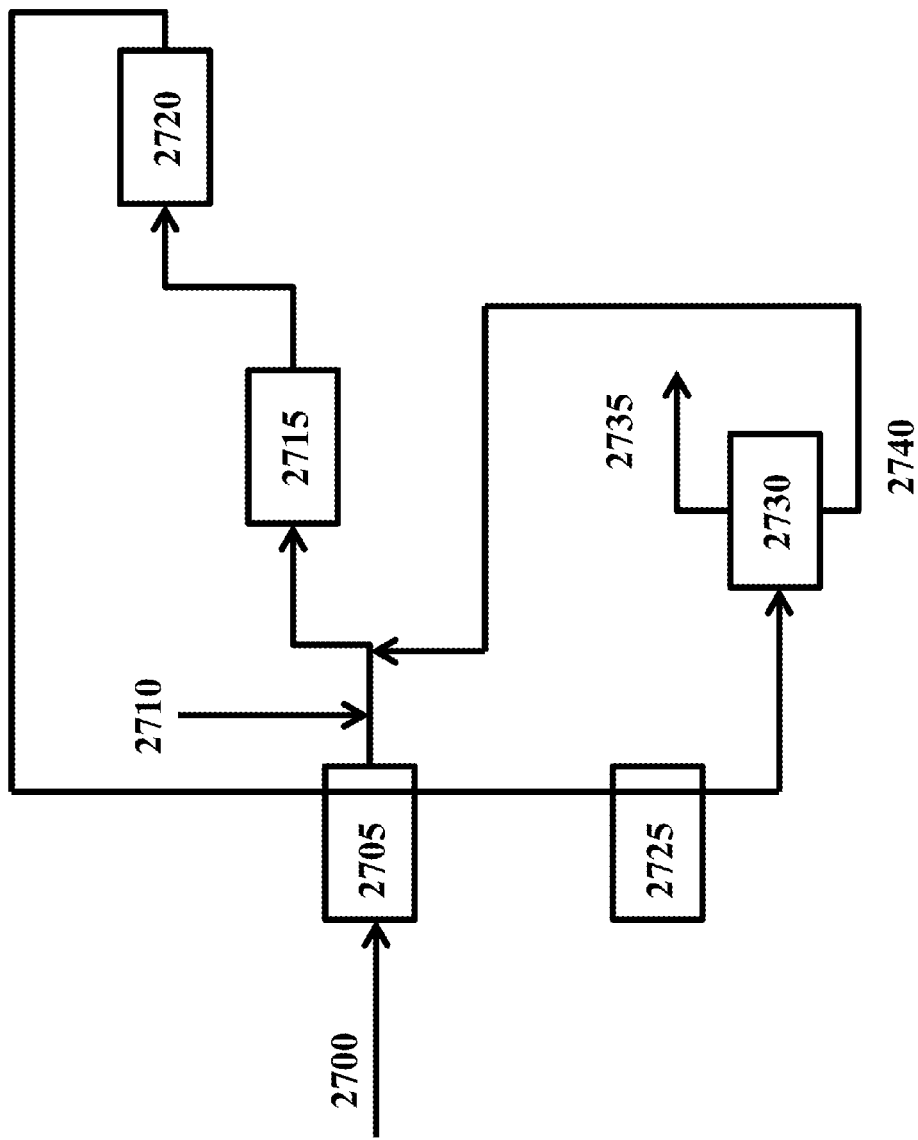
FIG. 27 shows an example of methanation systems for OCM and ETL.

With reference to FIG. 27, the methanation system can be designed to use a catalyst that is not necessarily optimized for the OCM and/or ETL process streams. The methanation feed stream 2700 is first sent to a first heat exchanger 2705 where its temperature is increased to the methanation reactor inlet temperature, typically between 150 and 300° C. Steam is injected 2710 immediately downstream of the heat exchanger to increase water concentration in the methanation feed stream. Then the heated stream is fed to a first adiabatic reactor 2715 where ethylene, acetylene and any other hydrocarbon that presents multiple carbon-carbon bonds are hydrogenated via reaction with the $H_2$ present in the stream itself.

The effluent from 2715 is then fed to a second reactor 2720, where CO and $CO_2$ react with $H_2$ until a desired approach to equilibrium is achieved, typically 0-15° C. to equilibrium. The adiabatic temperature increase that results from CO and $CO_2$ methanation can depend on the composition of the feed stream, and is typically in the 50-150° C. range.

The effluent from the second reactor 2720 is then sent to the first heat exchanger 2705 and a second heat exchanger 2725 where it is cooled down to a temperature below water condensation. The stream is then fed to a phase separator 2730 where the condensed water and a portion of the longer hydrocarbons is separated from the vapors.

The vapor stream from the phase separator 2735 is sent to the final product purification and recovery section or injected into a natural gas pipeline, depending on its concentration. Alternatively, the vapor stream 2735 from the phase separator 2730 can be further methanated in a second methanation reactor to further reduce CO, $CO_2$ and $H_2$ concentration (not shown).

The liquid stream from the phase separator 2740 is re-injected into the methanation feed stream alongside the steam. Alternatively, it can be first vaporized and then re-injected, or it can be sent to a water treatment system for water recovery and purification (not shown).

The reactors 2715, 2720 (and a third reactor, if present) or any combination of them can be physically situated in the same vessel or can be arranged in separate individual vessels.

In processes, systems, and methods of the present disclosure, a Fischer-Tropsch (F-T) reactor can be used to replace a methanation reactor, for example in a methane recycle stream. CO and $H_2$, such as that found in a methane recycle stream, can be converted to a variety of paraffinic linear hydrocarbons, including methane, in an F-T reaction. Higher levels of linear hydrocarbons, such as ethane, can improve OCM process efficiency and economics. For example, effluent from an OCM reactor can be directed through a cooling/compression system and other processes before removal of a recycle stream in a de-methanizer. The recycle stream can comprise $CH_4$, CO, and $H_2$, and can be directed into an F-T reactor. The F-T reactor can produce $CH_4$ and $C_{2+}$ paraffins for recycling into the OCM reactor. A range of catalysts, including any suitable F-T catalyst, can be employed. Reactor designs, including those discussed in the present disclosure, can be employed. F-T reactor operation conditions, including temperature and pressure, can be optimized. This approach can reduce $H_2$ consumption compared to a methanation reactor.

Hydrocarbon Separations

In natural gas processing plants, methane can be separated from ethane and higher carbon-content hydrocarbons (conventionally called natural gas liquids or NGLs) to produce a methane-rich stream that can meet the specifications of pipelines and sales gas. Such separation can be performed using cryogenic separation, such as with the aid of one or more cryogenic units.

The raw natural gas fed to gas processing plants can have a molar composition of 70% to 95% methane and 4% to 20% NGLs, the balance being inert gas(ses) (e.g., $CO_2$ and $N_2$). The ratio of methane to ethane can be in the range of 5-25:1. Given the relatively large amount of methane present in the stream fed to cryogenic sections of gas processing plants, at least some or substantially all of the cooling duty required for the separation is provided by a variety of compression and expansion steps performed on the feed stream and the methane product stream. None or a limited portion of the cooling duty can be supplied by external refrigeration units.

There are various approaches for separating higher carbon alkanes (e.g., ethane) from natural gas, such as recycle split vapor (RSV) and gas sub-cooled process (GSP) processes, which can maximize the recovery of ethane (e.g., >95% recovery) while providing most or all of the cooling duty via internal compression and expansion of the methane itself. However, the application of such approach in separating alkenes (e.g., ethylene) from an OCM product stream comprising methane may result in a limited recovery (e.g., provide less than 95% recovery) of the alkene product, due at least in part to (i) the different vapor pressure of alkenes and alkanes, and/or (ii) the presence of significant amounts of $H_2$ in the OCM product stream, which can change the boiling curve and, particularly, the Joule-Thomson coefficient of the methane stream that needs to be compressed and expanded to provide the cooling duty. Hydrogen can display a negative or substantially low Joule-Thomson coefficient, which can cause a temperature increase or a substantially low temperature decrease in temperature when a hydrogen-reach stream is expanded.

In some embodiments, the design of a cryogenic separation system of an OCM-based plant can feature a different combination of compression/expansion steps for internal refrigeration and, in some cases, external refrigeration. The present disclosure provides a separation system comprising one or more cryogenic separation units and one or more de-methanizer units. Such a system can maximize alkene recovery (e.g., provide greater than 95% recovery) from a stream comprising a mixture of alkanes, alkenes, and other gases (e.g., $H_2$), such as in an OCM product stream (see FIGS. 24 and 25 and the associated text).

In such separation system, the cooling duty can be supplied by a combination of expansion of the OCM effluent (feed stream to the cryogenic section) when the OCM effluent pressure is higher than a de-methanizer column; expansion of at least a portion or all of the de-methanizer overhead methane-rich stream; compression and expansion of a portion of the de-methanizer overhead methane-rich stream; and/or external propane, propylene or ethylene refrigeration units.

FIGS. 28-33 show various separation systems, as can be employed with various systems and methods of the present disclosure. Such systems can be employed for use in the OCM-ETL systems described herein, such as used as the vapor-liquid separator 320 described above in the context of FIGS. 3 and 4.

Figure 28:
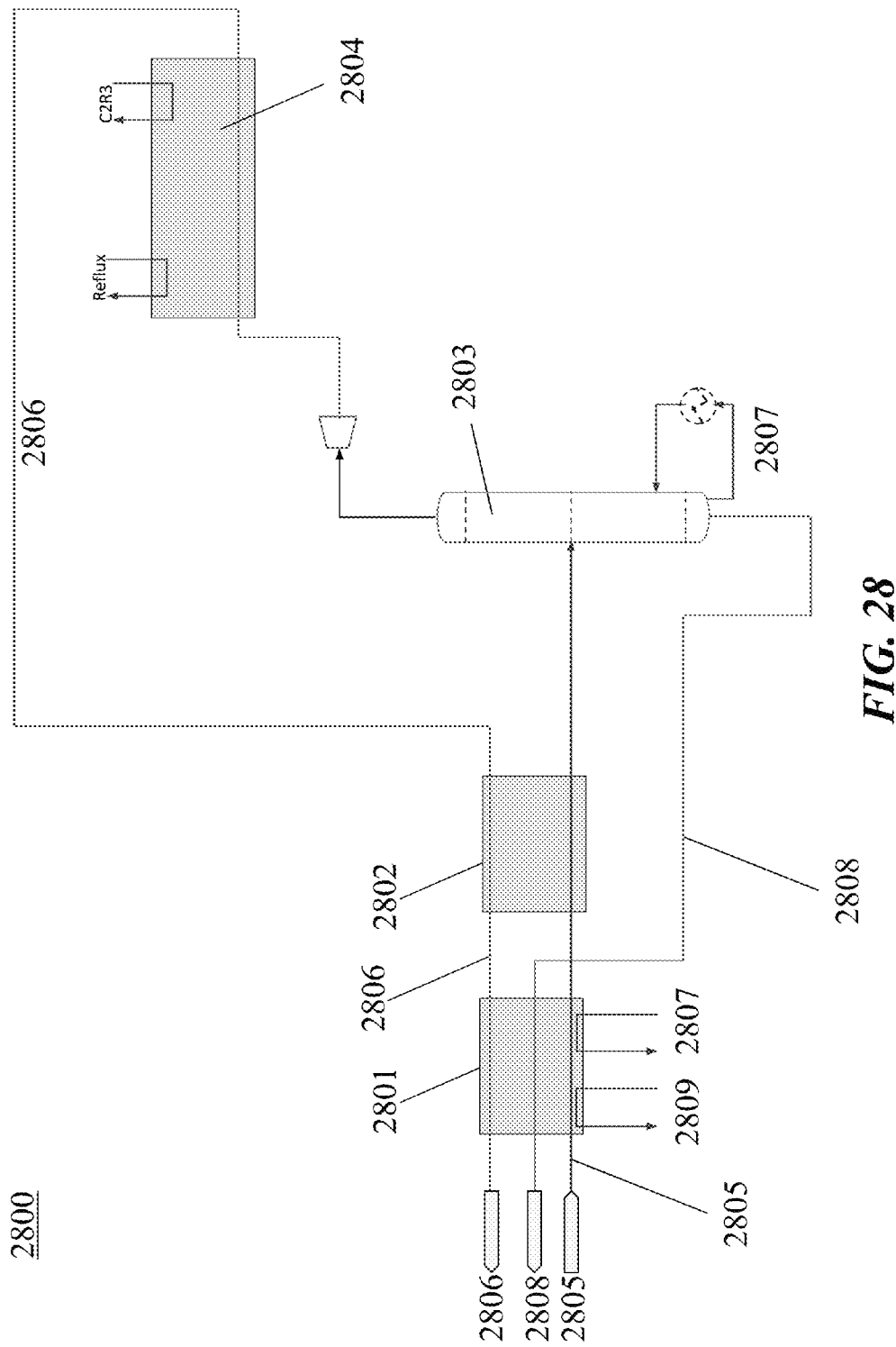
FIG. 28 shows a separation system that may be employed for use with systems and methods of the present disclosure.

FIG. 28 shows a separation system 2800 comprising a first heat exchanger 2801, a second heat exchanger 2802, a de-methanizer 2803, and a third heat exchanger 2804. The direction of fluid flow is shown in the figure. The de-methanizer 2803 can be a distillation unit or multiple distillation units (e.g., in series). In such a case, the de-methanizer can include a reboiler and a condenser, each of which can be a heat exchanger. An OCM effluent stream 2805 is directed to the first heat exchanger 2801 at a pressure from about 10 to 100 bar (absolute), or 20 to 40 bar. The OCM effluent stream 2805 can include methane and $C_{2+}$ compounds, and may be provided in an OCM product stream from an OCM reactor (not shown). The OCM effluent stream 2805 is then directed from the first heat exchanger 2801 to the second heat exchanger 2802. In the first heat exchanger 2801 and the second heat exchanger 2802, the OCM effluent stream 2805 is cooled upon heat transfer to a de-methanizer overhead stream 2806, a de-methanizer reboiler stream 2807, a de-methanizer bottom product stream 2808, and a refrigeration stream 2809 having a heat exchange fluid comprising propane or an equivalent cooling medium, such as, but not limited to, propylene or a mixture of propane and propylene.

The cooled OCM effluent 2805 can be directed to the de-methanizer 2803, where light components, such as $CH_4$, $H_2$ and CO, are separated from heavier components, such as ethane, ethylene, propane, propylene and any other less volatile component present in the OCM effluent stream 2805. The light components are directed out of the de-methanizer along the overhead stream 2806. The heavier components are directed out of the de-methanizer along the bottom product stream 2808. The de-methanizer can be designed such that at least about 60%, 70%, 80%, 90%, or 95% of the ethylene in the OCM effluent stream 2805 is directed to the bottom product stream 2808.

The de-methanizer overhead stream 2806 can contain at least 60%, 65%, or 70% methane. The overhead stream 2806 can be expanded (e.g., in a turbo-expander or similar machine or flashed over a valve or similar device) to decrease the temperature of the overhead stream 2806 prior to directing the overhead stream 2806 to the second heat exchanger 2802 and subsequently the first heat exchanger 2801. The overhead stream 2806 can be cooled in the third heat exchanger 2804, which can be cooled using a reflux stream and a hydrocarbon-containing cooling fluid, such as, for example, ethylene.

The overhead stream 2806, which can include methane, can be recycled to an OCM reactor and/or directed for other uses, such as a natural gas pipeline. In some examples, the bottom product stream, which can contain $C_{2+}$ compounds (e.g., ethylene), can be directed to an ETL system.

Figure 29:
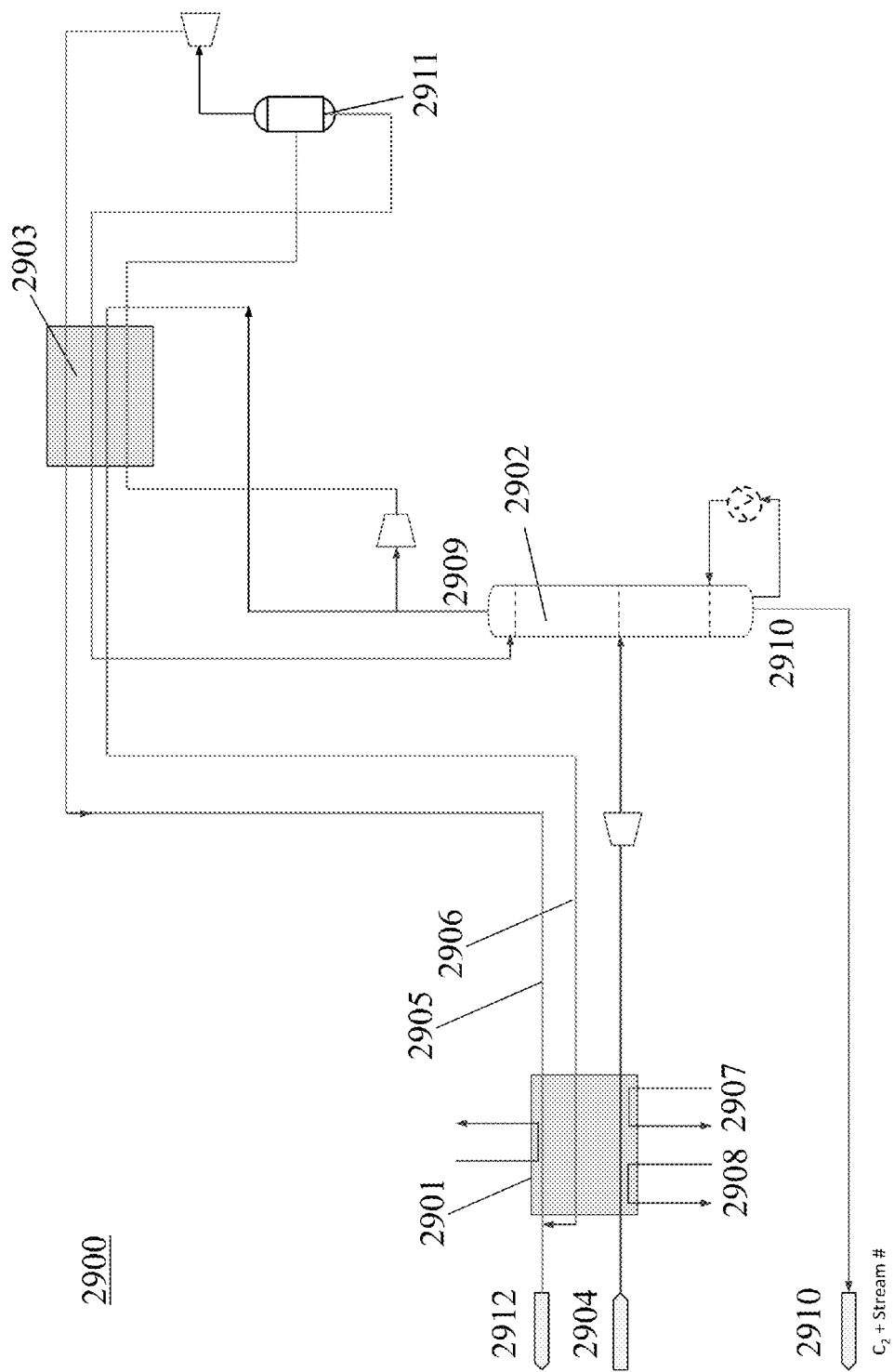
FIG. 29 shows another separation system that may be employed for use with systems and methods of the present disclosure.

FIG. 29 shows another separation system 2900 that may be employed for use with systems and methods of the present disclosure. The direction of fluid flow is shown in the figure. The system 2900 comprises a first heat exchanger 2901, de-methanizer 2902 and a second heat exchanger 2903. The de-methanizer 2902 can be a distillation unit or multiple distillation units (e.g., in series). An OCM effluent stream 2904 is directed into the first heat exchanger 2901. The OCM effluent stream 2904 can include methane and $C_{2+}$ compounds, and may be provided in an OCM product stream from an OCM reactor (not shown). The OCM effluent stream 2904 can be provided at a pressure from about 10 bar (absolute) to 100 bar, or 40 bar to 70 bar. The OCM effluent stream 2904 can be cooled upon heat transfer to a de-methanizer overhead streams 2905 and 2906 from the second heat exchanger 2903, a de-methanizer reboiler stream 2907, and a refrigeration stream having a cooling fluid comprising, for example, propane or an equivalent cooling medium, such as, but not limited to, propylene or a mixture of propane and propylene. In some cases, the de-methanizer overhead streams 2905 and 2906 are combined into an output stream 2912 before or after passing through the first heat exchanger 2901.

Subsequent to cooling in the first heat exchanger 2901, the OCM effluent stream 2904 can be expanded in a turbo-expander or similar device or flashed over a valve or similar device to a pressure of at least about 5 bar, 6 bar, 7 bar, 8 bar, 9 bar, or 10 bar. The cooled OCM effluent stream 2904 can then be directed to the de-methanizer 2902, where light components (e.g., $CH_4$, $H_2$ and CO) are separated from heavier components (e.g., ethane, ethylene, propane, propylene and any other less volatile component present in the OCM effluent stream 2904). The light components are directed to an overhead stream 2909 while the heavier components (e.g., $C_{2+}$) are directed along a bottoms stream 2910. A portion of the overhead stream 2909 is directed to second heat exchanger 2903 and subsequently to the first heat exchanger 2901 along stream 2906. A remainder of the overhead stream 2909 is pressurized in a compressor and directed to the second heat exchanger 2903. The remainder of the overhead stream 2909 is then directed to a phase separation unit 2911 (e.g., distillation unit or vapor-liquid separator). Liquids from the phase separation unit 2911 are directed to the second heat exchanger 2903 and subsequently returned to the de-methanizer 2902. Vapors from the phase separation unit 2911 are expanded (e.g., in a turbo-expander or similar device) and directed to the second heat exchanger 2903, and thereafter to the first heat exchanger along stream 2905. The de-methanizer 2902 can be designed such that at least about 60%, 70%, 80%, 90%, or 95% of the ethylene in the OCM effluent stream 2904 is directed to the bottom product stream 2910.

Figure 30:
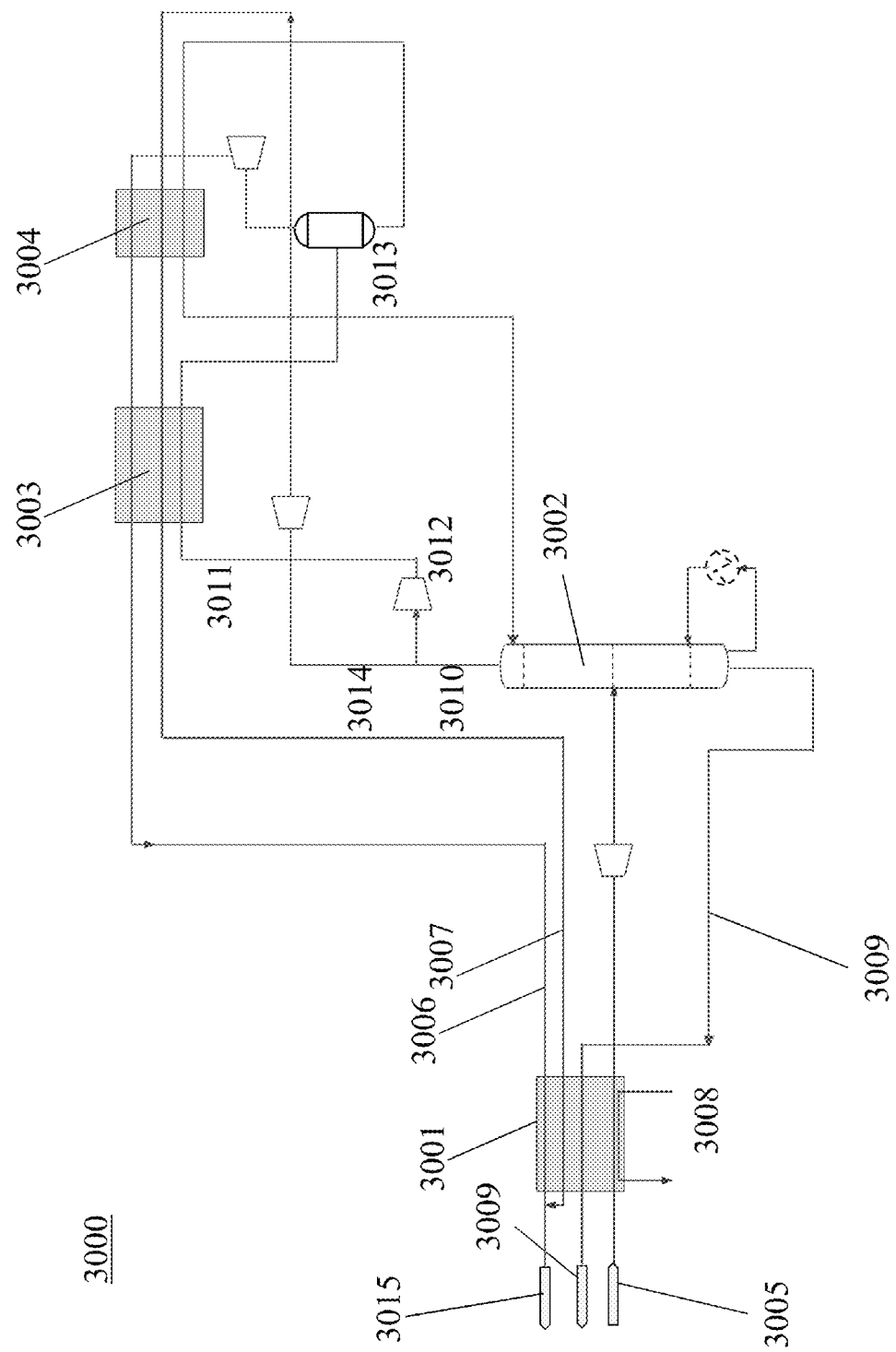
FIG. 30 shows another separation system that may be employed for use with systems and methods of the present disclosure.

FIG. 30 shows another separation system 3000 that may be employed for use with systems and methods of the present disclosure. The direction of fluid flow is shown in the figure. The system 3000 comprises a first heat exchanger 3001, a de-methanizer 3002, a second heat exchanger 3003 and a third heat exchanger 3004. The system 3000 may not require any external refrigeration. The de-methanizer 3002 can be a distillation unit or multiple distillation units (e.g., in series). An OCM effluent stream 3005 is directed to the first heat exchanger 3001 at a pressure from about 10 bar (absolute) to 100 bar, or 40 bar to 70 bar. In the first heat exchanger 3001, the OCM effluent stream 3005 can be cooled upon heat transfer to de-methanizer overhead streams 3006 and 3007, a de-methanizer reboiler stream 3008 and a de-methanizer bottom product stream 3009. In some cases, the de-methanizer overhead streams 3006 and 3007 are combined into a common stream 3015 before or after they are passed through the first heat exchanger 3001. The OCM effluent stream 3005 is then expanded to a pressure of at least about 5 bar, 6 bar, 7 bar, 8 bar, 9 bar, or 10 bar, such as, for example, in a turbo-expander or similar machine or flashed over a valve or similar device. The cooled OCM effluent stream 3005 is then directed to the de-methanizer 3002, where light components (e.g., $CH_4$, $H_2$ and CO) are separated from heavier components (e.g., ethane, ethylene, propane, propylene and any other less volatile component present in the OCM effluent stream 3005). The light components are directed to an overhead stream 3010 while the heavier components are directed along the bottom product stream 3009. The de-methanizer 3002 can be designed such that at least about 60%, 70%, 80%, 90%, or 95% of the ethylene in the OCM effluent stream 3005 is directed to the bottom product stream 3009.

The de-methanizer overhead stream 3010, which can contain at least 50%, 60%, or 70% methane, can be divided into two streams. A first stream 3011 is compressed in compressor 3012 and cooled in the second heat exchanger 3003 and phase separated in a phase separation unit 3013 (e.g., vapor-liquid separator or distillation column). Vapors from the phase separation unit 3013 are expanded (e.g., in a turbo-expander or similar device) to provide part of the cooling duty required in heat exchangers 3001, 3003 and 3004. Liquids from the phase separation unit 3013 are sub-cooled in the third heat exchanger 3004 and recycled to the de-methanizer 3002. A second stream 3014 from the overhead stream 3010 can be expanded (e.g., in a turbo-expander or similar device) to decrease its temperature and provide additional cooling to the heat exchangers 3001, 3003 and 3004.

Figure 31:
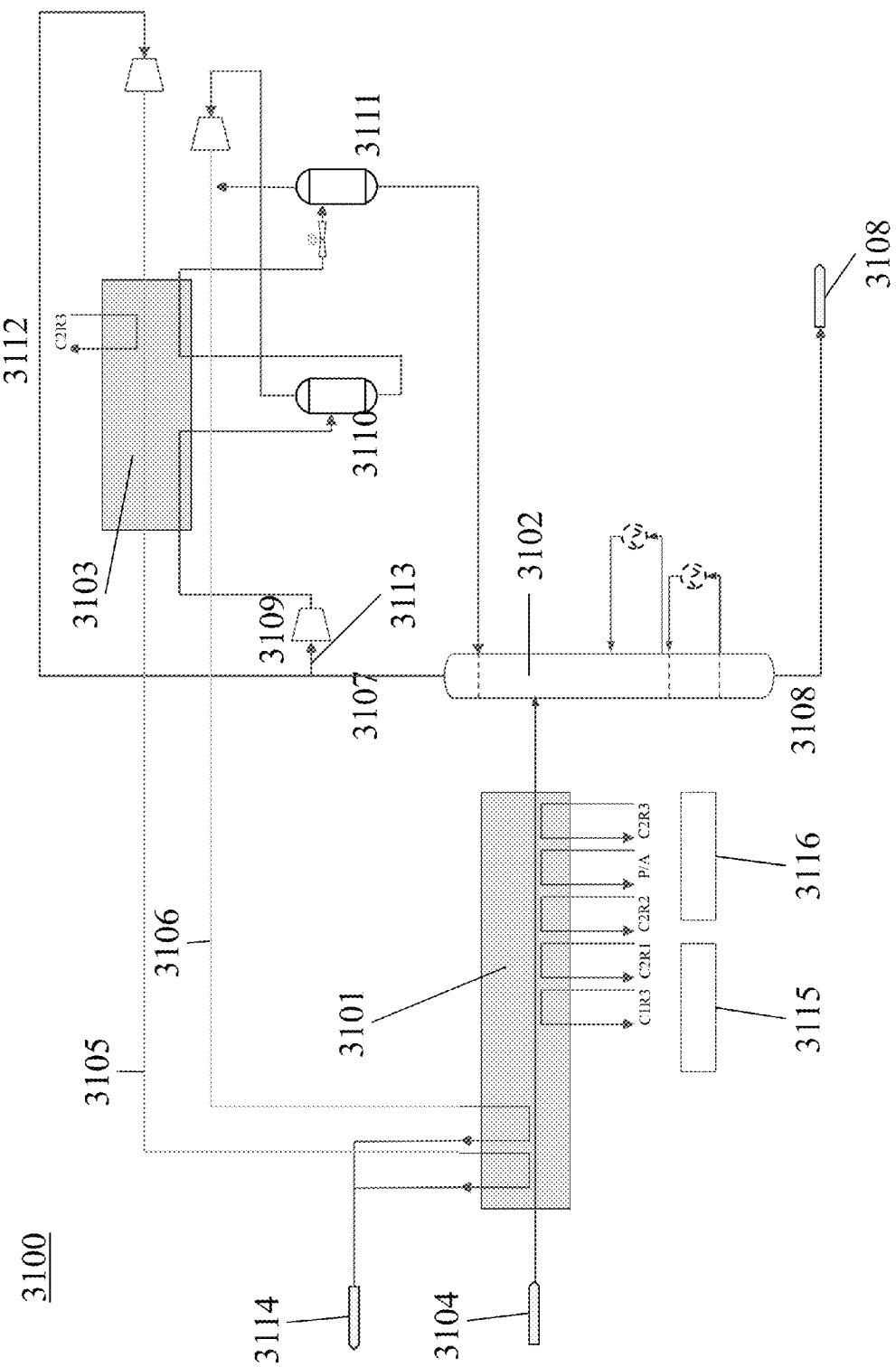
FIG. 31 shows another separation system that may be employed for use with systems and methods of the present disclosure.

FIG. 31 shows another separation system 3100 that may be employed for use with systems and methods of the present disclosure. The direction of fluid flow is shown in the figure. The system 3100 comprises a first heat exchanger 3101, a de-methanizer 3102, and a second heat exchanger 3103. An OCM effluent stream 3104 is directed to the first heat exchanger 3101 at a pressure from about 2 bar (absolute) to 100 bar, or 3 bar to 10 bar. The first heat exchanger 3101 can interface with a propane refrigeration unit 3115 and/or an ethylene refrigeration unit 3116. In the first heat exchanger 3101, the OCM effluent stream 3104 can be cooled upon heat transfer to de-methanizer overhead streams 3105 and 3106, a de-methanizer reboiler stream, a de-methanizer pump-around stream, and various levels of external refrigeration, such as using cooling fluids comprising ethylene and propylene. In some cases, the de-methanizer overhead streams 3105 and 3106 are combined into a single stream 3114 before or after they are cooled. The cooled OCM effluent stream 3104 is then directed to the de-methanizer 3102, where light components (e.g., $CH_4$, $H_2$ and CO) are separated from heavier components (e.g., ethane, ethylene, propane, propylene and any other less volatile component present in the OCM effluent stream 3104). The light components are directed to an overhead stream 3107 and the heavier components are directed along a bottom product stream 3108. The de-methanizer 3102 can be designed such that at least about 60%, 70%, 80%, 90%, or 95% of the ethylene in the OCM effluent stream 3104 is directed to the bottom product stream 3108.

The de-methanizer overhead stream, which can contain at least about 50%, 60%, or 70% methane, can be divided into two streams. A first stream 3113 can be compressed in a compressor 3109, cooled in the second heat exchanger 3103 and phase-separated in a phase separation unit 3110 (e.g., distillation column or vapor-liquid separator). Vapors from the phase separation unit 3110 can be expanded (e.g., in a turbo-expander or similar device) to provide part of the cooling duty required for the heat exchanger 3101 and 3103. Liquids from the phase separation unit 3110 can be sub-cooled and flashed (e.g., over a valve or similar device), and the resulting two-phase stream is separated in an additional phase separation unit 3111. Liquids from the additional phase separation unit 3111 are recycled to the de-methanizer 3102 and vapors from the additional phase separation unit are mixed with expanded vapors from the phase separation unit 3110 prior to being directed to the second heat exchanger 3103.

A second stream 3112 from the overhead stream 3107 can be expanded (e.g., in a turbo-expander or similar device) to decrease its temperature and provide additional cooling for the heat exchanger 3101 and 3103. Any additional cooling that may be required for the second heat exchanger 3103 can be provided by an external refrigeration system, which may employ a cooling fluid comprising ethylene or an equivalent cooling medium.

In some cases, recycle split vapor (RSV) separation can be performed in combination with de-methanization.

In some instances, the methane undergoes an OCM and/or ETL process to produce liquid fuel or aromatic compounds (e.g., higher hydrocarbon liquids) and contains molecules that have gone through methanation. In some embodiments, the compounds have been through a recycle split vapor (RSV) separation process. In some cases, alkanes (e.g., ethane, propane, butane) are cracked in a post-bed cracker.

Systems above and elsewhere herein are not limited to ethylene and may be configured to operate with other olefins, such as propylene, butenes, pentene, or other alkenes. Although various systems and methods herein have been described in the context of ethylene to liquids, it will be appreciated that other alkenes may be used. For example, an OCM reactor may generate an OCM effluent stream comprising propylene and/or one or more butenes, which may be used to provide one or more streams comprising higher molecular weight hydrocarbons.

Systems of the present disclosure may be suitable for generating liquids at less than or equal to about 250 kilotons per annum (KTA) ("small scale"), or generating liquids at greater than about 250 KTA ("world scale"). In some examples, a world scale OCM-ETL system generates at least about 1000, 1100, 1200, 1300, 1400, 1500, or 1600 KTA of liquids.

Ethane Skimmers

The systems and methods described herein can process natural gas into gas that is suitable for sale (i.e., "sales gas" that meets the specifications required for transportation by pipeline). In some cases, the systems and methods of the present disclosure can convert methane and/or ethane (e.g., from natural gas) to sales gas as well as products such as LPG, gasoline, distillate fuels, and/or aromatic chemicals. Such a system or method is referred to as an "ethane skimmer".

Ethane can be fed directly into a post-bed cracker (PBC), which can be a portion of an OCM reactor downstream of the OCM catalyst, where the heat generated in the OCM reaction can be used to crack the ethane to ethylene. As an alternative, the PBC can be a unit that is separate from the OCM reactor and in some cases in thermal communication with the OCM reactor. The ethane feed stream to the OCM reactor can include (a) ethane recycled to the OCM reactor from an OCM reactor effluent stream, which can be separated in at least one downstream separation module and recycled to the OCM reactor, (b) ethane present in other feed streams (e.g., natural gas), which can be separated in at least one separation module and recycled to the OCM reactor, and (c) any additional (i.e., fresh) ethane feed.

The maximum amount of ethane that can be converted in the PBC can be limited by the flow rate of material exiting the OCM catalyst and/or its temperature. It can be advantageous to utilize a high proportion of the maximum amount of PBC. In some cases, the amount of ethane converted to ethylene is about 50%, about 60%, about 70%, about 80%, about 85%, about 90%, about 95%, or about 99% of the maximum amount of ethane that can be converted to ethylene in the PBC. In some instances, the amount of ethane converted to ethylene is at least about 50%, at least about 60%, at least about 70%, at least about 80%, at least about 85%, at least about 90%, at least about 95%, or at least about 99% of the maximum amount of ethane that can be converted to ethylene in the PBC.

Achieving a high proportion of the maximum PBC capacity can be accomplished by adding natural gas to the system, which can have a concentration of ethane that depends on many factors, including the geography and type and age of the natural gas well. The treatment and separation modules of the process described herein can be used to purify or fractionate the ETL effluent, and can additionally be used to treat (e.g., remove water and $CO_2$) and purify the natural gas that is added to the system along with the ETL effluent, such as, e.g., by separating $C_{2+}$ compounds from methane and separating ethane from ethylene. In some cases, ethane contained in the natural gas feed can be recycled to the OCM reactor (e.g., PBC region) as pure ethane and the system may not be sensitive to the purity and composition of the natural gas, making raw natural gas a suitable input to the system.

The maximal PBC capacity can depend on the ratio between methane and ethane in the input to the OCM reactor, including in some instances the PBC portion. In some cases, the PBC capacity is saturated when the molar ratio of methane to ethane is about 1, about 2, about 3, about 4, about 5, about 6, about 7, about 8, about 9, about 10, about 11, about 12, about 13, about 14, or about 15. In some cases, the PBC capacity is saturated when the molar ratio of methane to ethane is at least about 1, at least about 2, at least about 3, at least about 4, at least about 5, at least about 6, at least about 7, at least about 8, at least about 9, at least about 10, at least about 11, at least about 12, at least about 13, at least about 14, or at least about 15. In some cases, the PBC capacity is saturated when the molar ratio of methane to ethane is at most about 5, at most about 6, at most about 7, at most about 8, at most about 9, at most about 10, at most about 11, at most about 12, at most about 13, at most about 14 or at most about 15. In some cases, the PBC capacity is saturated when the molar ratio of methane to ethane is between about 7 and 10 parts methane to one part ethane.

Natural gas (raw gas or sales gas) can have a concentration of ethane of less than about 30 mol %, 25 mol %, 20 mol %, 15 mol %, 10 mol %, 9 mol %, 8 mol %, 7 mol %, 6 mol %, 5 mol %, 4 mol %, 3 mol %, 2 mol % or 1 mol %. In some cases, natural gas has a methane to ethane ratio greater than about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1 or 40:1. The ethane skimmer implementation described herein can be used to inject more natural gas feed into the system than what may be required to produce the desired or predetermined amount of ethylene or other products. The excess methane can be drawn from a stream downstream of the methanation unit and sold as sales gas (which may lack an appreciable amount of ethane but can still meet pipeline specifications and/or can be directed to a power plant for power production). The ethane in the additional natural gas feed can be used to saturate the PBC capacity. Any excess ethane can be drawn from the $C_2$ splitter and exported as pure ethane. The ethane skimmer implementation described herein can result in additional product streams from the system (namely sales gas, natural gas liquids, gasoline, diesel or jet fuels and/or aromatic chemicals). In such a case, the process can be used to achieve both natural gas processing and production of $C_{2+}$ chemicals or fuels.

Figure 32:
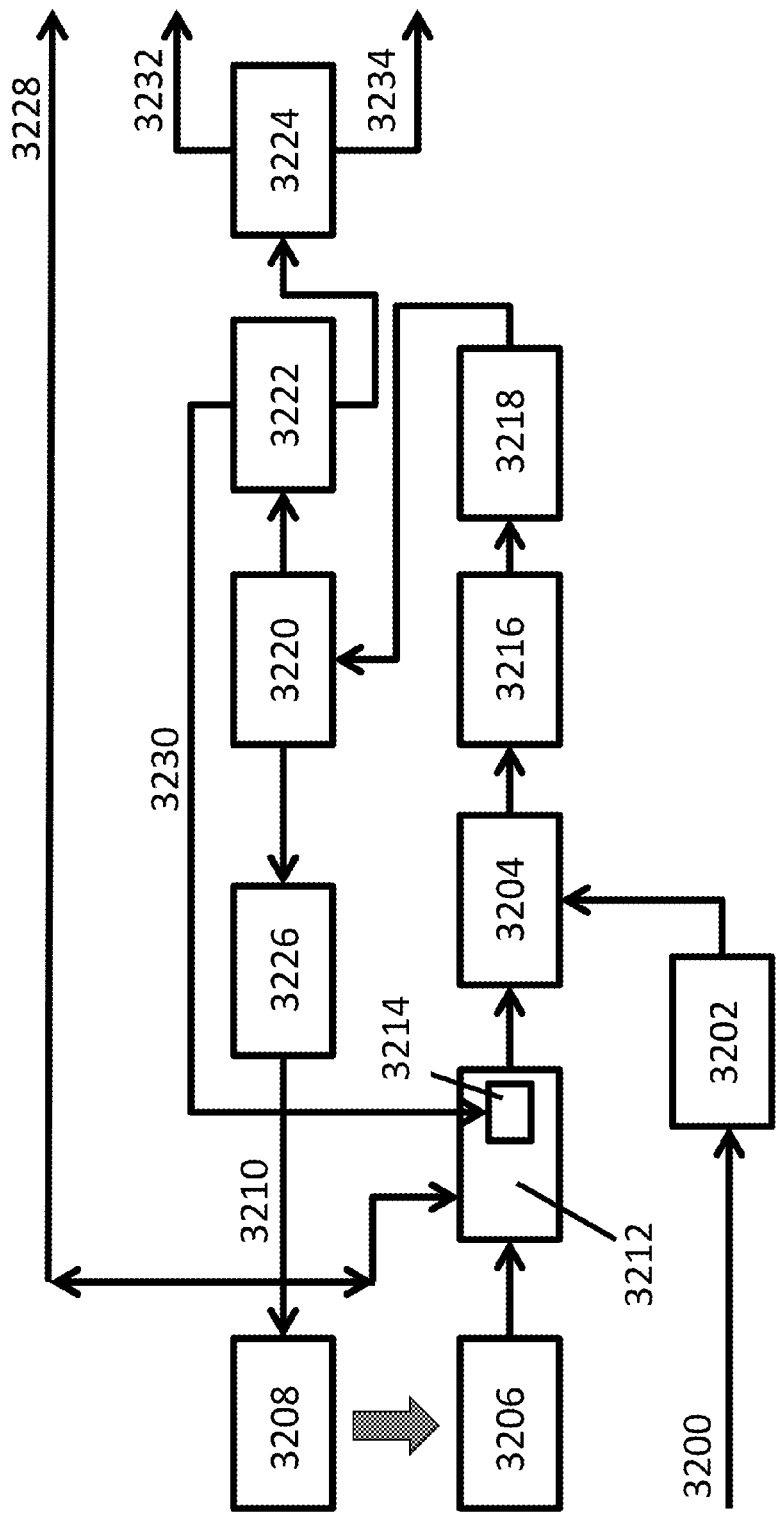
FIG. 32 shows an example of an ethane skimmer implementation of OCM and ETL.

The ethane skimmer implementation can be readily understood by reference to FIG. 32. Natural gas 3200 can be fed into a desulfurization unit 3202 and then into a gas compressor 3204. Oxygen can be provided from an air separation unit 3206 that can be powered by a gas turbine and combination cycle 3208 that is powered by combustion of a portion of the natural gas and/or methane. The oxygen and methane 3210 produced by the process can be injected into an OCM reactor 3212 having a PBC portion 3214. The OCM effluent can be fed into the process gas compressor 3204 and then into the ETL module 3216. Products of the ETL module can be dried in a drier 3218. The separation module can comprise a de-methanizer 3220, a de-ethanizer 3222 and a de-butanizer 3224. The de-methanizer can separate $C_1$ compounds from $C_{2+}$ compounds and direct the $C_1$ compounds (e.g., methane, carbon monoxide and carbon dioxide) to a methanator 3226. The $C_1$ compound stream can have any amount of $C_{2+}$ compounds (e.g., about 0.5%, about 1%, about 1.5%, about 2%, about 2.5%, about 3%, or about 3.5%). The methanator can convert the carbon monoxide and/or carbon dioxide to methane (e.g., using hydrogen generated in the process). The methane can be divided into any number of streams that can be directed to the OCM reactor 3212, the gas turbine 3208, and/or a pipeline 3228 or other means for delivering a methane product to the market (i.e., sales gas). The ethane 3230 from the separation module can be directed to the PBC. The system can produce $C_{3+}$ products such as liquified petroleum gas (LPG; having $C_3$ and $C_4$ molecules) 3232 and $C_{5+}$ products 3234 such as gasoline, diesel fuel, jet fuel, and/or aromatic chemicals.

Overall, in the ethane skimmer process as shown in FIG. 32, at least some or most (e.g., >70%, >80%, >85%, >90%, >95%, or >99%) of the methane in the natural gas feed 3200 ends up in the methane recycle 3210, at least some or most (e.g., >70%, >80%, >85%, >90%, >95%, or >99%) of the ethane in the natural gas feed ends up in the ethane recycle stream 3230, at least some or most (e.g., >70%, >80%, >85%, >90%, >95%, or >99%) propane in the natural gas feed ends up in the $C_{3+}$ products streams 3232 and 3234. In some cases, and ethane is added (not shown in FIG. 32) up to the point where the PBC cracking capacity is saturated or nearly saturated (e.g., >70%, >80%, >85%, >90%, >95%, or >99%). Excess ethane (e.g., beyond what is needed to saturate the PBC) can end up in an ethane product stream (not shown). The ethane skimmer implementation does not require a separate (i.e., fresh) ethane stream to saturate or nearly saturate the PBC capacity of the system.

Additional Products and Processes

In addition to the ethylene conversion processes described herein, components other than ethylene that are produced in an ethylene production process, e.g., contained within an OCM effluent gas, may be directed to, and thus fluidly connected to additional conversion processes. In particular, the OCM reaction process generates a number of additional products, other than ethylene, including for example, hydrogen gas ($H_2$) and carbon monoxide (CO). In some cases, the $H_2$ and CO components of the OCM reaction product slate are subjected to additional processing to produce other products and intermediates, e.g., dimethylether (DME), methanol, and hydrocarbons. These components may be useful in a variety of different end products, including liquid fuels, lubricants and propellants. In some embodiments, the $H_2$ and CO components of the OCM reaction effluent are separated from the other OCM products. The $H_2$ and CO can then be subjected to any of a variety of syngas-like conversion processes to produce a variety of different products, e.g., methanol, dimethylether, hydrocarbons, lubricants, waxes and fuels or fuel blendstocks. In one example, the $H_2$ and CO components are subjected to a catalytic process to produce DME via a methanol intermediate. The catalytic process is described in detail in, e.g., U.S. Pat. No. 4,481,305, the full disclosure of which is incorporated herein by reference in its entirety for all purposes.

As noted herein, the ethylene conversion processes employed in the integrated processes and systems of the invention may produce olefinic products for use in a variety of different end products or applications. For example, a portion or all of the ethylene produced by the OCM process may be routed through one or more catalytic processes or systems to oligomerize ethylene into LAOs of ranging carbon numbers. These compounds can be particularly useful in chemical manufacturing, e.g., in the production of amines, amine oxides, oxo-alcohols, alkylated aromatics epoxides, tanning oils, synthetic lubricants, lubricant additives, alpha olefin sulfonates, mercaptans, organic alkyl aluminum, hydrogenated oligomers, and synthetic fatty acids. Alternatively or additionally, the ethylene may be oligomerized through LAO processes to produce $C_4$-$C_{20}$ LAOs for use as liquid blend stocks for gasoline, diesel or jet fuels. These LAOs can also be hydrogenated to linear alkanes for fuel blend stocks for gasoline, jet, and diesel fuel.

Processes used for the production of product ranges, e.g., $C_4$-$C_{30}$ LAOS, are generally referred to herein as "full range processes" or "narrow range processes", as they produce a range of chemical species, e.g., LAOs of varying chain length such as 1-butene, 1-hexene, 1-octene, 1-decene, etc., in a single process. Products from full range or narrow range processes may be distilled or fractionated into, e.g., $C_4$-$C_{10}$ LAOs for use as chemical process feedstocks, $C_{10}$-$C_{20}$ LAOs for use as a jet fuel blendstock, diesel fuel blendstock, and chemical feedstock. By contrast, processes that produce a single product species in high yield, e.g., LAO of a single chain length such as 1-butene, 1-hexene, 1-octene, 1-decene or the like, are referred to generally as selective processes.

Full and narrow ranges of products may be prepared from ethylene using a variety of LAO processes, such as, for example, the α-Sablin® process (See, e.g., Published International Patent Application No. WO 2009/074203, European Patent No. EP 1749806B1, and U.S. Pat. No. 8,269,055, the full disclosures of which are incorporated herein by reference in their entirety for all purposes), the Shell higher olefin process (SHOP), the Alphabutol process, the Alphahexol process, the AlphaSelect process, the Alpha-Octol process, Linear-1 process, the Linealene process, the Ethyl Process, the Gulftene process, and the Phillips 1-hexene process.

Briefly, the α-Sablin process employs a two-component catalyst system of a zirconium salt and an aluminum alkyl co-catalyst, for homogenous, liquid phase oligomerization of ethylene to a narrow range of LAOS. The catalytic cycle comprises a chain growth step by an ethylene insertion reaction at the co-ordination site and displacement of the coordinated hydrocarbon from the organometallic complex. The ratio of zirconium to aluminum can be used to adjust between chain growth and displacement, thereby adjusting the product spectrum more toward lighter or heavier LAOS. For example, with a high Zr:Al ratio, the product spectrum can be shifted to upwards of 80% C4-C8 LAOS, while lower Zr:Al ratios will shift the product spectrum towards heavier LAOS. The reaction is generally carried out in a bubble column reactor with a solvent, such as toluene, and catalyst being fed into the liquid phase at temperatures of between about 60° C. and 100° C. and pressures of between about 20 bar and 30 bar. The liquid LAOs are then sent to a separation train to deactivate the catalyst, separate the solvent and optionally perform any additional product separations that are desired.

Additionally, all or a portion of these olefinic products may be hydrogenated prior to distillation to convert the olefins into the corresponding alkanes for use as alkane blendstocks for fuel products, and then again, subjected to a distillation or other separation process to produce the desired products.

In various embodiments, a wide range of other ethylene conversion processes may be integrated at the back end of the OCM processes described above, depending upon the desired product or products for the overall process and system. For example, in alternative or additional aspects, an integrated ethylene conversion process for production of LAOs may include the SHOP system, a full range ethylene conversion process which may be used to produce LAOs in the $C_6$-$C_{16}$ range. Briefly, the SHOP system employs a nickel-phosphine complex catalyst to oligomerize ethylene at temperatures of from about 80° C. to about 120° C., and pressures of from about 70 bar to about 140 bar.

A variety of other full-range ethylene conversion processes may be employed, including without limitation, the AlphaSelect process, the Alpha-Octol process, Linear-1 process, the Linealene process, the Synthol process, the Ethyl Process, the Gulftene process, the Phillips 1-hexene process, and others. These processes are well characterized in the literature, and reported, for example at the Nexant/Chemsystems PERP report, Alpha Olefins, January 2004, the full disclosure of which are incorporated herein by reference in their entirety for all purposes.

As an alternative or in addition to full and/or narrow range ethylene conversion processes, ethylene conversion processes that may be integrated into the overall systems of the invention include processes for the selective production of high purity single compound LAO compositions. As used herein, processes that are highly selective for the production of a single chemical species are generally referred to as selective or "on purpose" processes, as they are directed at production of a single chemical species in high selectivity. In the context of LAO production, such on purpose processes will typically produce a single LAO species, e.g., 1-butene, 1-hexene, 1-octene, etc., at selectivities of greater than 50%, in some cases greater than 60%, greater than 75%, and even greater than 90% selectivity for the single LAO species.

Examples of such on purpose processes for ethylene conversion to LAOs include, for example, the Alphahexol process from IFP, the Alphabutol process, or the Phillips 1-hexene process for the oligomerization of ethylene to high purity 1-hexene, as well as a wide range of other processes that may be integrated with the overall OCM reactor system.

The Alphahexol process, for example, is carried out using phenoxide ligand processes. In particular, ethylene trimerization may be carried out using a catalytic system that involves a chromium precursor, a phenoxyaluminum compound or alkaline earth phenoxide and a trialkylaluminum activator at 120° C. and 50 bar ethylene pressure (See, e.g., U.S. Pat. No. 6,031,145, and European Patent No. EP1110930, the full disclosures of which are incorporated herein by reference in their entirety for all purposes). Likewise, the Phillips 1-hexene process employs a chromium (III) alkanoate, such as chromium tris(2-ethylhexanoate, pyrrole, such as 2,5-dimethylpyrrole, and Et3Al to produce 1-hexene at high selectivity, e.g., in excess of 93%. See, e.g., European Patent No. EP0608447 and U.S. Pat. No. 5,856,257, the full disclosures of which are incorporated herein by reference in their entirety for all purposes. A variety of other ethylene trimerization processes may be similarly integrated to the back end of the OCM systems described herein. These include, for example, the British Petroleum PNP trimerization system (see, e.g., Published International Patent Application No. WO 2002/04119, and Carter et al., Chem. Commun. 2002, 858), and Sasol PNP trimerization system (see, e.g., Published International Patent Application No. WO2004/056479, discussed in greater detail), the full disclosures of which are incorporated herein by reference in their entirety for all purposes.

The Alphabutol process employs a liquid phase proprietary soluble catalyst system of Ti(IV)/AlEt3, in the dimerization of ethylene to 1-butene at relatively high purity, and is licensed through Axens (Rueil-Malmaison, France). Ethylene is fed to a continuous liquid phase dimerization reactor. A pump-around system removes the exothermic heat of reaction from the reactor. The reactor operates between 50-60° C. at 300-400 psia. The catalyst is removed from the product effluent and is ultimately fed to the 1-butene purification column where comonomer-grade 1-butene is produced.

Still other selective ethylene conversion processes include the catalytic tetramerization of ethylene to 1-octene. For example, one exemplary tetramerization process employs a liquid phase catalytic system using a Cr(III) precursor, such as [Cr(acac)3] or [CrCl3(THF)3] in conjunction with a bis(phosphine)amine ligand and a methylaluminooxane (MAO) activator at temperatures of between about 40° C. and 80° C. and ethylene pressures of from 20 to 100 bar, to produce 1-octene with high selectivity. See, e.g., Published International Patent Application No. WO2004/056479 and Bollmann, et al., "Ethylene Tetramerization: A New Route to Produce 1-Octene in Exceptionally High Selectivities" J. Am. Chem. Soc., 2004, 126 (45), pp 14712-14713, the full disclosures of which are incorporated herein by reference in their entirety for all purposes.

In addition to the LAO processes described herein, ethylene produced from the integrated OCM reactor systems can also be used to make olefinic non-LAO linear hydrocarbons and branched olefinic hydrocarbons through the same or different integrated processes and systems. For example, the ethylene product from the OCM reactor system may be passed through integrated reactor systems configured to carry out the SHOP process, the Alphabutol process, the Alphahexol process, the AlphaSelect process, the Alpha-Octol process, Linear-1 process, the Linealene process, the Ethyl Process, the Gulftene process, and/or the Phillips 1-hexene process, to yield the resultant LAO products. The output of these systems and processes may then be subjected to an olefin isomerization step to yield linear olefins other than LAOS, branched olefinic hydrocarbons, or the like. In addition, olefinic non-LAO linear hydrocarbons and branched olefinic hydrocarbons can be prepared by ethylene oligomerization over heterogeneous catalysts such as zeolites, amorphous silica/alumina, solid phosphoric acid catalysts, as well as doped versions of the foregoing catalysts.

Other oligomerization processes have been described in the art, including the olefin oligomerization processes set forth in Published U.S. Patent Application No. 2012/0197053 (incorporated herein by reference in its entirety for all purposes), which describes processes used for production of liquid fuel components from olefinic materials.

Although a number of processes are described with certain specificity, that description is by way of example and not limitation. In particular, it is envisioned that the full range of ethylene oligomerization and/or conversion processes may be readily integrated onto the back end of the OCM reactor systems for conversion of methane to ethylene product, and subsequently to a wide range of different higher hydrocarbon products. As noted previously, certain embodiments of the ethylene conversion processes that are integrated into the overall systems of the invention are those that yield liquid hydrocarbon products. Other embodiments of the ethylene conversion processes that are integrated in the overall systems include process that are particularly well-suited for use with dilute ethylene feed stocks which optionally comprise additional components such as higher hydrocarbons, unreacted OCM starting material (methane and/or other natural gas components) and/or side products of the OCM reactions. Examples of such other components are provided herein.

In addition to or as an alternative, the ethylene product produced from the OCM reactor system may be routed through one or more catalytic or other systems and processes to make non-olefinic hydrocarbon products. For example, saturated linear and branched hydrocarbon products may be produced from the ethylene product of the OCM reactor system through the hydrogenation of the products of the olefinic processes described above, e.g., the SHOP process, the Alphabutol process, the Alphahexol process, the AlphaSelect process, the Alpha-Octol process, Linear-1 process, the Linealene process, the Ethyl Process, the Gulftene process, and/or the Phillips 1-hexene process.

Other catalytic ethylene conversions systems that may be employed include reacting ethylene over heterogeneous catalysts, such as zeolites, amorphous silica/alumina, solid phosphoric acid catalysts, and/or doped forms of these catalysts, to produce mixtures of hydrocarbons, such as saturated linear and/or branched hydrocarbons, saturated olefinic cyclic hydrocarbons, and/or hydrocarbon aromatics. By varying the catalysts and or the process conditions, selectivity of the processes for specific components may be enhanced. For example, ethylene purified from OCM effluent or unpurified OCM effluent containing ethylene can be flowed across a zeolite catalyst, such as ZSM-5, or amorphous silica/alumina material with $SiO_2/Al_2O_3$ ratios of 23-280, at ethylene partial pressures between 0.01 bar to 100 bar (undoped, or doped with Zn and/or Ga in some embodiments or some combination thereof) at temperatures above 350° C. to give high liquid hydrocarbon yield (80+%) and high aromatic selectivity (benzene, toluene, xylene (BTX) selectivity>90% within the liquid hydrocarbon fraction). Ethylene purified from OCM effluent or unpurified OCM effluent containing ethylene can be flowed across a zeolite catalyst, such as ZSM-5, or amorphous silica/alumina material with $SiO_2/Al_2O_3$ ratios of 23-280, at ethylene partial pressures between 0.01 bar to 100 bar (undoped, or with dopants including but not limited to, e.g., Ni, Mg, Mn, Ca, and Co, or some combination of these) at temperatures above 200° C., to give high liquid hydrocarbon yield (80+%) and high gasoline selectivity (gasoline selectivity>90% within the liquid hydrocarbon fraction). Ethylene purified from OCM effluent or unpurified OCM effluent containing ethylene can be flowed across a zeolite catalyst, such as ZSM-5, or amorphous silica/alumina material with $SiO_2/Al_2O_3$ ratios of 23-280 or a solid phosphoric acid catalyst, at ethylene partial pressures between 0.01 bar to 100 bar at temperatures above 200° C. to give high liquid hydrocarbon yield (80+%) and high distillate selectivity (gasoline selectivity>90% within the liquid hydrocarbon fraction).

In some embodiments, to achieve high jet/diesel fuel yields, a two oligomerization reactor system is used in series. The first oligomerization reactor takes the ethylene and oligomerizes it to $C_3$-$C_6$ olefins over modified ZSM-5 catalysts, e.g., Mg, Ca, or Sr doped ZSM-5 catalysts. The $C_3$-$C_6$ olefins can be the end products of the process or alternatively can be placed in a second oligomerization reactor to be coupled into jet/diesel fuel range liquid.

In addition, some embodiments of the ethylene conversion processes also include processes for production of oxygenated hydrocarbons, such as alcohols and/or epoxides. For example, the ethylene product can be routed through an integrated system that includes a heterogeneous catalyst system, such as a solid phosphoric acid catalyst in the presence of water, to convert the ethylene to ethanol. This process has been routinely used to produce 200 proof ethanol in the process used by LyondellBasell. In other embodiments, longer chain olefins and/or LAO's, derived from OCM ethylene by oligomerization, can be likewise converted to alkyl alcohols using this same process. See, e.g., U.S. Pat. Nos. 2,486,980; 3,459,678; 4,012,452, the full disclosures of which are incorporated herein by reference in their entirety for all purposes. In alternate embodiments, ethylene undergoes a vapor oxidation reaction to make ethylene oxide over a silver based catalyst at 200-300° C. at 10-30 atmospheres of pressure with high selectivity (80+%). Ethylene oxide is an important precursor for synthesis of ethylene glycol, polyethylene glycol, ethylene carbonate, ethanolamines, and halohydrins. See, e.g., Chemsystems PERP Report Ethylene Oxide/Ethylene Glycol 2005, which is herein incorporated by reference.

In still other aspects, the ethylene product produced from the OCM reactor system may be routed to a reactor system that reacts the ethylene with various halogen sources (acids, gases, and others) to make halogenated hydrocarbons useful, for example, as monomers in producing halogenated polymers, such as polyvinyl chloride (PVC). For example, in one ethylene dichloride (EDC) process, available from Thyssen-Krupp Uhde, ethylene can be reacted with chlorine gas to make EDC, an important precursor to vinyl-chloride monomer (VCM) for polyvinylchloride (PVC) production. This process also can be modified EDC to react ethylene with hydrochloric acid (HCl) to make EDC via oxychlorination.

In still other exemplary ethylene conversion processes, the ethylene product of the OCM reactor system may be converted to alkylated aromatic hydrocarbons, which are also useful as chemical and fuel feedstocks. For example, in the Lummus CD-Tech EB process and the Badger EB process, benzene can be reacted with OCM ethylene, in the presence of a catalyst, to make ethylbenzene. See, e.g., U.S. Pat. No. 4,107,224, the full disclosure of which is incorporated herein by reference in its entirety for all purposes. Ethylbenzene can be added to gasoline as a high-octane gasoline blendstock or can be dehydrogenated to make styrene, the precursor to polystyrene.

In addition to the liquid and other hydrocarbons described above, in certain aspects, one or more of the integrated ethylene conversion processes is used to convert ethylene product from the OCM reactor system to one or more hydrocarbon polymers or polymer precursors. For example, in some embodiments ethylene product from the integrated OCM reactor systems is routed through an integrated Innovene process system, available through Ineos Technologies, Inc., where the ethylene is polymerized in the presence of a catalyst, in either a slurry or gas phase system, to make long hydrocarbon chains or polyethylene. By varying the process conditions and catalyst the process and system can be used to produce high density polyethylene or branched low density polyethylene, etc. The Innovene G and Innovene S processes are described at, for example, at "Ineostechnologies.com". See also Nexant/Chemsystems HDPE Report, PERP 09/10-3, January 2011, the full disclosure of which is incorporated herein by reference in its entirety for all purposes.

Alternatively, ethylene from OCM can be introduced, under high pressure, into an autoclave or tubular reactor in the presence of a free radical initiator, such as $O_2$ or peroxides, to initiate polymerization for the preparation of low-density polyethylene (LDPE). See e.g., "Advanced Polyethylene Technologies" Adv Polym Sci (2004) 169:13-27, the full disclosure of which is incorporated herein by reference in its entirety for all purposes. Alternatively, ethylene from OCM can be introduced, under low pressure in the presence of a chromium oxide based catalyst, Ziegler-Natta catalyst, or a single-site (metallocene or non metallocene based) catalyst, to prepare HDPE, MDPE, LLDPE, mLLDPE, or bimodal polyethylene. The reactor configurations for synthesis of HDPE, LLDPE, MDPE, and biomodal PE can be a slurry process, in which ethylene is polymerized to form solid polymer particles suspended in a hydrocarbon diluent, a solution process in which dissolved ethylene is polymerized to form a polymer dissolved in solvent, and/or a gas phase process in which ethylene is polymerized to form a solid polymer in a fluidized bed of polymer particles. Ethylene from OCM can be co-polymerized with different monomers to prepare random and block co-polymers. Co-monomers for ethylene copolymerization include but are not limited to: at least one olefin comonomer having three to fifteen carbons per molecule (examples are propylene and LAO's such as 1-butene, 1-hexene, 1-octene), oxygenated co-monomers such as: carbon oxide; vinyl acetate, methyl acrylate; vinyl alcohols; allyl ethers; cyclic monomers such as norbornene and derivatives thereof; aromatic olefins such as: styrene and derivatives thereof. These ethylene or LAO copolymerization processes, e.g., where ethylene is copolymerized with different monomers, are generally referred to herein as copolymerization processes or systems.

More exemplary ethylene conversion processes that may be integrated with the OCM reactor systems include processes and systems for carrying out olefin metathesis reactions, also known as disproportionation, in the production of propylene. Olefin metathesis is a reversible reaction between ethylene and butenes in which double bonds are broken and then reformed to form propylene. "Propylene Production via Metathesis, Technology Economics Program" by Intratec, ISBN 978-0-615-61145-7, Q2 2012, the full disclosure of which is incorporated herein by reference in its entirety for all purposes. Propylene yields of about 90 wt % are achieved. This option may also be used when there is no butene feedstock. In this case, part of the ethylene from the OCM reaction feeds into an ethylene-dimerization unit that converts ethylene into butene.

As noted herein, one, two, three, four or more different ethylene conversion processes are provided integrated into the overall systems of the invention, e.g., as shown in FIG. 1. As will be appreciated, these ethylene conversion systems will include fluid communications with the OCM systems described herein, and may be within the same facility or within an adjacent facility. Further, these fluid communications may be selective. In particular, in certain embodiments the interconnect between the OCM system component and the ethylene conversion system component(s) is able to selectively direct all of an ethylene product from the OCM system to any one ethylene conversion system at a given time, and then direct all of the ethylene product to a second different ethylene conversion system component at a different time. Alternatively, such selective fluid communications may also simultaneously direct portions of the ethylene product to two or more different ethylene conversion systems to which the OCM system is fluidly connected.

These fluid communications will typically comprise interconnected piping and manifolds with associated valving, pumps, thermal controls and the like, for the selective direction of the ethylene product of the OCM system to the appropriate ethylene conversion system component or components.

In an example, ethylene produced by the methods described herein (e.g., by OCM) can be converted into 1-butene or 2-butene. In some cases, ETL methods and systems provided herein can be used to form 1-butene but no appreciable 2-butene, or 2-butene but no appreciable 1-butene. Methods for generating 1-butene from ethylene are disclosed in U.S. Pat. No. 2,943,125, U.S. Pat. No. 3,686,350, U.S. Pat. No. 4,101,600, U.S. Pat. No. 8,624,042, and U.S. Pat. No. 5,792,895, each of which is entirely incorporated herein by reference.

As an alternative or in addition to, ethylene produced by the methods described herein (e.g., by OCM) can be converted into 1-hexene. Methods for converting ethylene to 1-hexene are described in U.S. Pat. No. 6,380,451, U.S. Pat. No. 7,157,612, U.S. Pat. No. 5,057,638, U.S. Pat. No. 8,658,750, and U.S. Pat. No. 5,811,618, each of which is entirely incorporated herein by reference. As an alternative or in addition to, ethylene produced by the methods described herein (e.g., by OCM) can be converted into 1-octene. Methods for converting ethylene to 1-Octene are described in U.S. Pat. No. 5,292,979, U.S. Pat. No. 5,811, 619, U.S. Pat. No. 5,817,905, and U.S. Pat. No. 6,103,654, each of which is entirely incorporated herein by reference.

In some cases, ethylene produced by the methods described herein (e.g., by OCM) can be converted into C4 to C18 and higher α-olefins (1-butene, 1-hexene, 1-octene, 1-decene and higher). Oligomerization of ethylene into linear alpha olefins (LAO) can be carried out in a bubble column reactor with the solvent and the dissolved catalyst components fed to the liquid phase. Methods for converting ethylene to $C_4$-$C_{18}$ and higher α-olefins are described in Canadian Patent Application Number CA 2,765,769, German Patent Number DE 4338414, German Patent Number DE 4338416, U.S. Pat. No. 3,862,257, U.S. Pat. No. 4,966, 874, and U.S. Pat. No. 5,449,850, each of which is entirely incorporated herein by reference.

As an alternative or in addition to, ethylene produced by the methods described herein (e.g., by OCM) can be converted into $C_4$ to $C_{10}$ α-olefins (1-butene, 1-hexene, 1-octene, and 1-decene). Methods for converting ethylene to $C_4$-$C_{10}$ α-olefins are described in U.S. Pat. No. 3,660,519, U.S. Pat. No. 3,584,071, European Patent Number EP 0,722, 922, U.S. Pat. No. 4,314,090, U.S. Pat. No. 5,345,023, and U.S. Pat. No. 6,221,986, each of which is entirely incorporated herein by reference.

In another example, ethylene produced by the methods described herein (e.g., by OCM) can be converted into propylene (propene). For example, n-butenes can be reacted with ethylene using a heterogeneous catalyst system in a fixed bed reactor process. Methods for converting ethylene to propylene are described in U.S. Pat. No. 6,683,019, U.S. Pat. No. 7,214,841, U.S. Pat. No. 8,153,851, and U.S. Pat. No. 8,258,358, each of which is entirely incorporated herein by reference.

As an alternative or in addition to, ethylene produced by the methods described herein (e.g., by OCM) can be converted into ethylene dichloride (EDC). For example, ethylene can be reacted with chlorine in liquid phase in presence of a catalyst system. Methods for converting ethylene to EDC are described in German Patent Number DE 19 05 517, German Patent Number DE 25 40 257, German Patent Number DE 40 39 960 A16, U.S. Pat. No. 7,579,509, U.S. Pat. No. 7,671,244, and U.S. Pat. No. 6,841,708, each of which is entirely incorporated herein by reference.

Ethylene produced by the methods described herein (e.g., by OCM) can be converted into high density polyethylene (HDPE) or other types of polyethylene. For example, ethylene or a mixture of ethylene with one or more alpha olefins can be reacted in the gas phase in the presence of a catalyst system. Methods for converting ethylene to HDPE are described in U.S. Pat. No. 5,473,027, U.S. Pat. No. 5,473,027, U.S. Pat. No. 6,891,001, and U.S. Pat. No. 4,882,400, each of which is entirely incorporated herein by reference.

The ethylene produced by the methods described herein (e.g., by OCM) can be converted into ethanol. For example, a mixture of ethylene and water is reacted over a heterogeneous catalyst (e.g., solid phosphoric acid catalyst) in a reactor to form ethanol by direct hydration of ethylene. Methods for converting ethylene to ethanol are described in U.S. Pat. No. 2,486,980, U.S. Pat. No. 2,579,601, U.S. Pat. No. 2,673,221, and U.S. Pat. No. 3,686,334, each of which is entirely incorporated herein by reference.

Acetylene can be selectively hydrogenated to ethylene while present in a mixture containing ethylene and other components without hydrogenating ethylene. For example, a feed containing acetylene and ethylene is reacted in the presence of hydrogen over a heterogeneous catalyst in a fixed bed reactor system. Methods for selective hydrogenating acetylene are described in U.S. Pat. No. 3,128,317, U.S. Pat. No. 4,126,645, U.S. Pat. No. 4,367,353, U.S. Pat. No. 4,329,530, U.S. Pat. No. 4,440,956, U.S. Pat. No. 5,414,170, U.S. Pat. No. 6,509,292, and Xu, Ling, et al. "Maximise ethylene gain and acetylene selective hydrogenation efficiency," Petroleum technology quarterly 18.3 (2013): 39-42, each of which is entirely incorporated herein by reference.

Acetylene and dienes, such as butadiene, can be selectively hydrogenated while present in a mixture containing ethylene and other components without hydrogenating the ethylene present. For example, a feed containing acetylene and dienes is reacted in the presence of hydrogen over a heterogeneous catalyst in a fixed bed reactor system. Methods for selective hydrogenating acetylene and dienes are described in U.S. Pat. No. 3,900,526, U.S. Pat. No. 5,679,241, U.S. Pat. No. 6,759,562, U.S. Pat. No. 5,877,363, U.S. Pat. No. 7,838,710, and U.S. Pat. No. 8,227,650, each of which is entirely incorporated herein by reference.

Olefin to Liquids Reactors
Control Systems

The present disclosure provides computer control systems that can be employed to regulate or otherwise control the methods and systems provided herein. A control system of the present disclosure can be programmed to control process parameters to, for example, effect a given product distribution, such as a higher concentration of alkenes as compared to alkanes in a product stream out of an OCM and/or ETL reactor.

Figure 33:
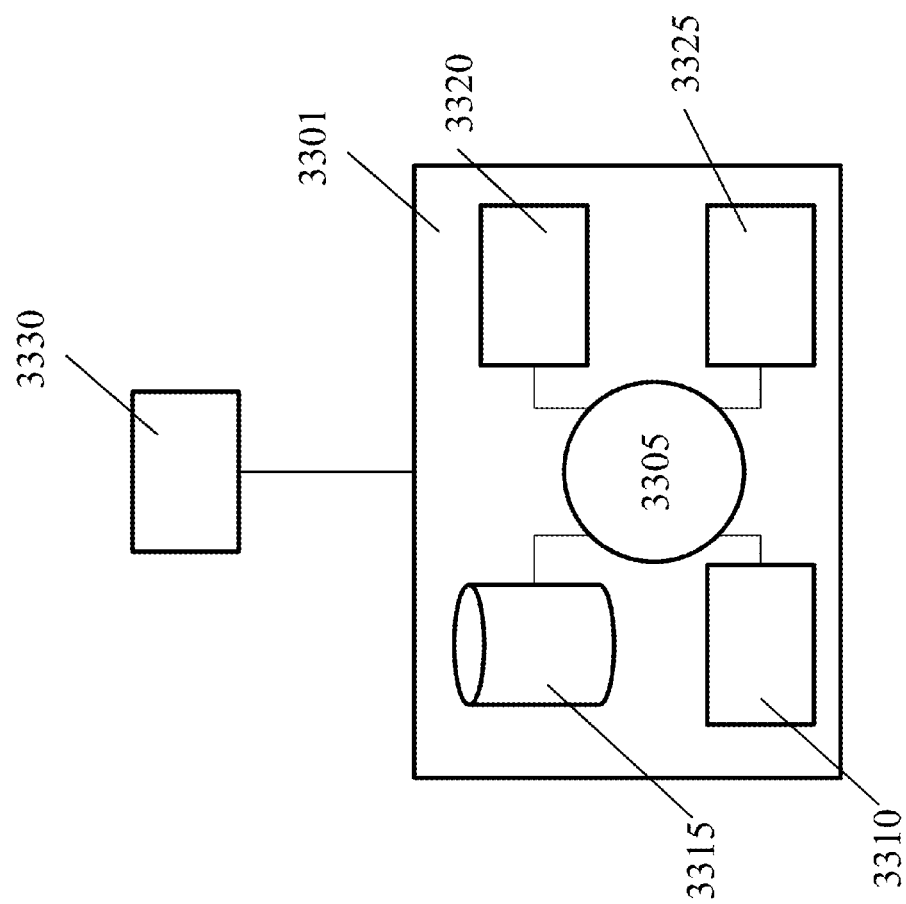
FIG. 33 shows a computer system that is programmed or otherwise configured to regulate OCM reactions.

FIG. 33 shows a computer system 3301 that is programmed or otherwise configured to regulate OCM and/or ETL reactions, such as regulate fluid properties (e.g., temperature, pressure and stream flow rate(s)), mixing, heat exchange and OCM and/or ETL reactions. The computer system 3301 can regulate, for example, fluid stream ("stream") flow rates, stream temperatures, stream pressures, OCM and/or ETL reactor temperature, OCM and/or ETL reactor pressure, the quantity of products that are recycled, and the quantity of a first stream (e.g., methane stream) that is mixed with a second stream (e.g., air stream).

The computer system 3301 includes a central processing unit (CPU, also "processor" and "computer processor" herein) 3305, which can be a single core or multi core processor, or a plurality of processors for parallel processing. The computer system 3301 also includes memory or memory location 3310 (e.g., random-access memory, read-only memory, flash memory), electronic storage unit 3315 (e.g., hard disk), communication interface 3320 (e.g., network adapter) for communicating with one or more other systems, and peripheral devices 3325, such as cache, other memory, data storage and/or electronic display adapters. The memory 3310, storage unit 3315, interface 3320 and peripheral devices 3325 are in communication with the CPU 3305 through a communication bus (solid lines), such as a motherboard. The storage unit 3315 can be a data storage unit (or data repository) for storing data.

The CPU 3305 can execute a sequence of machine-readable instructions, which can be embodied in a program or software. The instructions may be stored in a memory location, such as the memory 3310. Examples of operations performed by the CPU 3305 can include fetch, decode, execute, and writeback.

The storage unit 3315 can store files, such as drivers, libraries and saved programs. The storage unit 3315 can store programs generated by users and recorded sessions, as well as output(s) associated with the programs. The storage unit 3315 can store user data, e.g., user preferences and user programs. The computer system 3301 in some cases can include one or more additional data storage units that are external to the computer system 3301, such as located on a remote server that is in communication with the computer system 3301 through an intranet or the Internet.

The computer system 3301 can be in communication with an OCM and/or ETL system 3330, including an OCM and/or ETL reactor and various process elements. Such process elements can include sensors, flow regulators (e.g., valves), and pumping systems that are configured to direct a fluid.

Methods as described herein can be implemented by way of machine (e.g., computer processor) executable code stored on an electronic storage location of the computer system 3301, such as, for example, on the memory 3310 or electronic storage unit 3315. The machine executable or machine readable code can be provided in the form of software. During use, the code can be executed by the processor 3305. In some cases, the code can be retrieved from the storage unit 3315 and stored on the memory 3310 for ready access by the processor 3305. In some situations, the electronic storage unit 3315 can be precluded, and machine-executable instructions are stored on memory 3310.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 3301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

Example 1

Fuel Production from OCM Produced Ethylene

Figure 34:
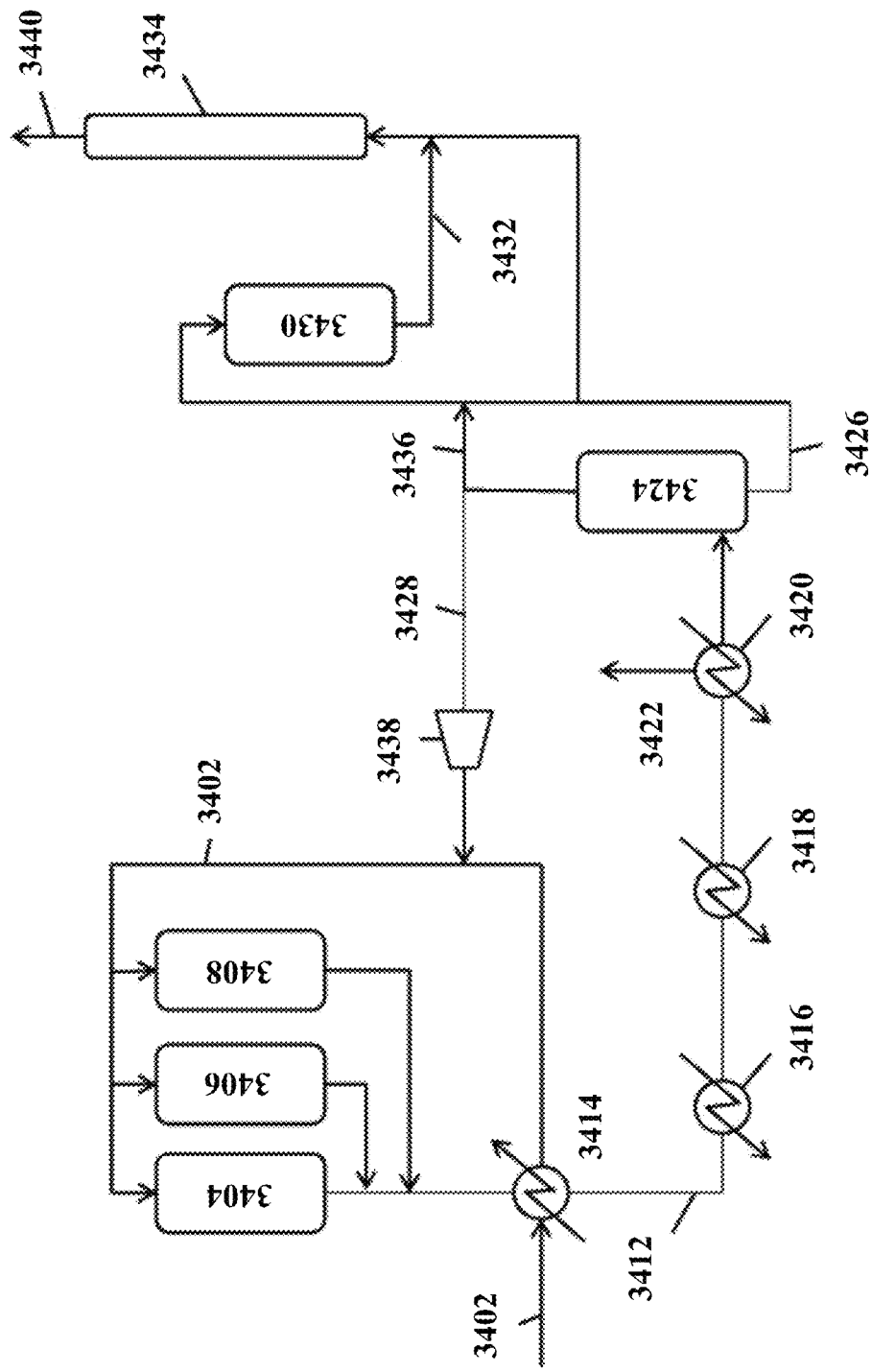
FIG. 34 schematically illustrates a process flow for conversion of ethylene to higher liquid hydrocarbons for use in, e.g., fuels and fuel blendstocks.

An example liquid fuel production process is shown in FIG. 34 and described in greater detail below. In this example, an OCM product gas containing ethylene 3402 is preheated to 200° C. to 500° C. depending upon the desired process. The ethylene may be from 0.05% to 100% pure. For less than 100% pure, the ethylene containing gas may include $CO_2$, CO, $H_2$, $H_2O$, $C_2H_6$, $CH_4$, $C_3$ or higher hydrocarbons (i.e., $C_{3+}$ hydrocarbons), or combinations thereof.

The heated ethylene containing gas 3402 is then flowed through one or more ethylene conversion reactors, e.g., reactors 3404, 3406 and 3408, each containing a solid acid catalyst. The different reactors may include reactors having the same catalyst for performing a parallel reaction to produce a single product. Alternatively, and in accordance with certain aspects of the invention, the different reactors may include different catalysts and/or be operated under different reaction conditions to produce different reaction products or product ranges. The catalysts may include crystalline catalysts, such as zeolites, e.g., zeolites ZSM-5, Y, Beta, ZSM-22, ZSM-48, SAPO-34, SAPO-5, SAPO-11, Mordenite, Ferrierite, and others. Alternatively or additionally, the catalysts may include crystalline mesoporous materials, such as SBA-15, SBA-16, MCM-22, MCM-41, and Al-MCM-41 catalysts, among others. Zeolites and mesoporous materials can be modified with metals, metal oxides, or metal ions to enhance ethylene reactivity, product slate selectivity, and/or catalyst stability.

The ethylene reacts with the solid catalyst to make higher carbon oligomers/products ($C_3$-$C_{30}$). Carbon number ranges can be targeted depending on catalyst type and process conditions.

The oligomerized ethylene product stream 3412 exits from the ethylene conversion reactor(s) and may be used to heat the incoming ethylene containing gas 3402, e.g., via a heat exchanger 3414. The product stream is otherwise passed through a series of heat exchangers 3416, 3418, and 3420 to cool the oligomerized product and to generate steam 3422. The product stream 3412 is then passed through a flash drum 3424 to condense heavier products into liquids 3426. Light products 3436, such as $C_3$-$C_4$'s, can be recycled back to the ethylene conversion reactor in stream 3428 through compressor 3438 for reaction if the $C_3$-$C_4$'s are olefinic and/or to control the heat of reaction of the ethylene conversion reactors 3404, 3406 and 3408. Alternatively, they may be routed through downstream processes, e.g., through hydrogenation reactor 3430 in stream 3436. If desired, the liquid fraction 3426 is passed through a hydrogenation reactor 3430 to hydrogenate olefins to paraffins/isoparaffins using a Co/Mo, Pd, Ni/Mo or other hydrogenation catalyst. The oligomerized product 3426 (or optionally hydrogenated fraction 3432) may then be routed to a distillation column 3434 to fractionate different cuts of products 3440, such as gasoline, jet, and diesel fuel, fuel blendstocks or aromatics.

Example 2

Performance of an ETL Reaction

In another example, the performance of an ETL reaction is assessed. The ETL reaction is performed in an ETL reactor to yield a gasoline product. Ethylene is introduced to a packed bed of extruded H—Mg-ZSM-5 catalyst at a WHSV of about 0.7 hr$^{-1}$ and a temperature of about 350° C. The ethylene partial pressure is about 1 bar. The reactor effluent is chilled to a condenser temperature of about −5° C., and a portion of the non-condensing vapors are recycled by a gas pump to the reactor inlet. In this example, the volumetric recycle-to-feed ratio is about 2:1. The feed to the reactor is comprised of the combination of ethylene feed and recycled vapors, yielding an ethylene concentration at the reactor inlet of about 25%. The product slate and performance of the catalyst prepared according to the methods described herein are detailed in FIG. 5.

Example 3

ETL Reaction Products

Figure 35:
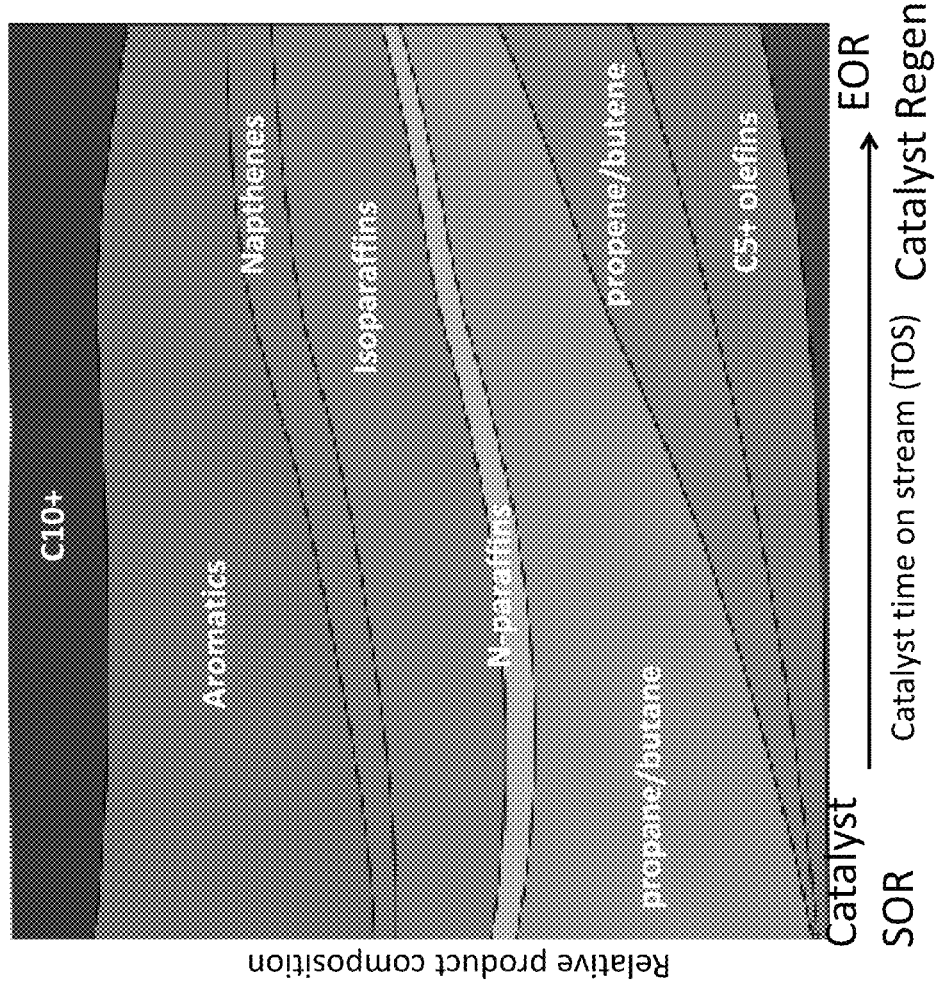
FIG. 35 shows a graph of exemplary product compositions over time on stream.

ETL processes are conducted as described in this disclosure, and the reaction product properties are measured. During the ETL oligomerization process, a small amount of coke is produced. Over time, the coke will deactivate the catalyst below desired levels. Catalyst activity can be restored to full activity by removing the coke by oxidation. The catalyst is robust to coke and decoke cycles. As the catalyst deactivates, the product slate changes. A freshly regenerated catalyst bed will be more selective to aromatics and paraffins. Overtime, the catalyst bed will become less selective toward aromatics and paraffins and more selective toward olefins. FIG. 35 shows the effect that catalyst time on stream for a single reactor has on the product slate composition. Time on stream (TOS) progresses along the x-axis from start of run (SOR) to end of run (EOR), and the width of product bands on the y-axis shows their relative abundance. From top to bottom, the products shown are $C_{10+}$ compounds, aromatics, naphthenes, isoparaffins, N-paraffins, propane/butane, propene/butene, $C_{5+}$ olefins, and other compounds.

Figure 36:
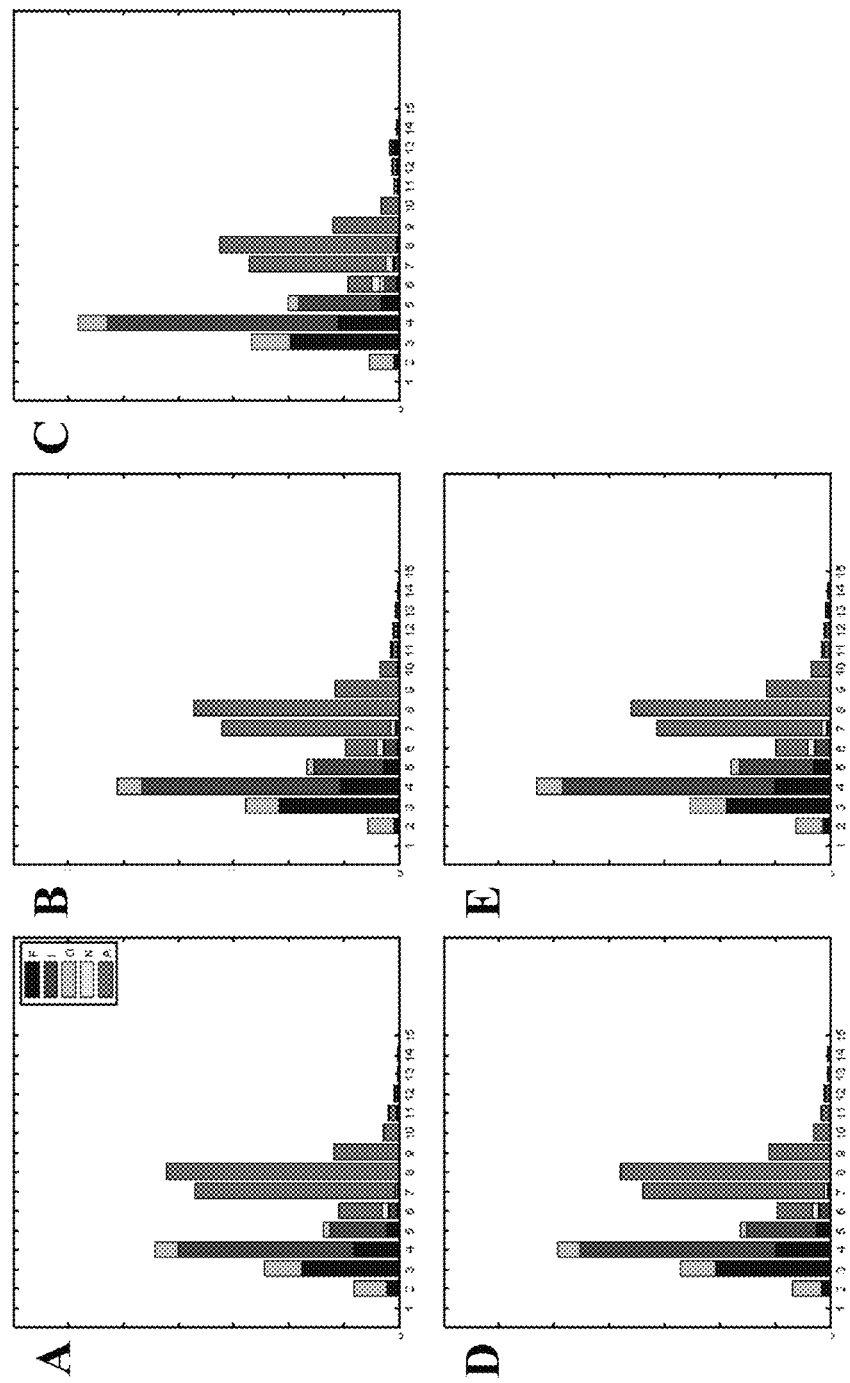
FIGS. 36A-36E shows graphs of ETL products with various feedstocks.

ETL processes are conducted with different feedstocks, and the reactor output is compared with PIONA analysis (paraffin content, isoparaffin content, olefins content, naphthenes content, and aromatics content), as shown in FIGS. 36A-36E. The feedstocks compared are ethylene (FIG. 36A), propylene (FIG. 36B), butylene (FIG. 36C), 50:50 ethylene/propylene (FIG. 36D), and 50:50 ethylene/butylene (FIG. 36E). The liquid products from the different feeds are comparable in composition and carbon number distribution, showing the robustness of the process with respect to feed composition.

Figure 37:
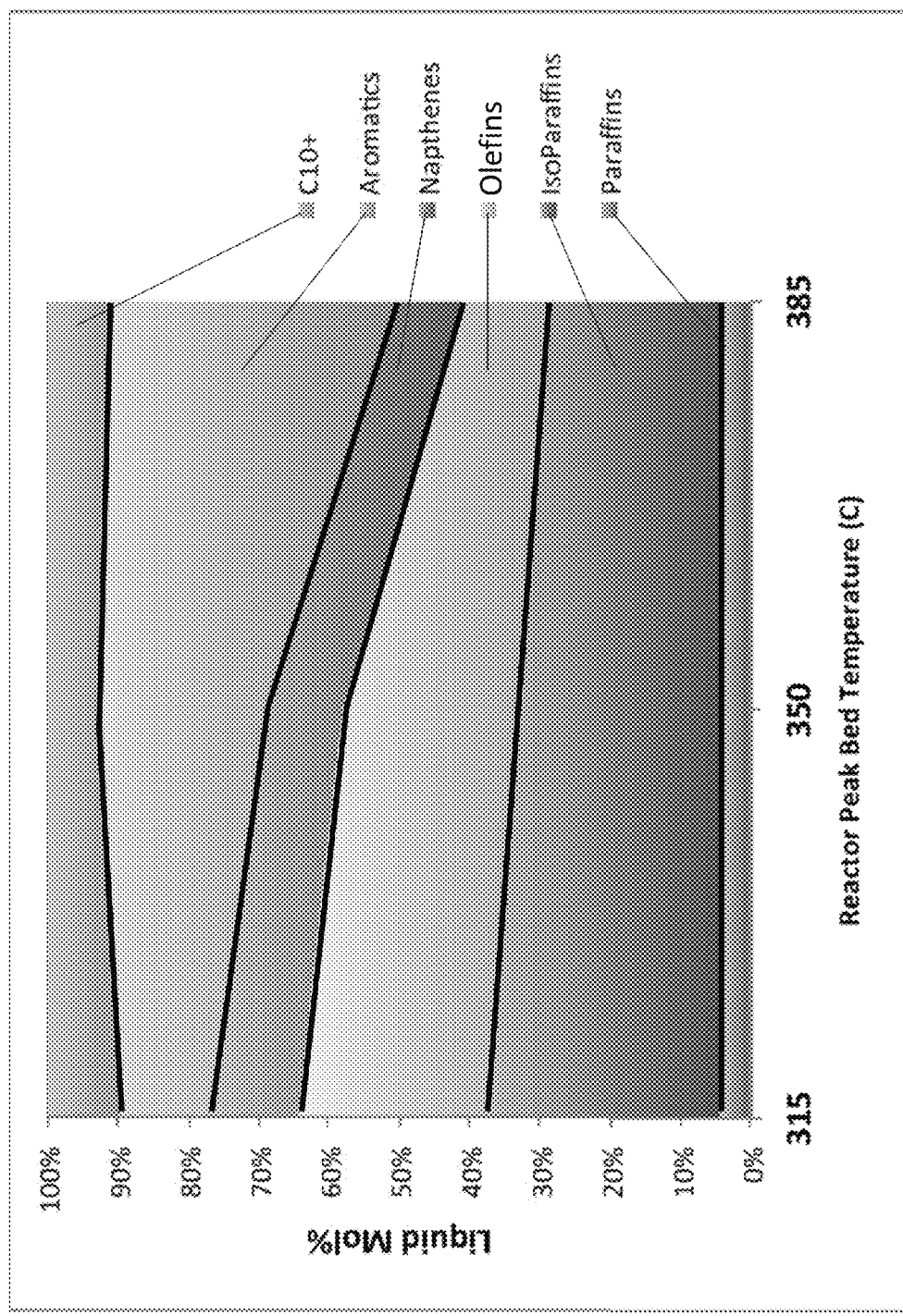
FIG. 37 shows a graph of product composition versus catalyst bed peak temperature.

ETL processes are conducted at different peak catalyst bed temperatures, and the effect on product composition is evaluated, as shown in FIG. 37. The x-axis shows the temperature from 315° C. to 385° C., and the y-axis shows the liquid mol % of various product components. From top to bottom, the product components are C10+ compounds, aromatics, naphthenes, olefin, isoparaffins, and paraffins.

Figure 38:
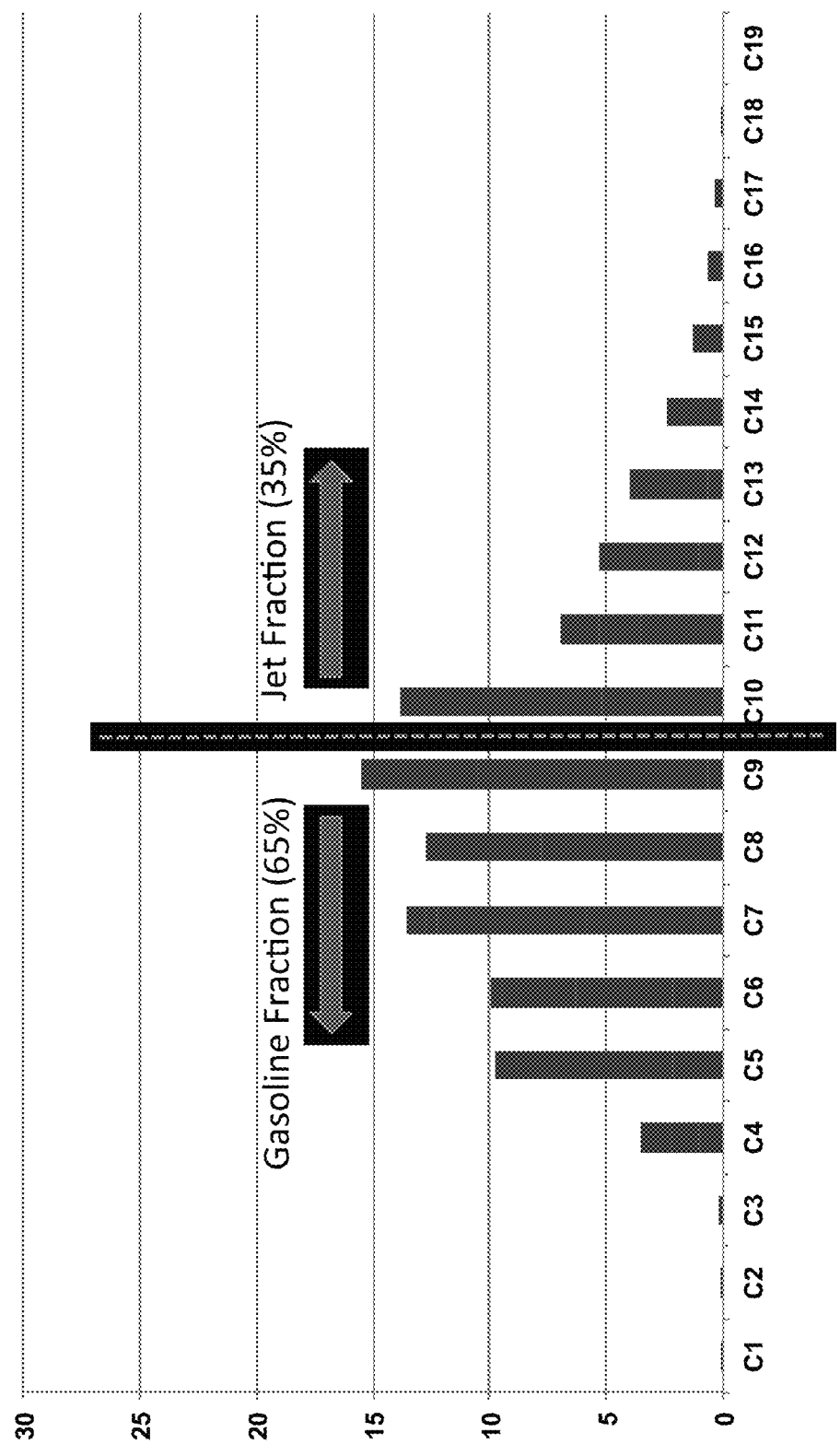
FIG. 38 shows a graph of ETL product divided into a gasoline fraction and a jet fraction.

Different segments of ETL product components can be directed for use in different fractions. For example, a separations process can be employed to separate a jet fraction (comprising, e.g., $C_{10+}$ compounds) from a gasoline fraction (comprising, e.g., $C_{9-}$ compounds), as shown in FIG. 38. In some cases, the ETL product stream can comprise about 65% gasoline fraction components and about 35% jet fraction components.

Reactor operating conditions can impact the reactor performance, and can favor the production of components for a particular product slate. For example, operating conditions and reactor performance for the production can be those shown in Table 3, favoring the production of gasoline components. The resulting product can have a stream composition as shown in Table 4, and can be characterized by the properties shown in Table 5 (center column), with reference to the specification for RBOB (left column).

In another example, operating conditions can favor the production of aromatics, such as the operating conditions and reactor performance shown in Table 6. The resulting product can have a stream composition as shown in Table 7.

TABLE 3

Operating conditions and reactor performance, gasoline

| | ETL Gasoline |
|---|---|
| Inlet T (° C.) | 300 |
| Outlet T (° C.) | 383 |
| Inlet P (Barg) | 25 |
| Outlet P (Barg) | 25 |
| WHSV (h$^{-1}$) | 1.4 |
| $C_{2-}$ conversion | >99% |
| $C_{5+}$ Selectivity | 63% |
| Composition mol % | Inlet |
| $CH_4$ | 95 |
| $C_2H_4$ | 5 |
| C balance | 99.1% |

TABLE 4

Outlet stream composition, gasoline (in C mol %)

| | n-paraffins | i-paraffins | olefins | napthenes | aromatics | Total |
|---|---|---|---|---|---|---|
| C1 | 0.00% | 0.00% | 0.00% | 0.00% | 0.00% | 0.00% |
| C2 | 0.00% | 0.00% | 0.00% | 0.00% | 0.00% | 0.00% |
| C3 | 9.62% | 0.00% | 1.90% | 0.00% | 0.00% | 11.52% |
| C4 | 7.51% | 14.92% | 2.93% | 0.00% | 0.00% | 25.36% |
| C5 | 2.87% | 8.20% | 1.70% | 2.00% | 0.00% | 14.77% |
| C6 | 0.45% | 6.88% | 1.57% | 1.46% | 0.00% | 10.36% |
| C7 | 0.16% | 3.34% | 0.91% | 0.90% | 3.35% | 8.65% |
| C8 | 0.08% | 1.02% | 0.26% | 1.06% | 6.63% | 9.06% |
| C9 | 0.03% | 0.91% | 0.24% | 0.48% | 6.53% | 8.19% |
| C10 | 0.03% | 0.76% | 0.02% | 0.18% | 4.14% | 5.12% |
| C11+ | | | | | | 6.96% |

TABLE 5

Gasoline fuel properties

| | RBOB specification | product properties |
|---|---|---|
| Chemical [max.] | | |
| Benzene (Vol %) | 1.30% | 0.97% |
| Aromatics (Vol %) | 50% | 35.31% |
| Olefins (Vol %) | 25% | 24.6% |
| Octane [min] | | |
| RON | — | 96.9 |
| MON | 82 | 84.9 |
| Tot. Octane | 87 | 90.9 |
| Distillation [max] | | |
| RVP (psi) | 15 | 9.37 |
| 10% (° C.) | 70 | 57.67 |
| 50% (° C.) | 121 | 113.78 |
| 90% (° C.) | 190 | 161.28 |
| FBP (° C.) | 221 | 192.39 |
| Oxidation stability | | |
| Induction time (min) | 240 | >240 |

TABLE 6

Operating conditions and reactor performance, aromatics

| | ETL Gasoline |
|---|---|
| Inlet T (° C.) | 300 |
| Outlet T (° C.) | 383 |
| Inlet P (Barg) | 25 |
| Outlet P (Barg) | 25 |
| WHSV (h$^{-1}$) | 1.4 |
| C$_{2-}$ conversion | >99% |
| C$_{5+}$ Selectivity | 63% |
| Composition mol % | Inlet |
| CH$_4$ | 95 |
| C$_2$H$_4$ | 5 |
| C balance | 99.1% |

TABLE 7

Outlet stream composition, aromatics (in C mol %)

| | n-paraffins | i-paraffins | olefins | napthenes | aromatics | Total |
|---|---|---|---|---|---|---|
| C1 | 0.00% | 0.00% | 0.00% | 0.00% | 0.00% | 0.00% |
| C2 | 0.00% | 0.00% | 0.00% | 0.00% | 0.00% | 0.00% |
| C3 | 9.62% | 0.00% | 1.90% | 0.00% | 0.00% | 11.52% |
| C4 | 7.51% | 14.92% | 2.93% | 0.00% | 0.00% | 25.36% |
| C5 | 2.87% | 8.20% | 1.70% | 2.00% | 0.00% | 14.77% |
| C6 | 0.45% | 6.88% | 1.57% | 1.46% | 0.00% | 10.36% |
| C7 | 0.16% | 3.34% | 0.91% | 0.90% | 3.35% | 8.65% |
| C8 | 0.08% | 1.02% | 0.26% | 1.06% | 6.63% | 9.06% |
| C9 | 0.03% | 0.91% | 0.24% | 0.48% | 6.53% | 8.19% |
| C10 | 0.03% | 0.76% | 0.02% | 0.18% | 4.14% | 5.12% |
| C11+ | | | | | | 6.96% |

Example 4

ETL Catalyst Formation and Use

Figure 39:
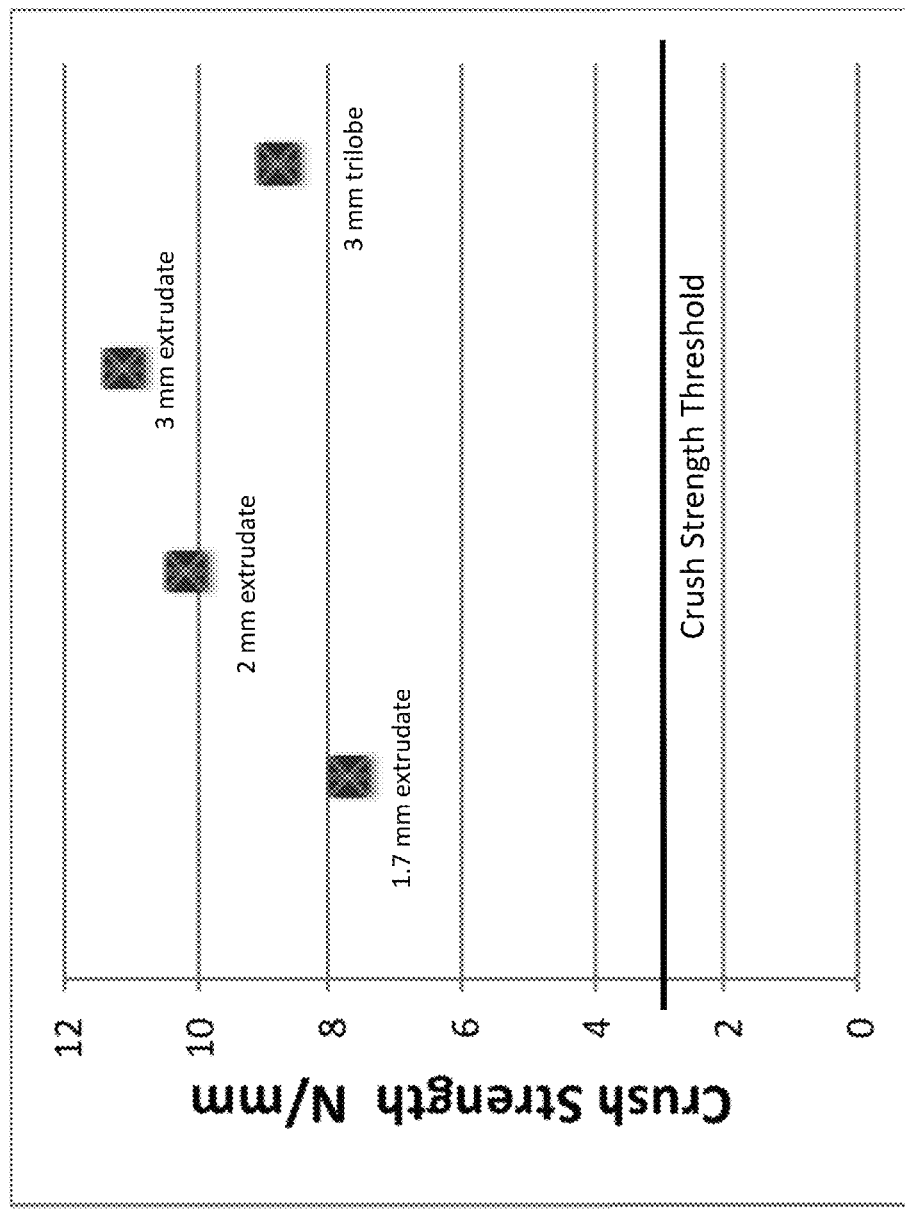
FIG. 39 shows a graph of crush strength for various catalyst formulations.

To form ETL catalyst, base material, dopant, and binder are mixed in desired ratios and then extruded. The target catalyst form strength is to maintain particle crush strength above 3 N/mm. The crush strength threshold is selected based upon the expected stress on individual particles in a commercial scale reactor. As shown in FIG. 39, the ETL catalyst baseline formulation is above the crush strength threshold. If desired, stronger catalyst forms can be achieved by tailoring the active catalyst to binder ratio.

Figure 40:
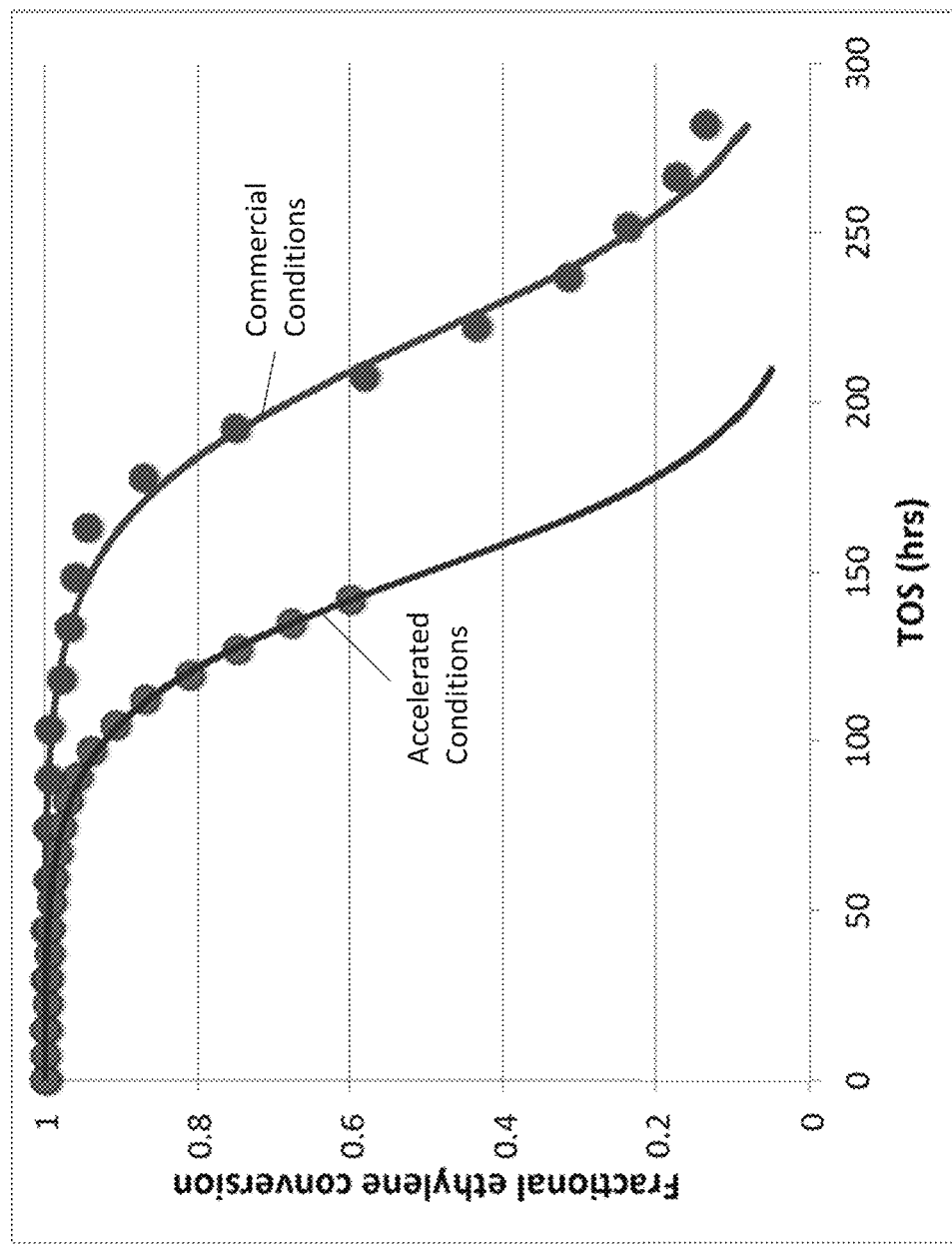
FIG. 40 shows a graph comparing catalyst aging under commercial and accelerated conditions.

Catalyst aging can be accelerated by changing process conditions, such as WHSV. Catalyst aging can be accelerated without changing process inputs. FIG. 40 shows catalyst aging measured by fractional ethylene conversion (y-axis) as a function of time on stream (TOS, x-axis) in hours. Catalyst aging under typical commercial conditions is shown by the curve on the right, and catalyst aging under accelerated conditions is shown by the curve on the left.

Figure 41:
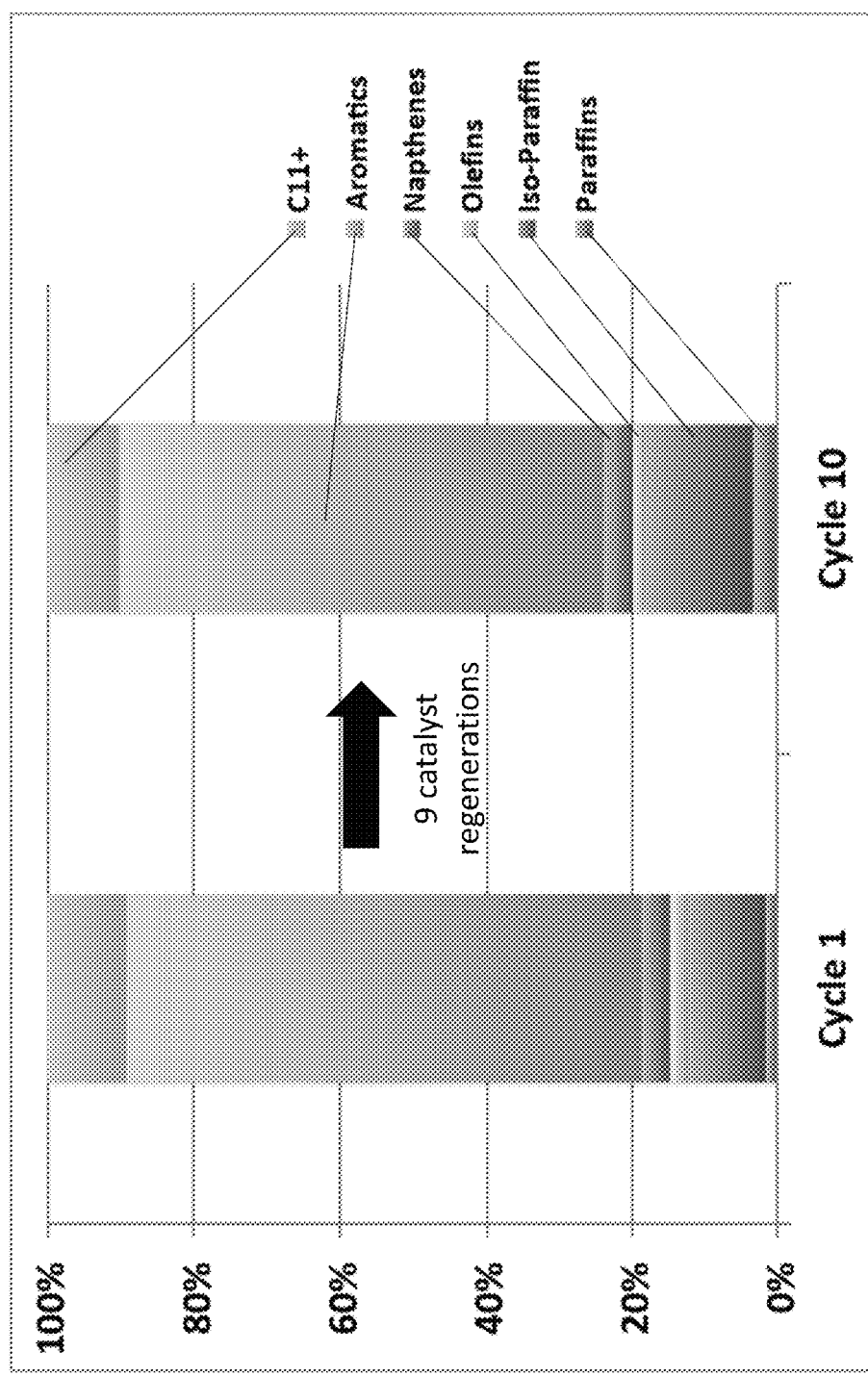
FIG. 41 shows a graph comparing product composition over catalyst regeneration cycles.

The catalyst used can be robust to a number of process and regeneration cycles, with little to no impact on the product composition. FIG. 41 shows the product composition produced by a reactor in its first cycle, i.e. no catalyst regeneration (left side) compared to a reactor in its tenth cycle, i.e. nine catalyst regenerations (right side). The product components graphed, from top to bottom, are C$_{11+}$ compounds, aromatics, naphthenes, olefins, iso-paraffins, and paraffins.

Systems and methods of the present disclosure can be combined with or modified by other systems and methods, such as those described in U.S. Pat. No. 2,943,125, U.S. Pat. No. 3,686,350, U.S. Pat. No. 4,101,600, U.S. Pat. No. 8,624,042, and U.S. Pat. No. 5,792,895, U.S. patent application Ser. No. 14/099,614 and PCT/US2013/073657, each of which is entirely incorporated herein by reference.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for performing oxidative coupling of methane (OCM), comprising:
   (a) directing oxygen (O$_2$) and methane (CH$_4$) to an OCM unit that is upstream of a separations unit, wherein said OCM unit is integrated with and in fluid communication with a cracking unit, and wherein in said OCM unit, said O$_2$ and said CH$_4$ react in an OCM process to yield compounds with two or more carbon atoms (C$_{2+}$ compounds), including ethylene (C$_2$H$_4$);
   (b) directing at least a portion of said C$_{2+}$ compounds to said cracking unit to yield a first stream comprising (i) compounds having triple bonds or (ii) compounds having more than one double bond, wherein said cracking unit operates substantially adiabatically, and wherein said at least said portion of said C$_{2+}$ compounds is directed to said cracking unit without passage through said separations unit; and
   (c) directing said first stream to said separations unit to yield a second stream having a lower concentration of said (i) compounds having triple bonds or (ii) compounds having more than one double bond with respect to said first stream.

2. The method of claim 1, wherein said OCM unit has an inlet temperature between about 450° C. and about 600° C.

3. The method of claim 1, wherein said OCM unit has a pressure between about 15 pounds per square inch gauge (psig) and about 125 psig.

4. The method of claim 1, wherein said OCM process has a C$_{2+}$ selectivity of at least about 50%.

5. The method of claim 1, further comprising directing said second stream to an ethylene-to-liquids (ETL) unit to convert C$_2$H$_4$ in said second stream to yield an ETL product stream comprising higher hydrocarbon product(s).

6. The method of claim 5, wherein said second stream, when directed to said ETL unit, has less than about 100 parts per million (ppm) of acetylene.

7. The method of claim 5, wherein said second stream, when directed to said ETL unit, has less than or equal to about 5 mol % carbon monoxide (CO).

8. The method of claim 5, wherein said ETL product stream has less than about 50 weight percent (wt %) water.

9. The method of claim 5, wherein said ETL unit is operated at a temperature greater than or equal to about 200° C.

10. The method of claim 5, wherein said ETL unit is operated at a pressure greater than or equal to about 200 pounds per square inch.

11. The method of claim 5, further comprising directing at least a portion of said ETL product stream to an additional separations unit that recovers a liquid stream comprising said higher hydrocarbon product(s) and a gas stream comprising hydrogen ($H_2$) and CO or carbon dioxide ($CO_2$).

12. The method of claim 11, further comprising directing said gas stream to a methanation unit to react said $H_2$ with said CO or $CO_2$ to form $CH_4$.

13. The method of claim 12, further comprising directing at least a portion of said $CH_4$ from said methanation unit to said OCM unit.

14. The method of claim 1, wherein said at least said portion of said $C_{2+}$ compounds is directed to a treatment unit prior to being directed to said cracking unit.

15. The method of claim 1, wherein an inlet temperature of said OCM unit is at most about 600° C.

16. The method of claim 1, wherein said OCM unit comprises a plurality of OCM reactors.

17. The method of claim 1, wherein said cracking unit comprises a plurality of cracking vessels.

18. The method of claim 1, further comprising directing one or more alkanes to said cracking unit along a stream external to said OCM unit.

19. The method of claim 1, wherein said first stream comprises said compounds having triple bonds and said compounds having more than one double bond.

* * * * *